United States Patent
McFarland et al.

(10) Patent No.: US 9,453,213 B2
(45) Date of Patent: *Sep. 27, 2016

(54) METHODS OF INCREASING THE CELLULOLYTIC ENHANCING ACTIVITY OF A POLYPEPTIDE

(75) Inventors: Keith McFarland, Davis, CA (US); Paul Harris, Carnation, WA (US)

(73) Assignee: Novozymes, Inc., Davis, CA (US)

( * ) Notice: Subject to any disclaimer, the term of this patent is extended or adjusted under 35 U.S.C. 154(b) by 692 days.

This patent is subject to a terminal disclaimer.

(21) Appl. No.: 12/598,723

(22) PCT Filed: May 30, 2008

(86) PCT No.: PCT/US2008/065360
§ 371 (c)(1),
(2), (4) Date: Nov. 3, 2009

(87) PCT Pub. No.: WO2008/151043
PCT Pub. Date: Dec. 11, 2008

(65) Prior Publication Data
US 2010/0129860 A1 May 27, 2010

Related U.S. Application Data

(60) Provisional application No. 60/941,243, filed on May 31, 2007.

(51) Int. Cl.
| | | |
|---|---|---|
| *C12N 9/14* | (2006.01) | |
| *C12N 9/42* | (2006.01) | |
| *C12P 1/00* | (2006.01) | |
| *C07H 21/04* | (2006.01) | |
| *C12P 7/10* | (2006.01) | |
| *C12P 19/02* | (2006.01) | |

(52) U.S. Cl.
CPC ........... *C12N 9/2437* (2013.01); *C12N 9/2445* (2013.01); *C12P 7/10* (2013.01); *C12P 19/02* (2013.01); *C12Y 302/01004* (2013.01); *C12Y 302/01021* (2013.01); *Y02E 50/16* (2013.01); *Y02E 50/17* (2013.01); *Y02P 20/52* (2015.11)

(58) Field of Classification Search
None
See application file for complete search history.

(56) References Cited

U.S. PATENT DOCUMENTS

2006/0005279 A1* 1/2006 Dotson et al. ................ 800/284
2007/0077630 A1 4/2007 Harris et al.

FOREIGN PATENT DOCUMENTS

WO    WO 2005/074647    8/2005
WO    WO 2005/074656    8/2005

OTHER PUBLICATIONS

Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Horn et al. Novel enzymes for the degradation of cellulose, Biotechnology for Biofuels (2012), 5: 45-56.*
Westereng et al. The putative endoglucanase PcGH61D from Phanerochaete Chrysosporium is a metal-dependent oxidative enzyme that cleaves cellulose, PLOS One, 6(11), p. 1-11, 2011).*
Ohmura et al. JBC, (1957), 227, p. 181-190).*
Szumilo et al. Acta Biochemica Polanica (1980), 31: p. 401-408.*
Au et al., "Purification and properties of the Endo-1 4-Beta Glucanase from Bacillus-subtilis," Journal of General Microbiology, vol. 133, No. 8, 1987, pp. 2155-2162.
MacKenzie et al., Location and kinetic properties of the cellulose system of acetivibrio cellulolyticus, Canadian Journal of Microbiology, Ottawa, vol. 28, No. 10, Jan. 1, 1982, pp. 1158-1164.
Wallecha et al., Purification and characterization of two beta-glucosidases from a thermo-tolerant yeast Pichia etchellsil, Biochimica et Biophysica ACTA (BBA)-Proteins & Proteomics, Elsevier, vol. 1649, No. 1, Jun. 26, 2003, pp. 74-84.
Bhat et al., Cellulose degrading enzymes and their potential industrial applications, Biotechnology Advances, Elsevier, vol. 15, No. 3-4, Jan. 1, 1997, pp. 583-620.

* cited by examiner

*Primary Examiner* — Iqbal H Chowdhury
(74) *Attorney, Agent, or Firm* — Robert L. Starnes

(57) ABSTRACT

The present invention relates to methods of increasing the activity of a polypeptide having cellulolytic enhancing activity, comprising: adding a soluble activating divalent metal cation to a composition comprising the polypeptide having cellulolytic enhancing activity, wherein the presence of the soluble activating divalent metal cation and the polypeptide having cellulolytic enhancing activity increases degradation or conversion of a cellulose-containing material by a cellulolytic enzyme composition compared to the polypeptide having cellulolytic enhancing activity without the soluble activating divalent metal cation. The present invention also relates to compositions, methods for degrading or converting a cellulose-containing material, and methods for producing a fermentation product.

20 Claims, 24 Drawing Sheets

ATG AAG CTT GGT TGG ATC GAG GTG GCC GCA TTG GCG GCT GCC TCA GTA GTC AGT GCC
M   K   L   G   W   I   E   V   A   A   L   A   A   A   S   V   V   S   A

Fig. 7

ATG CGT TCC CCC CTC CTC CGC TCC GCC GTT GTG GCC GCC CTG CCG GTG TTG GCC CTT GCC
 M   R   S   P   L   L   R   S   A   V   V   A   A   L   P   V   L   A   L   A

METHODS OF INCREASING THE CELLULOLYTIC ENHANCING ACTIVITY OF A POLYPEPTIDE

CROSS-REFERENCE TO RELATED APPLICATIONS

This application is a 35 U.S.C. 371 national application of PCT/US2008/065360 filed on May 30, 2008 and claims priority from U.S. provisional application Ser. No. 60/941,243 filed on May 31, 2007, which applications are fully incorporated herein by reference.

REFERENCE TO A SEQUENCE LISTING

This application contains a Sequence Listing in computer readable form. The computer readable form is incorporated herein by reference.

REFERENCE TO A DEPOSIT OF BIOLOGICAL MATERIAL

This application contains a reference to a deposit of biological material, which deposit is incorporated herein by reference.

BACKGROUND OF THE INVENTION

1. Field of the Invention

The present invention relates to methods and compositions for increasing the activity of a polypeptide having cellulolytic enhancing activity.

2. Description of the Related Art

Cellulose is a polymer of the simple sugar glucose covalently bonded by beta-1,4-linkages. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of cellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the cellulose is converted to glucose, the glucose is easily fermented by yeast into ethanol.

WO 2005/074647 discloses isolated polypeptides having cellulolytic enhancing activity and polynucleotides thereof from *Thielavia terrestris*, WO 2005/074656 discloses an isolated polypeptide having cellulolytic enhancing activity and a polynucleotide thereof from *Thermoascus aurantiacus*. U.S. Published Application Serial No. 2007/0077630 discloses an isolated polypeptide having cellulolytic enhancing activity and a polynucleotide thereof from *Trichoderma reesei*.

It would be an advantage in the art to improve the activity of polypeptides having cellulolytic enhancing activity.

The present invention relates to methods and compositions for increasing the activity of a polypeptide having cellulolytic enhancing activity.

SUMMARY OF THE INVENTION

The present invention relates to methods of increasing the activity of a polypeptide having cellulolytic enhancing activity, comprising: adding a soluble activating divalent metal cation to a composition comprising the polypeptide having cellulolytic enhancing activity, wherein the soluble activating divalent metal cation is present at an effective concentration of about 0.001 mM to about 50 mM during degradation or conversion of a cellulose-containing material and the presence of the soluble activating divalent metal cation and the polypeptide having cellulolytic enhancing activity increases the degradation or conversion of the cellulose-containing material by a cellulolytic enzyme composition compared to the polypeptide having cellulolytic enhancing activity without the soluble activating divalent metal cation.

The present invention also relates to methods for degrading or converting a cellulose-containing material, comprising: treating the cellulose-containing material with an effective amount of a cellulolytic enzyme composition comprising an effective amount of a polypeptide having cellulolytic enhancing activity and a soluble activating divalent metal cation, wherein the soluble activating divalent metal cation is present at an effective concentration of about 0.001 mM to about 50 mM.

The present invention also relates to methods for producing a fermentation product, comprising: (a) saccharifying a cellulose-containing material with an effective amount of a cellulolytic enzyme composition comprising an effective amount of a polypeptide having cellulolytic enhancing activity and a soluble activating divalent metal cation, wherein the soluble activating divalent metal cation is present at an effective concentration of about 0.001 mM to about 50 mM; (b) fermenting the saccharified cellulose-containing material of step (a) with one or more fermenting microorganisms to produce the fermentation product; and (c) recovering the fermentation product from the fermentation.

The present invention also relates to compositions comprising a polypeptide having cellulolytic enhancing activity and a soluble activating divalent metal cation, wherein the soluble activating divalent metal cation is present at an effective concentration of about 0.001 mM to about 50 mM during degradation or conversion of a cellulose-containing material and the presence of the soluble activating divalent metal cation and the polypeptide having cellulolytic enhancing activity increases the degradation or conversion of the cellulose-containing material by a cellulolytic enzyme composition compared to the polypeptide having cellulolytic enhancing activity without the soluble activating divalent metal cation.

The present invention also relates to cellulolytic enzyme compositions comprising an effective amount of a polypeptide having cellulolytic enhancing activity and a soluble activating divalent metal cation, wherein the soluble activating divalent metal cation is present at an effective concentration of about 0.001 mM to about 50 mM during degradation or conversion of a cellulose-containing material and the presence of the soluble activating divalent metal cation and the polypeptide having cellulolytic enhancing activity increases the degradation or conversion of the cellulose-containing material by the cellulolytic enzyme compositions compared to the polypeptide having cellulolytic enhancing activity without the soluble activating divalent metal cation.

BRIEF DESCRIPTION OF THE FIGURES

FIG. 7 shows the DNA sequence and amino acid sequence of an *Aspergillus oryzae* beta-glucosidase native signal sequence (SEQ ID NOs: 57 and 58).

FIG. 8 shows the DNA sequence and amino acid sequence of a *Humicola insolens* endoglucanase V signal sequence (SEQ ID NOs: 61 and 62).

Figure 12A:
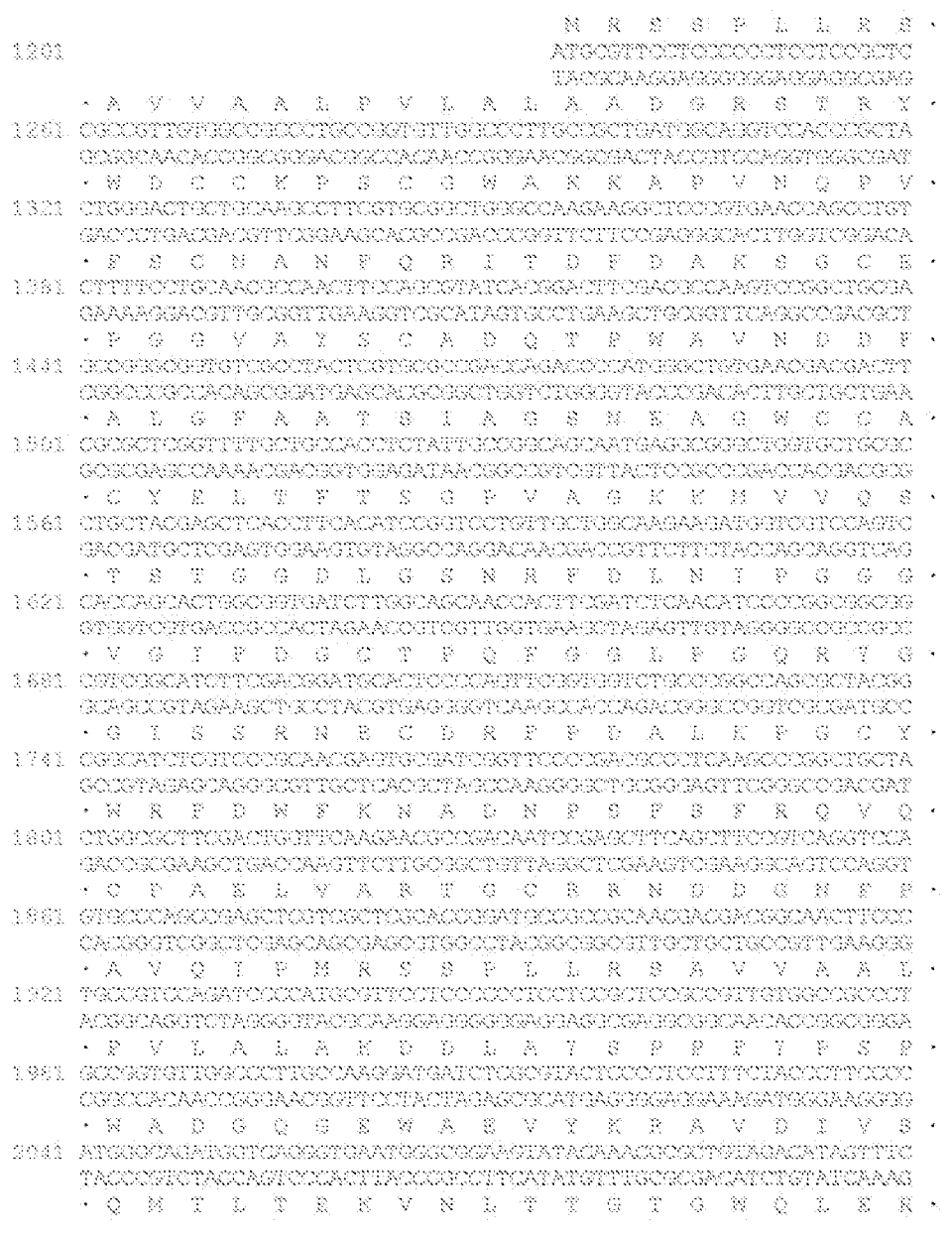
Figure 12B:
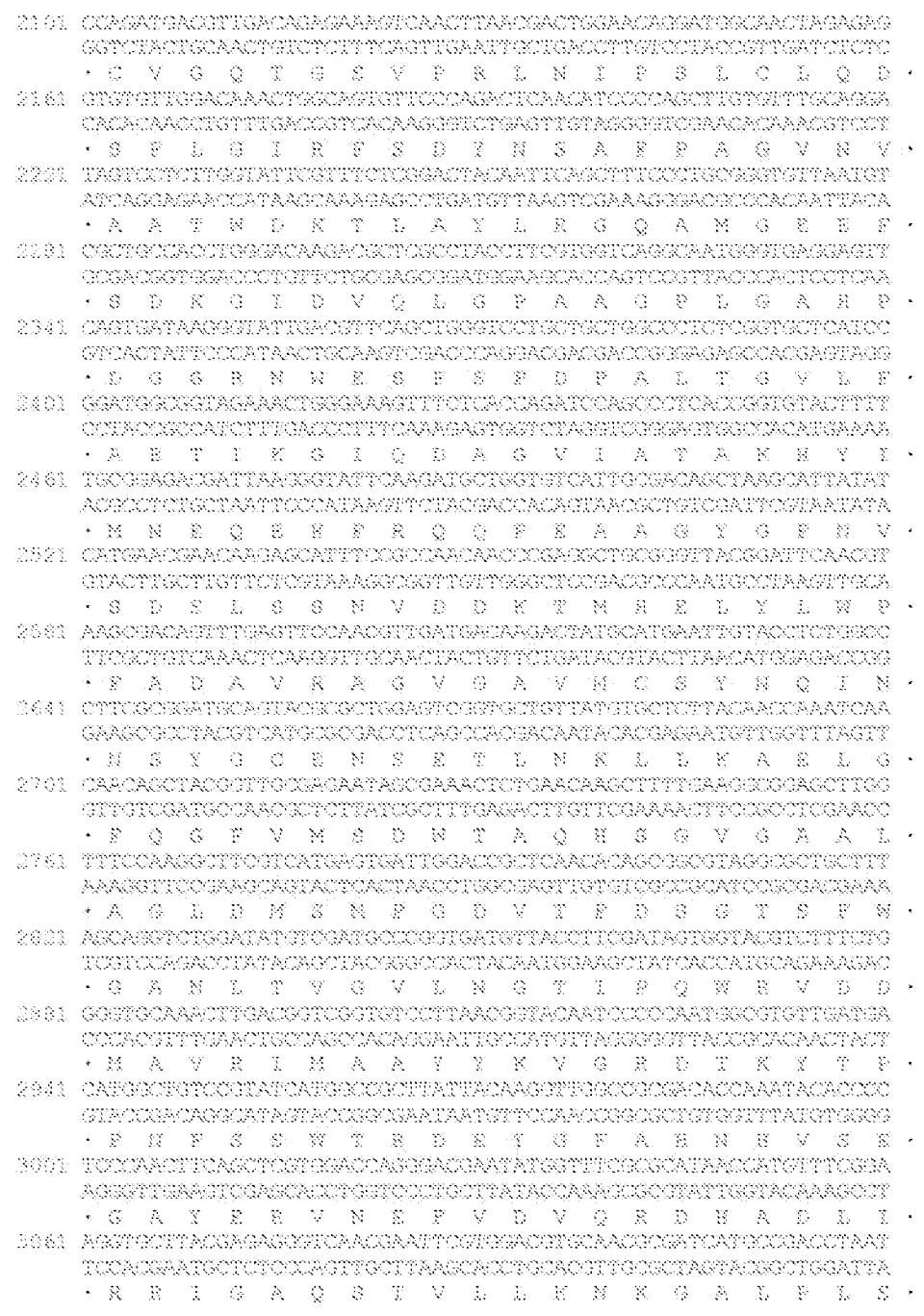
Figure 12C:
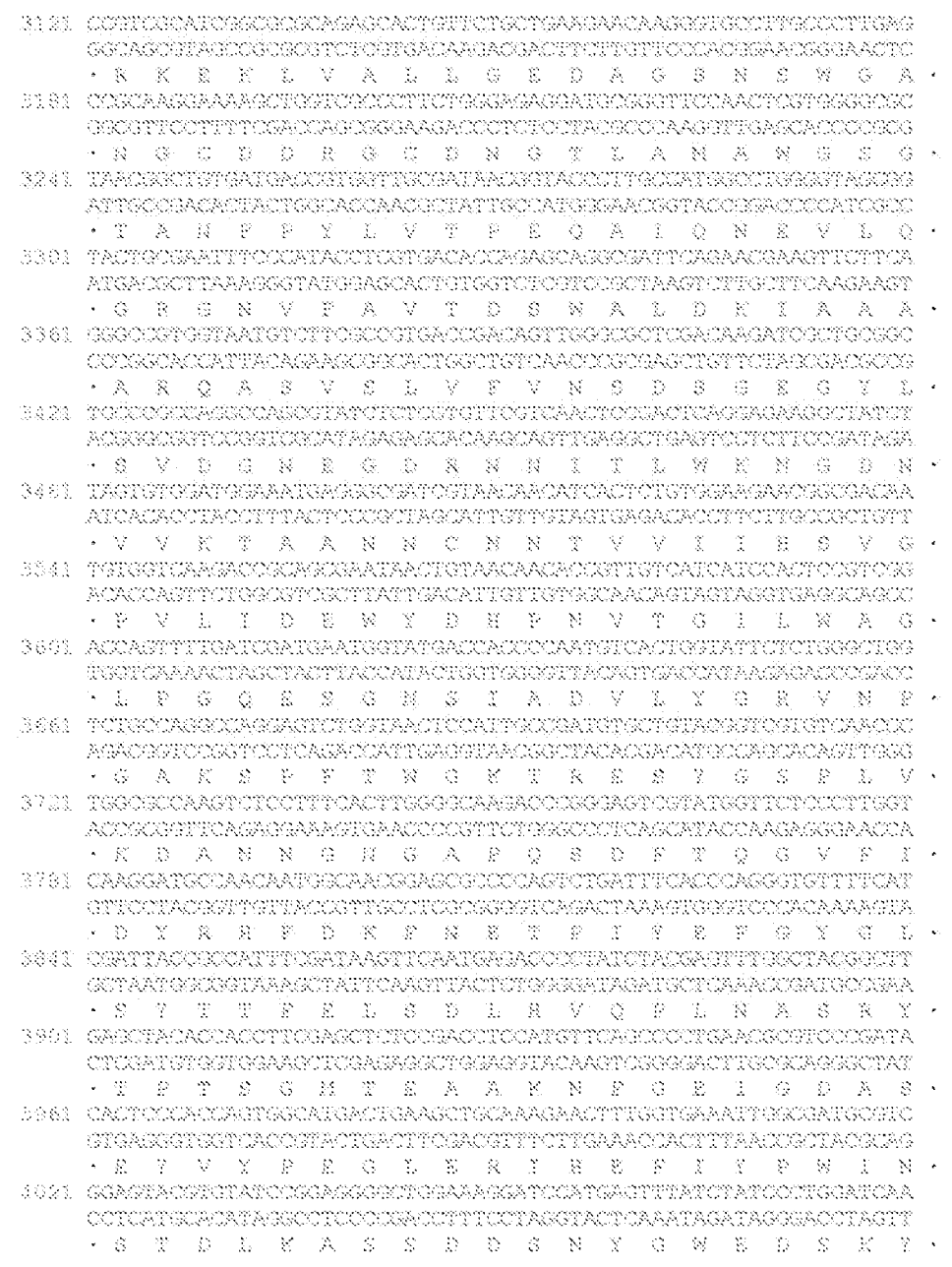
Figure 12D:
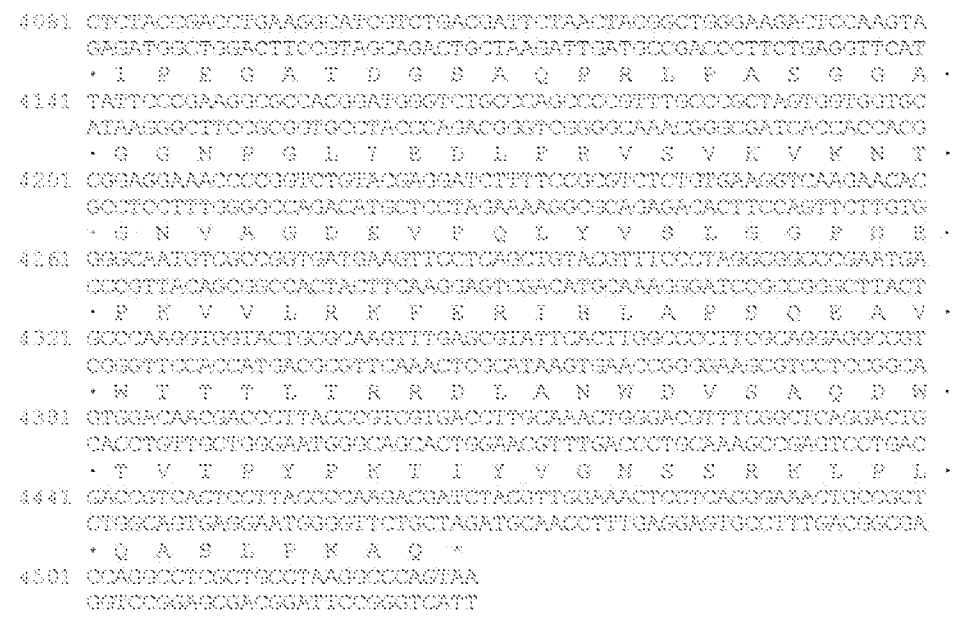

FIGS. 12A, 12B, 12C, and 12D show the DNA sequence and deduced amino acid sequence of an *Aspergillus oryzae* beta-glucosidase variant BG fusion protein (SEQ ID NOs: 25 and 26, respectively).

Figure 14A:
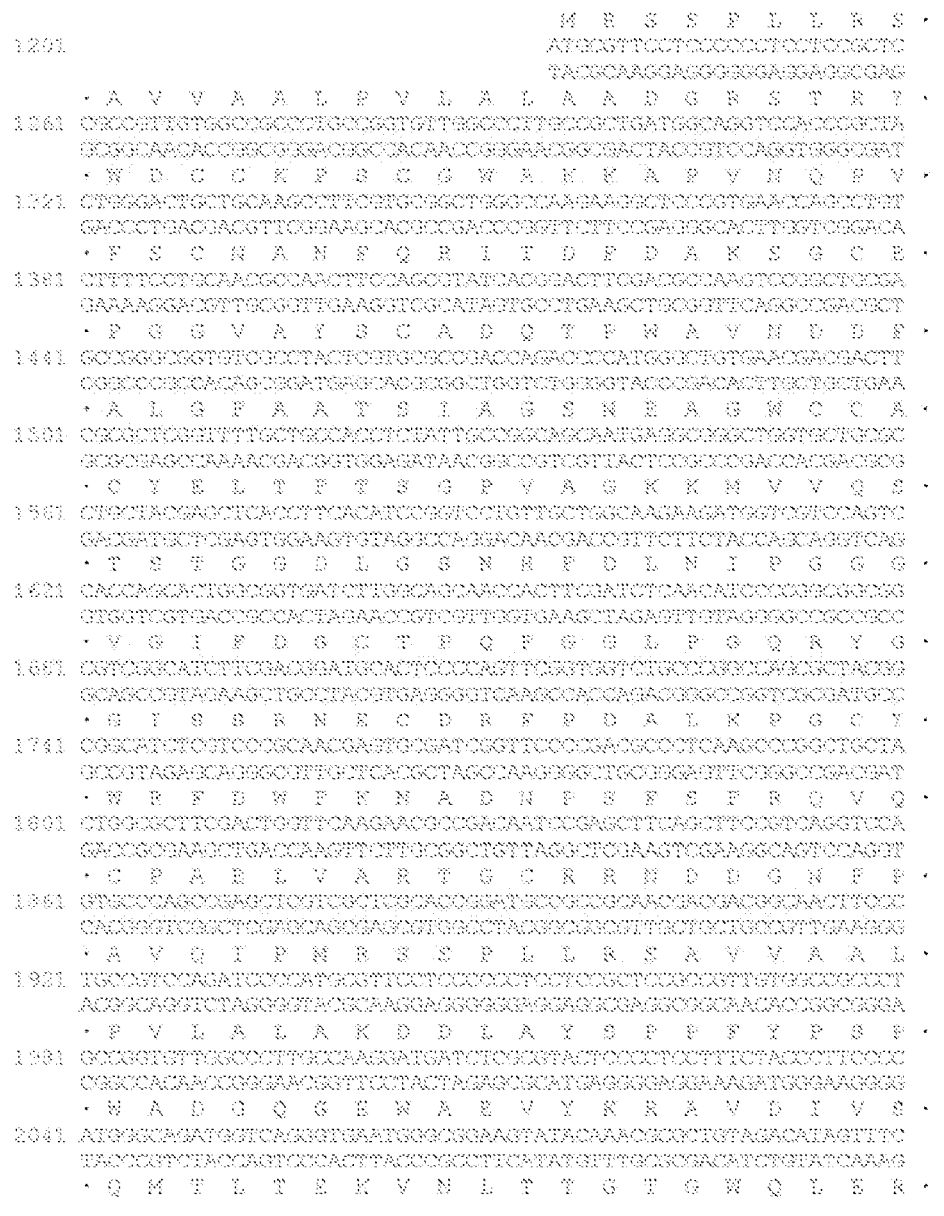
Figure 14B:
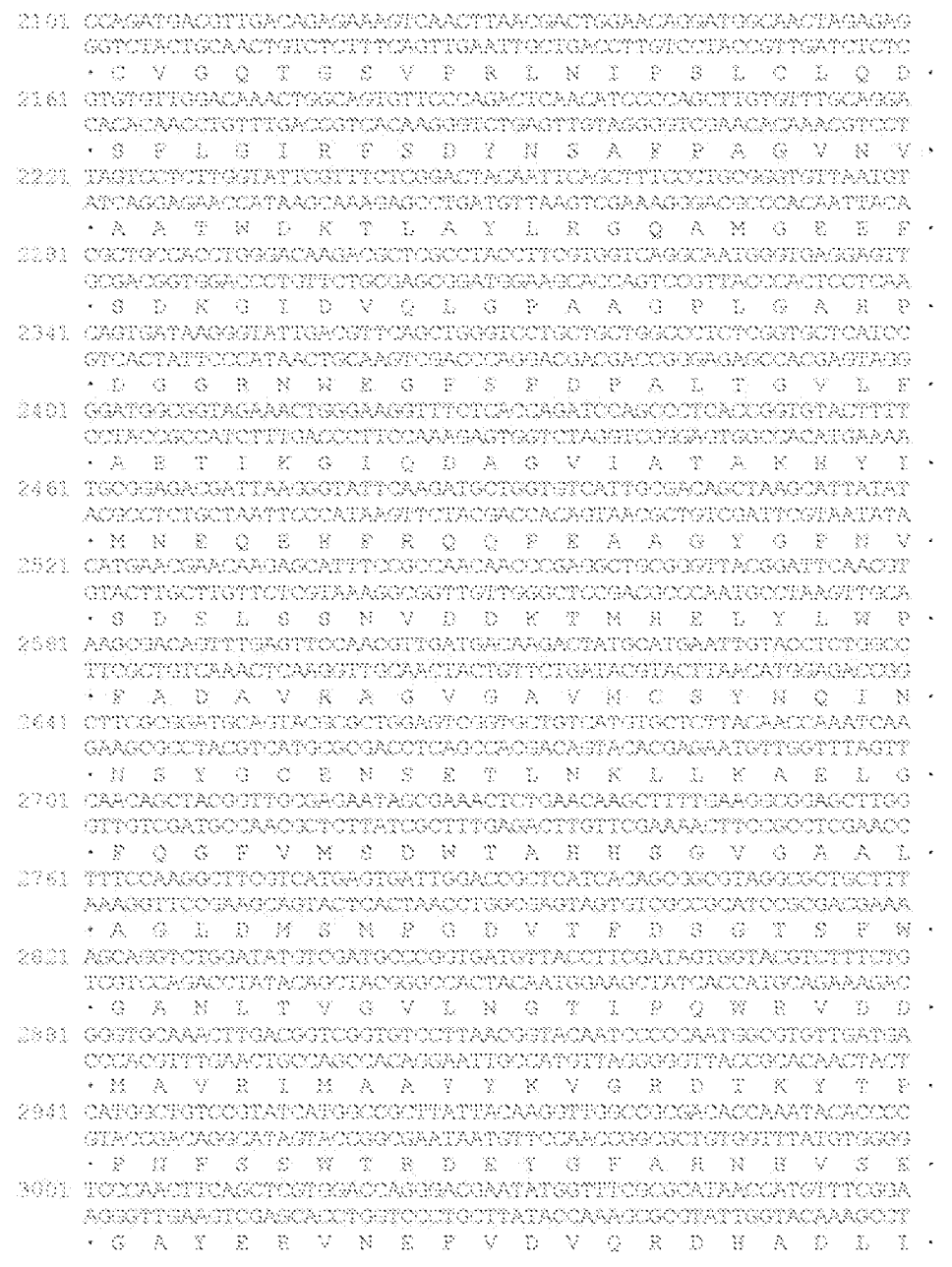
Figure 14C:
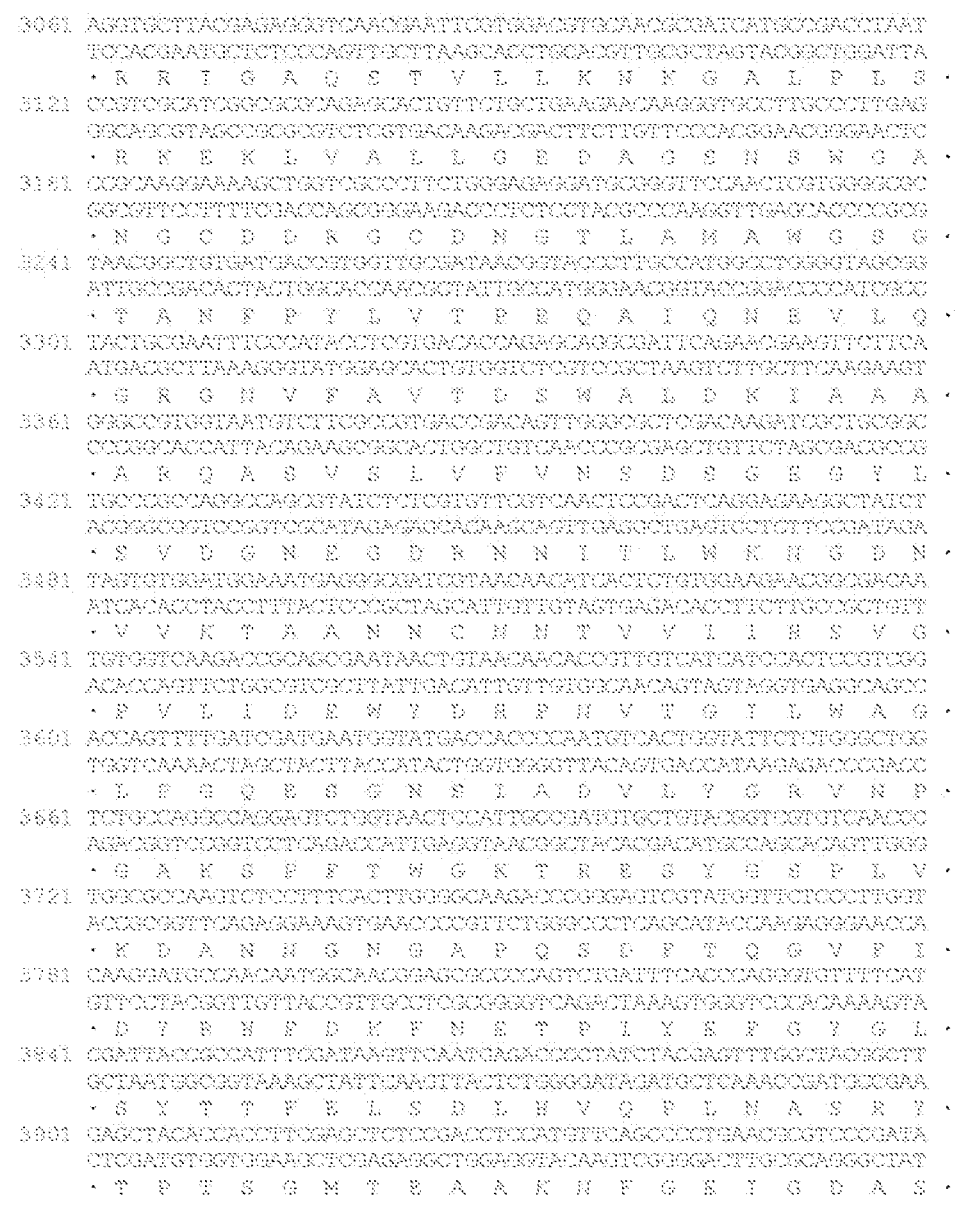

FIGS. 14A, 14B, 14C, and 14D show the DNA sequence and deduced amino add sequence of the *Aspergillus oryzae* beta-glucosidase fusion protein (SEQ ID NOs: 27 and 28, respectively).

DEFINITIONS

Figure 1:
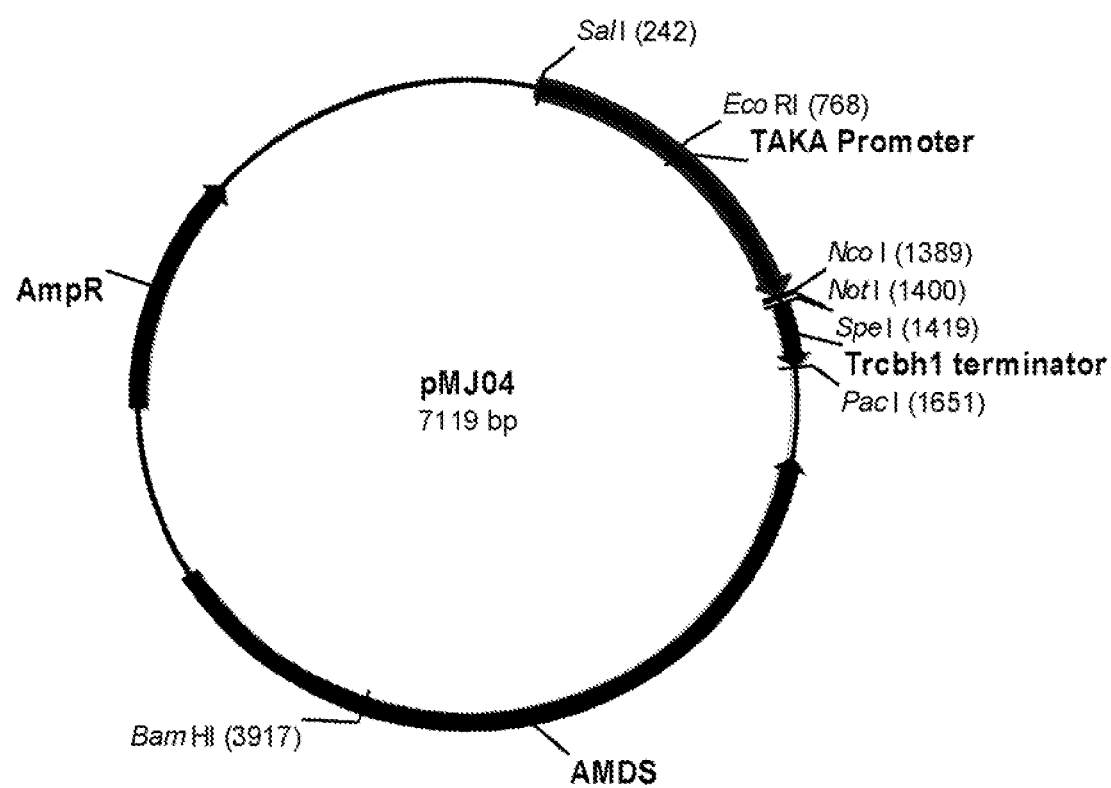
FIG. 1 shows a restriction map of pMJ04.

Cellulolytic enhancing activity: The term "cellulolytic enhancing activity" is defined herein as a biological activity that enhances the hydrolysis of a cellulose-containing material by proteins having cellulolytic activity. For purposes of the present invention, cellulolytic enhancing activity is determined by measuring the increase in reducing sugars or the increase of the total of cellobiose and glucose from the hydrolysis of a cellulose-containing material by cellulolytic protein under the following conditions: 1-50 mg of total protein containing 80-99.5% w/w cellulolytic protein/g of cellulose in PCS and 0.5-20% w/w protein of cellulolytic enhancing activity for 1-7 day at 50° C. compared to a control hydrolysis with equal total protein loading without cellulolytic enhancing activity (1-50 mg of cellulolytic protein/9 of cellulose in PCS). In a preferred aspect, a mixture of CELLUCLAST® 1.5L, (Novozymes A/S, Bagsværd, Denmark) in the presence of 3% *Aspergillus oryzae* beta-glucosidase (recombinantly produced in *Aspergillus oryzae* according to WO 02/095014) or 3% *Aspergillus fumigatus* beta-glucosidase (recombinantly produced in *Aspergillus oryzae* according to Example 22 of WO 02/095014) of cellulose protein loading is used as a standard of the cellulolytic activity.

The polypeptides having cellulolytic enhancing activity have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the cellulolytic enhancing activity of the mature polypeptide of SEC ID NO: 2, 4, 6, 8, 10, 12, or 14.

The polypeptides having cellulolytic enhancing activity enhance the hydrolysis of a cellulose-containing material catalyzed by proteins having cellulolytic activity by reducing the amount of cellulolytic enzyme required to reach the same degree of hydrolysis preferably at least 0.1-fold, more at least 0.2-fold, more preferably at least 0.3-fold, more preferably at least 0.4-fold, more preferably at least 0.5-fold, more preferably at least 1-fold, more preferably at least 3-fold, more preferably at least 4-fold, more preferably at least 5-fold, more preferably at least 10-fold, more preferably at least 20-fold, even more preferably at least 30-fold, most preferably at least 50-fold, and even most preferably at least 100-fold.

Cellulolytic activity: The term "cellulolytic activity" is defined herein as cellulase activity (e.g., endoglucanase(s), cellobiohydrolase(s), beta-glucosidase(s), or combinations thereof) that hydrolyzes a cellulose-containing material. Cellulolytic protein may hydrolyze or hydrolyzes carboxymethyl cellulose (CMC), thereby decreasing the viscosity of the incubation mixture. The resulting reduction in viscosity may be determined by a vibration viscosimeter (e.g., MIVI 3000 from Sofraser, France). Determination of cellulase activity, measured in terms of Cellulase Viscosity Unit (CEVU), quantifies the amount of catalytic activity present in a sample by measuring the ability of the sample to reduce the viscosity of a solution of carboxymethyl cellulose (CMC). The assay is performed at the temperature and pH suitable for the cellulolytic protein and substrate.

For purposes of the present invention, cellulolytic activity is determined by measuring the increase in hydrolysis of a cellulose-containing material by a cellulolytic composition under the following conditions: 1-50 mg of cellulolytic protein/g of cellulose in PCS for 1-7 day at 50° C. compared to a control hydrolysis without addition of cellulolytic protein.

Endoglucanase: The term "endoglucanase" is defined herein as an endo-1,4-(1,3;1,4)-beta-D-glucan 4-glucanohydrolase (E.C. No. 3.2.1.4), which catalyses endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. For purposes of the present invention, endoglucanase activity is determined using carboxymethyl cellulose (CMC) hydrolysis according to the procedure of Ghose, 1987, *Pure and App. Chem.* 59: 257-268.

Cellobiohydrolase: The term "cellobiohydrolase" is defined herein as a 1,4-beta-D-glucan cellobiohydrolase (E.C. 3.2.1.91), which catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain. For purposes of the present invention, cellobiohydrolase activity is determined according to the procedures described by Lever et al., 1972, *Anal. Biochem.* 47: 273-279 and by van Tilbeurgh et al., 1982, *FEBS Letters* 149: 152-156; van Tilbeurgh and Claeyssens, 1985, *FEBS Letters* 187: 283-288. In the present invention, the Lever et al. method was employed to assess hydrolysis of cellulose in corn stover, while the method of van Tilbeurgh et al. was used to determine the cellobiohydrolase activity on a fluorescent disaccharide derivative.

Beta-glucosidase: The term "beta-glucosidase" is defined herein as a beta-D-glucoside glucohydrolase (E.C. 3.2.1.21), which catalyzes the hydrolysis of terminal non-reducing beta-D-glucose residues with the release of beta-D-glucose. For purposes of the present invention, beta-glucosidase activity is determined according to the basic procedure described by Venturi et al., 2002, *J. Basic Microbiol.* 42: 55-66, except different conditions were employed as described herein. One unit of beta-glucosidase activity is defined as 1.0 μmole of p-nitrophenol produced per minute at 50° C., pH 5 from 4 mM p-nitrophenyl-beta-D-glucopyranoside as substrate in 100 mM sodium citrate, 0.01% TWEEN® 20.

Family 7, 12, 45, or 61 glycoside hydrolase: The term "Family 7 glycoside hydrolase" or "Family GH7", "Family 12 glycoside hydrolase" or "Family GH12", "Family 45 glycoside hydrolase" or "Family GH45", and "Family 61 glycoside hydrolase" or "Family GH61" is defined herein as a polypeptide falling into the glycoside hydrolase Family 7, Family 12, Family 45, and Family 61, respectively, according to Henrissat, 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696. Presently, Henrissat lists the GH61 Family as unclassified indicating that properties such as mechanism, catalytic nucleophile/base, catalytic proton donors, and 3-D structure are not known for polypeptides belonging to this family, A GH7, GH12, or GH45 protein is also referred to as a CEL7, CEL12, or CEL45 protein, respectively.

Cellulose-containing material: The predominant polysaccharide in the primary cell wall of biomass is cellulose, the second most abundant is hemi-cellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

The cellulose-containing material can be any material containing cellulose. Cellulose is generally found, for example, in the stems, leaves, hulls, husks, and cobs of plants or leaves, branches, and wood of trees. The cellulose-containing material can be, but is not limited to, herbaceous material, agricultural residues, forestry residues, municipal solid wastes, waste paper, and pulp and paper mill residues. The cellulose-containing material can be any type of biomass including, but not limited to, wood resources, municipal solid waste, wastepaper, crops, and crop residues (see, for example, Wiselogel et al., 1995, in Handbook on Bioethanol (Charles E. Wyman, editor), pp. 105-118, Taylor & Francis, Washington D.C.; Wyman, 1994, Bioresource Technology 50; 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose-containing material is preferably in the form of lignocellulose, e.g., a plant cell wall material containing lignin, cellulose, and hemicellulose in a mixed matrix.

In a preferred aspect, the cellulose-containing material is corn stover. In another preferred aspect, the cellulose-containing material is corn fiber. In another preferred aspect, the cellulose-containing material is corn cobs. In another preferred aspect, the cellulose-containing material is switch grass. In another preferred aspect, the cellulose-containing material is rice straw. In another preferred aspect, the cellulose-containing material is paper and pulp processing waste. In another preferred aspect, the cellulose-containing material is woody or herbaceous plants. In another preferred aspect, the cellulose-containing material is bagasse.

The cellulose-containing material may be used as is or may be subjected to pretreatment, using conventional methods known in the art. For example, physical pretreatment techniques can include various types of milling, irradiation, steaming/steam explosion, and hydrothermolysis; chemical pretreatment techniques can include dilute acid, alkaline, organic solvent, ammonia, sulfur dioxide, carbon dioxide, and pH-controlled hydrothermolysis; and biological pretreatment techniques can involve applying lignin-solubilizing microorganisms (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh, P., and Singh, A., 1993, Physicochemical and biological treatments for enzymatic/microbial conversion of lignocellulosic biomass, *Adv. Appl. Microbiol.* 39: 295-333: McMillan, J. D. 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T 1999. Ethanol production from renewable resources, in *Advances in Biochemical Engineering/Biotechnology*, Scheper, T., ed., Springer-Verlag Berlin Heidelberg, Germany, 65: 207-241: Olsson, L., and Hahn-Hagerdal, B., 1996, Fermentation of lignocellulosic hydrolysates for ethanol production, *Enz. Microb. Tech,* 18: 312-331: and Vallander, L., and Eriksson, K.-E, L. 1990, Production of ethanol from lignocellulosic materials: State of the art, *Adv. Biochem. Eng./Biotechnol.* 42: 63-95).

Pre-treated corn stover: The term "PCS" or "Pre-treated Corn Stover" is defined herein as a cellulose-containing material derived from corn stover by treatment with heat and dilute acid. For purposes of the present invention, PCS is made by the method described in Example 20, or variations thereof in time, temperature and amount of acid.

Isolated polypeptide: The term "isolated polypeptide" as used herein refers to a polypeptide that is isolated from a source. In a preferred aspect, the polypeptide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by SDS-PAGE.

Substantially pure polypeptide: The term "substantially pure polypeptide" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation. The polypeptides of the present invention are preferably in a substantially pure form, i.e., that the polypeptide preparation is essentially free of other polypeptide material with which it is natively or recombinantly associated. This can be accomplished, for example, by preparing the polypeptide by well-known recombinant methods or by classical purification methods.

Mature polypeptide: The term "mature polypeptide" is defined herein as a polypeptide having biological activity, e.g., enzyme activity, which is in its final form following translation and any post-translational modifications, such as N-terminal processing, C-terminal truncation, glycosylation, phosphorylation, etc.

Mature polypeptide coding sequence: The term "mature polypeptide coding sequence" is defined herein as a nucleotide sequence that encodes a mature polypeptide having biological activity.

Identity: The relatedness between two amino acid sequences or between two nucleotide sequences is described by the parameter "identity".

For purposes of the present invention, the degree of identity between two amino acid sequences is determined using the Needleman-Wunsch algorithm (Needleman and Wunsch, 1970, *J. Mol. Blot.* 48: 443-453) as implemented in the Needle program of the EMBOSS package (EMBOSS: The European Molecular Biology Open Software Suite. Rice et at, 2000, *Trends in Genetics* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the-nobrief option) is used as the percent identity and is calculated as follows:

(Identical Residues×100)/(Length of Alignment−
Total Number of Gaps in Alignment)

For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice at., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the-no brief option) is used as the percent identity and is calculated as follows:

(identical Deoxyribonucleotides×100/(Length of
Alignment−Total Number of Gaps in Alignment)

Homologous sequence: The term "homologous sequence" is defined herein as sequences with an E value (or expectancy score) of less than 0.001 using the blastp (for protein databases) or tblastn (for nucleic acid databases) algorithms with the BLOSUM62 matrix, wordsize 3, gap existence cost 11, gap extension cost 1, no low complexity filtration, and a mature protein sequence as query. See Altschul et al., 1997, *Nucleic Acids Res.* 25: 3389-3402.

Polypeptide Fragment: The term "polypeptide fragment" is defined herein as a polypeptide having one or more (several) amino acids deleted from the amino and/or carboxyl terminus of the mature polypeptide or a homologous sequence thereof; wherein the fragment has activity as the mature polypeptide thereof.

Subsequence: The term "subsequence" is defined herein as a nucleotide sequence having one or more (several) nucleotides deleted from the 5' and/or 3' end of the mature polypeptide coding sequence or a homologous sequence thereof; wherein the subsequence encodes a polypeptide fragment having activity as the mature polypeptide thereof.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide that is isolated from a source. In a preferred aspect, the polynucleotide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively or recombinantly associated. A substantially pure polynucleotide may, however, include naturally occurring 5 and 3' untranslated regions, such as promoters and terminators. It is preferred that the substantially pure polynucleotide is at least 98% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form, i.e., that the polynucleotide preparation is essentially free of other polynucleotide material with which it is natively or recombinantly associated. The polynucleotides may be of genomic, cDNA. RNA, semisynthetic, synthetic origin, or any combinations thereof.

cDNA: The term "cDNA" is defined herein as a DNA molecule that can be prepared by reverse transcription from a mature, spliced, mRNA molecule obtained from a eukaryotic cell. cDNA lacks intron sequences that are usually present in the corresponding genomic DNA. The initial, primary RNA transcript is a precursor to mRNA that is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequence: The term "control sequences" is defined herein to include all components necessary for the expression of a polynucleotide encoding a polypeptide of the present invention. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant nucleotide sequence.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the present invention and is operably linked to additional nucleotides that provide for its expression.

Host cell: The term "host cell", as used herein, includes any cell type that is susceptible to transformation, transfection, transduction, and the like with a nucleic acid construct or expression vector comprising a polynucleotide.

Modification: The term "modification" means herein any chemical modification of a mature polypeptide or a homologous sequence thereof; as well as genetic manipulation of the DNA encoding such a polypeptide. The modification can be a substitution, a deletion and/or an insertion of one or more (several) amino acids as well as replacements of one or more (several) amino acid side chains.

Artificial variant: When used herein, the term "artificial variant" means a polypeptide produced by an organism expressing a modified nucleotide sequence of a mature polypeptide coding sequence or a homologous sequence thereof. The modified nucleotide sequence is obtained through human intervention by modification of the polynucleotide sequence or a homologous sequence thereof.

DETAILED DESCRIPTION OF THE INVENTION

The present invention relates to methods of increasing the activity of a polypeptide having cellulolytic enhancing activity, comprising: adding a soluble activating divalent metal cation to a composition comprising the polypeptide having cellulolytic enhancing activity, wherein the soluble activating divalent metal cation is present at an effective concentration of about 0.001 mM to about 50 mM during degradation or conversion of a cellulose-containing material and the presence of the soluble activating divalent metal cation and the polypeptide having cellulolytic enhancing activity increases the degradation or conversion of the cellulose-containing material by a cellulolytic enzyme composition compared to the polypeptide having cellulolytic enhancing activity without the soluble activating divalent metal cation.

The present invention also relates to methods for degrading or converting a cellulose-containing material, comprising: treating the cellulose-containing material with an effective amount of a cellulolytic enzyme composition comprising an effective amount of a polypeptide having cellulolytic enhancing activity and a soluble activating divalent metal cation, wherein the soluble activating divalent metal cation is present at an effective concentration of about 0.001 mM to about 50 mM.

The present invention also relates to methods for producing a fermentation product, comprising: (a) saccharifying a cellulose-containing material with an effective amount of a cellulolytic enzyme composition comprising an effective amount of a polypeptide having cellulolytic enhancing activity and a soluble activating divalent metal cation, wherein the soluble activating divalent metal cation is present at an effective concentration of about 0.001 mM to about 50 mM: (b) fermenting the saccharified cellulose-containing material of step (a) with one or more fermenting microorganisms to produce the fermentation product; and (c) recovering the fermentation product from the fermentation.

The present invention also relates to compositions comprising a polypeptide having cellulolytic enhancing activity and a soluble activating divalent metal cation, wherein the soluble activating divalent metal cation is present at an effective concentration of about 0.001 mM to about 50 mM during degradation or conversion of a cellulose-containing material and the presence of the soluble activating divalent metal cation and the polypeptide having cellulolytic enhancing activity increases the degradation or conversion of the cellulose-containing material by a cellulolytic enzyme composition compared to the polypeptide having cellulolytic enhancing activity without the soluble activating divalent metal cation.

The present invention also relates to cellulolytic enzyme compositions comprising an effective amount of a polypeptide having cellulolytic enhancing activity and a soluble activating divalent metal cation, wherein the soluble activating divalent metal cation is present at an effective concentration of about 0.001 mM to about 50 mM during degradation or conversion of a cellulose-containing material and the presence of the soluble activating divalent metal cation and the polypeptide having cellulolytic enhancing activity increases the degradation or conversion of the cellulose-containing material by the cellulolytic enzyme compositions compared to the polypeptide having cellulolytic enhancing activity without the soluble activating divalent metal cation.

Divalent Metal Cations

Any soluble activating divalent metal cation can be used in the present invention. In a preferred aspect, the soluble activating divalent metal cation is selected from the group consisting of $Mn^{++}$, $Co^{++}$, $Mg^{++}$, $Ca^{++}$, and a combination thereof. In a more preferred aspect, the soluble activating divalent metal cation is $Mn^{++}$. In another more preferred aspect, the soluble activating divalent metal cation is $Co^{++}$. In another more preferred aspect, the soluble activating divalent metal cation is $Mg^{++}$. In another more preferred aspect, the soluble activating divalent metal cation is $Ca^{++}$. In another more preferred aspect, the soluble activating divalent metal cation is two or more (several) cations selected from the group consisting of $Mn^{++}$, $Co^{++}$, $Mg^{++}$, and $Ca^{++}$. In a most preferred aspect, the soluble activating divalent metal cation is $Mn^{++}$. In another most preferred aspect, the soluble activating divalent metal cation is $Mg^{++}$.

The soluble activating divalent metal cation is added during the degradation or conversion of a cellulose-containing substrate at an effective concentration of preferably about 0.001 mM to about 50 mM, more preferably about 0.01 mM to about 25 mM, more preferably about 0.1 mM to about 25 mM, more preferably about 0.1 mM to about 10 mM, even more preferably about 0.3 mM to about 5 mM, most preferably about 0.3 mM to about 2.5 mM, and even most preferably about 0.3 mM to about 1 mM.

In a preferred aspect, the soluble activating divalent metal cation is added during the degradation or conversion of a cellulose-containing substrate at an effective concentration of about 0.001 mM to about 50 mM. In a more preferred aspect, the soluble activating divalent metal cation is added during the degradation or conversion of a cellulose-containing substrate at an effective concentration of about 0.01 mM to about 25 mM. In a more preferred aspect, the soluble activating divalent metal cation is added during the degradation or conversion of a cellulose-containing substrate at an effective concentration of about 0.1 mM to about 25 mM. In a more preferred aspect, the soluble activating divalent metal cation is added during the degradation or conversion of a cellulose-containing substrate at an effective concentration of about 0.1 mM to about 10 mM. In a even more preferred aspect, the soluble activating divalent metal cation is added during the degradation or conversion of a cellulose-containing substrate at an effective concentration of about 0.3 mM to about 5 mM. In a most preferred aspect, the soluble activating divalent metal cation is added during the degradation or conversion of a cellulose-containing substrate at an effective concentration of about 0.3 mM to about 2.5 mM. In a even most preferred aspect, the soluble activating divalent metal cation is added during the degradation or conversion of a cellulose-containing substrate at an effective concentration of about 0.3 mM to about 1 mM.

The soluble activating divalent metal cation is preferably added as a soluble salt, such as, for example, a sulfate, carbonate, chloride, citrate, nitrate, nitrite, fluoride, or iodide salt. It is well known in the art, however, that cellulosic biomass can comprise a number of divalent metal cations. See, for example, F. B. Salisbury and C. W. Ross: Plant Physiology, Wadsworths Publishing Company, Belmont, Calif. (1992). The cellulosic biomass can, therefore, be used, in part or wholly, as a source of the metal cations. The activating divalent metal cations may be soluble or insoluble, The term "soluble activating divalent metal cation" is defined herein as a divalent metal cation that is available in solution to increase the activity of a polypeptide having cellulolytic enhancing activity. The term "insoluble activating divalent metal cation" is defined herein as a divalent metal cation that is unavailable in solution to increase the activity of a polypeptide having cellulolytic enhancing activity. The divalent metal cation may be unavailable because, for example, it is chelated by, for example, EDTA or EGTA, or it is complexed with a component of the cellulosic biomass, for example, pyrophosphate.

The cellulosic biomass can also supply soluble divalent metal cations that inhibit the cellulolysis (hereinafter "soluble inhibitory divalent metal cation"). For example, an inhibitory divalent metal cation is $Zn^{++}$ or $Fe^{++}$. Consequently, under conditions where a mixture of soluble divalent metal cations are present, some that activate and others that inhibit cellulolysis, an excess of a soluble activating divalent metal cation is added to overcome the inhibitory effect of the inhibitory divalent metal cations. In such a situation to prevent inhibitory divalent metal cations from adversely affecting the polypeptide having cellulolytic enhancing activity, the methods of the present invention further comprise supplementing the concentration of the soluble activating divalent metal cation to maintain the effective concentration of the soluble activating divalent metal cation in the range of preferably about 0.001 mM to about 50 mM, more preferably about 0.01 mM to about 25 mM, more preferably about 0.1 mM to about 25 mM, more preferably about 0.1 mM to about 10 mM, even more preferably about 0.3 mM to about 5 mM, most preferably about 0.3 mM to about 2.5 mM, and even most preferably about 0.3 mM to about 1 mM for a period sufficient to degrade or convert the cellulose-containing material.

In a preferred aspect, the concentration of the soluble activating divalent metal cation is supplemented during the degradation or conversion of a cellulose-containing substrate to maintain an effective concentration of about 0.001 mM to about 50 mM. In a more preferred aspect, the concentration of the soluble activating divalent metal cation is supplemented during the degradation or conversion of a cellulose-containing substrate to maintain an effective concentration of about 0.01 mM to about 25 mM. In a more preferred aspect, the concentration of the soluble activating divalent metal cation is supplemented during the degradation or conversion of a cellulose-containing substrate to maintain an effective concentration of about 0.1 mM to about 25 mM. In a more preferred aspect, the concentration of the soluble activating divalent metal cation is supplemented during the degradation or conversion of a cellulose-containing substrate to maintain an effective concentration of about 0.1 mM to about 10 mM. In a even more preferred aspect, the concentration of the soluble activating divalent metal cation is supplemented during the degradation or conversion of a cellulose-containing substrate to maintain an effective concentration of about 0.3 mM to about 5 mM. In a most preferred aspect, the concentration of the soluble activating divalent metal cation is supplemented during the degradation or conversion of a cellulose-containing substrate to maintain an effective concentration of about 0.3 mM to about 2.5 mM. In a even most preferred aspect, the concentration of the soluble activating divalent metal cation is supplemented during the degradation or conversion of a cellulose-containing substrate to maintain an effective concentration of about 0.3 mM to about 1 mM.

The concentration of divalent metal cations in cellulosic biomass can be determined using any method known in the art, such as atomic absorption, electrochemical electrodes, metal ion biosensors, or optical sensors, or titration by chelation (see, for example, Methods in Enzymology, v. 158 (multiple chapters), Haugland, R. P. *Handbook of Fluorescent Probes and Research Chemicals,* 6th ed.; Molecular Probes, Inc.: Eugene, Oreg., 1996., Thompson et al. *Anal. Chem.,* 70 (22). 4717-4723, 1998, Inductively Coupled Plasma Mass Spectrometry, Akbar Montaser (Editor) May 1998).

In the methods of the present invention, a soluble activating divalent metal cation increases the activity of a polypeptide having cellulolytic enhancing activity preferably at least 0.1-fold, more preferably at least 0.2-fold, more preferably at least 0.3-fold, more preferably at least 0.4-fold, more preferably at least 0.5-fold, more preferably at least 1-fold, more preferably at least 3-fold, more preferably at least 4-fold, more preferably at least 5-fold, more preferably at least 10-fold, more preferably at least 20-fold, even more preferably at least 30-fold, most preferably at least 50-fold, and even most preferably at least 100-fold.

Cellulolytic Enzyme Compositions

The present invention also relates to compositions comprising a polypeptide having cellulolytic enhancing activity and a soluble activating divalent metal cation, wherein the soluble activating divalent metal cation is present at an effective concentration of preferably about 0.001 mM to about 50 mM, more preferably about 0.01 mM to about 25 mM, more preferably about 0.1 mM to about 25 mM, more preferably about 0.1 mM to about 10 mM, even more preferably about 0.3 mM to about 5 mM, most preferably about 0.3 mM to about 2.5 mM, and even most preferably about 0.3 mM to about 1 mM during degradation or conversion of a cellulose-containing material and the presence of the soluble activating divalent metal cation and the polypeptide having cellulolytic enhancing activity increases the degradation or conversion of the cellulose-containing material by a cellulolytic enzyme composition compared to the polypeptide having cellulolytic enhancing activity without the soluble activating divalent metal cation.

The present invention also relates to cellulolytic enzyme compositions comprising an effective amount of a polypeptide having cellulolytic enhancing activity and a soluble activating divalent metal cation, wherein the soluble activating divalent metal cation is present at an effective concentration of preferably about 0.001 mM to about 50 mM, more preferably about 0.01 mM to about 25 mM, more preferably about 0.1 mM to about 25 mM, more preferably about 0.1 mM to about 10 mM, even more preferably about 0.3 mM to about 5 mM, most preferably about 0.3 mM to about 2.5 mM, and even most preferably about 0.3 mM to about 1 mM during degradation or conversion of a cellulose-containing material and the presence of the soluble activating divalent metal cation and the polypeptide having cellulolytic enhancing activity increases the degradation or conversion of the cellulose-containing material by the cellulolytic enzyme compositions compared to the polypeptide having cellulolytic enhancing activity without the soluble activating divalent metal cation.

In the methods of the present invention, the cellulolytic enzyme composition may comprise any protein involved in the processing of a cellulose-containing material to glucose, or hemicellulose to xylose, mannose, galactose, and arabinose, their polymers, or products derived from them as described below. In one aspect, the cellulolytic enzyme composition comprises an endoglucanase, a cellobiohydrolase, a beta-glucosidase, or a combination thereof. In another aspect, the cellulolytic enzyme composition further comprises one or more additional enzyme activities to improve the degradation of the cellulose-containing material. Preferred additional enzymes are hemicellulases, esterases (e.g., lipases, phospholipases, and/or cutinases), proteases, laccases, peroxidases, or mixtures thereof.

The cellulolytic enzyme composition may be a monocomponent preparation, e.g., an endoglucanase, a multicomponent preparation, e.g., endoglucanase(s), cellobiohydrolase(s), and beta-glucosidase(s), or a combination of multicomponent and monocomponent protein preparations. The cellulolytic proteins may have activity, i.e. hydrolyze the cellulose-containing material, either in the acid, neutral, or alkaline pH-range.

As mentioned above, the cellulolytic proteins used in the present invention may be monocomponent preparations, i.e., a component essentially free of other cellulolytic components. The single component may be a recombinant component, i.e., produced by cloning of a DNA sequence encoding the single component and subsequent cell transformed with the DNA sequence and expressed in a host (see, for example, WO 91/17243 and WO 91/17244). The host cell may be a heterologous host (enzyme is foreign to host) or the host may also be a wild-type host (enzyme is native to host). Monocomponent cellulolytic proteins may also be prepared by purifying such a protein from a fermentation broth.

The enzymes used in the present invention may be in any form suitable for use in the processes described herein, such as, for example, a crude fermentation broth with or without cells, a dry powder or granulate, a non-dusting granulate, a liquid, a stabilized liquid, or a protected enzyme. Granulates may be produced, e.g., as disclosed in U.S. Pat. Nos. 4,106,991 and 4,661,452, and may optionally be coated by process known in the art. Liquid enzyme preparations may, for instance, be stabilized by adding stabilizers such as a sugar, a sugar alcohol or another polyol, and/or lactic acid or another organic acid according to established process. Protected enzymes may be prepared according to the process disclosed in EP 238,216.

A polypeptide having cellulolytic enzyme activity may be obtained from microorganisms of any genus. The term "obtained from" means herein that the enzyme may have been isolated from an organism that naturally produces the enzyme as a native enzyme. The term "obtained from" also means herein that the enzyme may have been produced recombinantly in a host organism, wherein the recombinantly produced enzyme is either native or foreign to the host organism or has a modified amino acid sequence, e.g., having one or more amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained by chemical or recombinant mutagenesis, such as by site-directed mutagenesis or shuffling. Consequently, chemically modified or protein engineered mutants of cellulolytic proteins may also be used in the present invention. In a preferred aspect, the polypeptide obtained from a given source is secreted extracellularly.

A polypeptide having cellulolytic enzyme activity may be a bacterial polypeptide. For example, the polypeptide may be a gram positive bacterial polypeptide such as a *Bacillus, Streptococcus, Streptomyces, Staphylococcus, Enterococcus, Lactobacillus, Lactococcus, Clostridium, Geobacillus,* or *Oceanobacillus* polypeptide having cellulolytic enzyme activity, or a Gram negative bacterial polypeptide such as an *E. coli. Pseudomonas, Salmonella, Campylobacter, Helicobacter, Flavobacterium, Fusobacterium, Ilyobacter, Neisseria,* or *Ureaplasma* polypeptide having cellulolytic enzyme activity.

In a preferred aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* polypeptide having cellulolytic enzyme activity.

In another preferred aspect, the polypeptide is a *Streptococcus equisimilis, Streptococcus pyogenes, Streptococcus uberis,* or *Streptococcus equi* subsp. *Zooepidemicus* polypeptide having cellulolytic enzyme activity.

In another preferred aspect, the polypeptide is a *Streptomyces achromogenes, Streptomyces avermitilis, Streptomyces coelicolor, eptomyces griseus,* or *Streptomyces lividans* polypeptide having cellulolytic enzyme activity.

The polypeptide having cellulolytic enzyme activity may also be a fungal polypeptide, and more preferably a yeast polypeptide such as a *Candida, Kluyveromyces, Pichia, Saccharomyces, Schizosaccharomyces,* or *Yarrowia* polypeptide having cellulolytic enzyme activity; or more preferably a filamentous fungal polypeptide such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Mycelioplithora, Neocallimastix, Neurospora, Paecilomyces, Penicillium, Phanerochaete, Piromyces, Poitrasia, Pseudopiectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* polypeptide having cellulolytic enzyme activity.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* polypeptide having cellulolytic enzyme activity.

In another preferred aspect, the polypeptide is an *Acremonium cellulolyticus, Aspergillus acuteatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinurn, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophlia, Neurospora crassa, Penicillium funiculosum, Penicillium purpurogenurn, Phanerochaete chrysosparium, Thielavia achromatica, Thielavia albomyces, Thielavia albopilosa, Thielavia australeinsis, Thielavia fimeti, Thielavia microspore, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei, Trichoderma viride,* or *Trichophaea saccata* polypeptide having cellulolytic enzyme activity.

In the methods of the present invention, any endoglucanase, cellobiohydrolase, and/or beta-glucosidase, as well as any other cellulolytic enzyme, can be used.

Examples of bacterial endoglucanases that can be used in the present invention, include, but are not limited to an *Acidothermus cellulolyticus* endoglucanase (WO 91/05039; WO 93/15186: U.S. Pat. No. 5,275,944; WO 96/02551; U.S. Pat. No. 5,536,655, WO 00/70031, WO 05/093050); *Thermobifida fusca* endoglucanase III (WO 05/093050); and *Thermobifida fusca* endoglucanase V (WO 05/093050).

Examples of fungal endoglucanases that can be used in the present invention, include, but are not limited to, a *Trichoderma reesei* endoglucanase I (Penttila et al., 1986, *Gene* 45: 253-263: GenBank™ accession no. M15665); *Trichoderma reesei* endoglucanase II (Saloheimo et al., 1988, *Gene* 63:11-22; GenBank™ accession no, M19373); *Trichoderma reesei* endoglucanase III (Okada et al, 1988, *Appl. Environ. Microbiol.* 64: 555-563; GenBank™ accession no. AB003694); *Trichoderma reesei* endoglucanase IV (Saloheimo et al., 1997, *Eur. J. Biochem,* 249: 584-591; GenBank™ accession no. Y11113); and *Trichoderma reesei* endoglucanase V (Saloheimo et al. 1994, *Molecular Microbiology* 13: 219-228; GenBank™ accession no. Z33381): *Aspergillus aculeatus* endoglucanase (Ooi et al., 1990, *Nucleic Acids Research* 18: 5884); *Aspergillus kawachii* endoglucanase (Sakamoto et al. 1995; *Current Genetics* 27: 435-439); *Chrysosporium* sp. Cl (U.S. Pat. No. 6,573,086; GenPept accession no. AAQ38150), *Corynascus heterothallicus* (U.S. Pat. No. 6,855,531; GenPept accession no. AAY00344); *Erwinia carotovara* endoglucanase (Saarilahti et al., 1990, *Gene* 90: 9-14); *Fusarium oxysporum* endoglucanase (GenBank™ accession no. L29381); *Humicola grisea* var. *thermoidea* endoglucanase (GenBank™ accession no. AB003107); *Melanocarpus albomyces* endoglucanase (GenBank™ accession no. MAL515703); *Neurospora crassa* endoglucanase (GenBank™ accession no. XM_324477); *Piromyces equi* (Eberhardt et al., 2000, *Microbiology* 146: 1999-2008: GenPept accession no. CAB92325); *Rhizopus oryzae* (Moriya et al., 2003, *J. Bacteriology* 185: 1749-1756; GenBank™ accession nos. AB047927, AB056667, and AB056668); and *Thielavia terrestris* (WO 2004/053039; EMBL accession no, CQ827970).

Other endoglucanases are disclosed in more than 13 of the Glycosyl Hydrolase families using the classification according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696.

In a preferred aspect, the endoglucanase is a *Trichoderma reesei* endoglucanase I (CEL7B). In another preferred aspect, the endoglucanase is a *Trichoderma reesei* endoglucanase II (CEL5A). In another preferred aspect, the endoglucanase is a *Trichoderma reesei* endoglucanase III (CEL12A). In another preferred aspect, the endoglucanase is a *Trichoderma reesei* endoglucanase V (CEL45A). In another preferred aspect, the endoglucanase is a *Myceliophthora thermophila* CEL7 endoglucanase, In another preferred aspect, the endoglucanase is a *Chrysosporium lucknowense* CEL12 endoglucanase. In another preferred aspect, the endoglucanase is a *Chrysosporium lucknowense* CEL45 endoglucanase.

In a more preferred aspect, the *Trichoderma reesei* endoglucanase I (CEL7B) is the mature polypeptide of SEQ ID NO: 74 or an ortholog or variant thereof. In another more preferred aspect, the *Trichoderma reesei* endoglucanase II (CEL5A) is the mature polypeptide of SEQ ID NO: 76 or an ortholog or variant thereof. In another more preferred aspect, the *Trichoderma reesei* endoglucanase III (CEL12A) is the mature polypeptide of SEQ ID NO: 78 or an ortholog or variant thereof. In another more preferred aspect, the *Trichoderma reesei* endoglucanase V (CEL45A) is the mature polypeptide of SEQ ID NO. 80 or an ortholog or variant thereof. In another more preferred aspect, the *Myceliophthora thermophila* CEL7 endoglucanase is the mature polypeptide of SEQ ID NO: 82 or an ortholog or variant thereof. In another more preferred aspect, the *Myceliophthora thermophila* CEL12 endoglucanase is the mature polypeptide of SEQ ID NO: 84 or an ortholog or variant thereof. In another more preferred aspect, the *Myceliophthora thermophila* CEL45 endoglucanase is the mature polypeptide of SEQ ID NO: 86 or an ortholog or variant thereof.

In another more preferred aspect, the *Trichoderma reesei* endoglucanase (CEL7B) is encoded by the mature polypeptide coding sequence of SEQ ID NO: 73 or an ortholog or variant thereof. In another more preferred aspect, the *Trichoderma reesei* endoglucanase II (CEL5A) is encoded by the mature polypeptide coding sequence of SEQ ID NO: 75 or an ortholog or variant thereof. In another more preferred aspect, the *Trichoderma reesei* endoglucanase III (CEL12A) is encoded by the mature polypeptide coding sequence of SEQ ID NO: 77 or an ortholog or variant thereof. In another more preferred aspect, the *Trichoderma reesei* endoglucanase V (CEL45A) is encoded by the mature polypeptide coding sequence of SEQ ID NO: 79 or an ortholog or variant thereof. In another more preferred aspect, the *Myceliophthora thermophila* CEL7 endoglucanase is encoded by the mature polypeptide coding sequence of SEQ ID NO: 81 or an ortholog or variant thereof. In another more preferred aspect, the *Chrysosporium* CEL12 endoglucanase is encoded by the mature polypeptide coding sequence of SEQ ID NO: 83 or an ortholog or variant thereof. In another more preferred aspect, the *Chrysosporium* CEL45 endoglucanase is encoded by the mature polypeptide coding sequence of SEQ ID NO: 85 or an ortholog or variant thereof.

The *Trichoderma reesei* endoglucanase I (CEL7B) can be obtained according to Penttila et al., 1986, *Gene* 45: 253-263. The *Trichoderma reesei* endoglucanase (CEL5A) can be obtained according to Saloheimo et al., 1988, *Gene* 63:11-22. The *Trichoderma reesei* endoglucanase III (CEL12A) can be obtained according to Okada et al., 1988, *Appl. Environ. Microbiol.* 64: 555-563. The *Trichoderma reesei* endoglucanase V (CEL45A) can be obtained according to Saloheimo et al., 1994. *Molecular Microbiology* 13: 219-228. The *Myceliophthora thermophila* CEL7 endoglucanase can be obtained according to WO 95/024471. The *Chrysosporium lucknowense* CEL12 endoglucanase can be obtained according to WO 2001/25468. The *Chrysosporium lucknowense* CEL45 endoglucanase can be obtained according to WO 2000/20555.

In another preferred aspect, the cellobiohydrolase is a *Trichoderma reesei* cellobiohydrolase I (CEL7A). In another preferred aspect, the cellobiohydrolase is a *Trichoderma reesei* cellobiohydrolase II (CEL6A). In another preferred aspect, the cellobiohydrolase is a *Chrysosporium lucknowense* CEL7 cellobiohydrolase with a cellulose binding domain. In another preferred aspect, the cellobiohydrolase is a *Myceliophthora thermophila* CEL7 cellobiohydrolase without a cellulose binding domain. In another preferred aspect, the cellobiohydrolase is a *Thielavia terrestris* cellobiohydrolase.

In another more preferred aspect, the *Trichoderma reesei* cellobiohydrolase I (CEL7A) is the mature polypeptide of SEQ ID NO: 88 or an ortholog or variant thereof. In another preferred aspect, the *Trichoderma reesei* cellobiohydrolase II (CEL6A) is the mature polypeptide of SEQ ID NO: 90 or an ortholog or variant thereof. In another more preferred aspect, the *Chrysosporium lucknowense* CEL7 cellobiohydrolase with a cellulose binding domain is the mature polypeptide of SEQ ID NO: 92 or an ortholog or variant thereof. In another more preferred aspect, the *Myceliophthora thermophila* CEL7 cellobiohydrolase without a cellulose binding domain is the mature polypeptide of SEQ ID NO: 94 or an ortholog or variant thereof. In another more preferred aspect, the *Thielavia terrestris* cellobiohydrolase is the mature polypeptide of SEQ ID NO: 96 or an ortholog or variant thereof.

In another more preferred aspect, the *Trichoderma reesei* cellobiohydrolase I (CEL7A) cellobiohydrolase is encoded by the mature polypeptide coding sequence of SEQ ID NO: 87 or an ortholog or variant thereof. In another more preferred aspect, the *Trichoderma reesei* cellobiohydrolase II (CEL6A) cellobiohydrolase is encoded by the mature polypeptide coding sequence of SEQ ID NO: 89 or an ortholog or variant thereof. In another more preferred aspect, the *Chrysosporium lucknowense* CEL7 cellobiohydrolase with a cellulose binding domain is encoded by the mature polypeptide coding sequence of SEQ ID NO: 91 or an ortholog or variant thereof. In another more preferred aspect, the *Myceliophthora thermophila* CEL7 cellobiohydrolase without a cellulose binding domain is encoded by the mature polypeptide coding sequence of SEQ ID NO: 93 or an ortholog or variant thereof. In another more preferred aspect, the *Thielavia terrestris* cellobiohydrolase is encoded by the mature polypeptide coding sequence of SEQ ID NO: 95 or an ortholog or variant thereof.

The *Trichoderma reesei* cellobiohydrolase I (CEL7A) can be obtained according to Shoemaker et al., 1983, *Biotechnology* (N.Y.) 1: 691-696. The *Trichoderma reesei* cellobiohydrolase II (CEL6A) can be obtained according to Terri et al., 1987, *Gene* 51: 43-52. The *Chrysosporium lucknowense* CEL7 cellobiohydrolase with a cellulose binding domain can be obtained according to WO 2001/79507. The *Myceliophthora thermophila* CEL7 cellobiohydrolase without a cellulose binding domain can be obtained according to WO 2003/000941. The *Thielavia terrestris* cellobiohydrolase can be obtained according to WO 2006/074435.

In another preferred aspect, the beta-glucosidase is obtained from *Aspergillus oryzae*. In another preferred aspect, the beta-glucosidase is obtained from *Aspergillus fumigatus*. In another preferred aspect, the beta-glucosidase is obtained from *Penicillium brasilianum*, e.g., *Penicillium brasilianum* strain IBT 20888. In another preferred aspect, the beta-glucosidase is obtained from *Aspergillus niger*. In another preferred aspect, the beta-glucosidase is obtained from *Aspergillus aculeatus*.

In a more preferred aspect, the *Aspergillus oryzae* beta-glucosidase is the mature polypeptide of SEQ ID NO: 16 or an ortholog or variant thereof. In another more preferred aspect, the *Aspergillus fumigates* beta-glucosidase is the mature polypeptide of SEQ ID NO: 18 or an ortholog or variant thereof. In another more preferred aspect, the *Penicillium brasilianum* beta-glucosidase is the mature polypeptide of SEQ ID NO: 20 or an ortholog or variant thereof. In another more preferred aspect, the *Aspergillus niger* beta-glucosidase is the mature polypeptide of SEQ ID NO: 22 or an ortholog or variant thereof. In another more preferred aspect, the *Aspergillus aculeatus* beta-glucosidase is the mature polypeptide of SEQ ID NO: 24 or an ortholog or variant thereof. In another more preferred aspect, the *Aspergillus oryzae* beta-glucosidase is encoded by the mature polypeptide coding sequence of SEQ ID NO: 15 or an ortholog or variant thereof. In another more preferred aspect, the *Aspergillus fumigatus* beta-glucosidase is encoded by the mature polypeptide coding sequence of SEQ ID NO: 17 or an ortholog or variant thereof. In another more preferred aspect, the *Penicillium brasilianum* beta-glucosidase is encoded by the mature polypeptide coding sequence of SEQ ID NO: 19 or an ortholog or variant thereof. In another more preferred aspect, the *Aspergillus niger* beta-glucosidase is encoded by the mature polypeptide coding sequence of SEQ ID NO: 21 or an ortholog or variant thereof. In another more preferred aspect, the *Aspergillus aculeatus* beta-glucosidase is encoded by the mature polypeptide coding sequence of SEQ ID NO: 23 or an ortholog or variant thereof.

The *Aspergillus oryzae* polypeptide having beta-glucosidase activity can be obtained according to WO 2002/095014. The *Aspergillus fumigatus* polypeptide having beta-glucosidase activity can be obtained according to WO 2005/047499, The *Penicillium brasilianum* polypeptide having beta-glucosidase activity can be obtained according to WO 2007/019442. The *Aspergillus niger* polypeptide having beta-glucosidase activity can be obtained according to Dan et al., 2000, *J. Biol. Chem.* 275: 4973-4980. The *Aspergillus aculeatus* polypeptide having beta-glucosidase activity can be obtained according to Kawaguchi et al., 1996, *Gene* 173: 287-288.

In another preferred aspect, the mature polypeptide of SEQ ID NO: 16 encoded by a polynucleotide contained in the plasmid which is contained in *E. coli* DSM 14240. In another preferred aspect, the mature polypeptide of SEQ ID NO: 18 is encoded by the polynucleotide contained in plasmid pEJG113 which is contained in *E. coli* NRRL B-30695. In another preferred aspect, the mature polypeptide of SEQ ID NO: 20 is encoded by a polynucleotide contained in plasmid pKKAB which is contained in *E. coli* NRRL B-30860.

In another preferred aspect, the beta-glucosidase is the *Aspergillus oryzae* beta-glucosidase variant BG fusion protein of SEQ ID NO: 26. In another preferred aspect, the *Aspergillus oryzae* beta-glucosidase variant BG fusion protein is encoded by the polynucleotide of SEQ ID NO: 25. In another preferred aspect, the beta-glucosidase is the *Aspergillus oryzae* beta-glucosidase fusion protein of SEQ ID NO:

28. In another preferred aspect, the *Aspergillus oryzae* beta-glucosidase fusion protein is encoded by the polynucleotide of SEQ ID NO: 27.

Examples of other beta-glucosidases that can be used in the present invention, include, but are not limited to an *Aspergillus oryzae* beta-glucosidase (WO 02/095014; WO 04/099228); *Aspergillus aculeatus* beta-glucosidase (Kawaguchi et al., 1996. Gene 173: 287-288); *Aspergillus avenaceus* beta-glucosidase (GenBank™ accession no. AY943971): *Aspergillus fumigatus* beta-glucosidase (GenBank™ accession no. XM745234); *Aspergillus kawachii* beta-glucosidase (GenBank™ accession no. AB003470); *Aspergillus niger* beta-glucosidase (GenBank™ AJ132386); *Magnaporthe grisea* beta-glucosidase (GenBank™ no accession no. AY849670); *Phanerochaete chrysosporium* beta-glucosidase (GenBank™ accession no. AB253327); *Talaromyces emersonii* beta-glucosidase (GenBank™ accession no. AY072918), and *Trichoderma reesei* beta-glucosidase (GenBank™ accession nos. U09580, AB003110, AY281374, AY281375, AY281377, AY281378, and AY281379). Variants of beta-glucosidases may also be used such as those described in WO 04/099228.

Other beta-glucosidases are disclosed in more than 13 of the Glycosyl Hydrolase families using the classification according to Henrissat B., 1991. A classification of glycosyl hydrolases based on amino-acid sequence similarities, *Biochem. J.* 280: 309-316, and Henrissat B., and Bairoch A., 1996. Updating the sequence-based classification of glycosyl hydrolases, *Biochem. J.* 316: 695-696.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcuitures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of such a microorganism. Once a polynucleotide sequence encoding a polypeptide has been detected with the probe(s), the polynucleotide can be isolated or cloned by utilizing techniques that are well known to those of ordinary skill in the art (see, e.g., Sambrook et al., 1989, supra).

Polypeptides having cellulolytic enzyme activity also include fused polypeptides or cleavable fusion polypeptides in which another polypeptide is fused at the N-terminus or the C-terminus of the polypeptide or fragment thereof having cellulolytic enzyme activity. A fused polypeptide is produced by fusing a nucleotide sequence (or a portion thereof) encoding another polypeptide to a nucleotide sequence (or a portion thereof) encoding a polypeptide having cellulolytic enzyme activity. Techniques for producing fusion polypeptides are known in the art, and include ligating the coding sequences encoding the polypeptides so that they are in frame and that expression of the fused polypeptide is under control of the same promoter(s) and terminator.

A fusion polypeptide can further comprise a cleavage site. Upon secretion of the fusion protein, the site is cleaved releasing the polypeptide having cellulolytic enzyme activity from the fusion protein. Examples of cleavage sites include, but are not limited to, a Kex2 site that encodes the dipeptide Lys-Arg (Martin et al., 2003, *J. Ind. Microbiol. Biotechnol.* 3: 568-76, Svetina et al., 2000, *J. Biotechnol.* 76: 245-251; Rasmussen-Wilson et al., 1997, *Appl. Environ. Microbiol,* 63: 3488-3493; Ward et al., 1995, *Biotechnology* 13: 498-503; and Contreras et al., 1991, *Biotechnology* 9: 378-381), an Ile-(Glu or Asp)-Gly-Arg site, which is cleaved by a Factor protease after the arginine residue (Eaton et al., 1986, *Biochem.* 25: 505-512); a Asp-Asp-Asp-Asp-Lys site, which is cleaved by an enterokinase after the lysine (Collins-Racie et al., 1995, *Biotechnology* 13: 982-987); a His-Tyr-Glu site or His-Tyr-Asp site, which is cleaved by Genenase I (Carter et al., 1989, *Proteins: Structure, Function, and Genetics* 6: 240-248); a Leu-Val-Pro-Arg-Gly-Ser site, which is cleaved by thrombin after the Arg (Stevens, 2003, *Drug Discovery World* 4: 35-48); a Glu-Asn-Leu-Tyr-Phe-Gln-Gly site, which is cleaved by TEV protease after the Gln (Stevens. 2003, supra); and a Leu-Glu-Val-Leu-Phe-Gln-Gly-Pro site, which is cleaved by a genetically engineered form of human rhinovirus 3C protease after the Gln (Stevens, 2003, supra).

In a preferred aspect, the cellulolytic enzyme composition comprises a beta-glucosidase; a *Trichoderma reesei* cellobiohydrolase I (CEL7A), a *Trichoderma reesei* cellobiohydrolase II (CEL6A), and a *Trichoderma reesei* endoglucanase I (CEL7B).

In another preferred aspect, the cellulolytic enzyme composition comprises a beta-glucosidase; a *Trichoderma reesei* cellobiohydrolase I (CEL7A), a *Trichoderma reesei* cellobiohydrolase II (CEL6A), and a *Trichoderma reesei* endoglucanase I (CEL7B), and further comprises one or more enzymes selected from the group consisting of a *Trichoderma reesei* endoglucanase II (CEL5A), a *Trichoderma reesei* endoglucanase V (CEL45A), and a *Trichoderma reesei* endoglucanase III (CEL12A).

In another preferred aspect, the cellulolytic enzyme composition comprises a beta-glucosidase; a *Trichoderma reesei* cellobiohydrolase I (CEL7A), a *Trichoderma reesei* cellobiohydrolase II (CEL6A), and a *Trichoderma reesei* endoglucanase (CEL7B), and further comprises a *Thielavia terrestris* cellobiohydrolase.

In another preferred aspect, the cellulolytic enzyme composition comprises a beta-glucosidase: a *Trichoderma reesei* cellobiohydrolase 1 (CEL7A), a *Trichoderma reesei* cellobiohydrolase II (CEL6A), and a *Trichoderma reesei* endoglucanase (CEL7B), and further comprises (1) one or more enzymes selected from the group consisting of a *Trichoderma reesei* endoglucanase II (CEL5A), a *Trichoderma reesei* endoglucanase V (CEL45A), and a *Trichoderma reesei* endoglucanase III (CEL12A), and/or further comprises (2) a *Thielavia terrestris* cellobiohydrolase.

In another preferred aspect, the cellulolytic enzyme composition comprises one or more (several) components selected from the group consisting of a *Myceliophthora thermophila* CEL7 polypeptide having endoglucanase activity, a *Chrysosporiurn lucknowense* CEL12 polypeptide having endoglucanase activity, a *Chrysosporium lucknowense* CEL45 polypeptide having endoglucanase activity, a *Chrysosporium lucknowense* CEL7 polypeptide having cellobio- hydrolase activity with a cellulose binding domain, and a *Myceliophthora thermophila* CEL7 polypeptide having cellobiohydrolase activity without a cellulose binding domain. In another preferred aspect, the cellulolytic enzyme composition comprises a *Myceliophthora thermophila* CEL7 polypeptide having endoglucanase activity, a *Chrysosporium lucknowense* CEL12 polypeptide having endoglucanase activity, a *Chrysosporiurn lucknowense* CEL45 polypeptide having endoglucanase activity, a CEL7 polypeptide having cellobiohydrolase activity with a cellulose binding domain, and a *Myceliophthora thermophila* CEL7 polypeptide having cellobiohydrolase activity without a cellulose binding domain. In another preferred aspect, the composition above further comprises one or more (several) polypeptides having beta-glucosidase activity.

The cellulolytic enzyme composition can also be a commercial preparation. Examples of commercial cellulolytic enzyme preparations suitable for use in the present invention include, for example. CELLUCLAST™ (available from Novozymes A/S) and NOVOZYM™ 188 (available from Novozymes A/S), Other commercially available preparations that may be used include CELLUZYME™, CEREFLO™ and ULTRAFLO™ (Novozymes A/S), LAMINEX™ and SPEZYME™ CP (Genencor Int.), ROHAMENT™ 7069 W (Röhm GmbH), and FIBREZYME® LDI, FIBREZYME® LBR, or VISCOSTAR® 150L (Dyadic international, Inc., Jupiter, Fla., USA).

Other cellulolytic proteins that may be useful in the present invention are described in EP 495,257, EP 531,315, EP 531,372, WO 89/09259, WO 94/07998, WO 95/24471, WO 96/11262, WO 96/29397, WO 96/034108, WO 97/14804, WO 98/08940, WO 98/012307, WO 98/13465, WO 98/015619, WO 98/015633, WO 98/028411, WO 99/06574, WO 99/10481, WO 99/025846, WO 99/025847, WO 99/031255, WO 2000/009707, WO 2002/050245, WO 2002/076792, WO 2002/101078, WO 2003/027306, WO 2003/052054, WO 2003/052055, WO 2003/052056, WO 2003/052057, WO 2003/052118, WO 2004/016760, WO 2004/043980, WO 2004/048692, WO 2005/001065, WO 2005/028636, WO 2006/093050, WO 2005/093073, WO 2006/074005, WO 2006/117432, WO 2007/071818, WO 2007/071820, WO 2008/008070, WO 2008/008793, U.S. Pat. Nos. 4,435,307, 5,457,046, 6,648,263, 5,686,593, 5,691,178, 5,763,254, and 5,776,757.

The cellulolytic proteins used in the methods of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.). *More Gene Manipulations in Fungi*, Academic Press, CA, 1991). Suitable media are available from commercial suppliers or may be prepared according to published compositions (e.g., in catalogues of the American Type Culture Collection). Temperature ranges and other conditions suitable for growth and cellulolytic protein production are known in the art (see, e.g., Bailey. J. E., and 011 is, D. F., *Biochemical Engineering Fundamentals*, McGraw-Hill Book Company, NY, 1986).

The fermentation can be any method of cultivation of a cell resulting in the expression or isolation of a cellulolytic protein. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the cellulolytic protein to be expressed or isolated. The resulting cellulolytic proteins produced by the methods described above may be recovered from the fermentation medium and purified by conventional procedures as described herein.

Polypeptides Having Cellulolytic Enhancing Activity

In a first aspect, the isolated polypeptides having cellulolytic enhancing activity comprise the following motifs:

[ILMV]-P-X(4,5)-G-X-Y-[ILMV]-X-R-X-[EQ]-X(4)-[HNQ]
and

[FW]-[TF]-K-[AIV], wherein X is any amino acid, X(4,5) is any amino acid at 4 or 5 contiguous positions, and X(4) is any amino acid at 4 contiguous positions.

The isolated polypeptide comprising the above-noted motifs may further comprise:

(SEQ ID NO: 99 or SEQ ID NO: 100)
H-X(1,2)-G-P-X(3)-[YW]-[AILMV], (SEQ ID NO: 101)
[EQ]-X-Y-X(2)-C-X-[EHQN]-[FILV]-X-[ILV],
or (SEQ ID NO: 99 or SEQ ID NO: 100)
H-X(1,2)-G-P-X(3)-[YW]-[AILMV] and [EQ]-X-Y-X(2)-
C-X-[EHQN]-[FILV]-X-[ILV],(SEQ ID NO: 101)

wherein X is any amino acid, X(1,2) is any amino acid at 1 position or 2 contiguous positions, X(3) is any amino acid at 3 contiguous positions, and X(2) is any amino acid at 2 contiguous positions. In the above motifs, the accepted IUPAC single letter amino acid abbreviation is employed.

In a preferred aspect, the isolated polypeptide having cellulolytic enhancing activity further comprises H-X(1,2)-G-P-X(3)-[YW]-[AILMV] (SEQ ID NO: 99 or SEQ ID NO: 100). In another preferred aspect, the isolated polypeptide having cellulolytic enhancing activity further comprises [EQ]-X-Y-X(2)-C-X-[EHQN]-[FILV]-X-[ILV] (SEQ ID NO: 101). In another preferred aspect, the isolated polypeptide having cellulolytic enhancing activity further comprises H-X(1,2)-G-P-X(3)-[YW]-[AILMV] (SEQ ID NO: 99 or SEQ ID NO: 100) and [EQ]-X-Y-X(2)-C-X-[EHQN]-[FILV]-X-[ILV] (SEQ ID NO: 101).

In a second aspect, the isolated polypeptides having cellulolytic enhancing activity comprise the following motif:

(SEQ ID NO: 102 or SEQ ID NO: 103)
[ILMV]-P-x(4,5)-G-x-Y-[ILMV]-x-R-x-[EQ]-x(3)-A-
[HNQ], wherein x is any amino acid, x(4,5) is any amino acid at 4 or 5 contiguous positions, and x(3) is any amino acid at 3 contiguous positions. In the above motif, the accepted IUPAC single letter amino acid abbreviation is employed.

In a third aspect, the isolated polypeptides having cellulolytic enhancing activity have an amino acid sequence that has a degree of identity to the mature polypeptide of SEQ ID NO: 2, SEQ ID NO: 4, SEQ ID NO: 6, SEQ ID NO: 8, or SEQ ID NO: 10, SEQ ID NO: 12, or SEQ ID NO: 14 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, 97%, 98%, or 99%, which have cellulolytic enhancing activity (hereinafter "homologous polypeptides"). In a preferred aspect, the homologous polypeptides have an amino acid sequence that differs by ten amino acids, preferably by five amino acids, more preferably by four amino acids, even more preferably by three amino acids, most preferably by two amino acids, and even most preferably by one amino acid from the mature polypeptide of SEQ ID NO; 2, SEQ ID NO: 4, SEQ ID NO: 6, SEQ ID NO: 8, or SEQ ID NO: 10, SEQ ID NO: 12, or SEQ ID NO: 14.

A polypeptide having cellulolytic enhancing activity preferably comprises the amino acid sequence of SEQ ID NO: 2 or an allelic variant thereof; or a fragment thereof that has cellulolytic enhancing activity. In a preferred aspect, the polypeptide comprises the amino acid sequence of SEQ ID NO: 2. In another preferred aspect, the polypeptide comprises the mature polypeptide of SEQ ID NO: 2. In another preferred aspect, the polypeptide comprises amino acids 20 to 326 of SEQ ID NO: 2, or an allelic variant thereof; or a fragment thereof that has cellulolytic enhancing activity. In another preferred aspect, the polypeptide comprises amino acids 20 to 326 of SEQ ID NO: 2. In another preferred aspect, the polypeptide consists of the amino acid sequence of SEQ ID NO: 2 or an allelic variant thereof; or a fragment thereof that has cellulolytic enhancing activity. In another preferred aspect, the polypeptide consists of the amino acid sequence of SEQ ID NO: 2. In another preferred aspect, the polypeptide consists of the mature polypeptide of SEQ ID NO: 2. In another preferred aspect, the polypeptide consists of amino acids 20 to 326 of SEQ ID NO: 2 or an allelic variant thereof; or a fragment thereof that has cellulolytic enhancing activity. In another preferred aspect, the polypeptide consists of amino acids 20 to 326 of SEQ ID NO: 2.

A polypeptide having cellulolytic enhancing activity preferably comprises the amino acid sequence of SEQ ID NO: 4 or an allelic variant thereof; or a fragment thereof that has cellulolytic enhancing activity. In a preferred aspect, the polypeptide comprises the amino acid sequence of SEQ ID NO: 4. In another preferred aspect, the polypeptide comprises the mature polypeptide of SEQ ID NO: 4. In another preferred aspect, the polypeptide comprises amino acids 18 to 240 of SEQ ID NO: 4, or an allelic variant thereof; or a fragment thereof that has cellulolytic enhancing activity. In another preferred aspect, the polypeptide comprises amino acids 18 to 240 of SEQ ID NO: 4. In another preferred aspect, the polypeptide consists of the amino acid sequence of SEQ ID NO: 4 or an allelic variant thereof; or a fragment thereof that has cellulolytic enhancing activity. In another preferred aspect, the polypeptide consists of the amino acid sequence of SEQ ID NO: 4. In another preferred aspect, the polypeptide consists of the mature polypeptide of SEQ ID NO: 4. In another preferred aspect, the polypeptide consists of amino acids 18 to 240 of SEQ ID NO: 4 or an allelic variant thereof; or a fragment thereof that has cellulolytic enhancing activity. In another preferred aspect, the polypeptide consists of amino acids 18 to 240 of SEQ ID NO: 4.

A polypeptide having cellulolytic enhancing activity preferably comprises the amino acid sequence of SEQ ID NO: 6 or an allelic variant thereof; or a fragment thereof that has cellulolytic enhancing activity. In a preferred aspect, the polypeptide comprises the amino acid sequence of SEQ ID NO: 6. In another preferred aspect, the polypeptide comprises the mature polypeptide of SEQ ID NO: 6. In another preferred aspect, the polypeptide comprises amino acids 20 to 258 of SEQ ID NO: 6, or an allelic variant thereof; or a fragment thereof that has cellulolytic enhancing activity. In another preferred aspect, the polypeptide comprises amino acids 20 to 258 of SEQ ID NO: 6. In another preferred aspect, the polypeptide consists of the amino acid sequence of SEQ ID NO: 6 or an allelic variant thereof; or a fragment thereof that has cellulolytic enhancing activity. In another preferred aspect, the polypeptide consists of the amino acid sequence of SEQ ID NO: 6. In another preferred aspect, the polypeptide consists of the mature polypeptide of SEQ ID NO: 6. In another preferred aspect, the polypeptide consists of amino acids 20 to 258 of SEQ ID NO: 6 or an allelic variant thereof; or a fragment thereof that has cellulolytic enhancing activity. In another preferred aspect, the polypeptide consists of amino acids 20 to 258 of SEQ ID NO: 6.

A polypeptide having cellulolytic enhancing activity preferably comprises the amino acid sequence of SEQ ID NO: 8 or an allelic variant thereof; or a fragment thereof that has cellulolytic enhancing activity. In a preferred aspect, the polypeptide comprises the amino acid sequence of SEQ ID NO: 8. In another preferred aspect, the polypeptide comprises the mature polypeptide of SEQ ID NO: 8. In another preferred aspect, the polypeptide comprises amino acids 19 to 226 of SEQ ID NO. 8, or an allelic variant thereof; or a fragment thereof that has cellulolytic enhancing activity. In another preferred aspect, the polypeptide comprises amino acids 19 to 226 of SEQ ID NO: 8. In another preferred aspect, the polypeptide consists of the amino acid sequence of SEQ ID NO: 8 or an allelic variant thereof; or a fragment thereof that has cellulolytic enhancing activity. In another preferred aspect, the polypeptide consists of the amino acid sequence of SEQ ID NO: 8. In another preferred aspect, the polypeptide consists of the mature polypeptide of SEQ ID NO: 8. In another preferred aspect, the polypeptide consists of amino acids 19 to 226 of SEQ ID NO: 8 or an allelic variant thereof; or a fragment thereof that has cellulolytic enhancing activity. In another preferred aspect, the polypeptide consists of amino acids 19 to 226 of SEQ ID NO: 8.

A polypeptide having cellulolytic enhancing activity preferably comprises the amino acid sequence of SEQ ID NO: 10 or an allelic variant thereof; or a fragment thereof that has cellulolytic enhancing activity. In a preferred aspect, the polypeptide comprises the amino acid sequence of SEQ ID NO: 10. In another preferred aspect, the polypeptide comprises the mature polypeptide of SEQ ID NO: 10. In another preferred aspect, the polypeptide comprises amino acids 20 to 304 of SEQ ID NO: 10, or an allelic variant thereof; or a fragment thereof that has cellulolytic enhancing activity. In another preferred aspect, the polypeptide comprises amino acids 20 to 304 of SEQ ID NO: 10. In another preferred aspect, the polypeptide consists of the amino acid sequence of SEQ ID NO: 10 or an allelic variant thereof; or a fragment thereof that has cellulolytic enhancing activity. In another preferred aspect, the polypeptide consists of the amino acid sequence of SEQ ID NO: 10. In another preferred aspect, the polypeptide consists of the mature polypeptide of SEQ ID NO: 10. In another preferred aspect, the polypeptide consists of amino acids 20 to 304 of SEQ ID NO: 10 or an allelic variant thereof; or a fragment thereof that has cellulolytic enhancing activity. In another preferred aspect, the polypeptide consists of amino acids 20 to 304 of SEQ ID NO: 10.

A polypeptide having cellulolytic enhancing activity preferably comprises the amino add sequence of SEQ ID NO: 12 or an allelic variant thereof; or a fragment thereof that has cellulolytic enhancing activity. In a preferred aspect, the polypeptide comprises the amino acid sequence of SEQ ID NO: 12. In another preferred aspect, the polypeptide comprises the mature polypeptide of SEQ ID NO: 12. In another preferred aspect, the polypeptide comprises amino acids 23 to 250 of SEQ ID NO: 12, or an allelic variant thereof; or a fragment thereof that has cellulolytic enhancing activity. In another preferred aspect, the polypeptide comprises amino acids 23 to 250 of SEQ ID NO: 12. In another preferred aspect, the polypeptide consists of the amino acid sequence of SEQ ID NO: 12 or an allelic variant thereof; or a fragment thereof that has cellulolytic enhancing activity. In another preferred aspect, the polypeptide consists of the amino acid sequence of SEQ ID NO: 12. In another preferred aspect, the polypeptide consists of the mature polypeptide of SEQ ID NO: 12. In another preferred aspect, the polypeptide consists of amino acids 23 to 250 of SEQ ID NO: 12 or an allelic variant thereof; or a fragment thereof that has cellulolytic enhancing activity. In another preferred aspect, the polypeptide consists of amino acids 23 to 250 of SEQ ID NO: 12.

A polypeptide having cellulolytic enhancing activity preferably comprises the amino acid sequence of SEQ ID NO: 14 or an allelic variant thereof; or a fragment thereof that has cellulolytic enhancing activity. In a preferred aspect, the polypeptide comprises the amino acid sequence of SEQ ID NO: 14. In another preferred aspect, the polypeptide comprises the mature polypeptide of SEQ ID NO: 14. In another preferred aspect, the polypeptide comprises amino acids 20 to 249 of SEQ ID NO: 14, or an allelic variant thereof; or a fragment thereof that has cellulolytic enhancing activity. In another preferred aspect, the polypeptide comprises amino acids 20 to 249 of SEQ ID NO: 14. In another preferred aspect, the polypeptide consists of the amino acid sequence of SEQ ID NO: 14 or an allelic variant thereof; or a fragment thereof that has cellulolytic enhancing activity. In another preferred aspect, the polypeptide consists of the amino acid sequence of SEQ ID NO: 14. In another preferred aspect, the polypeptide consists of the mature polypeptide of SEQ ID NO: 14. In another preferred aspect, the polypeptide consists of amino acids 20 to 249 of SEQ ID NO: 14 or an allelic variant thereof; or a fragment thereof that has cellulolytic enhancing activity. In another preferred aspect, the polypeptide consists of amino acids 20 to 249 of SEQ ID NO: 14.

Preferably, a fragment of the mature polypeptide of SEQ ID NO: 2 contains at least 277 amino acid residues, more preferably at least 287 amino acid residues, and most preferably at least 297 amino acid residues. Preferably, a fragment of the mature polypeptide of SEQ ID NO: 4 contains at least 185 amino acid residues, more preferably at least 195 amino acid residues, and most preferably at least 205 amino acid residues. Preferably, a fragment of the mature polypeptide of SEQ ID NO: 6 contains at least 200 amino acid residues, more preferably at least 212 amino acid residues, and most preferably at least 224 amino acid residues. Preferably, a fragment of the mature polypeptide of SEQ ID NO: 8 contains at least 175 amino acid residues, more preferably at least 185 amino acid residues, and most preferably at least 195 amino acid residues. Preferably, a fragment of the mature polypeptide of SEQ ID NO: 10 contains at least 240 amino acid residues, more preferably at least 255 amino acid residues, and most preferably at least 270 amino acid residues. Preferably, a fragment of the mature polypeptide of SEQ ID NO: 12 contains at least 175 amino acid residues, more preferably at least 190 amino acid residues, and most preferably at least 205 amino acid residues. Preferably, a fragment of the mature polypeptide of SEQ ID NO: 14 contains at least 200 amino acid residues, more preferably at least 210 amino acid residues, and most preferably at least 220 amino acid residues.

Preferably, a subsequence of the mature polypeptide coding sequence of SEQ ID NO: 1 contains at least 831 nucleotides, more preferably at least 861 nucleotides, and most preferably at least 891 nucleotides. Preferably, a subsequence of the mature polypeptide coding sequence of SEQ ID NO: 3 contains at least 555 nucleotides, more preferably at least 585 nucleotides, and most preferably at least 615 nucleotides. Preferably, a subsequence of the mature polypeptide coding sequence of SEQ ID NO: 5 contains at least 600 nucleotides, more preferably at least 636 nucleotides, and most preferably at least 672 nucleotides. Preferably, a subsequence of the mature polypeptide coding sequence of SEQ ID NO: 7 contains at least 525 nucleotides, more preferably at least 555 nucleotides, and most preferably at least 585 nucleotides. Preferably, a subsequence of the mature polypeptide coding sequence of SEQ ID NO: 9 contains at least 720 nucleotides, more preferably at least 765 nucleotides, and most preferably at least 810 nucleotides, Preferably, a subsequence of the mature polypeptide coding sequence of nucleotides 67 to 796 of SEQ ID NO: 11 contains at least 525 nucleotides, more preferably at least 570 nucleotides, and most preferably at least 615 nucleotides. Preferably, a subsequence of the mature polypeptide coding sequence of SEQ ID NO: 13 contains at least 600 nucleotides, more preferably at least 630 nucleotides, and most preferably at least 660 nucleotides.

In a fourth aspect, the isolated polypeptides having cellulolytic enhancing activity are encoded by polynucleotides that hybridize under at least very low stringency conditions, preferably at least low stringency conditions, more preferably at least medium stringency conditions, more preferably at least medium-high stringency conditions, even more preferably at least high stringency conditions, and most preferably at least very high stringency conditions with (i) the mature polypeptide coding sequence of SEQ ID NO: 1, SEQ ID NO: 3, SEQ ID NO: 5, SEQ ID NO: 7, SEQ ID NO: 9, SEQ ID NO: 11, or SEQ ID NO: 13. (ii) the cDNA sequence contained in the mature polypeptide coding sequence of SEQ ID NO: 1, SEQ ID NO: 3, SEQ ID NO: 5, or SEQ ID NO: 11, or the genomic DNA sequence comprising the mature polypeptide coding sequence of SEQ ID NO: 7, SEQ ID NO: 9, or SEQ ID NO: 13, (iii) a subsequence of (i) or (ii), or (iv) a full-length complementary strand of (i), (ii), or (iii) (J. Sambrook, E. F. Fritsch, and T. Maniatus, 1989, supra). A subsequence of the mature polypeptide coding sequence of SEQ ID NO: 1, SEQ ID NO: 3, SEQ ID NO: 5, SEQ ID NO: 7. SEQ ID NO: 9, SEQ ID NO: 11, or SEQ ID NO: 13 contains at least 100 contiguous nucleotides or preferably at least 200 contiguous nucleotides. Moreover, the subsequence may encode a polypeptide fragment that has cellulolytic enhancing activity. In a preferred aspect, the mature polypeptide coding sequence is nucleotides 388 to 1332 of SEQ ID NO: 1, nucleotides 98 to 821 of SEQ ID NO: 3, nucleotides 126 to 978 of SEQ ID NO: 5, nucleotides 55 to 678 of SEQ ID NO: 7, nucleotides 58 to 912 of SEQ ID NO: 9, nucleotides 67 to 796 of SEQ ID NO: 11, or nucleotides 77 to 766 of SEQ ID NO: 13.

The nucleotide sequence of SEQ ID NO: 1, SEQ ID NO: 3, SEQ ID NO: 5, SEQ ID NO: 7, SEQ ID NO: 9, SEQ ID NO: 11, or SEQ ID NO: 13, or a subsequence thereof; as well as the amino acid sequence of SEQ ID NO: 2, SEQ ID NO: 4, SEQ ID NO: 6, SEQ ID NO: 8, or SEQ ID NO: 10, SEQ ID NO: 12, or SEQ ID NO: 14, or a fragment thereof, may be used to design a nucleic acid probe to identify and clone DNA encoding polypeptides having cellulolytic enhancing activity from strains of different genera or species, as described supra.

For purposes of the present invention, hybridization indicates that the nucleotide sequence hybridizes to a labeled nucleic acid probe corresponding to the mature polypeptide coding sequence of SEQ ID NO: 1, SEQ ID NO: 3, SEQ ID NO: 5, SEQ ID NO: 7, SEQ ID NO: 9, SEQ ID NO: 11, or SEQ ID NO: 13, the cDNA sequence contained in the mature polypeptide coding sequence of SEQ ID NO: 1, SEQ ID NO: 3, SEQ ID NO: 5, or SEQ ID NO: 11, or the genomic DNA sequence comprising the mature polypeptide coding sequence of SEQ ID NO: 7, SEQ ID NO: 9, or SEQ ID NO: 13, its full-length complementary strand, or a subsequence thereof, under very low to very high stringency conditions, as described supra.

In a preferred aspect, the nucleic acid probe is the mature polypeptide coding sequence of SEQ ID NO: 1. In another preferred aspect, the nucleic acid probe is nucleotides 388 to 1332 of SEQ ID NO: 1. In another preferred aspect, the nucleic acid probe is a polynucleotide sequence that encodes the polypeptide of SEQ ID NO: 2, or a subsequence thereof. In another preferred aspect, the nucleic acid probe is SEQ ID NO: 1. In another preferred aspect, the nucleic acid probe is the polynucleotide sequence contained in plasmid pEJG120 which is contained in *E. coli* NRRL B-30699. wherein the polynucleotide sequence thereof encodes a polypeptide having cellulolytic enhancing activity. In another preferred aspect, the nucleic acid probe is the mature polypeptide coding sequence contained in plasmid pEJG120 which is contained in *E. coli* NRRL B-30699.

In another preferred aspect, the nucleic acid probe is the mature polypeptide coding sequence of SEQ ID NO: 3. In another preferred aspect, the nucleic acid probe is nucleotides 98 to 821 of SEQ ID NO: 3. In another preferred aspect, the nucleic acid probe is a polynucleotide sequence that encodes the polypeptide of SEQ ID NO: 4, or a subsequence thereof. In another preferred aspect, the nucleic acid probe is SEQ ID NO: 3. In another preferred aspect, the nucleic acid probe is the polynucleotide sequence contained in plasmid pTter61C which is contained in *E. coli* NRRL B-30813, wherein the polynucleotide sequence thereof encodes a polypeptide having cellulolytic enhancing activity. In another preferred aspect, the nucleic acid probe is the mature polypeptide coding sequence contained in plasmid pTter61 C which is contained in *E. coli* NRRL B-30813.

In another preferred aspect, the nucleic acid probe is the mature polypeptide coding sequence of SEQ ID NO: 5. In another preferred aspect, the nucleic acid probe is nucleotides 126 to 978 of SEQ ID NO: 5. In another preferred aspect, the nucleic acid probe is a polynucleotide sequence that encodes the polypeptide of SEQ ID NO: 6, or a subsequence thereof, in another preferred aspect, the nucleic acid probe is SEQ ID NO: 5. In another preferred aspect, the nucleic acid probe is the polynucleotide sequence contained in plasmid pTter61D which is contained in *E. coli* NRRL 8-30812, wherein the polynucleotide sequence thereof encodes a polypeptide having cellulolytic enhancing activity. In another preferred aspect, the nucleic acid probe is the mature polypeptide coding sequence contained in plasmid pTter61D which is contained in *E. coli* NRRL B-30812.

In another preferred aspect, the nucleic acid probe is the mature polypeptide coding sequence of SEQ ID NO: 7. In another preferred aspect, the nucleic acid probe is nucleotides 55 to 678 of SEQ ID NO: 7. In another preferred aspect, the nucleic acid probe is a polynucleotide sequence that encodes the polypeptide of SEQ ID NO: 8, or a subsequence thereof. In another preferred aspect, the nucleic acid probe is SEQ ID NO: 7. In another preferred aspect, the nucleic acid probe is the polynucleotide sequence contained in plasmid pTter61E which is contained in *E. coli* NRRL B-30814, wherein the polynucleotide sequence thereof encodes a polypeptide having cellulolytic enhancing activity in another preferred aspect, the nucleic acid probe is the mature polypeptide coding sequence contained in plasmid pTter61E which is contained in *E. coli* NRRL 8-30814.

In another preferred aspect, the nucleic acid probe is the mature polypeptide coding sequence of SEQ ID NO: 9. In another preferred aspect, the nucleic acid probe is nucleotides 58 to 912 of SEQ ID NO: 9 In another preferred aspect, the nucleic acid probe is a polynucleotide sequence that encodes the polypeptide of SEQ ID NO: 10, or a subsequence thereof. In another preferred aspect, the nucleic acid probe is SEQ ID NO: 9. In another preferred aspect, the nucleic acid probe is the polynucleotide sequence contained in plasmid pTter61G which is contained in *E. coli* NRRL B-30811. wherein the polynucleotide sequence thereof encodes a polypeptide having cellulolytic enhancing activity. In another preferred aspect, the nucleic acid probe is the mature polypeptide coding sequence contained in plasmid pTter61G which is contained in *E. coli* NRRL 8-30811.

In another preferred aspect, the nucleic acid probe is the mature polypeptide coding sequence of SEQ ID NO: 11. In another preferred aspect, the nucleic acid probe is nucleotides 67 to 796 of SEQ ID NO: 11. In another preferred aspect, the nucleic acid probe is a polynucleotide sequence that encodes the polypeptide of SEQ ID NO: 12, or a subsequence thereof. In another preferred aspect, the nucleic acid probe is SEQ ID NO: 11. In another preferred aspect, the nucleic acid probe is the polynucleotide sequence contained in plasmid pDZA2-7 which is contained in *E. coli* NRRL B-30704, wherein the polynucleotide sequence thereof encodes a polypeptide having cellulolytic enhancing activity. In another preferred aspect, the nucleic acid probe is the mature polypeptide coding sequence contained in plasmid pDZA2-7 which is contained in *E. coli* NRRL 8-30704.

In another preferred aspect, the nucleic acid probe is the mature polypeptide coding sequence of SEQ ID NO: 13. In another preferred aspect, the nucleic acid probe is nucleotides 77 to 766 of SEQ ID NO: 13. In another preferred aspect, the nucleic acid probe is a polynucleotide sequence that encodes the polypeptide of SEQ ID NO: 14, or a subsequence thereof. In another preferred aspect, the nucleic acid probe is SEQ ID NO: 13. In another preferred aspect, the nucleic acid probe is the polynucleotide sequence contained in plasmid pTr333 which is contained in *E. coli* NRRL B-30878, wherein the polynucleotide sequence thereof encodes a polypeptide having cellulolytic enhancing activity. In another preferred aspect, the nucleic acid probe is the mature polypeptide coding sequence contained in plasmid pTr333 which is contained in *E. coli* NRRL 8-30878.

For long probes of at least 100 nucleotides in length, very low to very high stringency conditions are as defined herein.

For long probes of at least 100 nucleotides in length, the carrier material is finally washed as defined herein.

For short probes of about 15 nucleotides to about 70 nucleotides in length, stringency conditions are as defined herein.

For short probes of about 15 nucleotides to about 70 nucleotides n length, the carrier material is washed as defined herein.

In a fifth aspect, the polypeptides having cellulolytic enhancing activity are encoded by polynucleotides comprising or consisting of nucleotide sequences that have a degree of identity to the mature polypeptide coding sequence of SEQ ID NO: 1, SEQ ID NO: 3, SEQ ID NO: 5, SEQ ID NO: 7, SEQ ID NO: 9, SEQ ID NO: 11, or SEQ ID NO: 13 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, 97%, 98%, or 99%, which encode an active polypeptide having cellulolytic enhancing activity.

In a preferred aspect, the mature polypeptide coding sequence is nucleotides 388 to 1332 of SEQ ID NO; 1, nucleotides 98 to 821 of SEQ ID NO; 3, nucleotides 126 to 978 of SEQ ID NO: 5, nucleotides 55 to 678 of SEQ ID NO: 7, nucleotides 58 to 912 of SEQ ID NO: 9, nucleotides 67 to 796 of SEQ ID NO: 11, or nucleotides 77 to 766 of SEQ ID NO: 13. See polynucleotide section herein.

In a sixth aspect, the polypeptides having cellulolytic enhancing activity are artificial variants comprising a substitution, deletion, and/or insertion of one or more (or several) amino acids of the mature polypeptide of SEQ ID NO: 2, SEQ ID NO: 4, SEQ ID NO: 6, SEQ ID NO: 8, or SEQ ID NO: 10, SEQ ID NO: 12, or SEQ ID NO; 14; or a homologous sequence thereof. Methods for preparing such artificial variants are described supra.

The total number of amino acid substitutions, deletions and/or insertions of the mature polypeptide of SEQ ID NO: 2, SEQ ID NO: 4, SEQ ID NO: 6, SEQ ID NO: 8, SEQ ID NO: 10, SEQ ID NO: 12, or SEQ ID NO: 14, is 10, preferably 9, more preferably 8, more preferably 7, more preferably at most 6, more preferably 5, more preferably 4, even more preferably 3, most preferably 2, and even most preferably 1, Sources for Polypeptides Having Cellulolytic Enhancing Activity A polypeptide having cellulolytic enhancing activity may be obtained from microorganisms of any genus. In a preferred aspect, the polypeptide obtained from a given source is secreted extracellularly.

A polypeptide having cellulolytic enhancing activity may be a bacterial polypeptide. For example, the polypeptide may be a gram positive bacterial polypeptide such as a *Bacillus*, *Streptococcus*, *Streptomyces*, *Staphylococcus*, *Enterococcus*, *Lactobacillus*, *Lactocaccus*, *Clostridium*, *Geobacillus*, or *Oceanobacillus* polypeptide having cellulolytic enhancing activity, or a Gram negative bacterial polypeptide such as an *E. coli*, *Pseudomonas*, *Salmonella*, *Campylobacter*, *Helicobacter*, *Flavobacterium*, *Fusobacterium*, *Ilyabacter*, *Neisseria*, or *Ureaplasma* polypeptide having cellulolytic enhancing activity.

In a preferred aspect, the polypeptide is a *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, or *Bacillus thuringiensis* polypeptide having cellulolytic enhancing activity.

In another preferred aspect, the polypeptide is a *Streptococcus equisimilis*, *Streptococcus pyogenes*, *Streptococcus uberis*, or *Streptococcus equi* subsp. *Zooepidemicus* polypeptide having cellulolytic enhancing activity.

In another preferred aspect, the polypeptide is a *Streptomyces achromogenes*, *Streptomyces avermitilis*, *Streptomyces coelicolor*, *Streptomyces griseus*, or *Streptomyces lividans* polypeptide having cellulolytic enhancing activity.

The polypeptide having cellulolytic enhancing activity may also be a fungal polypeptide, and more preferably a yeast polypeptide such as a *Candida*, *Kluyveromyces*, *Pichia*, *Saccharomyces*, *Schizosaccharomyces*, or *Yarrowia* polypeptide having cellulolytic enhancing activity; or more preferably a filamentous fungal polypeptide such as an *Acremonium*, *Agaricus*, *Alternaria*, *Aspergillus*, *Aureoba-*

*sidium, Betryospaerla, Cariporiopsis, Chaatomidium, Chrysosporium, Claviceps, Cochliobolus, Coprinopsis, Coptotermes, Corynascus, Cryphonectra, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* polypeptide having cellulolytic enhancing activity.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* polypeptide having cellulolytic enhancing activity.

In another preferred aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporiurn queenslandicum, Chrysosporiurn zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii. Trichoderma longibrachiatum, Trichoderma reesei, Trichoderma viride,* or *Trichophaea saccata* polypeptide having cellulolytic enhancing activity.

In a more preferred aspect, the polypeptide is a *Thielavia terrestris* polypeptide having cellulolytic enhancing activity. In a most preferred embodiment, the polypeptide is a *Thielavia terrestris* NRRL 8126 polypeptide having cellulolytic enhancing activity, e.g., the mature polypeptide of SEQ ID NO: 2, 4, 6, 8, or 10, or fragments thereof that have cellulolytic enhancing activity.

In another more preferred aspect, the polypeptide is a *Thermoascus aurantiacus* polypeptide, e.g., the mature polypeptide of SEQ ID NO: 12.

In another more preferred aspect, the polypeptide is a *Trichoderma reesei* polypeptide having cellulolytic enhancing activity. In another most preferred aspect, the polypeptide is a *Trichoderma reesei* RutC30 (ATCC 56765) polypeptide, having cellulolytic enhancing activity e.g., the mature polypeptide of SEQ ID NO: 14, or fragments thereof that have cellulolytic enhancing activity.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC). Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes, as described herein.

Polypeptides having cellulolytic enhancing activity also include fused polypeptides or cleavable fusion polypeptides in which another polypeptide is fused at the N-terminus or the C-terminus of the polypeptide or fragment thereof having cellulolytic enhancing activity, and can further comprise a cleavage site, as described herein.

For further details on polypeptides having cellulolytic enhancing activity and polynucleotides thereof, see WO 2005/074647, WO 2005/074656, and U.S. Published Application Serial No. 2007/0077630, which are incorporated herein by reference.

Polynucleotides Encoding Polypeptides Having Cellulolytic Enhancing Activity

Polynucleotides comprising nucleotide sequences that encode polypeptides having cellulolytic enhancing activity can be isolated and utilized to practice the methods of the present invention, as described herein.

The polynucleotides comprise nucleotide sequences that have a degree of identity to the mature polypeptide coding sequence of SEQ ID NO: 1, SEQ ID NO: 3, SEQ ID NO: 5, SEQ ID NO: 7, SEQ ID NO: 9, SEQ ID NO: 11, or SEQ ID NO: 13 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, 97%, 98%, or 99%, which encode a polypeptide having cellulolytic enhancing activity.

In a preferred aspect, the nucleotide sequence comprises or consists of SEQ ID NO: 1. In another more preferred aspect, the nucleotide sequence comprises or consists of the sequence contained in plasmid pEJG120 that is contained in *Escherichia coli* NRRL B-30699, in another preferred aspect, the nucleotide sequence comprises or consists of the mature polypeptide coding sequence of SEQ ID NO: 1. In another more preferred aspect, the nucleotide sequence comprises or consists of the mature polypeptide coding sequence contained in plasmid pEJG120 that is contained in *Escherichia coli* NRRL B-30699. The present invention also encompasses nucleotide sequences that encode a polypeptide having the amino acid sequence of SEQ ID NO: 2 or the mature polypeptide thereof, which differ from SEQ ID NO: 1 by virtue of the degeneracy of the genetic code. The present invention also relates to subsequences of SEQ ID NO: 1 that encode fragments of SEQ ID NO: 2 that have cellulolytic enhancing activity.

In another preferred aspect, the nucleotide sequence comprises or consists of SEQ ID NO: 3. In another more preferred aspect, the nucleotide sequence comprises or consists of the sequence contained in plasmid pTter61C that is contained in *Escherichia coli* NRRL B-30813. In another preferred aspect, the nucleotide sequence comprises or consists of the mature polypeptide coding sequence of SEQ ID NO: 3. In another more preferred aspect, the nucleotide sequence comprises or consists of the mature polypeptide coding sequence contained in plasmid pTter61C that is contained in *Escherichia coli* NRRL B-30813. The present invention also encompasses nucleotide sequences that encode a polypeptide having the amino acid sequence of SEQ ID NO: 4 or the mature polypeptide thereof, which differ from SEQ ID NO: 3 by virtue of the degeneracy of the genetic code. The present invention also relates to subsequences of SEQ ID NO: 3 that encode fragments of SEQ ID NO: 4 that have cellulolytic enhancing activity.

In another preferred aspect, the nucleotide sequence comprises or consists of SEQ ID NO: 5. In another more preferred aspect, the nucleotide sequence comprises or consists of the sequence contained in plasmid pTter61D that is contained in *Escherichia coli* NRRL B-30812. In another preferred aspect, the nucleotide sequence comprises or consists of the mature polypeptide coding sequence of SEQ ID NO: 5. In another more preferred aspect, the nucleotide sequence comprises or consists of the mature polypeptide coding sequence contained in plasmid pTter61D that is contained in *Escherichia coli* NRRL B-30812. The present invention also encompasses nucleotide sequences that encode a polypeptide having the amino acid sequence of SEQ ID NO: 6 or the mature polypeptide thereof, which differ from SEQ ID NO. 5 by virtue of the degeneracy of the genetic code. The present invention also relates to subsequences of SEQ ID NO: 5 that encode fragments of SEQ ID NO: 6 that have cellulolytic enhancing activity.

In another preferred aspect, the nucleotide sequence comprises or consists of SEQ ID NO: 7. In another more preferred aspect, the nucleotide sequence comprises or consists of the sequence contained in plasmid pTter61E that is contained in *Escherichia coli* NRRL B-30814. In another preferred aspect, the nucleotide sequence comprises or consists of the mature polypeptide coding sequence of SEQ ID NO: 7. In another more preferred aspect, the nucleotide sequence comprises or consists of the mature polypeptide coding sequence contained in plasmid pTter61E that is contained in *Escherichia coli* NRRL B-30814. The present invention also encompasses nucleotide sequences that encode a polypeptide having the amino acid sequence of SEQ ID NO: 8 or the mature polypeptide thereof, which differ from SEQ ID NO: 7 by virtue of the degeneracy of the genetic code. The present invention also relates to subsequences of SEQ ID NO: 7 that encode fragments of SEQ ID NO: 8 that have cellulolytic enhancing activity.

In another preferred aspect, the nucleotide sequence comprises or consists of SEQ ID NO: 9. In another more preferred aspect, the nucleotide sequence comprises or consists of the sequence contained in plasmid pTter61G that is contained in *Escherichia coli* NRRL B-30811. In another preferred aspect, the nucleotide sequence comprises or consists of the mature polypeptide coding sequence of SEQ ID NO: 9. In another more preferred aspect, the nucleotide sequence comprises or consists of the mature polypeptide coding sequence contained in plasmid pTter61G that is contained in *Escherichia coli* NRRL B-30811. The present invention also encompasses nucleotide sequences that encode a polypeptide having the amino acid sequence of SEQ ID NO: 10 or the mature polypeptide thereof, which differ from SEQ ID NO: 9 by virtue of the degeneracy of the genetic code. The present invention also relates to subsequences of SEQ ID NO: 9 that encode fragments of SEQ ID NO: 10 that have cellulolytic enhancing activity.

In another preferred aspect, the nucleotide sequence comprises or consists of SEQ ID NO: 11. In another more preferred aspect, the nucleotide sequence comprises or consists of the sequence contained in plasmid pDZA2-7 that is contained in *Escherichia coli* NRRL B-30704. In another preferred aspect, the nucleotide sequence comprises or consists of the mature polypeptide coding sequence of SEQ ID NO: 11. In another more preferred aspect, the nucleotide sequence comprises or consists of the mature polypeptide coding sequence contained in plasmid pDZA2-7 that is contained in *Escherichia coli* NRRL B-30704. The present invention also encompasses nucleotide sequences that encode a polypeptide having the amino acid sequence of SEQ ID NO: 12 or the mature polypeptide thereof, which differ from SEQ ID NO: 11 by virtue of the degeneracy of the genetic code. The present invention also relates to subsequences of SEQ ID NO: 11 that encode fragments of SEQ ID NO: 12 that have cellulolytic enhancing activity.

In another preferred aspect, the nucleotide sequence comprises or consists of SEQ ID NO: 13. In another more preferred aspect, the nucleotide sequence comprises or consists of the sequence contained in plasmid pTr3337 which is contained in *Escherichia coli* NRRL B-30878. In another preferred aspect, the nucleotide sequence comprises or consists of the mature polypeptide coding sequence of SEQ ID NO: 13. In another more preferred aspect, the nucleotide sequence comprises or consists of the mature polypeptide coding sequence contained in plasmid pTr3337 which is contained *Escherichia coli* NRRL B-30878. The present invention also encompasses nucleotide sequences that encode a polypeptide having the amino acid sequence of SEQ ID NO: 14 or the mature polypeptide thereof, which differ from SEQ ID NO: 13 or the mature polypeptide coding sequence thereof by virtue of the degeneracy of the genetic code.

The present invention also relates to subsequences of SEQ ID NO: 13 that encode fragments of SEQ ID NO: 14 that have cellulolytic enhancing activity. The present invention also relates to mutant polynucleotides comprising at least one mutation in the mature polypeptide coding sequence of SEQ ID NO: 1, SEQ ID NO: 3, SEQ ID NO: 5, SEQ ID NO: 7, SEQ ID NO: 9, SEQ ID NO: 11, or SEQ ID NO: 13, in which the mutant nucleotide sequence encodes the mature polypeptide of SEQ ID NO: 2, SEQ ID NO: 4, SEQ ID NO: 6, SEQ ID NO: 8, or SEQ ID NO: 10, SEQ ID NO: 12, or SEQ ID NO: 14. In a preferred aspect, the mature polypeptide is amino acids 20 to 326 of SEQ ID NO: 2, amino acids 18 to 240 of SEQ ID NO: 4, amino acids 20 to 258 of SEQ ID NO: 6, amino acids 19 to 226 of SEQ ID NO: 8, or amino acids 20 to 304 of SEQ ID NO: 10, amino acids 23 to 250 of SEQ ID NO: 12, or amino acids 20 to 249 of SEQ ID NO: 14. In another preferred aspect, the mature polypeptide coding sequence is nucleotides 388 to 1332 of SEQ ID NO: 1, nucleotides 98 to 821 of SEQ ID NO: 3, nucleotides 126 to 978 of SEQ ID NO: 5, nucleotides 55 to 678 of SEQ ID NO: 7, nucleotides 58 to 912 of SEQ ID NO: 9, nucleotides 67 to 796 of SEQ ID NO: 11, or nucleotides 77 to 766 of SEQ ID NO: 13.

As described earlier, the techniques used to isolate or clone a polynucleotide encoding a polypeptide are known in the art and include isolation from genomic DNA, preparation from cDNA, or a combination thereof.

The polynucleotide may also be a polynucleotide encoding a polypeptide having cellulolytic enhancing activity that hybridizes under at least very low stringency conditions, preferably at least low stringency conditions, more preferably at least medium stringency conditions, more preferably at least medium-high stringency conditions, even more preferably at least high stringency conditions, and most preferably at least very high stringency conditions with (i) the mature polypeptide coding sequence of SEQ ID NO: 1, SEQ ID NO: 3, SEQ ID NO: 5, SEQ ID NO: 7, SEQ ID NO: 9, SEQ ID NO: 11, or SEQ ID NO: 13, (ii) the cDNA sequence contained in the mature polypeptide coding sequence of SEQ ID NO: 1, SEQ ID NO: 1, SEQ ID NO: 5, or SEQ ID NO: 11, or the genomic DNA sequence comprising the mature polypeptide coding sequence of SEQ ID NO: 7, SEQ ID NO: 9, or SEQ ID NO: 13, or (iii) a full-length complementary strand of (i) or (ii); or allelic variants and subsequences thereof (Sambrook et al., 1989, supra), as defined herein. In a preferred aspect, the mature polypeptide coding sequence is nucleotides 388 to 1332 of SEQ ID NO: 1, nucleotides 98 to 821 of SEQ ID NO: 3, nucleotides 126 to 978 of SEQ ID NO: 5, nucleotides 55 to 678 of SEQ ID NO: 7, nucleotides 58 to 912 of SEQ ID NO: 9, nucleotides 67 to 796 of SEQ ID NO: 11, or nucleotides 77 to 766 of SEQ ID NO: 13.

Nucleic Acid Constructs

An isolated polynucleotide encoding a polypeptide having cellulolytic enhancing activity or a polypeptide having cellulolytic enzyme activity may be manipulated in a variety of ways to provide for expression of the polypeptide by constructing a nucleic acid construct comprising an isolated polynucleotide encoding the polypeptide operably linked to one or more control sequences that direct the expression of the coding sequence in a suitable host cell under conditions compatible with the control sequences. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence that is recognized by a host cell for expression of a polynucleotide encoding such a polypeptide. The promoter sequence contains transcriptional control sequences that mediate the expression of the polypeptide. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American*, 1980, 242: 74-94; and in Sambrook et al., 1989, supra.

Examples of suitable promoters for directing the transcription of the nucleic acid constructs in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase. *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAO), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator that is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase. *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH21GAP).

The control sequence may also be a polyadenylation sequence, a sequence operably linked to the 3' terminus of the nucleotide sequence and, when transcribed, is recognized by the host cell as a signal to add polyadenosine residues to transcribed mRNA. Any polyadenylation sequence that is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding sequence that codes for an amino acid sequence linked to the amino terminus of a polypeptide and directs the encoded polypeptide into the cell's secretory pathway. The 5' end of the coding sequence of the nucleotide sequence may inherently contain a signal peptide coding sequence naturally linked in translation reading frame with the segment of the coding region that encodes the secreted polypeptide. Alternatively, the 5' end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice, i.e., secreted into a culture medium, may be used in the present invention.

Effective signal peptide coding sequences for bacterial host cells are the signal peptide coding sequences obtained from the genes for *Bacillus* NCIB 11837 maltogenic amylase, *Bacillus stearothetmophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase.

In a preferred aspect, the signal peptide comprises or consists of amino acids 1 to 19 of SEQ ID NO: 2. In another preferred aspect, the signal peptide coding region comprises or consists of nucleotides 330 to 387 of SEQ ID NO: 1.

In another preferred aspect, the signal peptide comprises or consists of amino acids 1 to 17 of SEQ ID NO: 4. In another preferred aspect, the signal peptide coding region comprises or consists of nucleotides 47 to 97 of SEQ ID NO: 3.

In another preferred aspect, the signal peptide comprises or consists of amino acids coding region is amino acids 1 to 19 of SEQ ID NO: 6. In another preferred aspect, the signal peptide coding region comprises or consists of nucleotides 69 to 125 of SEQ ID NO: 5.

In another preferred aspect, the signal peptide comprises or consists of amino acids 1 to 18 of SEQ ID NO: 8. In another preferred aspect, the signal peptide coding region comprises or consists of nucleotides 1 to 54 of SEQ ID NO: 7.

In another preferred aspect, the signal peptide comprises or consists of amino acids 1 to 19 of SEQ ID NO: 10. In another preferred aspect, the signal peptide coding region comprises or consists of nucleotides 1 to 57 of SEQ ID NO: 9.

In another preferred aspect, the signal peptide comprises or consists of amino acids 1 to 22 of SEQ ID NO: 12. In another preferred aspect, the signal peptide coding region comprises or consists of nucleotides 1 to 66 of SEQ ID NO: 11.

In another preferred aspect, the signal peptide comprises or consists of amino acids 1 to 19 of SEQ ID NO: 14. In another preferred aspect, the signal peptide coding region comprises or consists of nucleotides 20 to 76 of SEQ ID NO: 13.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding sequence may be obtained from the genes for *Bacillus subtilis* alkaline protease (aprE). *Bacillus subtilis* neutral protease (npr7). *Saccharomyces cerevisiae* alpha-factor, *Rhizomucor miehei* aspartic proteinase, and *Myceliophthora thermophila* laccase (WO 95/33836).

Where both signal peptide and propeptide sequences are present at the amino terminus of a polypeptide, the propeptide sequence is positioned next to the amino terminus of a polypeptide and the signal peptide sequence is positioned next to the amino terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the nucleotide sequence encoding the polypeptide would be operably linked with the regulatory sequence.

Expression Vectors

The various nucleic acids and control sequences described herein may be joined together to produce a recombinant expression vector comprising a polynucleotide encoding a polypeptide having cellulolytic enhancing activity or a polypeptide having cellulolytic enzyme activity, a promoter, and transcriptional and translational stop signals. The expression vectors may include one or more convenient restriction sites to allow for insertion or substitution of the polynucleotide sequence encoding the polypeptide at such sites. Alternatively, a polynucleotide encoding such a polypeptide may be expressed by inserting the polynucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide sequence. The choice of the vector will typically depend on the compatibility of the vector with the host cell into which the vector is to be introduced. The vectors may be linear or closed circular plasmids.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vectors preferably contain one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, kanamycin, chloramphenicol, or tetracycline resistance. Suitable markers for yeast host cells are ADE2, HIS3, LEU2, LYS2, MET3, TRP1, and URA3. Selectable markers for use in a filamentous fungal host cell include, but are not limited to amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyftransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity to the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67: Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide encoding such a polypeptide may be inserted into the host cell to increase production of the polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors are well known to one skilled in the art (see, e.g., Sambrook et al., 1989, supra).

Host Cells

Recombinant host cells comprising a polynucleotide encoding a polypeptide having cellulolytic enhancing activity or a polypeptide having cellulolytic enzyme activity can be advantageously used in the recombinant production of the polypeptide. A vector comprising such a polynucleotide is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

The bacterial host cell may be any Gram positive bacterium or a Gram negative bacterium, Gram positive bacteria include, but not limited to, *Bacillus, Streptococcus, Streptomyces, Staphylococcus, Enterococcus, Lactobacillus, Lac-* tococcus, *Clostridium*, *Geobacillus*, and *Oceanobacillus*. Gram negative bacteria include, but not limited to, *E. coli*, *Pseudomonas*, *Salmonella*, *Campylobacter*, *Helicobacter*, *Flavobacterium*, *Fusobacterium*, *Ilyobacter*, *Neisseria*, and *Ureaplasma*.

The bacterial host cell may be any *Bacillus* cell. *Bacillus* cells useful in the practice of the present invention include, but are not limited to, *Bacillus alkalophilus*, *Bacillus amyloliquefaciens*, *Bacillus brevis*, *Bacillus circulans*, *Bacillus clausii*, *Bacillus coagulans*. *Bacillus firmus*, *Bacillus lautus*. *Bacillus lentus*, *Bacillus licheniformis*, *Bacillus megaterium*, *Bacillus pumilus*, *Bacillus stearothermophilus*, *Bacillus subtilis*, and *Bacillus thuringiensis* cells.

In a preferred aspect, the bacterial host cell is a *Bacillus amyloliquefaciens*, *Bacillus lentus*, *Bacillus licheniformis*, *Bacillus stearothermophilus* or *Bacillus subtilis* cell. In a more preferred aspect, the bacterial host cell is a *Bacillus amyloliquefaciens* cell. In another more preferred aspect, the bacterial host cell is a *Bacillus clausii* cell. In another more preferred aspect, the bacterial host cell is a *Bacillus licheniformis* cell. In another more preferred aspect, the bacterial host cell is a *Bacillus subtilis* cell.

The bacterial host cell may also be any *Streptococcus* cell. *Streptococcus* cells useful in the practice of the present invention include, but are not limited to, *Streptococcus equisimilis*, *Streptococcus pyogenes*, *Streptococcus uberis*, and *Streptococcus equi* subsp. *Zooepidemicus* cells.

In a preferred aspect, the bacterial host cell is a *Streptococcus* equisimilis cell. In another preferred aspect, the bacterial host cell is a *Streptococcus pyogenes* cell. In another preferred aspect, the bacterial host cell is a *Streptococcus uberis* cell. In another preferred aspect, the bacterial host cell is a *Streptococcus* equi subsp. *Zooepidemicus* cell.

The bacterial host cell may also be any *Streptomyces* cell. *Streptomyces* cells useful in the practice of the present invention include, but are not limited to, *Streptomyces achromogenes*, *Streptomyces avermitilis*, *Streptomyces coelicolor*, *Streptomyces griseus*, and *Streptomyces lividans* cells.

In a preferred aspect, the bacterial host cell is a *Streptomyces achromogenes* cell. In another preferred aspect, the bacterial host cell is a *Streptomyces avermitilis* cell. In another preferred aspect, the bacterial host cell is a *Streptomyces coelicolor* cell. In another preferred aspect, the bacterial host cell is a *Streptomyces griseus* cell. In another preferred aspect, the bacterial host cell is a *Streptomyces lividans* cell.

The introduction of DNA into a *Bacillus* cell may, for instance, be effected by protoplast transformation (see, e.g., Chang and Cohen, 1979, *Molecular General Genetics* 168: 111-115), by using competent cells (see, e.g., Young and Spizizen, 1961, *Journal of Bacteriology* 81: 823-829, or Dubnau and Davidoff-Abelson, 1971, *Journal of Molecular Biology* 56: 209-221), by electroporation (see, e.g., Shigekawa and Dower, 1988, *Biotechniques* 6: 742-751), or by conjugation (see, e.g., Koehler and Thorne, 1987, *Journal of Bacteriology* 169: 5271-5278). The introduction of DNA into an *E coli* cell may, for instance, be effected by protoplast transformation (see, e.g., Hanahan, 1983, *J. Mol. Biol.* 166: 557-580) or electroporation (see, e.g. Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol.* (Praha) 49: 399-405), by conjugation (see, e.g. Mazodier et al., 1989, *J. Bacterial*, 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios.* 68: 189-2070, by electroporation (see, e.g. Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995. supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidlosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteria. Symposium Series* No. 9, 1980).

In an even more preferred aspect, the yeast host cell is a *Candida*, *Hansenula*, *Kluyveromyces*, *Pichia*, *Saccharomyces*, *Schizosaccharomyces*, or *Yarrowia* cell.

In a most preferred aspect, the yeast host cell is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth at, 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium*, *Aspergillus*, *Aureobasidium*, *Bjerkandera*, *Ceriporiopsis*, *Chrysosporium*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium*, *Trametes*, or *Trichoderma* cell.

In a most preferred aspect, the filamentous fungal host cell is an *Aspergillus awamori*, *Aspergillus fumigatus*, *Aspergil-* lus foetidus, Aspergillus japonicus, Aspergillus nidulans, Aspergillus niger or Aspergillus oryzae cell. In another most preferred aspect, the filamentous fungal host cell is a Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum. Fusarium sporotrichiodes, Fusarium sulphureum, Fusarium torulosum, Fusarium trichothecioides, or Fusarium venenatum cell. In another most preferred aspect, the filamentous fungal host cell is a Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiate, Pleurotus eryngii, Thielavia terrestris, Trametes villosa, Trametes versicolor, Trichoderma harzianum, Trichoderma koningil, Trichoderma longibrachiatum, Trichoderma reesei, or Trichoderma viride cell.

Fungal cells may be transformed by a process involving protoplast formation, transformation of the protoplasts, and regeneration of the cell wall in a manner known per se. Suitable procedures for transformation of Aspergillus and Trichoderma host cells are described in EP 238 023 and Yelton et al., 1984, Proceedings of the National Academy of Sciences USA 81: 1470-1474. Suitable methods for transforming Fusarium species are described by et al., 1989, Gene 78: 147-156, and WO 96/00787, Yeast may be transformed using the procedures described by Becker and Guarente. In Abelson, J. N. and Simon. M. I., editors, Guide to Yeast Genetics and Molecular Biology, Methods in Enzymology, Volume 194. pp 182-187, Academic Press, Inc., New York; Ito et al., 1983. Journal of Bacteriology 153: 163; and Hinnen et al., 1978, Proceedings of the National Academy of Sciences USA 75: 1920.

Methods of Production

Methods for producing a polypeptide having cellulolytic enhancing activity or a polypeptide having cellulolytic enzyme activity, comprise (a) cultivating a cell, which in its wild-type form is capable of producing the polypeptide, under conditions conducive for production of the polypeptide; and (b) recovering the polypeptide.

Alternatively, methods for producing a polypeptide having cellulolytic enhancing activity or a polypeptide having cellulolytic enzyme activity, comprise (a) cultivating a recombinant host cell under conditions conducive for production of the polypeptide: and (b) recovering the polypeptide.

In the production methods, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted into the medium, it can be recovered from cell lysates.

The polypeptides having cellulolytic enhancing activity or cellulolytic enzyme activity are detected using the methods described herein.

The resulting broth may be used as is or the polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J.-C. Janson and Lars Ryden, editors. VCH Publishers, New York, 1989) to obtain substantially pure polypeptides.

Methods for Processing Cellulose-Containing Material

The compositions and methods of the present invention can be used to hydrolyze (saccharify) a cellulose-containing material, e.g., lignocellulose, to fermentable sugars and convert the fermentable sugars to many useful substances, e.g., chemicals and fuels. The production of a desired fermentation product from cellulose-containing material typically involves pretreatment, enzymatic hydrolysis (saccharification), and fermentation.

The processing of cellulose-containing material according to the present invention can be accomplished using processes known in the art. Moreover, the methods of the present invention can be implemented using any biomass processing apparatus configured to operate in accordance with the invention.

Hydrolysis (saccharification) and fermentation, separate or simultaneous, include, but are not limited to, separate hydrolysis and fermentation (SHF), simultaneous saccharification and fermentation (SSF), simultaneous saccharification and cofermentation (SSCF), hybrid hydrolysis and fermentation (HHF), SHCF (separate hydrolysis and co-fermentation). HHCF (hybrid hydrolysis and fermentation), and direct microbial conversion (DMC). It is understood herein that any method known in the art comprising pretreatment, enzymatic hydrolysis (saccharification), fermentation, or a combination thereof, can be used in the practicing the methods of the present invention.

A conventional apparatus can include a fed-batch stirred reactor, a batch stirred reactor, a continuous flow stirred reactor with ultrafiltration, and/or a continuous plug-flow column reactor (Fernando de Castilhos Corazza, Flávio Faria de Moraes, Gisella Maria Zanin and Ivo Neitzel, 2003, Optimal control in fed-batch reactor for the cellobiose hydrolysis, Acta Sclentiarum. Technology 25: 33-38; Gusakov, A. V., and Sinitsyn, A. P., 1985, Kinetics of the enzymatic hydrolysis of cellulose: 1. A mathematical model for a batch reactor process, Enz. Microb. Technol. 7: 346-352), an attrition reactor (Ryu, S. K. and Lee, J. M., 1983, Bioconversion of waste cellulose by using an attrition bioreactor, Biotechnol. Bioeng. 25; 53-65), or a reactor with intensive stirring induced by an electromagnetic field (Gusakov, A. V., Sinitsyn, A. P., Davydkin, I. Y., Davydkin, V. Y., Protas, O. V., 1996, Enhancement of enzymatic cellulose hydrolysis using a novel type of bioreactor with intensive stirring induced by electromagnetic field, *Appl. Biochem. Biotechnol.* 56: 141-153). Additional reactor types include, for example, fluidized bed, upflow blanket, immobilized, and extruder type reactors for hydrolysis and/or fermentation.

Pretreatment. In practicing the methods of the present invention, any pretreatment process known in the art can be used to disrupt the plant cell wall components of the cellulose-containing material. The cellulose-containing material can also be subjected to pre-soaking, wetting, or conditioning prior to pretreatment using methods known in the art. Conventional pretreatments include, but are not limited to, steam pretreatment (with or without explosion), dilute acid pretreatment, hot water pretreatment, lime pretreatment, wet oxidation, wet explosion, ammonia fiber explosion, organosolv pretreatment, and biological pretreatment. Additional pretreatments include ultrasound, electroporation, microwave, supercritical $CO_2$, supercritical $H_2O$, and ammonia percolation.

The cellulose-containing material can be pretreated before hydrolysis and/or fermentation. Pretreatment is preferably performed prior to the hydrolysis. Alternatively, the pretreatment can be carried out simultaneously with hydrolysis, such as simultaneously with treatment of the cellulose-containing material with one or more cellulolytic enzymes, or other enzyme activities, to release fermentable sugars, such as glucose and/or maltose. In most cases the pretreatment step itself results in some conversion of biomass to fermentable sugars (even in absence of enzymes).

Steam Pretreatment. In steam pretreatment, the cellulose-containing material is heated to disrupt the plant cell wall components, including lignin, hemicellulose, and cellulose to make the cellulose and other fractions, e.g., hemicellulase, accessible to enzymes. The cellulose material is passed to or through a reaction vessel where steam is injected to increase the temperature to the required temperature and pressure and is retained therein for the desired reaction time. Steam pretreatment is preferably done at 140-230° C., more preferably at 160-200° C., and most preferably at 170-190° C., where the optimal temperature range depends on addition of a chemical catalyst. Residence time for the steam pretreatment is preferably 1-15 minutes, more preferably 3-12 minutes, and most preferably 4-10 minutes, where the optimal residence time depends on the temperature range and addition of a chemical catalyst. Steam pretreatment allows for relatively high solids loadings, so that the cellulose-containing material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33: Galbe and Zacchi, 2002, *Appl. Microbiol., Biotechnol.* 59: 618-628; U.S. Patent Application No. 20020164730).

A catalyst such as $H_2SO_4$ or $SO_2$ (typically 0.3 to 3% w/w) is often added prior to steam pretreatment, which decreases the time and temperature, increases recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762).

Chemical Pretreatment: The term "chemical treatment" refers to any chemical pretreatment that promotes the separation and/or release of cellulose, hemicellulose, and/or lignin. Examples of suitable chemical pretreatment processes include, for example, dilute acid pretreatment, lime pretreatment, wet oxidation, ammonia fiber/freeze explosion (AFEX), ammonia percolation (APR), and organosolv pretreatments.

In dilute acid pretreatment, the cellulose-containing material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, *Bioresource Technol.* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, lime pretreatment, wet oxidation, ammonia percolation (APR), and ammonia fiber/freeze explosion (AFEX).

Lime pretreatment is performed with calcium carbonate, sodium hydroxide, or ammonia at low temperatures of 85-150° C. and residence times from 1 hour to several days (Wyman et al., 2005, *Bioresource Technol.* 96: 1959-1966; Mosier et al., 2005, *Bioresource Technol.* 96: 673-686). WO 2006/110891, WO 2006/11899, WO 2006/11900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed at preferably 1-40% dry matter, more preferably 2-30% dry matter, and most preferably 5-20% dry matter, and often the initial pH is increased by the addition of alkali such as sodium carbonate.

A modification of the wet oxidation pretreatment method, known as wet explosion (combination of wet oxidation and steam explosion), can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating cellulose-containing material with liquid or gaseous ammonia at moderate temperatures such as 90-100° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng* 96: 219-231; Alizadeh at al, 2005, *Appl. Biochem. Biotechnol.* 121; 1133-1141, Teymouri at., 2005, *Bioresource Technol.* 96: 2014-2018).

Organosolv pretreatment delignifies cellulose-containing material by extraction using aqueous ethanol (40-60% ethanol) at 160-200° C. for 30-60 minutes (Pan et al., 2005, *Biotechnol. Bioeng.* 90: 473-481; Pan at, 2006, *Biotechnol. Bioeng.* 94: 851-861; Kurabi et al., 2005, *Appl. Biochem. Biotechnol.* 121:219-230). Sulphuric acid is usually added as a catalyst. In organosolv pretreatment, the majority of the hemicellulose is removed.

Other examples of suitable pretreatment methods are described by Schell et al., 2003, *Appl. Biochem, and Bio-*

*technol.* Vol. 105-108, p. 69-85, and Mosier et al., 2005, *Bioresource Technology* 96: 673-686, and U.S. Published Application 2002/0164730.

In one aspect, the chemical pretreatment is preferably carried out as an acid treatment, and more preferably as a continuous dilute and/or mild acid treatment. The acid is typically sulfuric acid: but other acids can also be used, such as acetic acid, citric acid, nitric acid, phosphoric acid, tartaric acid, succinic acid, hydrogen chloride or mixtures thereof. Mild acid treatment is conducted in the pH range of preferably 1-5, more preferably 1-4, and most preferably 1-3. In one aspect, the acid concentration is in the range from preferably 001 to 20 wt % acid, more preferably 0.05 to 10 wt % acid, even more preferably 0.1 to 5 wt % acid, and most preferably 0.2 to 2.0 wt % acid. The acid is contacted with the cellulose-containing material and held at a temperature, for example, in the range of 160-220° C., preferably 165-195° C., for periods ranging from seconds to minutes to, e.g., 1 second to 60 minutes.

In another aspect, pretreatment is carried out as an ammonia fiber explosion step (AFEX pretreatment step).

In another aspect, pretreatment takes place in an aqueous slurry. In preferred aspects, the cellulose-containing material is present during pretreatment in amounts preferably between 10-80 wt %, more preferably between 20-70 wt %, and most preferably between 30-60 wt %, such as around 50 wt %. The pretreated cellulose-containing material can be unwashed or washed using any method known in the art, e.g., washed with water.

Mechanical Pretreatment The term "mechanical pretreatment" refers to various types of grinding or milling (e.g. dry milling, wet milling, or vibratory ball milling).

Physical Pretreatment: The term "physical pretreatment" refers to any pretreatment that promotes the separation and/or release of cellulose, hemicellulose, and/or lignin from cellulose-containing material. For example, physical pretreatment can involve irradiation (e.g., microwave irradiation), steaming/steam explosion, hydrothermolysis, and combinations thereof.

Physical pretreatment can involve high pressure and/or high temperature (steam explosion). In one aspect, high pressure means pressure in the range of preferably about 300 to about 600 psi, more preferably about 350 to about 550 psi, and most preferably about 400 to about 500 psi, such as around 450 psi. In another aspect, high temperature means temperatures in the range of about 100 to about 300° C., preferably about 140 to about 235° C. In a preferred aspect, mechanical pretreatment is performed in a batch-process, steam gun hydrolyzer system that uses high pressure and high temperature as defined above, e.g., a Sunds Hydrolyzer available from Sunds Defibrator AB, Sweden.

Combined Physical and Chemical Pretreatment: The cellulose-containing material can be pretreated both physically and chemically. For instance, the pretreatment step can involve dilute or mild acid treatment and high temperature and/or pressure treatment. The physical and chemical pretreatments can be carried out sequentially or simultaneously, as desired. A mechanical pretreatment can also be included.

Accordingly, in a preferred aspect, the cellulose-containing material is subjected to mechanical, chemical, or physical pretreatment, or any combination thereof, to promote the separation and/or release of cellulose, hemicellulose and/or lignin.

Biological Pretreatment: The term "biological pretreatment" refers to any biological pretreatment that promotes the separation and/or release of cellulose, hemicellulose, and/or lignin from the cellulose-containing material. Biological pretreatment techniques can involve applying lignin-solubilizing microorganisms (see, for example, Hsu, T.-A., 1996, Pretreatment of biomass, in *Handbook on Bioethanol: Production and Utilization*, Wyman, C. E., ed., Taylor & Francis, Washington, D.C., 179-212: Ghosh and Singh, 1993, Physicochemical and biological treatments for enzymatic/microbial conversion of lignocellulosic biomass, *Adv. Appt Microbiol.* 39: 295-333; McMillan, J. D., 1994, Pretreating lignocellulosic biomass: a review, in *Enzymatic Conversion of Biomass for Fuels Production*, Himmel, M. E Baker, J. O., and Overend, R. P., eds., ACS Symposium Series 566, American Chemical Society, Washington, D.C., chapter 15; Gong, C. S., Cao, N. J., Du, J. and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem, Eng./Biotechnol.* 42: 63-95).

Saccharification. In the hydrolysis step, also known as saccharification, the pretreated cellulose-containing material is hydrolyzed to break down cellulose and alternatively also hemicellulose to fermentable sugars, such as glucose, xylose, xylulose, arabinose, maltose, mannose, galactose, and/or soluble oligosaccharides. The hydrolysis is performed enzymatically using a cellulolytic enzyme composition of the present invention comprising an effective amount of a polypeptide having cellulolytic enhancing activity and soluble activating divalent metal cation. The enzyme components of the composition can also be added sequentially.

Enzymatic hydrolysis is preferably carried out in a suitable aqueous environment under conditions that can be readily determined by one skilled in the art. In a preferred aspect, hydrolysis is performed under conditions suitable for the activity of the enzyme(s), optimal for the enzyme(s). The hydrolysis can be carried out as a fed batch or continuous process where the pretreated cellulose-containing material (substrate) is fed gradually to, for example, an enzyme containing hydrolysis solution.

The saccharification is generally performed in stirred-tank reactors or fermentors under controlled pH, temperature, and mixing conditions. Suitable process time, temperature, and pH conditions can readily be determined by one skilled in the art. For example, the saccharification can last up to 200 hours, but is typically performed for preferably at 12 to about 96 hours, more preferably about 16 to about 72 hours, and most preferably about 24 to about 48 hours. The temperature is in the range of preferably about 25° C. to about 70° C., more preferably about 30° C. to about 65° C., and more preferably about 40° C. to 60° C. in particular about 50° C. The pH is in the range of preferably about 3 to about 8, more preferably about 3.5 to about 7, and most preferably about 4 to about 6, in particular about pH 5. The dry solids content is in the range of preferably about 5 to about 50 wt %, more preferably about 10 to about 40 wt %, and most preferably about 20 to about 30 wt %.

The optimum amounts of the enzymes and polypeptides having cellulolytic enhancing activity depend on several factors including, but not limited to, the mixture of component cellulolytic proteins, the cellulosic substrate, the concentration of cellulosic substrate, the pretreatment(s) of the cellulosic substrate, temperature, time, pH, and inclusion of fermenting organism (e.g., yeast for Simultaneous Saccharification and Fermentation).

In a preferred aspect, an effective amount of cellulolytic protein(s) to cellulose-containing material is about 0.5 to about 50 mg, preferably at about 0.5 to about 40 mg, more preferably at about 0.5 to about 25 mg, more preferably at about 0.75 to about 20 mg, more preferably at about 0.75 to about 15 mg, even more preferably at about 0.5 to about 10 mg, and most preferably at about 2.5 to about 10 mg per g of cellulose-containing material.

In another preferred aspect, an effective amount of a polypeptide having cellulolytic enhancing activity to cellulose-containing material is about 0.5 to about 50 mg, preferably at about 0.5 to about 40 mg, more preferably at about 0.5 to about 25 mg, more preferably at about 0.75 to about 20 mg, more preferably at about 0.75 to about 15 mg, even more preferably at about 0.5 to about 10 mg, and most preferably at about 2.5 to about 10 mg per g of cellulose-containing material.

In another preferred aspect, an effective amount of polypeptide(s) having cellulolytic enhancing activity to cellulose-containing material is about 0.01 to about 50.0 mg, preferably about 0.01 to about 40 mg, more preferably about 0.01 to about 30 mg, more preferably about 0.01 to about 20 mg, more preferably about 0.01 to about 10 mg, more preferably about 0.01 to about 5 mg, more preferably at about 0.025 to about 1.5 mg, more preferably at about 0.05 to about 1.25 mg, more preferably at about 0.075 to about 1.25 mg, more preferably at about 0.1 to about 1.25 mg, even more preferably at about 0.15 to about 1.25 mg, and most preferably at about 0.25 to about 1.0 mg per g of cellulose-containing material.

In another preferred aspect, an effective amount of polypeptide(s) having cellulolytic enhancing activity to cellulolytic protein(s) is about 0.005 to about 1.0 g, preferably at about 0.01 to about 1.0 g, more preferably at about 0.15 to about 0.759, more preferably at about 0.15 to about 0.5 g, more preferably at about 0.1 to about 0.5 g, even more preferably at about 0.1 to about 0.5 g, and most preferably at about 0.05 to about 0.2 g per g of cellulolytic protein(s).

Fermentation. The fermentable sugars obtained from the pretreated and hydrolyzed cellulose-containing material can be fermented by one or more fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the biofuel industry, consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulose-containing material as a result of the pretreatment and enzymatic hydrolysis steps, are fermented to a product, e.g., ethanol, by a fermenting organism, such as yeast. Hydrolysis (saccharification) and fermentation can be separate or simultaneous. Such methods include, but are not limited to, separate hydrolysis and fermentation (SHF), simultaneous saccharification and fermentation (SSF), simultaneous saccharification and cofermentation (SSCF), hybrid hydrolysis and fermentation (HHF), SHCF (separate hydrolysis and co-fermentation), HHCF (hybrid hydrolysis and fermentation), and direct microbial conversion (DMC).

Any suitable hydrolyzed cellulose-containing material can be used in the fermentation step in practicing the present invention. The material is generally selected based on the desired fermentation product, i.e., the substance to be obtained from the fermentation, and the process employed, as is well known in the art.

The term "fermentation medium" is understood herein to refer to a medium before the fermenting microorganism(s) is(are) added, such as, a medium resulting from a saccharification process, as well as a medium, for example, used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be $C_6$ and/or $C_5$ fermenting organisms, or a combination thereof. Both $C_6$ and $C_5$ fermenting organisms are well known in the art. Suitable fermenting microorganisms are able to ferment, i.e., convert, sugars, such as glucose, xylose, xylulose, arabinose, maltose, mannose, galactose, or oligosaccharides, directly or indirectly into the desired fermentation product.

Examples of bacterial and fungal fermenting organisms producing ethanol are described by Lin et al., 2006. *Appl. Microbiol. Biotechnol.* 69: 627-642.

Examples of fermenting microorganisms that can ferment C6 sugars include bacterial and fungal organisms, such as yeast. Preferred yeast includes strains of *Saccharomyces* spp., preferably *Saccharomyces cerevisiae*.

Examples of fermenting organisms that can ferment C5 sugars include bacterial and fungal organisms, such as yeast. Preferred C5 fermenting yeast include strains of *Pichia*, preferably *Pichia stipitis*, such as *Pichia stipitis* CBS 5773; strains of *Candida*, preferably *Candida boidinii*, *Candida brassicae*, *Candida sheatae*, *Candida diddensii*, *Candida pseudotropicalis*, or *Candida utilis*.

Other fermenting organisms include strains of *Zymomonas*, such as *Zymomonas mobilis*; *Hansenula*, such as *Hansenula anomala*; *Klyveromyces*, such as *K. fragilis*; *Schizosaccharomyces*, such as *S. pombe*; and *E. coli*, especially *E. coli* strains that have been genetically modified to improve the yield of ethanol.

In a preferred aspect, the yeast is a *Saccharomyces* spp. In a more preferred aspect, the yeast is *Saccharomyces cerevisiae*. In another more preferred aspect, the yeast is *Saccharomyces distaticus*. In another more preferred aspect, the yeast is *Saccharomyces uvarum*. In another preferred aspect, the yeast is a *Kluyveromyces*. In another more preferred aspect, the yeast is *Kluyveromyces marxianus*. In another more preferred aspect, the yeast is *Kluyveromyces fragilis*. In another preferred aspect, the yeast is a *Candida*. In another more preferred aspect, the yeast is *Candida boidinii*. In another more preferred aspect, the yeast is *Candida brassicae*. In another more preferred aspect, the yeast is *Candida diddensii*. In another more preferred aspect, the yeast is *Candida pseudotropicalis*. In another more preferred aspect, the yeast is *Candida utilis*. In another preferred aspect, the yeast is a *Clavispora*. In another more preferred aspect, the yeast is *Clavispora lusitaniae*. In another more preferred aspect, the yeast is *Clavispora opuntiae*. In another preferred aspect, the yeast is a *Pachysolen*. In another more preferred aspect, the yeast is *Pachysolen tannophilus*. In another preferred aspect, the yeast is a *Pichia*. In another more preferred aspect, the yeast is a *Pichia stipitis*. In another preferred aspect, the yeast is a *Bretannomyces*. In another more preferred aspect, the yeast is *Bretannomyces clausenii* (Philippidis, G. P., 1996, Cellulose bioconversion technology, in *Handbook on Bioethanol: Production and Utilization*, Wyman, C. E., ed., Taylor & Francis, Washington, D.C., 179-212).

Bacteria that can efficiently ferment hexose and pentose to ethanol include, for example, *Zymomonas mobilis* and *Clostridium thermocellum* (Philippidis, 1996, supra).

In a preferred aspect, the bacterium is a *Zymomonas*. In a more preferred aspect, the bacterium is *Zymomonas mobilis*. In another preferred aspect, the bacterium is a *Clostridium*. In another more preferred aspect, the bacterium is *Clostridium thermocellum*.

Commercially available yeast suitable for ethanol production includes, e.g. ETHANOL RED™ yeast (available from Fermentis/Lesaffre, USA), FALI™ (available from Fleischmann's Yeast, USA), SUPERSTART™ and THERMOSACC™ fresh yeast (available from Ethanol Technology, Wis., USA), BIOFERM™ AFT and XR (available from NABC—North American Bioproducts Corporation. GA, USA), GERT STRAND™ (available from Gert Strand AB, Sweden), and FERMIOL™ (available from DSM Specialties).

In a preferred aspect, the fermenting microorganism has been genetically modified to provide the ability to ferment pentose sugars, such as xylose arabinose utilizing, and xylose and arabinose co-utilizing microorganisms.

The cloning of heterologous genes into various fermenting microorganisms has led to the construction of organisms capable of converting hexoses and pentoses to ethanol (cofermentation) (Chen and Ho. 1993, Cloning and improving the expression of *Pichia stipitis* xylose reductase gene in *Saccharomyces cerevisiae, App. Biochem. Biotechnol.* 39-40: 135-147; Ho et al., 1998. Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae, App. Microbiol. Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle. *FEMS Yeast Research* 4: 655-664; Beall et al., 1991, Parametric studies of ethanol production from xylose and other sugars by recombinant *Escherichia coli, Biotech. Bioeng.* 38: 296-303; Ingram et al., 1998, Metabolic engineering of bacteria for ethanol production, *Biotechnol. Bioeng* 58: 204-214; Zhang at, 1995, Metabolic engineering of a pentose metabolism pathway in ethanologenic *Zymomonas mobilis, Science* 267: 240-243: Deanda et al., 1996, Development of an arabinose-fermenting *Zymomonas mobilis* strain by metabolic pathway engineering, *Appl. Environ. Microbiol.* 62: 4465-4470).

In a preferred aspect, the genetically modified fermenting microorganism is *Saccharomyces cerevisiae*. In another preferred aspect, the genetically modified fermenting microorganism is *Zymomonas mobilis*. In another preferred aspect, the genetically modified fermenting microorganism is *Escherichia colt*. In another preferred aspect, the genetically modified fermenting microorganism is *Klebsiella oxytoca*.

The fermenting microorganism(s) is typically added to the degraded cellulose or hydrolysate and the fermentation is performed for about 8 to about 96 hours, such as about 24 to about 60 hours The temperature is typically between about 26° C. to about 60° C., in particular about 32° C. or 50° C., and at about pH 3 to about pH 8, such as around pH 4-5,6, or 7.

In a preferred aspect, the fermenting microorganism(s) is applied to the degraded cellulose or hydrolysate and the fermentation is performed for about 12 to about 96 hours, such as typically 24-60 hours. In a preferred aspect, the temperature is preferably between about 20° C. to about 60° C., more preferably about 25° C. to about 50° C., and most preferably about 32° C. to about 50° C., in particular about 32° C. or 50° C., and the pH is generally from about pH 3 to about pH 7, preferably around pH 4-7. However, some, e.g., bacterial fermenting organisms have higher fermentation temperature optima. The fermenting microorganism(s) is preferably applied in amounts of approximately $10^5$ to $10^{12}$, preferably from approximately $10^7$ to $10^{10}$, especially approximately $2\times10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

For ethanol production, following the fermentation the fermented slurry is distilled to extract the ethanol. The ethanol obtained according to the methods of the invention can be used as, e.g., fuel ethanol, drinking ethanol, i.e., potable neutral spirits, or industrial ethanol.

A fermentation stimulator can be used in combination with any of the enzymatic processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al. Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation products: A fermentation product can be any substance derived from the fermentation. The fermentation product can be, without limitation, an alcohol (e.g., arabinitol, butanol, ethanol, glycerol, methanol, 1,3-propanediol, sorbitol, and xylitol); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, propionic acid, succinic acid, and xylonic acid); a ketone (e.g., acetone): an aldehyde (e.g., formaldehyde); an amino acid (e.g., aspartic acid, glutamic acid, glycine, lysine, serine, and threonine); and a gas (e.g., methane, hydrogen ($H_2$), carbon dioxide ($CO_2$), and carbon monoxide (CO)). The fermentation product can also be protein as a high value product.

In a preferred aspect, the fermentation product is an alcohol. It will be understood that the term "alcohol" encompasses a substance that contains one or more hydroxyl moieties. In a more preferred aspect, the alcohol is arabinitol. In another more preferred aspect, the alcohol is butanol. In another more preferred aspect, the alcohol is ethanol. In another more preferred aspect, the alcohol is glycerol. In another more preferred aspect, the alcohol is methanol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P. 2003, Production of acetone, butanol and ethanol by *Clostridium beijerinckii* BA101 and in situ recovery by gas stripping, *World Journal of Microbiology and Biotechnology* 19 (6): 595-603.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid, in another more preferred aspect, the organic acid is ascorbic acid. In another more preferred aspect, the organic acid is citric acid. In another more preferred aspect, the organic acid is 2,5-diketo-D-gluconic acid in another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen, R., and Lee, Y. Y., 1997, Membrane-mediated extractive fermentation for lactic acid production from cellulosic biomass, *Appl. Biochem. Biotechnol.* 63-65: 435-448.

In another preferred aspect, the fermentation product is a ketone. It will be understood that the term "ketone" encompasses a substance that contains one or more ketone moieties. In another more preferred aspect, the ketone is acetone. See, for example, Qureshi and Blaschek, 2003, supra.

In another preferred aspect, the fermentation product is an aldehyde. In another more preferred aspect, the aldehyde is formaldehyde.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard, A., and Margaritis, A., 2004, Empirical modeling of batch fermentation kinetics for poly(glutamic acid) production and other microbial biopolymers, *Biotechnology and Bioengineering* 87 (4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka. N., A. Miya, and K. Kiriyama, 1997, Studies on hydrogen production by continuous culture system of hydrogen-producing anaerobic bacteria, Water Science and Technology 36 (6-7): 41-47; and Gunaseelan V. N. in *Biomass and Bioenergy*, Vol. 13 (1-2), pp. 83-114, 1997, Anaerobic digestion of biomass for methane production: A review.

Recovery. The fermentation product(s) can be optionally recovered from the fermentation medium using any method known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), distillation, or extraction. For example, ethanol is separated from the fermented cellulose-containing material and purified by conventional methods of distillation. Ethanol with a purity of up to about 96 vol. % can be obtained, which can be used as, for example, fuel ethanol, drinking ethanol, i.e., potable neutral spirits, or industrial ethanol.

The present invention is further described by the following examples that should not be construed as limiting the scope of the invention.

EXAMPLES

Materials

Chemicals used as buffers and substrates were commercial products of at least reagent grade.

DNA Sequencing

DNA sequencing was performed using an Applied Biosystems Model 3130X Genetic Analyzer (Applied Biosystems, Foster City, Calif. USA) using dye terminator chemistry (Giesecke et al., 1992, *Journal of Virol. Methods* 38: 47-60). Sequences were assembled using phred/phrap/consed (University of Washington. Seattle, Wash., USA) with sequence specific primers.

Media

NNCYP medium was composed per liter of 5.0 g of $NH_4NO_3$, 0.5 g of $MgSO_4.7H_2O$, 0.3 g of $CaCl_2$, 2.5 g of citric acid, 1.0 g of Bacto Peptone, 5.0 g of yeast extract, COVE trace metals solution, and sufficient $K_2HPO_4$ to achieve a final pH of approximately 5.4.

COVE trace metals solution was composed per liter of 0.04 g of $Na_2B_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_2.2H_2O$, and 10 g of $ZnSO_4.7H_2O$.

YP medium was composed per liter of 10 g of yeast extract and 20 g of bacto tryptone.

Cellulase-inducing medium was composed per liter of 20 g of cellulose, 10 g of corn steep solids, 145 g of $(NH_4)_2SO_4$, 2.08 g of $KH_2PO_4$, 0.28 g of $CaCl_2$, 0.42 g of $MgSO_4.7H_2O$, and 0.42 ml of trace metals solution.

Trace metals solution was composed per liter of 216 g of $FeCl_3.6H_2O$, 58 g of $ZnSO_4.7H_2O$, 27 g of $MnSO_4.H_2O$, 10 g of $CuSO_4.5H_2O$, 2.4 g of $H_3BO_3$, and 336 g of citric acid.

STC was composed of 1 M sorbitol, 10 mM $CaCl_2$, and 10 mM Tris-HCl, pH 7.5.

COVE plates were composed per liter of 342 g of sucrose, 10 ml of COVE salts solution, 10 ml of 1 M acetamide, 10 ml of 1.5 M CsCl, and 25 g of Noble agar.

COVE salts solution was composed per liter of 26 g of KCl, 26 g of MgSO$_4$, 76 g of KH$_2$PO$_4$, and 50 ml of COVE trace metals solution.

COVE2 plates were composed per liter of 30 g of sucrose, 20 ml of COVE salts solution, 25 g of Noble agar, and 10 ml of 1 M acetamide.

PDA plates were composed per liter of 39 grams of potato dextrose agar.

LB medium was composed per liter of 10 g of tryptone, 5 g of yeast extract, 5 g of sodium chloride.

2× YT-Amp plates were composed per liter of 10 g of tryptone, 5 g of yeast extract, 5 g of sodium chloride, and 15 g of Bacto Agar, followed by 2 ml of a filter-sterilized solution of 50 mg/ml ampicillin after autoclaving.

MDU2BP medium was composed per liter of 45 g of maltose, 1 g of MgSO$_4$.7H$_2$O, 1 g of NaCl, 2 g of 1K$_2$HSO$_4$, 12 g of KH$_2$PO$_4$, 2 g of urea, and 500 µl of AMG trace metals solution, the pH was adjusted to 5.0 and then filter sterilized with a 0.22 µm filtering unit.

AMG trace metals solution was composed per liter of 14.3 g of ZnSO$_4$.7H$_2$O, 2.5 g of CuSO$_4$.5H$_2$O, 0.5 g of NiCl$_2$.6H$_2$O, 13.8 g of FeSO$_4$.H$_2$O, 8.5 g of MnSO$_4$.7H$_2$O, and 3 g of citric acid.

Minimal medium plates were composed per liter of 6 g of NaNO$_3$, 0.52 of KCl. 1.52 g of KH$_2$PO$_4$, 1 ml of COVE trace metals solution, 20 g of Noble agar, 20 ml of 50% glucose, 2.5 ml of 20% MgSO$_4$.7H$_2$O, and 20 ml of biotin stock solution.

Biotin stock solution was composed per liter of 0.2 g of biotin.

SOC medium was composed of 2% tryptone, 0.5% yeast extract, 10 mM NaCl, 2.5 mM KCl, 10 mM MgCl$_2$, and 10 mM MgSO$_4$, followed by filter-sterilized glucose to 20 mM after autoclaving.

Example 1

Construction of pMJ04 Expression Vector

Expression vector pMJ04 was constructed by PCR amplifying the *Trichoderma reesei* exocellobiohydrolase 1 gene (cbh1, CEL7A) terminator from *Trichoderma reesei* RutC30 genomic DNA using primers 993429 (antisense) and 993428 (sense) shown below. The antisense primer was engineered to have a Pac I site at the 5'-end and a Spe I site at the 3'-end of the sense primer.

```
Primer 993429 (antisense):
                              (SEQ ID NO: 29)
5'-AACGTTAATTAAGGAATCGTTTTGTGTTT-3'

Primer 993428 (sense):
                              (SEQ ID NO: 30)
5'-AGTACTAGTAGCTCCGTGGCGAAAGCCTG-3'
```

*Trichoderma reesei* RutC30 genomic DNA was isolated using a DNEASY® Plant Maxi Kit (QIAGEN Inc., Valencia, Calif., USA).

The amplification reactions (50 µl) were composed of 1× ThermoPol Reaction Buffer (New England Biolabs, Beverly, Mass., USA), 0.3 mM dNTPs, 100 ng of *Trichoderma reesei* RutC30 genomic DNA, 0.3 µM primer 993429, 0.3 µM primer 993428, and 2 units of Vent DNA polymerase (New England Biolabs, Beverly, Mass., USA). The reactions were incubated in an EPPENDORF® MASTERCYCLER®, 5333 (Eppendorf Scientific, Inc., Westbury, N.Y., USA) programmed for 5 cycles each for 30 seconds at 94° C., 30 seconds at 50° C., and 60 seconds at 72° C., followed by 25 cycles each for 30 seconds at 94° C., 30 seconds at 65° C., and 120 seconds at 72° C. (5 minute final extension). The reaction products were isolated by 1.0% agarose gel electrophoresis using 40 mM Tris base-20 mM sodium acetate-1 mM disodium EDTA (TAE) buffer where a 229 by product band was excised from the gel and purified using a QIAQUICK® Gel Extraction Kit (QIAGEN Inc., Valencia, Calif., USA) according to the manufacturer's instructions.

The resulting PCR fragment was digested with Pac I and Spe I and ligated into pAILo1 (WO 05/067531) digested with the same restriction enzymes using a Rapid Ligation Kit (Roche. Indianapolis, Ind., USA), to generate pMJ04 (FIG. 1).

Example 2

Construction of pCaHj568

Plasmid pCaHj568 was constructed from pCaHj170 (U.S. Pat. No. 5,763,254) and pMT2188. Plasmid pCaHj170 comprises the *Humicola insolens* endoglucanase V (CEL45A) full-length coding region (SEQ ID NO: 31, which encodes the amino acid sequence of SEQ ID NO: 32). Construction of pMT2188 was initiated by PCR amplifying the pUC19 origin of replication from pCaHj483 (WO 98/00529) using primers 142779 and 142780 shown below. Primer 142780 introduces a Bbu I site in the PCR fragment.

```
Primer 142779:
                              (SEQ ID NO: 33)
5'-TTGAATTGAAAATAGATTGATTTAAAACTTC-3'

Primer 142780:
                              (SEQ ID NO: 34)
5'-TTGCATGCGTAATCATGGTCATAGC-3'
```

An EXPAND® FOR System (Roche Molecular Biochemicals, Basel, Switzerland) was used following the manufacturer's instructions for this amplification. PCR products were separated on an agarose gel and an 1160 bP fragment was isolated and purified using a Jetquick Gel Extraction Spin Kit (Genomed, Wielandstr, Germany).

The URA3 gene was amplified from the general *Saccharomyces cerevisiae* cloning vector pYES2 (Invitrogen, Carlsbad, Calif. USA) using primers 140288 and 142778 shown below using an EXPAND® PCR System. Primer 140288 introduced an Eco RI site into the PCR fragment.

```
Primer 140288:
                              (SEQ ID NO: 35)
5'-TTGAATTCATGGGTAATAACTGATAT-3'

Primer 142778:
                              (SEQ ID NO: 36)
5'-AAATCAATCTATTTTCAATTCAATTCATCATT-3'
```

PCR products were separated on an agarose gel and an 1126 by fragment was isolated and purified using a Jetquick Gel Extraction Spin Kit.

The two PCR fragments were fused by mixing and amplfied using primers 142780 and 140288 shown above by the overlap splicing method (Horton et al., 1989. *Gene* 77: 61-68). PCR products were separated on an agarose gel and a 2263 by fragment was isolated and purified using a Jetquick Gel Extraction Spin Kit.

Figure 2:
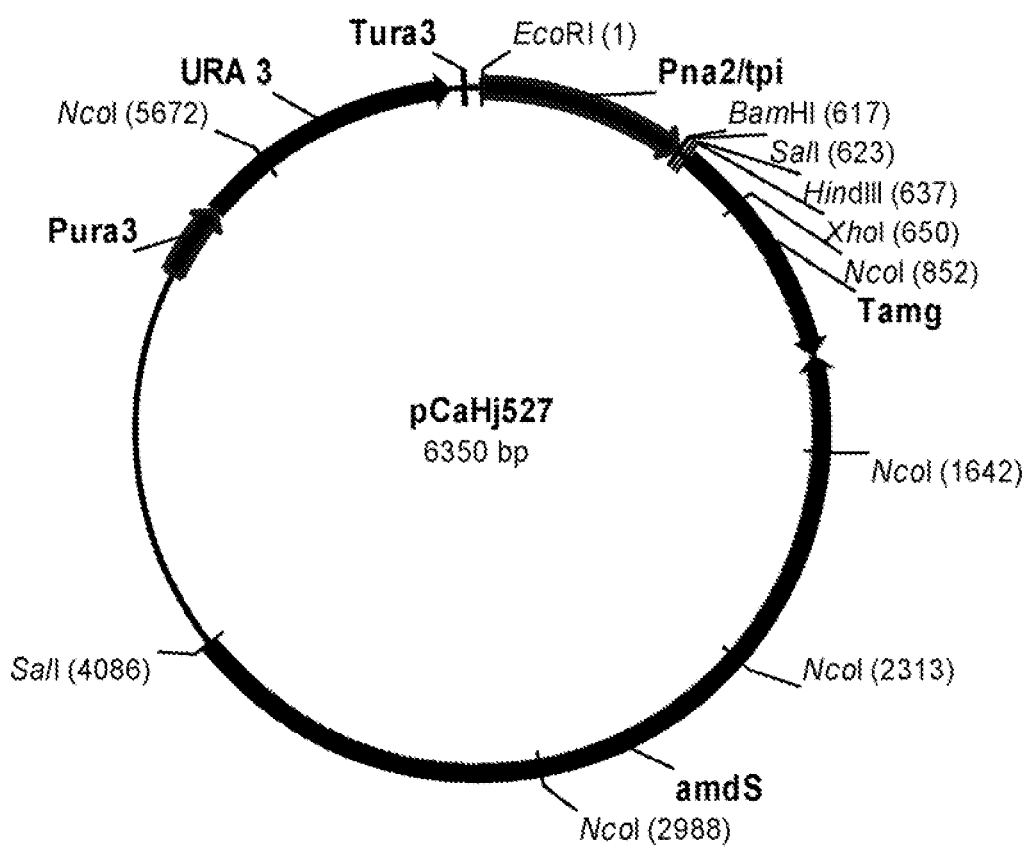
FIG. 2 shows a restriction map of pCaHj527.

The resulting fragment was digested with Eco RI and BIN, I and ligated using standard protocols to the largest fragment of pCaHj483 digested with the same restriction enzymes. The ligation mixture was transformed into pyrF-negative *E. coli* strain DB6507 (ATCC 35673) made competent by the method of Mandel and Higa, 1970, *J. Mol. Biol.* 45: 154. Transformants were selected on solid M9 medium (Sambrook et al., 1989, *Molecular Cloning, A Laboratory Manual,* 2nd edition, Cold Spring Harbor Laboratory Press) supplemented per liter with 1 g of casaminoacids, 500 μg of thiamine, and 10 mg of kanamycin. A plasmid from one transformant was isolated and designated pCaHj527 (FIG. 2).

The NA2-tpi promoter present on pCaHj527 was subjected to site-directed mutagenesis by PCR using an EXPAND® PCR System according to the manufacturer's instructions. Nucleotides 134-144 were converted from GTACTAAAACC (SEQ ID NO: 37) to CCGTTAAATTT (SEQ ID NO. 38) using mutagenic primer 141223 shown below.

```
Primer 141223:
                                    (SEQ ID NO: 39)
5'-GGATGCTGTTGACTCCGGAAATTTAACGGTTTGGTCTTGCA
TCCC-3'
```

Nucleotides 423-436 were converted from ATGCAATT-TAAACT (SEQ ID NO: 40) to CGGCAATTTAACGG (SEQ ID NO: 41) using mutagenic primer 141222 shown below.

```
Primer 141222:
                                    (SEQ ID NO: 42)
5'-GGTATTGTCCTGCAGACGGCAATTTAACGGCTTCTGCGAATCGC-3'
```

Figure 3:
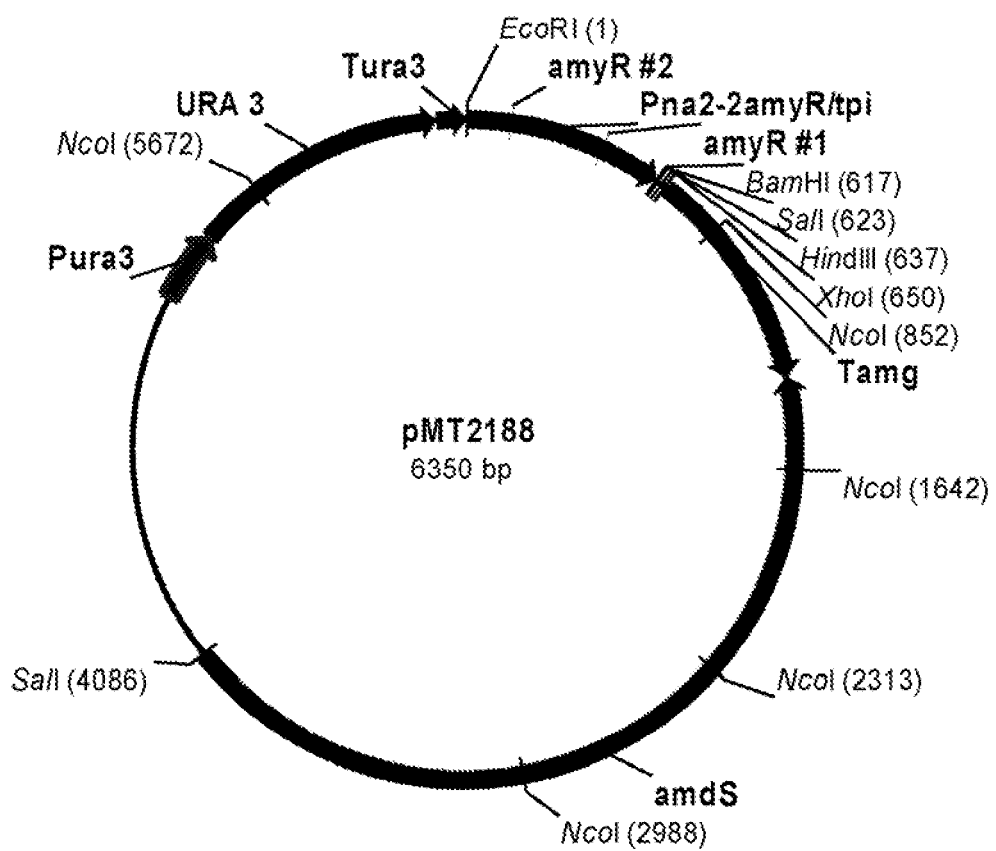
FIG. 3 shows a restriction map of pMT2188.

The resulting plasmid was designated pMT2188 (FIG. 3).

Figure 4:
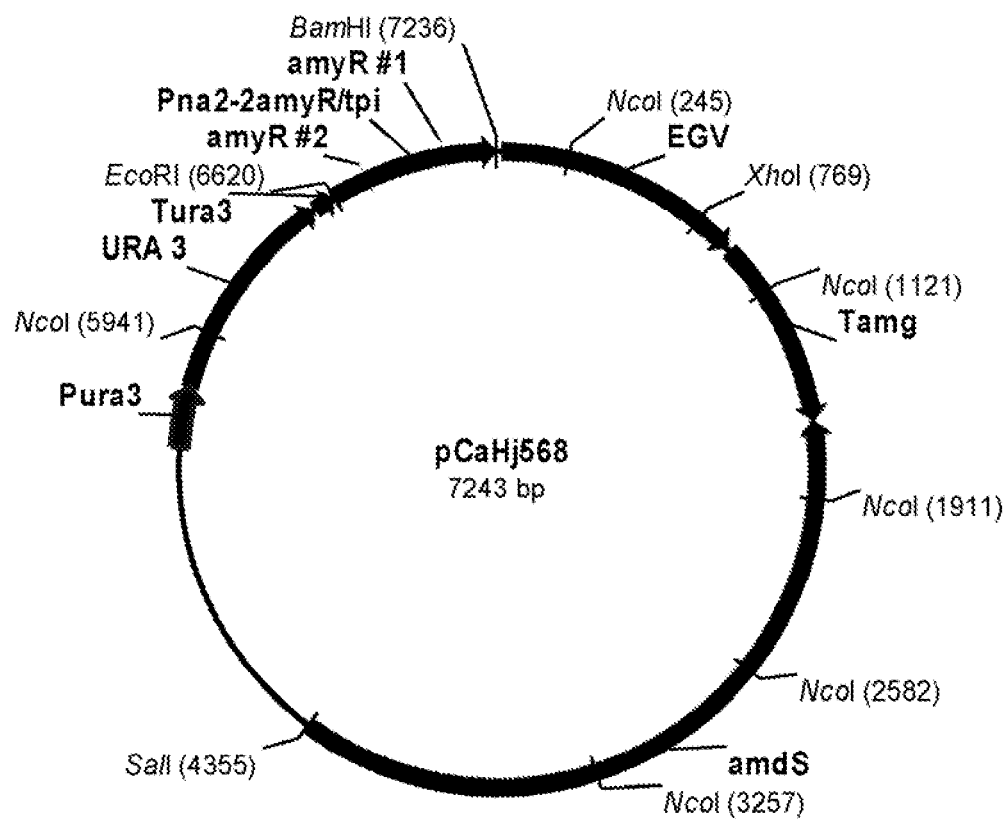
FIG. 4 shows a restriction map of pCaHj568.

The *Humicola insolens* endoglucanase V coding region was transferred from pCaHj170 as a Bam HI-Sal I fragment into pMT2188 digested with Bam HI and Xho I to generate pCaHj568 (FIG. 4). Plasmid pCaHj568 comprises a mutated NA2-tpi promoter operably linked to the *Humicola insolens* endoglucanase V full-length coding sequence.

Example 3

Construction of pMJ05

Plasmid pMJ05 was constructed by PCR amplifying the 915 by *Humicola insolens* endoglucanase V full-length coding region from pCaHj568 using primers HiEGV-F and HiEGV-R shown below.

```
Primer HiEGV-F (sense):
                                    (SEQ ID NO: 43)
5'-AAGCTTAAGCATGCGTTCCTCCCCCCTCC-3'

Primer HiEGV-R (antisense):
                                    (SEQ ID NO: 44)
5'-CTGCAGAATTCTACAGGCACTGATGGTACCAG-3'
```

The amplification reactions (50 μl) were composed of 1× ThermoPol Reaction Buffer (New England Biolabs, Beverly, Mass., USA), 0.3 mM dNTPs, 10 ng/μl of pCaHj568, 0.3 μM HiEGV-F primer. 0.3 μM HiEGV-R primer, and 2 units of Vent DNA polymerase (New England Biolabs, Beverly, Mass., USA). The reactions were incubated in an EPPENDORF® MASTERCYCLER® 5333 programmed for 5 cycles each for 30 seconds at 94° C., 30 seconds at 50° C., and 60 seconds at 72° C., followed by 25 cycles each for 30 seconds at 94° C., 30 seconds at 65° C., and 120 seconds at 72° C. (5 minute final extension). The reaction products were isolated by 1.0% agarose gel electrophoresis using TAE buffer where a 937 by product band was excised from the gel and purified using a QIAQUICK® Gel Extraction Kit according to the manufacturer's instructions.

The 937 bp purified fragment was used as template DNA for subsequent amplifications with the following primers:

```
Primer HiEGV-R (antisense):
                                    (SEQ ID NO: 45)
5'-CTGCAGAATTCTACAGGCACTGATGGTACCAG-3'

Primer HiEGV-F-overlap (sense):
                                    (SEQ ID NO: 46)
5'-ACCGCGGACTGCGCATCATGCGTTCCTCCCCCCTCC-3'
```

Primer sequences in italics are homologous to 17 by of the promoter of the *Trichoderma reesei* cellobiohydrolase I gene (cbh1) (WO 91/17243) and underlined primer sequences are homologous to 29 by of the *Humicola insolens* endoglucanase V coding region. A 36 by overlap between the promoter and the coding sequence allowed precise fusion of a 994 by fragment comprising the *Trichoderma reesei* cbh1 promoter to the 918 by fragment comprising the *Humicola insolens* endoglucanase V coding region.

The amplification reactions (50 μl) were composed of 1× ThermoPol Reaction Buffer, 0.3 mM dNTPs, 1 μl of the purified 937 by PCR fragment, 0.3 μM HiEGV-F-overlap primer, 0.3 μM HiEGV-R primer, and 2 units of Vent DNA polymerase. The reactions were incubated in an EPPENDORF® MASTERCYCLER® 5333 programmed for 5 cycles each for 30 seconds at 94° C., 30 seconds at 50° C., and 60 seconds at 72° C., followed by 25 cycles each for 30 seconds at 94° C., 30 seconds at 65° C., and 120 seconds at 72° C. (5 minute final extension). The reaction products were isolated by 1.0% agarose gel electrophoresis using TAE buffer where a 945 by product band was excised from the gel and purified using a QIAQUICK® Gel Extraction Kit according to the manufacturer's instructions.

A separate PCR was performed to amplify the *Trichoderma reesei* cbh1 promoter sequence extending from 994 by upstream of the ATG start codon of the gene from *Trichoderma reesei* RutC30 genomic DNA using the primers shown below (the sense primer was engineered to have a Sal I restriction site at the 5'-end). *Trichoderma reesei* RutC30 genomic DNA was isolated using a DNeasy Plant Maxi Kit.

```
Primer TrCBHIpro-F (sense):
                                    (SEQ ID NO: 47)
5'-AAACGTCGACCGAATGTAGGATTGTTATC-3'

Primer TrCBHIpro-R (antisense):
                                    (SEQ ID NO: 48)
5'-GATGCGCAGTCCGCGGT-3'
```

The amplification reactions (50 μl) were composed of 1× ThermoPol Reaction Buffer, 0.3 mM dNTPs, 100 ng/μl *Trichoderma reesei* RutC30 genomic DNA, 0.3 μM TrCBHIpro-F primer, 0.3 μM TrCBHIpro-R primer, and 2 units of Vent DNA polymerase. The reactions were incubated in an EPPENDORF® MASTERCYCLER® 5333 programmed for 30 cycles each for 30 seconds at 94° C., 30 seconds at 55° C., and 120 seconds at 72° C. (5 minute final extension). The reaction products were isolated by 1.0% agarose gel electrophoresis using TAE buffer where a 998 by product band was excised from the gel and purified using a QIAQUICK® Gel Extraction Kit according to the manufacturer's instructions.

The purified 998 by PCR fragment was used as template DNA for subsequent amplifications using the primers shown below.

```
Primer TrCBHIpro-F:
                                       (SEQ ID NO: 49)
5'-AAACGTCGACCGAATGTAGGATTGTTATC-3'

Primer TrCBHIpro-R-overlap:
                                       (SEQ ID NO: 50)
5'-GGAGGGGGAGGAACGCATGATGCGCAGTCCGCGGT-3'
```

Sequences in italics are homologous to 17 by of the *Trichoderma reesei* cbh1 promoter and underlined sequences are homologous to 29 by of the *Humicola insolens* endoglucanase V coding region A 36 by overlap between the promoter and the coding sequence allowed precise fusion of the 994 by fragment comprising the *Trichoderma reesei* cbh1 promoter to the 918 by fragment comprising the *Humicola insolens* endoglucanase V full-length coding region.

The amplification reactions (50 µl) were composed of 1× ThermoPol Reaction Buffer, 0.3 mM dNTPs, 1 µl of the purified 998 by PCR fragment, 0.3 µM TrCBH1pro-F primer, 0.3 µM TrCBH1 pro-R-overlap primer, and 2 units of Vent DNA polymerase. The reactions were incubated in an EPPENDORF® MASTERCYCLER® 5333 programmed for 5 cycles each for 30 seconds at 94° C., 30 seconds at 50° C., and 60 seconds at 72° C., followed by 25 cycles each for 30 seconds at 94° C., 30 seconds at 65° C., and 120 seconds at 72° C. (5 minute final extension). The reaction products were isolated by 1.0% agarose gel electrophoresis using TAE buffer where a 1017 by product band was excised from the gel and purified using a QIAQUICK® Gel Extraction Kit according to the manufacturer's instructions.

The 1017 by *Trichoderma reesei* cbh1 promoter PCR fragment and the 945 by *Humicola insolens* endoglucanase V PCR fragment were used as template DNA for subsequent amplification using the following primers to precisely fuse the 994 by cbh1 promoter to the 918 by endoglucanase V full-length coding region using overlapping PCR.

```
Primer TrCBHIpro-F:
                                       (SEQ ID NO: 51)
5'-AAACGTCGACCGAATGTAGGATTGTTATC-3'

Primer HiEGV-R:
                                       (SEQ ID NO: 52)
5'-CTGCAGAATTCTACAGGCACTGATGGTACCAG-3'
```

The amplification reactions (50 up were composed of 1× ThermoPol Reaction Buffer, 0.3 mM dNTPs, 0.3 µM TrCBH1pro-F primer. 0.3 µM HiEGV-R primer, and 2 units of Vent DNA polymerase. The reactions were incubated in an EPPENDORF® MASTERCYCLER® 5333 programmed for 5 cycles each for 30 seconds at 94° C., 30 seconds at 50° C., and 60 seconds at 72° C., followed by 25 cycles each for 30 seconds at 94° C., 30 seconds at 65° C., and 120 seconds at 72° c. (5 minute final extension). The reaction products were isolated by 1.0% agarose gel electrophoresis using TAE buffer where a 1926 by product band was excised from the gel and purified using a QIAQUICK® Gel Extraction Kit according to the manufacturer's instructions.

Figure 5:
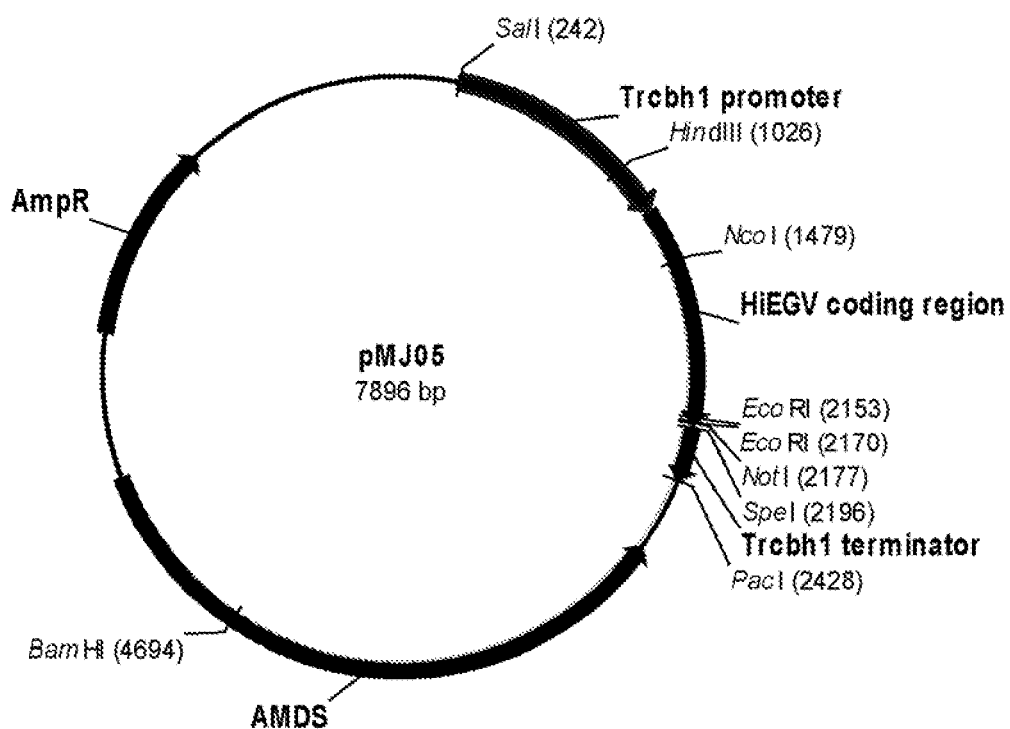
FIG. 5 shows a restriction map of pMJ05.

The resulting 1926 by fragment was cloned into a pCR®-Blunt-ii-TOPO® vector (Invitrogen, Carlsbad, Calif., USA) using a ZEROBLUNT® TOPO® PCR Cloning Kit (Invitrogen, Carlsbad, Calif., USA) following the manufacturer's protocol. The resulting plasmid was digested with Not I and Sal I and the 1926 by fragment was gel purified using a QIAQUICK® Gel Extraction Kit and ligated using T4 DNA ligase (Roche, Indianapolis, Ind., USA) into pMJ04, which was also digested with the same two restriction enzymes, to generate pMJ05 (FIG. 5). Plasmid pMJ05 comprises the *Trichoderma reesei* cellobiohydrolase I promoter and terminator operably linked to the *Humicola insolens* endoglucanase V full-length coding sequence.

Example 4

Construction of pSMai130 Expression Vector

A 2586 by DNA fragment spanning from the ATG start codon to the TM stop codon of an *Aspergillus oryzae* beta-glucosidase full-length coding sequence (SEQ ID NO: 15 for cDNA sequence and SEQ ID NO: 16 for the deduced amino acid sequence; *E. coli* DSM 14240) was amplified by PCR from pJaL660 (WO 2002/095014) as template with primers 993467 (sense) and 993456 (antisense) shown below. A Spe I site was engineered at the 5' end of the antisense primer to facilitate ligation. Primer sequences in italics are homologous to 24 by of the *Trichoderma reesei* cart promoter and underlined sequences are homologous to 22 by of the *Aspergillus oryzae* beta-glucosidase coding region.

```
Primer 993467:
                                       (SEQ ID NO: 53)
5'-ATAGTCAACCGCGGACTGCGCATCATGAAGCTTGGTTGGATCGAGG-
3'

Primer 993456:
                                       (SEQ ID NO: 54)
5'-ACTAGTTTACTGGGCCTTAGGCAGCG-3'
```

The amplification reactions (50 µl) were composed of Pfx Amplification Buffer (Invitrogen, Carlsbad, Calif., USA), 0.25 mM dNTPs, 10 ng of pJaL660, 6.4 µM primer 993467, 3.2 µM primer 993456, 1 mM MgCl$_2$, and 2.5 units of Pfx DNA polymerase (Invitrogen, Carlsbad, Calif., USA). The reactions were incubated in an EPPENDORF® MASTERCYCLER® 5333 programmed for 30 cycles each for 1 minute at 94'C, 1 minute at 55° C., and 3 minutes at 72° C. (15 minute final extension). The reaction products were isolated by 1.0% agarose gel electrophoresis using TAE buffer where a 2586 by product band was excised from the gel and purified using a QIAQUICK® Gel Extraction Kit according to the manufacturer's instructions.

A separate PCR was performed to amplify the *Trichoderma reesei* cbh1 promoter sequence extending from 1000 by upstream of the ATG start codon of the gene, using primer 993453 (sense) and primer 993463 (antisense) shown below to generate a 1000 by PCR fragment.

```
Primer 993453:
                                       (SEQ ID NO: 55)
5'-GTCGACTCGAAGCCCGAATGTAGGAT-3'

Primer 993463:
                                       (SEQ ID NO: 56)
5'-CCTCGATCCAACCAAGCTTCATGATGCGCAGTCCGCGGTTGACTA-
3'
```

Primer sequences in italics are homologous to 24 by of the *Trichoderma reesei* cbh1 promoter and underlined primer sequences are homologous to 22 by of the *Aspergillus*

*oryzae* beta-glucosidase full-length coding region. The 46 by overlap between the promoter and the coding sequence allowed precise fusion of the 1000 by fragment comprising the *Trichoderma reesei* cbh1 promoter to the 2586 by fragment comprising the *Aspergillus oryzae* beta-glucosidase coding region.

The amplification reactions (50 µl) were composed of Pfx Amplification Buffer. 0.25 mM dNTPs, 100 ng of *Trichoderma reesei* RutC30 genomic DNA, 6.4 µM primer 993453, 3.2 µM primer 993463, 1 mM MgCl$_2$, 2.5 units of Pfx DNA polymerase. The reactions were incubated in an EPPENDORF® MASTERCYCLER® 5333 programmed for 30 cycles each for 1 minute at 94° C., 1 minute at 55° C., and 3 minutes at 72° C. (15 minute final extension). The reaction products were isolated by 1.0% agarose gel electrophoresis using TAE buffer where a 1000 by product band was excised from the gel and purified using a QIAQUICK® Gel Extraction Kit according to the manufacturer's instructions.

The purified fragments were used as template DNA for subsequent amplification by overlapping PCR using primer 993453 (sense) and primer 993456 (antisense) shown above to precisely fuse the 1000 by fragment comprising the *Trichoderma reesei* cbh1 promoter to the 2586 by fragment comprising the *Aspergillus oryzae* beta-glucosidase full-length coding region.

The amplification reactions (50 µl) were composed of Pfx Amplification Buffer, 0.25 mM dNTPs, 6.4 µM primer 99353, 3.2 µM primer 993456, 1 mM MgCl$_2$, and 2.5 units of Pfx DNA polymerase. The reactions were incubated in an EPPENDORF® MASTERCYCLER® 5333 programmed for 30 cycles each for 1 minute at 94° C., 1 minute at 60° C., and 4 minutes at 72° C. (15 minute final extension).

Figure 6:
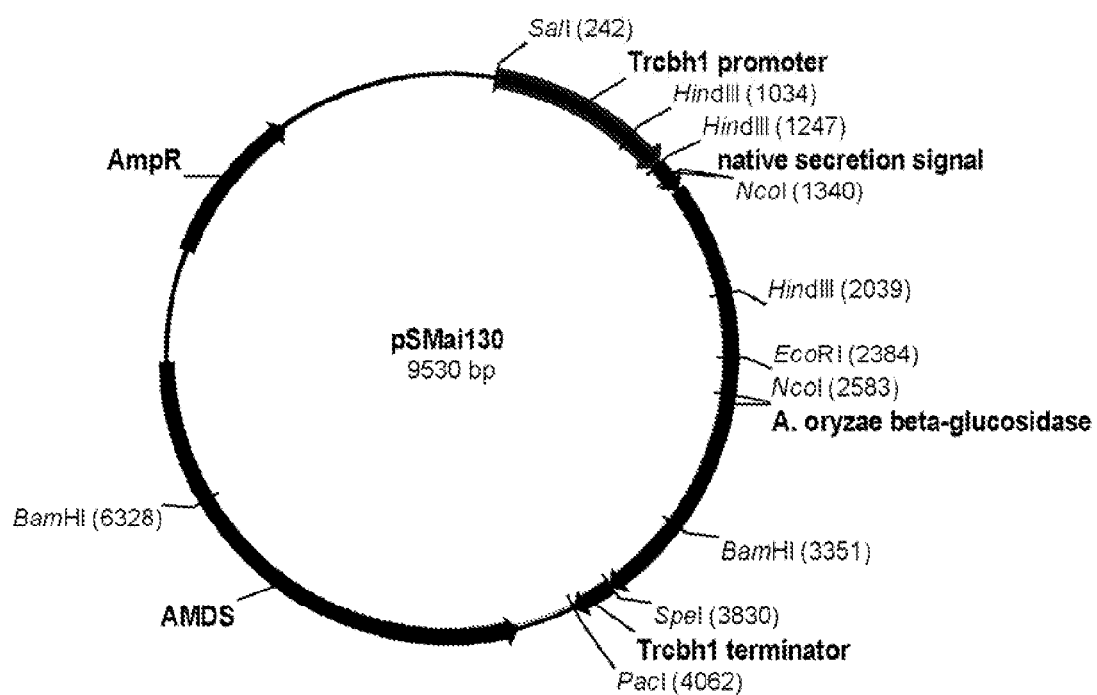
FIG. 6 shows a restriction map of pSMai130.

The resulting 3586 by fragment was digested with Sal I and Spe I and ligated into pMJ04, digested with the same two restriction enzymes, to generate pSMai130 (FIG. 6). Plasmid pSMai130 comprises the *Trichoderma reesei* cellobiohydrolase gene promoter and terminator operably linked to the *Aspergillus oryzae* native beta-glucosidase signal sequence and coding sequence (i.e., full-length *Aspergillus oryzae* beta-glucosidase coding sequence).

Example 5

Construction of pSMai135

The *Aspergillus oryzae* beta-glucosidase mature coding region (minus the native signal sequence, see FIG. 7; SEQ ID NOs. 57 and 58 for the signal peptide and coding sequence thereof) from Lys-20 to the TAA stop codon was PCR amplified from pJaL660 as template with primer 993728 (sense) and primer 993727 (antisense) shown below.

Primer 993728:
(SEQ ID NO: 59)
5'-*TGCCGGTGTTGGCCCTTGCC*AAGGATGATCTCGCGTACTCCC-3'

Primer 993727:
(SEQ ID NO: 60)
5'-GACTAGTCTTACTGGGCCTTAGGCAGCG-3'

Sequences in italics are homologous to 20 by of the *Humicola insolens* endoglucanase V signal sequence and sequences underlined are homologous to 22 by of the *Aspergillus oryzae* beta-glucosidase coding region. A Spe I site was engineered into the 5' end of the antisense primer.

The amplification reactions (50 µl) were composed of Pfx Amplification Buffer, 025 mM dNTPs, 10 ng/µl of pJaL660, 6.4 µM primer 993728, 3.2 µM primer 993727, 1 mM MgCl$_2$, and 2.5 units of Pfx DNA polymerase. The reactions were incubated in an EPPENDORF® MASTERCYCLER® 5333 programmed for 30 cycles each for 1 minute at 94° C., 1 minute at 55° C., and 3 minutes at 72° C. (15 minute final extension). The reaction products were isolated by 1.0% agarose gel electrophoresis using TAE buffer where a 2523 by product band was excised from the gel and purified using a QIAQUICK® Gel Extraction Kit according to the manufacturer's instructions.

A separate PCR amplification was performed to amplify 1000 by of the *Trichoderma reesei* cbh1 promoter and 63 by of the *Humicola insolens* endoglucanase V signal sequence (ATG start codon to Ala-21, FIG. 8, SEQ ID NOs: 61 and 62), using primer 993724 (sense) and primer 993729 (antisense) shown below.

Primer 993724;
(SEQ ID NO: 63)
5'-ACGCGTCGACCGAATGTAGGATTGTTATCC-3'

Primer 993729:
(SEQ ID NO: 64)
5'-GGGAGTACGCGAGATCATCCTTGGCAAGGGCCAACACCGGCA-3'

Primer sequences in italics are homologous to 20 by of the *Humicola insolens* endoglucanase V signal sequence and underlined primer sequences are homologous to the 22 by of the *Aspergillus oryzae* beta-glucosidase coding region.

Plasmid pMJ05, which comprises the *Humicola insolens* endoglucanase V coding region under the control of the cbh1 promoter, was used as template to generate a 1063 by fragment comprising the *Trichoderma reesei* cbh1 promoter and *Humicola insolens* endoglucanase V signal sequence fragment. A 42 by of overlap was shared between the *Trichoderma reesei* cbh1 promoter and *Humicola insolens* endoglucanase V signal sequence and the *Aspergillus oryzae* beta-glucosidase mature coding sequence to provide a perfect linkage between the promoter and the ATG start codon of the 2523 by *Aspergillus oryzae* beta-glucosidase coding region.

The amplification reactions (50 µl) were composed of Pfx Amplification Buffer, 0.25 mM dNTPs, 10 ng/µl of pMJ05, 6.4 µM primer 993728, 3.2 µM primer 993727, 1 mM MgCl$_2$, and 2.5 units of Pfx DNA polymerase. The reactions were incubated in an EPPENDORF® MASTERCYCLER® 5333 programmed for 30 cycles each for 1 minute at 94° C., 1 minute at 60° C. and 4 minutes at 72° C. (15 minute final extension). The reaction products were isolated by 1.0% agarose gel electrophoresis using TAE buffer where a 1063 by product band was excised from the gel and purified using a QIAQUICK® Gel Extraction Kit according to the manufacturer's instructions.

The purified overlapping fragments were used as templates for amplification using primer 993724 (sense) and primer 993727 (antisense) described above to precisely fuse the 1063 by fragment comprising the *Trichoderma reesei* cbh1 promoter and *Humicola insolens* endoglucanase V signal sequence to the 2523 by fragment comprising the *Aspergillus oryzae* beta-glucosidase mature coding region frame by overlapping PCR.

The amplification reactions (50 µl) were composed of Pfx Amplification Buffer, 0.25 mM dNTPs, 6.4 µM primer 993724, 3.2 µM primer 993727, 1 mM MgCl$_2$, and 2.5 units of Pfx DNA polymerase. The reactions were incubated in an EPPENDORF® MASTERCYCLER® 5333 programmed for 30 cycles each for 1 minute at 94° C., 1 minute at 60° C., and 4 minutes at 72° C. (15 minute final extension). The reaction products were isolated by 1.0% agarose gel electrophoresis using TAE buffer where a 3591 by product band was excised from the gel and purified using a QIAQUICK® Gel Extraction Kit according to the manufacturer's instructions.

Figure 9:
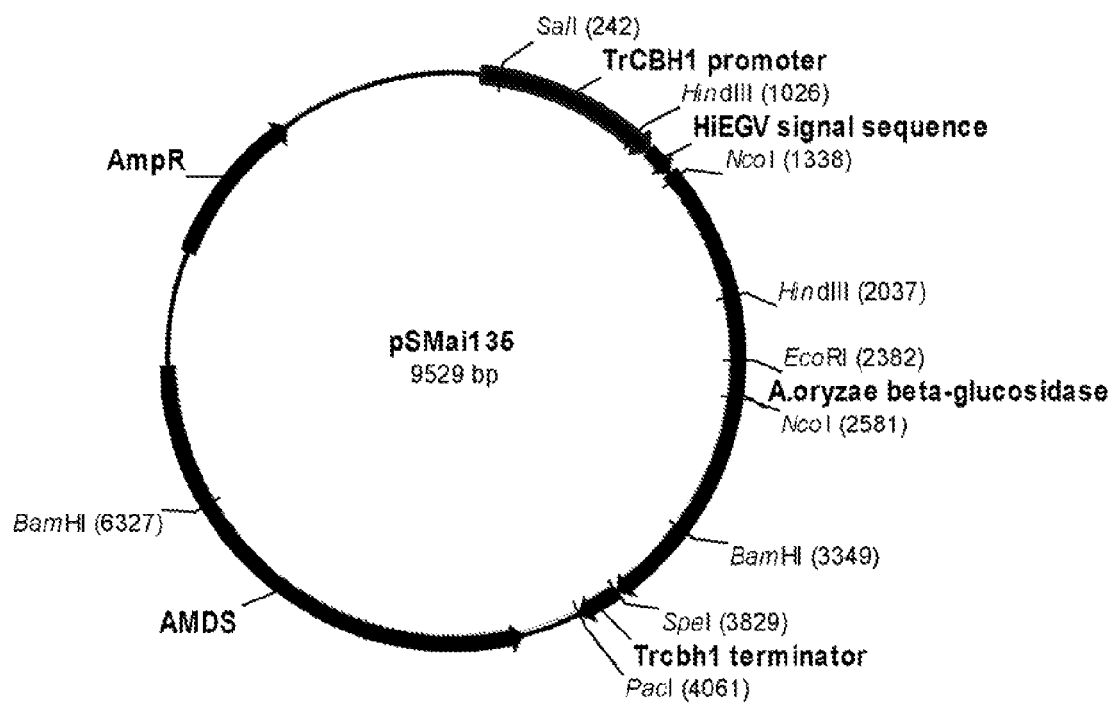
FIG. 9 shows a restriction map of pSMai135.

The resulting 3591 by fragment was digested with Sal I and Spe I and ligated into pMJ04 digested with the same restriction enzymes to generate pSMai135 (FIG. 9). Plasmid pSMai135 comprises the *Trichoderma reesei* cellobiohydrolase I gene promoter and terminator operably linked to the *Humicola insolens* endoglucanase V signal sequence and the *Aspergillus oryzae* beta-glucosidase mature coding sequence.

Example 6

Expression of *Aspergillus oryzae* Beta-Glucosidase with the *Humicola Insolens* Endoglucanase V Secretion Signal Plasmid pSMai135 encoding the mature *Aspergillus oryzae* beta-glucosidase linked to the *Humicola insolens* endoglucanase V secretion signal (FIG. 8) was introduced into *Trichoderma reesei* RutC30 by PEG-mediated transformation (Penttila et al., 1987, *Gene* 61 155-164). The plasmid contained the *Aspergillus nidulans* amdS gene to enable transformants to grow on acetamide as the sole nitrogen source.

*Trichoderma reesei* RutC30 was cultivated at 27° C. and 90 rpm in 25 ml of VP medium supplemented with 2% (w/v) glucose and 10 mM uridine for 17 hours. Mycelia was collected by filtration using a Vacuum Driven Disposable Filtration System (Millipore, Bedford. MA, USA) and washed twice with deionized water and twice with 1.2 M sorbitol. Protoplasts were generated by suspending the washed mycelia in 20 ml of 1.2 M sorbitol containing 15 mg of GLUCANEX® (Novozymes A/S, Bagsværd, Denmark) per ml and 0.36 units of chitinase (Sigma Chemical Co., St. Louis, Mo., USA) per ml and incubating for 15-25 minutes at 34° C. with gentle shaking at 90 rpm. Protoplasts were collected by centrifuging for 7 minutes at 400×g and washed twice with cold 1.2 M sorbitol. The protoplasts were counted using a haemacytometer and re-suspended in STC to a final concentration of $1 \times 10^8$ protoplasts per ml. Excess protoplasts were stored in a Cryo 1° C. Freezing Container (Nalgene, Rochester, N.Y., USA) at −80° C.

Approximately 7 μg of pSMai135 digested with Pme I was added to 100 μl of protoplast solution and mixed gently, followed by 260 μl of PEG buffer, mixed, and incubated at room temperature for 30 minutes. STC (3 ml) was then added and mixed and the transformation solution was plated onto COVE plates using *Aspergillus nidulans* amdS selection. The plates were incubated at 28° C. for 5-7 days. Transformants were sub-cultured onto COVE2 plates and grown at 28° C.

Sixty-seven transformants designated SMA135 obtained with pSMai135 were subcultured onto fresh plates containing acetamide and allowed to sporulate for 7 days at 28° C.

The 67 SMA135 *Trichoderma reesei* transformants were cultivated in 125 ml baffled shake flasks containing 25 ml of cellulase-inducing medium at pH 6.0 inoculated with spores of the transformants and incubated at 28° C. and 200 rpm for 7 days. *Trichoderma reesei* RutC30 was run as a control. Culture broth samples were removed at day 7. One ml of each culture broth was centrifuged at 15,700×g for 5 minutes in a micro-centrifuge and the supernatants transferred to new tubes. Samples were stored at 4° C. until enzyme assay. The supernatants were assayed for beta-glucosidase activity using p-nitrophenyl-beta-D-glucopyranoside as substrate, as described below.

Beta-glucosidase activity was determined at ambient temperature using 25 μl aliquots of culture supernatants, diluted 1:10 in 50 mM succinate pH 5.0, in 200 μl of 0.5 mg/ml p-nitrophenyl-beta-D-glucopyranoside as substrate in 50 mM succinate pH 5.0. After 15 minutes incubation the reaction was stopped by adding 100 μl of 1 M Tris-HCl pH 8.0 and the absorbance was read spectrophotometrically at 405 nm. One unit of beta-glucosidase activity corresponded to production of 1 μmol of p-nitrophenyl per minute per liter at pH 5.0, ambient temperature. *Aspergillus niger* beta-glucosidase (NOVOZYM™ 188, Novozymes A/S, Bagsværd, Denmark) was used as an enzyme standard.

A number of the SMA135 transformants produced beta-glucosidase activities several-fold higher than that of *Trichoderma reesei* RutC30. Transformant SMA135-04 produced the highest beta-glucosidase activity.

SDS-PAGE was carried out using CRITERION® Tris-HCl (5% resolving) gels (Bio-Rad, Hercules, Calif., USA) with the CRITERION® System (Bio-Rad, Hercules, Calif., USA). Five μl of day 7 supernatants (see above) were suspended in 2× concentration of Laemmli Sample Buffer (Bio-Rad, Hercules, Calif., USA) and boiled in the presence of 5% beta-mercaptoethanol for 3 minutes. The supernatant samples were loaded onto a polyacrylamide gel and subjected to electrophoresis with 1× Tris/Glycine/SDS as running buffer (Bio-Rad, Hercules, Calif., USA). The resulting gel was stained with BIO-SAFE® Coomassie Stain (Bio-Rad, Hercules, Calif., USA).

Totally, 26 of the 38 *Trichoderma reesei* SMA135 transformants produced a protein of approximately 110 kDa that was not visible in *Trichoderma reesei* RutC30 as control. Transformant *Trichoderma reesei* SMA135-04 produced the highest level of beta-glucosidase.

Example 7

Construction of Expression Vector pSMai140

Expression vector pSMai140 was constructed by digesting plasmid pSATe111BG41 (WO 04/099228), which carries the *Aspergillus oryzae* beta-glucosidase variant BG41 full-length coding region (SEQ ID NO: 25, which encodes the amino acid sequence of SEQ ID NO: 26), with Nco I. The resulting 1243 by fragment was isolated by 1.0% agarose gel electrophoresis using TAE buffer and purified using a QIAQUICK® Gel Extraction Kit according to the manufacturer's instructions.

Figure 10:
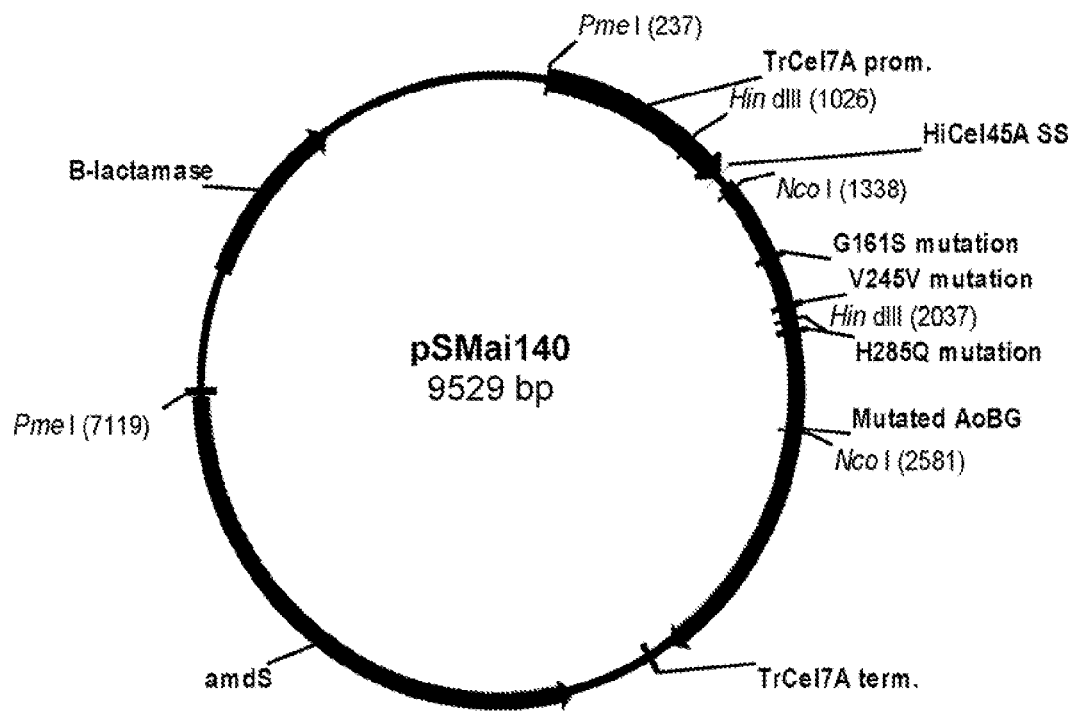
FIG. 10 shows a restriction map of pSMai140.

Expression vector pSMai135 was digested with Nco I and a 8286 by fragment was isolated by 1.0% agarose gel electrophoresis using TAE buffer and purified using a QIAQUICK® Gel Extraction Kit according to the manufacturer's instructions. The 1243 by Nco I digested *Aspergillus oryzae* beta-glucosidase variant BG41 fragment was then ligated to the 8286 by vector fragment, using T4 DNA ligase (Roche. Indianapolis, Ind., USA) according to manufacturer's protocol, to create the expression vector pSMai140 (FIG. 10). Plasmid pSMai140 comprises the *Trichoderma reesei* cellobiohydrolase I (CEL7A) gene promoter and terminator operably linked to the *Humicola insolens* endoglucanase V signal sequence and the *Aspergillus oryzae* beta-glucosidase variant mature coding sequence.

Example 8

Transformation of *Trichoderma reesei* RutC30 with pSMai140

Plasmid pSMai140 was linearized with Pme I and transformed into the *Trichoderma reesei* RutC30 strain as described in Example 6. A total of 100 transformants were obtained from 4 independent transformation experiments, all of which were cultivated in shake flasks on cellulase-inducing medium, and the beta-glucosidase activity was measured from the culture medium of the transformants as described in Example 6. A number of *Trichoderma reesei* SMA140 transformants showed beta-glucosidase activities several fold more than that of *Trichoderma reesei* RutC30.

The presence of the *Aspergillus oryzae* beta-glucosidase variant BG41 protein in the culture medium was detected by SDS-polyacrylamide gel electrophoresis as described in Example 6 and Coomassie staining from the same 13 culture supernatants from which enzyme activity were analyzed. All thirteen transformants that had high 11-glucosidase activity, also expressed the approximately 110 KDa *Aspergillus oryzae* beta-glucosidase variant BG41, at varying yields.

The highest beta-glucosidase variant expressing transformant, as evaluated by beta-glucosidase activity assay and SDS-polyacrylamide gel electrophoresis, was designated *Trichoderma reesei* SMA140-43.

Example 9

Construction of Expression Vector pSaMe-F1

A DNA fragment containing 209 by of the *Trichoderma reesei* cellobiohydrolase gene promoter and the core region (nucleotides 1 to 702 of SEQ ID NO: 31, which encodes amino acids 1 to 234 of SEQ ID NO: 32: WO 91/17243) of the *Humicola insolens* endoglucanase V gene was PCR amplified using pMJ05 as template and the primers shown below.

```
Primer 995103:
                                    (SEQ ID NO: 65)
5'-cccaagcttagccaagaaca-3'

Primer 995137:
                                    (SEQ ID NO: 66)
5'-gggggaggaacgcatgggatctggacggc-3'
```

The amplification reactions (50 µl) were composed of 1× Pfx Amplification Buffer, 10 mM dNTPs, 50 mM MgSO$_4$, 10 ng/µl of pMJ05, 50 picomoles of 995103 primer, 50 picomoles of 995137 primer, and 2 units of Pfx DNA polymerase. The reactions were incubated in an EPPENDORF® MASTERCYCLER® 5333 programmed for 30 cycles each for 30 seconds at 94° C., 30 seconds at 55° C., and 60 seconds at 72° C. (3 minute final extension).

The reaction products were isolated by 1.0% agarose gel electrophoresis using TAE buffer where a 911 by product band was excised from the gel and purified using a QIAQUICK® Gel Extraction Kit according to the manufacturer's instructions.

A DNA fragment containing 806 by of the *Aspergillus oryzae* beta-glucosidase variant BG41 gene was PCR amplified using pSMai140 as template and the primers shown below.

```
Primer 995133:
                                    (SEQ ID NO: 67)
5'-gccgtccagatccccatgcgttcctccccc-3'

Primer 995111:
                                    (SEQ ID NO: 68)
5'-ccaagcttgttcagagtttc-3'
```

The amplification reactions (50 µl) were composed of 1× Pfx Amplification Buffer, 10 mM dNTPs, 50 mM MgSO$_4$, 100 ng of pSMai140, 50 picomoles of 995133 primer, 50 picomoles of 995111 primer, and 2 units of Pfx DNA polymerase. The reactions were incubated in an EPPENDORF® MASTERCYCLER® 5333 programmed for 30 cycles each for 30 seconds at 94° C., 30 seconds at 55° C., and 120 seconds at 72° C. (3 minute final extension).

The reaction products were isolated by 1.0% agarose gel electrophoresis using TAE buffer where a 806 by product band was excised from the gel and purified using a QIAQUICK® Gel Extraction Kit according to the manufacturer's instructions.

The two PCR fragments above were then subjected to overlapping PCR. The purified overlapping fragments were used as templates for amplification using primer 995103 (sense) and primer 995111 (antisense) described above to precisely fuse the 702 by fragment comprising 209 by of the *Trichoderma reesei* cellobiohydrolase I gene promoter and the *Humicola insolens* endoglucanase V core sequence to the 806 by fragment comprising a portion of the *Aspergillus oryzae* beta-glucosidase variant BG41 coding region by overlapping PCR.

The amplification reactions (50 µl) were composed of 1× Pfx Amplification Buffer, 10 mM dNTPs, 50 mM MgSO$_4$, 2.5 µl of each fragment (20 ng/µl), 50 picomoles of 995103 primer, 50 picomoles of 995111 primer, and 2 units of high fidelity Pfx DNA polymerase. The reactions were incubated in an EPPENDORF® MASTERCYCLER® 5333 programmed for an initial denaturation of 3 minutes at 95° C. followed by 30 cycles each for 1 minute of denaturation, 1 minute annealing at 60° C., and a 3 minute extension at 72° C.

The reaction products were isolated by 1.0% agarose gel electrophoresis using TAE buffer where a 1.7 kb product band was excised from the gel and purified using a QIAQUICK® Gel Extraction Kit according to the manufacturer's instructions.

The 1.7 kb fragment was ligated into a pCR®4 Blunt vector (Invitrogen, Carlsbad, Calif., USA) according to the manufacturer's instructions. The construct was then transformed into ONE SHOT® TOP10 Chemically Competent *E. coli* cells (invitrogen, Carlsbad, Calif., USA) according to the manufacturer's rapid chemical transformation procedure. Colonies were selected and analyzed by plasmid isolation and digestion with Hind III to release the 1.7 kb overlapping PCR fragment.

Figure 11:
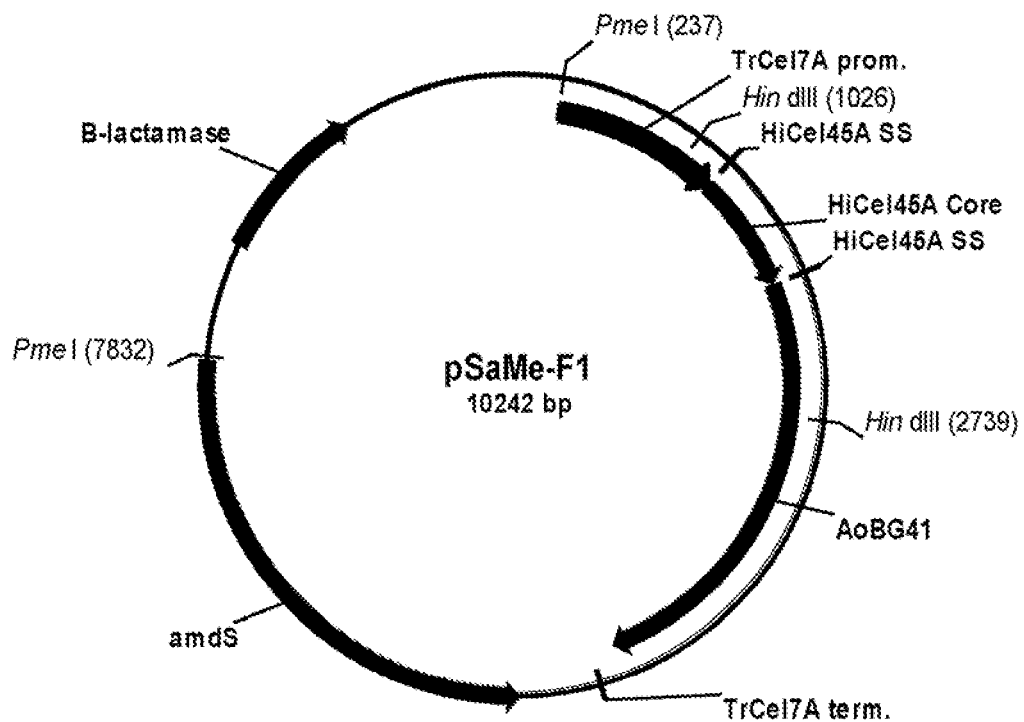
FIG. 11 shows a restriction map of pSaMe-F 1.

Plasmid pSMai140 was also digested with Hind III to linearize the plasmid. Both digested fragments were combined in a ligation reaction using a Rapid DNA Ligation Kit following the manufacturers instructions to produce pSaMe-F1 (FIG. 11).

*E. coli* XL1-Blue Subcloning-Grade Competent Cells (Stratagene, La Jolla, Calif., USA) were transformed with the ligation product. Identity of the construct was confirmed by DNA sequencing of the *Trichoderma reesei* cellobiohydrolase I gene promoter. *Humicola insolens* endoglucanase V signal sequence, *Humicola insolens* endoglucanase V core, *Humicola insolens* endoglucanase V signal sequence.

*Aspergillus oryzae* beta-glucosidase variant BG41, and the *Trichoderma reesei* cellobiohydrolase I gene terminator sequence from plasmids purified from transformed *E. coli*. One clone containing the recombinant plasmid was designated pSaMe-F1. Plasmid pSaMe-F1 comprises the *Trichoderma reesei* cellobiohydrolase I gene promoter and terminator and the *Humicola insolens* endoglucanase V signal peptide sequence linked directly to the *Humicola insolens* endoglucanase V core polypeptide, which are fused directly to the *Humicola insolens* endoglucanase V signal peptide, which is linked directly to the *Aspergillus oryzae* beta-glucosidase variant BG41 mature coding sequence. The DNA sequence and deduced amino acid sequence of the *Aspergillus oryzae* beta-glucosidase variant BG fusion protein is shown in FIGS. 12A, 12B, 12C, and 12D (SEQ ID NOs: 25 and 26, respectively).

Example 10

Transformation of *Trichoderma reesei* RutC30 with pSaMe-F1

Shake flasks containing 25 ml of YP medium supplemented with 2% glucose and 10 mM uridine were inoculated with $5 \times 10^7$ spores of *Trichoderma reesei* RutC30. Following incubation overnight for approximately 16 hours at 27° C., 90 rpm, the mycelia were collected using a Vacuum Driven Disposable Filtration System. The mycelia were washed twice in 100 ml of deionized water and twice in 1.2 M sorbitol. Protoplasts were generated as described in Example 6.

Two micrograms of pSaMe-F1 DNA linearized with Pme I, 100 μl of *Trichoderma reesei* RutC30 protoplasts, and 50% PEG (4000) were mixed and incubated for 30 minutes at room temperature. Then 3 ml of SIC were added and the contents were poured onto a COVE plate supplemented with 10 mM uridine. The plate was then incubated at 28° C. Transformants began to appear by day 6 and were picked to COVE2 plates for growth at 28° C. and 6 days. Twenty-two *Trichoderma reesei* transformants were recovered.

Transformants were cultivated in shake flasks on cellulase-inducing medium, and beta-glucosidase activity was measured as described in Example 6. A number of pSaMe-F1 transformants produced beta-glucosidase activity. One transformant, designated *Trichoderma reesei* SaMeF1-9, produced the highest amount of beta-glucosidase, and had twice the activity of a strain expressing the *Aspergillus oryzae* beta-glucosidase variant (Example 9).

Endoglucanase activity was assayed using a carboxymethyl cellulose (CMC) overlay assay according to Beguin, 1983, *Analytical Biochem,* 131(2): 333-336. Five μg of total protein from five of the broth samples (those having the highest beta-glucosidase activity) were diluted in Native Sample Buffer (Bio-Rad. Hercules, Calif., USA) and run on a CRITERION® 8-16% Tris-HCl gel (Bio-Rad, Hercules, Calif., USA) using 10× Tris/glycine running buffer (Bio-Rad, Hercules, Calif., USA) and then the gel was laid on top of a plate containing 1% carboxymethylcellulose (CMC). After 1 hour incubation at 37° C., the gel was stained with 0.1% Congo Red for 20 minutes. The plate was then destained using 1 M NaCl in order to identify regions of clearing indicative of endoglucanase activity. Two clearing zones were visible, one upper zone around 110 kDa and a lower zone around 25 kDa. The predicted protein size of the *Humicola insolens* endoglucanase V and *Aspergillus oryzae* beta-glucosidase variant BG41 fusion is 118 kDa if the two proteins are not cleaved and remain as a single polypeptide: glycosylation of the individual endoglucanase V core domain and of the beta-glucosidase leads to migration of the individual proteins at higher mw than predicted from the primary sequence. If the two proteins are cleaved then the predicted sizes for the *Humicola insolens* endoglucanase V core domain is 24 kDa and 94 kDa for *Aspergillus oryzae* beta-glucosidase variant BG41. Since there was a clearing zone at 110 kDa this result indicated that minimally a population of the endoglucanase and beta-glucosidase fusion protein remains intact as a single large protein. The lower clearing zone most likely represents the endogenous endoglucanase activity, and possibly additionally results from partial cleavage of the *Humicola insolens* endoglucanase V core domain from the *Aspergillus oryzae* beta-glucosidase.

The results demonstrated the *Humicola insolens* endoglucanase V core was active even though it was linked to the *Aspergillus oryzae* beta-glucosidase. In addition, the increase in beta-glucosidase activity appeared to result from increased secretion of protein relative to the secretion efficiency of the non-fusion beta-glucosidase. By linking the *Aspergillus oryzae* beta-glucosidase variant BG41 sequence to the efficiently secreted *Humicola insolens* endoglucanase V core, more beta-glucosidase was secreted.

Example 11

Construction of Vector pSaMe-FX

Plasmid pSaMe-FX was constructed by modifying pSaMe-F1 Plasmid pSaMe-F1 was digested with Bst Z17 and Eco RI to generate a 1 kb fragment that contained the beta-glucosidase variant BG41 coding sequence and a 9.2 kb fragment containing the remainder of the plasmid. The fragments were separated by 1.0% agarose gel electrophoresis using TAE buffer and the 9.2 kb fragment was excised and purified using a QIAQUICK® Gel Extraction Kit according to the manufacturers instructions. Plasmid pSMai135 was also digested with Bst Z17 and Eco RI to generate a 1 kb fragment containing bases homologous to the *Aspergillus oryzae* beta-glucosidase variant BG41 coding sequence and a 8.5 kb fragment containing the remainder of the plasmid. The 1 kb fragment was isolated and purified as above.

The 9.2 kb and 1 kb fragments were combined in a ligation reaction using a Rapid DNA Ligation Kit following the manufacturers instructions to produce pSaMe-FX, which is identical to pSaMe-F1 except that it contained the wild-type beta-glucosidase mature coding sequence rather than the variant mature coding sequence.

Figure 13:
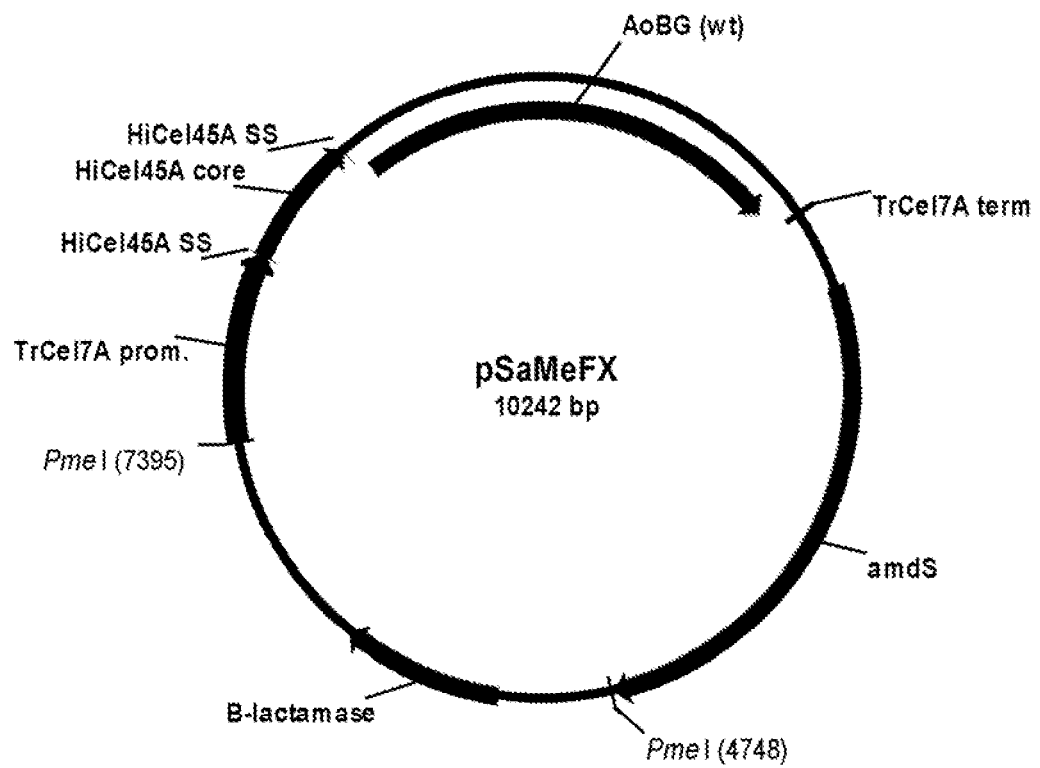
FIG. 13 shows a restriction map of pSaMe-FX.

*E. coli* SURE® Competent Cells (Stratagene, La Jolla, Calif., USA) were transformed with the ligation product. Identity of the construct was confirmed by DNA sequencing of plasmids purified from transformed *E. coli* demonstrating the presence of the *Trichoderma reesei* cellobiohydrolase I gene promoter, *Humicola insolens* endoglucanase V signal sequence, *Humicola insolens* endoglucanase V core sequence. *Humicola insolens* endoglucanase V signal sequence, *Aspergillus oryzae* beta-glucosidase mature coding sequence, and the *Trichoderma reesei* cellobiohydrolase I gene terminator sequence One clone containing the recombinant plasmid was designated pSaMe-FX (FIG. 13). The DNA sequence and deduced amino acid sequence of the *Aspergillus oryzae* beta-glucosidase fusion protein is shown in FIGS. 14A, 14B, 14C, and 14D (SEQ ID NOs: 27 and 28, respectively).

Example 12

Transformation and Expression of Trichoderma Transformants

The pSaMe-FX construct was linearized with Pme I and transformed into the *Trichoderma reesei* RutC30 strain as described in Example 10. A total of 63 transformants were obtained from a single transformation. Transformants were cultivated in shake flasks on cellulase-inducing medium, and beta-glucosidase activity was measured as described in Example 6. A number of pSaMe-FX transformants produced beta-glucosidase activity. One transformant designated SaMe-FX16 produced twice the amount of beta-glucosidase activity compared to *Trichoderma reesei* SaMeF1-9 (Example 10).

Example 13

Analysis of Trichoderma reesei Transformants

A fusion protein was constructed as described in Example 9 by fusing the *Humicola insolens* endoglucanase V core (containing its own native signal sequence) with the *Aspergillus oryzae* beta-glucosidase variant BG41 mature coding sequence linked to the *Humicola insolens* endoglucanase V signal sequence. This fusion construct resulted in a two-fold increase in secreted beta-glucosidase activity compared to the *Aspergillus oryzae* beta-glucosidase variant BG41 mature coding sequence linked to the *Humicola insolens* endoglucanase V signal sequence. A second fusion construct was made as described in Example 11 consisting of the *Humicola insolens* endoglucanase V core (containing its own signal sequence) fused with the *Aspergillus oryzae* wild-type beta-glucosidase coding sequence linked to the *Humicola insolens* endoglucanase V signal sequence, and this led to an even further improvement in beta-glucosidase activity. The strain transformed with the wild-type fusion had twice the secreted beta-glucosidase activity relative to the strain transformed with the beta-glucosidase variant BG41 fusion.

Example 14

Cloning of the Beta-Glucosidase Fusion Protein Encoding Sequence Into an Aspergillus oryzae Expression Vector Two synthetic oligonucleotide primers, shown below, were designed to PCR amplify the full-length open reading frame from pSaMeFX encoding the beta-glucosidase fusion protein.

```
PCR Forward primer:
                                    (SEQ ID NO: 69)
5'-GGACTGCGCAGCATGCGTTC-3'

PCR Reverse primer:
                                    (SEQ ID NO: 70)
5'-AGTTAATTAATTACTGGGCCTTAGGCAGCG-3'
```

Bold letters represent coding sequence. The underlined "G" in the forward primer represents a base change introduced to create an Sph I restriction site. The remaining sequence contains sequence identity compared with the insertion sites of pSaMeFX. The underlined sequence in the reverse primer represents a Pac I restriction site added to facilitate cloning into the expression vector pAILo2 (WO 04/099228).

Fifty picomoles of each of the primers above were used in a PCR reaction containing 50 ng of pSaMeFX DNA, 1× Pfx Amplification Buffer, 6 µl of 10 mM blend of dATP, dTTP, dGTP, and dCTP. 2.5 units of PLATINUM® Pfx DNA Polymerase, and 1 µl of 50 mM MgSO$_4$ in a final volume of 50 µl. An EPPENDORF® MASTERCYCLER® 5333 was used to amplify the fragment programmed for 1 cycle at 98° C. for 2 minutes; and 35 cycles each at 96° C. for 30 seconds, 61° C. for 30 seconds, and 68° C. for 3 minutes. After the 35 cycles, the reaction was incubated at 68° C. for 10 minutes and then cooled at 10° C. until further processed. A 3.3 kb PCR reaction product was isolated on a 0.8% GTG-agarose gel (Cambrex Bioproducts One Meadowlands Plaza East Rutherford, N.J., USA) using TAE buffer and 0.1 µg of ethidium bromide per ml. The DNA was visualized with the aid of a DARK READER™ (Clare Chemical Research, Dolores, Colo., USA) to avoid UV-induced mutations, A 3.3 kb DNA band was excised with a disposable razor blade and purified with an ULTRAFREE®-DA spin cup (Millipore, Billerica, Mass., USA) according to the manufacturer's instructions.

The purified 3.3 Kb PCR product was cloned into a pCR®4Blunt-TOPO® vector (invitrogen, Carlsbad, Calif., USA), Four microliters of the purified PCR product were mixed with 1 µl of a 2 M sodium chloride solution and 1 µl of the TOPO® vector. The reaction was incubated at room temperature for 15 minutes and then 2 µl of the reaction were used to transform One Shot® TOP10 Chemically Competent *E. coli* cells according to the manufacturer's instructions. Three aliquots of 83 each of the transformation reaction were spread onto three 150 mm 2×YT plates supplemented with 100 µg of ampicillin per ml and incubated overnight at 37° C.

Eight recombinant colonies were used to inoculate liquid cultures containing 3 ml of LB medium supplemented with 100 µg of ampicillin per ml. Plasmid DNA was prepared from these cultures using a BIOROBOT® 9600 (QIAGEN Inc., Valencia, Calif., USA). Clones were analyzed by restriction enzyme digestion with Pac I. Plasmid DNA from each clone was digested with Pac I and analyzed by 1.0% agarose gel electrophoresis using TAE buffer. All eight clones had the expected restriction digest pattern and clones 5, 6, 7, and 8 were selected to be sequenced to confirm that there were no mutations in the cloned insert Sequence analysis of their 5' and 3' ends indicated that all 4 clones had the correct sequence. Clones 5 and 7 were selected for further sequencing. Both clones were sequenced to Phred Q values of greater than 40 to ensure that there were no PCR induced errors. Clones 5 and 7 were shown to have the expected sequence and clone 5 was selected for re-cloning into pAILo2.

Plasmid DNA from clone 5 was linearized by digestion with Sph I. The linearized clone was then blunt-ended by adding 1.2 µl of a 10 mM blend of dATP, dTTP, dGTP, and dCTP and 6 units of T4 DNA polymerase (New England Biolabs, Inc., Ipswich, Mass., USA). The mixture was incubated at 12° C. for 20 minutes and then the reaction was stopped by adding 1 µl of 0.5 M EDTA and heating at 75° C. for 20 minutes to inactivate the enzyme. A 3.3 kb fragment encoding the beta-glucosidase fusion protein was purified by gel electrophoresis and ultrafiltration as described above.

The vector pAILo2 was linearized by digestion with Nco I. The linearized vector was then blunt-ended by adding 0.5 µl of a 10 mM blend of dATP, dTTP, dGTP, and dCTP and one unit of DNA polymerase I. The mixture was incubated at 25° C. for 15 minutes and then the reaction was stopped by adding 1 μl of 0.5 M EDTA and heating at 75° C. for 15 minutes to inactivate the enzyme. Then the vector was digested with Pac I. The blunt-ended vector was purified by gel electrophoresis and ultrafiltration as described above.

Figure 15:
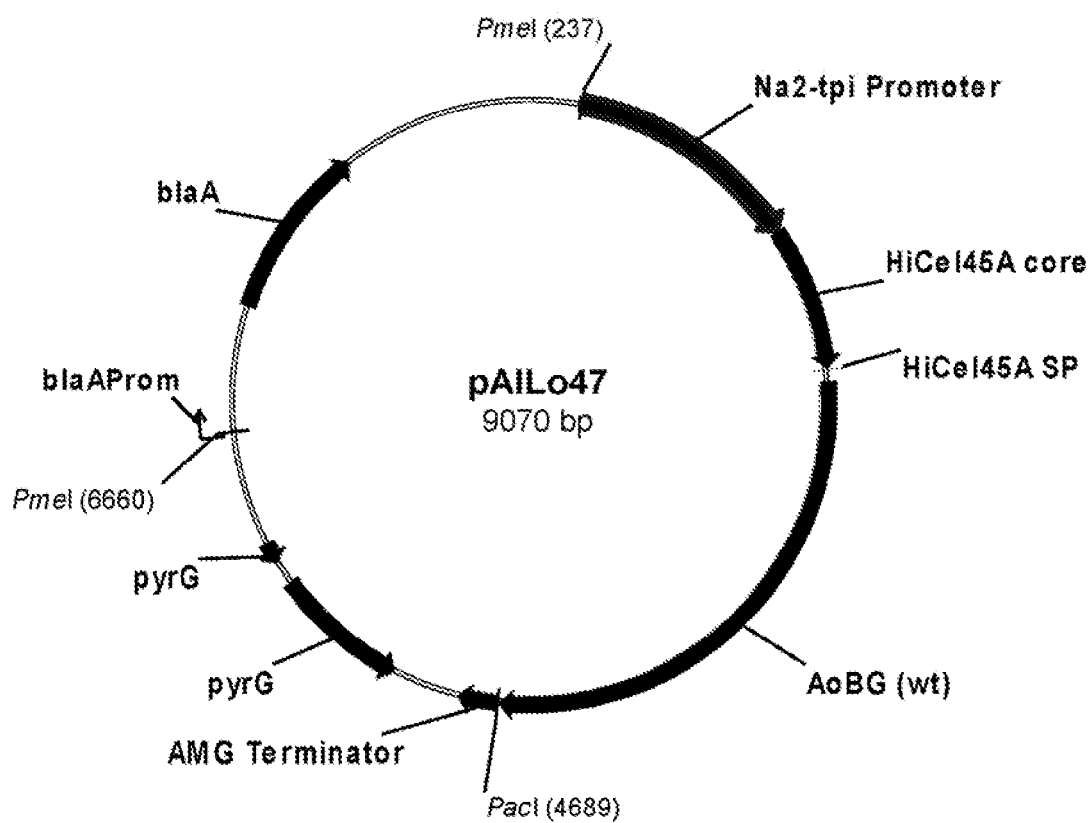
FIG. 15 shows a restriction map of pAILo47.

Cloning of the 3.3 kb fragment encoding the beta-glucosidase fusion protein into the linearized and purified pAILo2 vector was performed with a Rapid Ligation Kit. A 1 μl sample of the reaction was used to transform E call XL10 SOLOPACK® Gold cells (Stratagene, La Jolla, Calif., USA) according to the manufacturers instructions. After the recovery period, two 100 μl aliquots from the transformation reaction were plated onto two 150 mm 2×YT plates supplemented with 100 μg of ampicillin per ml and incubated overnight at 37° C. A set of eight putative recombinant clones was selected at random from the selection plates and plasmid DNA was prepared from each one using a BIORO-BOT® 9600. Clones 1-4 were selected for sequencing with pAILo2-specific primers to confirm that the junction vector/insert had the correct sequence. Clone 3 had a perfect vector/insert junction and was designated pAILo47 (FIG. 15).

In order to create a marker-free expression strain, a restriction endonuclease digestion was performed to separate the blaA gene that confers resistance to the antibiotic ampicillin from the rest of the expression construct. Thirty micrograms of pAILo47 were digested with Pme I. The digested DNA was then purified by agarose gel electrophoresis as described above. A 6.4 kb DNA band containing the expression construct but lacking the blaA gene was excised with a razor blade and purified with a QIAQUICK® Gel Extraction Kit.

Example 15

Expression of the *Humicola insolens/Aspergillus oryzae* cel45A-cel3a Fusion Gene in *Aspergillus oryzae* JaL355

*Aspergillus oryzae* JaL355 (WO 00/240694) protoplasts were prepared according to the method of Christensen of at. 1988, *Bio/Technology* 6: 1419-1422. Ten microliters of the purified expression construct of Example 14 were used to transform *Aspergillus oryzae* JaL355 protoplasts. The transformation of *Aspergillus oryzae* JaL355 yielded approximately 90 transformants. Fifty transformants were isolated to individual PDA plates and incubated for five days at 34° C.

Forty-eight confluent spore plates were washed with 3 ml of 0.01% TWEEN® 80 and the spore suspension was used to inoculate 25 ml of MDU2BP medium in 125 ml glass shake flasks. Transformant cultures were incubated at 34° C. with constant shaking at 200 rpm. After 5 days, 1 ml aliquots of each culture was centrifuged at 12,000×g and their supernatants collected. Five μl of each supernatant were mixed with an equal volume of 2× loading buffer (10% beta-mercaptoethanol) and loaded onto a 1.5 mm 8%-16% Tris-Glycine SDS-PAGE gel and stained with BIO-SAFE® Coomassie Blue G250 protein stain (Bio-Rad, Hercules, Calif., USA). SDS-PAGE profiles of the culture broths showed that 33 out of 48 transformants were capable of expressing a new protein with an apparent molecular weight very close to the expected 118 kDa. Transformant 21 produced the best yield and was selected for further studies.

Example 16

Single Spore Isolation of *Aspergillus oryzae* JaL355 Transformant 21

*Aspergillus oryzae* JaL355 transformant 21 spores were spread onto a PDA plate and incubated for five days at 34° C. A small area of the confluent spore plate was washed with 0.5 ml of 0.01% TWEEN® 80 to resuspend the spores. A 100 μl aliquot of the spore suspension was diluted to a final volume of 5 ml with 0.01% TWEEN® 80. With the aid of a hemocytometer the spore concentration was determined and diluted to a final concentration of 0.1 spores per microliter. A 200 μl aliquot of the spore dilution was spread onto 150 mm Minimal medium plates and incubated for 2-3 days at 34° C. Emerging colonies were excised from the plates and transferred to PDA plates and incubated for 3 days at 34° C. Then the spores were spread across the plates and incubated again for 5 days at 34° C.

The confluent spore plates were washed with 3 ml of 0.01% TWEEN® 80 and the spore suspension was used to inoculate 25 ml of MDU2BP medium in 125 ml glass shake flasks. Single-spore cultures were incubated at 34° C. with constant shaking at 200 rpm. After 5 days, a 1 ml aliquot of each culture was centrifuged at 12,000×g and their supernatants collected. Five μl of each supernatant were mixed with an equal volume of 2× loading buffer (10% beta-mercaptoethanol) and loaded onto a 1.5 mm 8%-16% Tris-Glycine SDS-PAGE gel and stained with BIO-SAFE® Commassie Blue G250 protein stain. SDS-PAGE profiles of the culture broths showed that all eight transformants were capable of expressing the beta-glucosidase fusion protein at very high levels and one of cultures designated *Aspergillus oryzae* JaL355AILo47 produced the best yield.

Example 17

Construction of pCW087

Two synthetic oligonucleotide primers shown below were designed to PCR amplify a *Thermoascus aurantiacus* GH61A polypeptide gene from plasmid pDZA2-7 (WO 2005/074656). The forward primer results in a blunt 5' end and the reverse primer incorporates a Pac I site at the 3' end.

Forward Primer
5'-ATGTCCTTTTCCAAGATAATTGCTACTG-3' (SEQ ID NO: 71)

Reverse Primer:
5'-GCTTAATTAACCAGTATACAGAGGAG-3' (SEQ ID NO: 72)

Fifty picomoles of each of the primers above were used in a PCR reaction consisting of 50 ng of pDZA2-7, 1 μl of 10 mM blend of dATP, dTTP, dGTP, and dCTP, 5 μl of 10× ACCUTAQ™ DNA Polymerase Buffer (Sigma-Aldrich, St. Louis, Mo., USA), and 5 units of ACCUTAQ™ DNA Polymerase (Sigma-Aldrich, St. Louis, Mo., USA), in a final volume of 50 μl. An EPPENDORF® MASTERCYCLER® 5333 was used to amplify the DNA fragment programmed for 1 cycle at 95° C. for 3 minutes; 30 cycles each at 94° C. for 45 seconds, 55° C. for 60 seconds, and 72° C. for 1 minute 30 seconds. After the 25 cycles, the reaction was incubated at 72° C. for 10 minutes and then cooled at 4° C. until further processing. The 3' end of the *Thermoascus aurantiacus* GH61A PCR fragment was digested using Pac I. The digestion product was purified using a MINELUTE™ Reaction Cleanup Kit (QIAGEN Inc., Valencia, Calif., USA) according to the manufacturer's instructions.

The GH61A fragment was directly cloned into pSMai155 (WO 2005/074647) utilizing a blunted Nco I site at the 5' end and a Pac 1 site at the 3' end. Plasmid pSMai155 was digested with Nco I and Pac I. The Nee I site was then rendered blunt using Klenow enzymes to fill in the 5' recessed Nco I site. The Klenow reaction consisted of 20 μl of the pSma155 digestion reaction mix plus 1 mM dNTPs and 1 μl of Klenow enzyme, which was incubated briefly at room temperature. The newly linearized pSMai155 plasmid was purified using a MINELUTE™ Reaction Cleanup Kit according to the manufacturer's instructions. These reactions resulted in the creation a 5' blunt end and 3' Pac 1 site compatible to the newly generated GH61A fragment. The GH61A fragment was then cloned into pSMai155 expression vector using a Rapid DNA Ligation Kit (Roche, Indianapolis, Ind., USA) following the manufacturer's instructions. E. coli XL1-Blue Subcloning-Grade Competent Cells (Stratagene, La Jolla, Calif., USA) were transformed with the ligation product. Identity of the construct was confirmed by DNA sequencing of the GH61A coding sequence from plasmids purified from transformed E. coli. One E. coli done containing the recombinant plasmid was designated pCW087-8.

Example 18

Construction of pSaMe-Ta61A

Expression vector pSaMe-Ta61 was constructed by digesting plasmid pMJ09 (WO 2005/056772), which harbors the amdS selectable marker, with Nsi I, which liberated a 2.7 kb amdS fragment. The 2.7 kb amdS fragment was then isolated by 1.0% agarose gel electrophoresis using TAE buffer and purified using a QIAQUICK® Gel Extraction Kit.

Expression vector pCW087 was digested with Nsi I and a 4.7 kb fragment was isolated by 1.0% agarose gel electrophoresis using TAE buffer and purified using a QIAQUICK® Gel Extraction Kit, The 2.7 kb amdS fragment was then ligated to the 4.7 kb vector fragment, using T4 DNA ligase (Roche. Indianapolis, Ind. USA) according to manufacturer's protocol, to create the expression vector pSaMe-Ta61A. Plasmid pSaMe-Ta61A comprises the *Trichoderma reesei* cellobiohydrolase I (CEL7A) gene promoter and terminator operably linked to the *Thermoascus aurantiacus* GH61A mature coding sequence.

Example 19

Construction of *Trichoderma reesei* Strain SaMe-MF268

A co-transformation was utilized to introduce plasmids pSaMe-FX and pSaMe-Ta61A into *Trichoderma reesei* RutC30. Plasmids pSaMe-FX and pSaMe-Ta61A were introduced into *Trichoderma reesei* RutC30 by PEG-mediated transformation (Penttila et al., 1987, supra). Each plasmid contained the *Aspergillus nidulans* amdS gene to enable transformants to grow on acetamide as the sole nitrogen source.

*Trichoderma reesei* RutC30 was cultivated at 27° C. and 90 rpm in 25 ml of VP medium supplemented with 2% (w/v) glucose and 10 mM uridine for 17 hours. Mycelia were collected by filtration using a Vacuum Driven Disposable Filtration System and washed twice with deionized water and twice with 1.2 M sorbitol. Protoplasts were generated by suspending the washed mycelia in 20 ml of 1.2 M sorbitol containing 15 mg of GLUCANEX® (Novozymes A/S, Bagsværd, Denmark) per ml and 0.36 units of chitinase (Sigma Chemical Co., St, Louis, Mo., USA) per ml and incubating for 15-25 minutes at 34° C. with gentle shaking at 90 rpm. Protoplasts were collected by centrifuging for 7 minutes at 400×g and washed twice with cold 1.2 M sorbitol.

The protoplasts were counted using a haemacytometer and re-suspended in STC to a final concentration of $1 \times 10^8$ protoplasts per ml. Excess protoplasts were stored in a Cryo 1° C. Freezing Container (Nalgene, Rochester. NY. USA) at −80° C.

Approximately 4 μg each of plasmids pSaMe-FX and pSaMe-Ta61A were digested with Pme I to facilitate removal of the antibiotic resistance marker, ampR. Following digestion with Pme I the linear fragments were run on a 1% agarose gel using TAE buffer to separate the various fragments. A 7.5 kb fragment from pSaMe-FX and a 4.7 kb fragment from pSaMe-Ta61A were cut out of the gel and purified using a QIAQUICK® Gel Extraction Kit according to the manufacturers instructions. These purified fragments contain the amdS selectable marker cassette, the *Trichoderma reesei* cbh1 gene promoter and terminator; additionally, the fragment includes the *Humicola insolens* EGV core/*Aspergillus oryzae* BG fusion coding sequence or the *T. aurantiacus* GH61A coding sequence. The fragments used in transformation did not contain antibiotic resistance markers, as the ampR fragment was removed by this gel purification step. The purified fragments were then added to 100 μl of protoplast solution and mixed gently, followed by 260 μl of PEG buffer, mixed, and incubated at room temperature for 30 minutes, STC (3 ml) was then added and mixed and the transformation solution was plated onto COVE plates using amdS selection. The plates were incubated at 28° C. for 5-7 days. Transformants were subcultured onto COVE2 plates and grown at 28° C.

Over 400 transformants were subcultured onto fresh plates containing acetamide and allowed to sporulate for 7 days at 28° C.

The *Trichoderma reesei* transformants were cultivated in 125 ml baffled shake flasks containing 25 ml of cellulase-inducing medium at pH 6.0 inoculated with spores of the transformants and incubated at 28° C. and 200 rpm for 5 days. *Trichoderma reesei* RutC30 was run as a control. Culture broth samples were removed at day 5. One ml of each culture broth was centrifuged at 15,700×g for 5 minutes in a micro-centrifuge and the supernatants transferred to new tubes.

SDS-PAGE was carried out using CRITERION® Tris-HCl (5% resolving) gels with the CRITERION® System. Five μl of day 5 supernatants (see above) were suspended in 2× concentration of Laemmli Sample Buffer (Bio-Rad, Hercules, Calif., USA) and boiled in the presence of 5% beta-mercaptoethanol for 3 minutes. The supernatant samples were loaded onto a polyacrylamide gel and subjected to electrophoresis with 1× Tris/Glycine/SDS as running buffer (Bio-Rad, Hercules, Calif., USA). The resulting gel was stained with BIO-SAFE® Coomassie Stain. Transformants showing expression of both the *Thermoascus aurantiacus* GH61A polypeptide and the fusion protein consisting of the *Humicola insolens* endoglucanase V core (Cel45A) fused with the *Aspergillus oryzae* beta-glucosidase as seen by visualization of bands on SDS-PAGE gels were then tested in PCS hydrolysis reactions to identify the strains producing the best hydrolytic broths.

Example 20

Identification of *Trichoderma reesei* Strain SaMe-MF268

The transformants showing expression of both the *Thermoascus aurantiacus* GH61A polypeptide and the *Aspergillus oryzae* beta-glucosidase fusion protein were cultivated in 125 ml baffled shake flasks containing 25 ml of cellulase-inducing medium at pH 6.0 inoculated with spores of the transformants and incubated at 28'C and 200 rpm for 5 days.

The shake flask culture broths were centrifuged at 6000×g and filtered using STERICUP™ EXPRESS™ (Millipore, Bedford, Mass., USA) to 0.22 μm prior to hydrolysis, The activity of the culture broths was measured by their ability to hydrolyze the PCS and produce sugars detectable by a chemical assay of their reducing ends.

Corn stover was pretreated at the U.S. Department of Energy National Renewable Energy Laboratory (NREL), Boulder. CO, USA, using dilute sulfuric acid. The following conditions were used for the pretreatment: 0.048 g sulfuric acid/g dry biomass at 190° C. and 25% w/w dry solids for around 1 minute. The water-insoluble solids in the pretreated corn stover (PCS) contained 59.2% cellulose as determined by a limit digest of PCS to release glucose and cellobiose. Prior to enzymatic hydrolysis, the PCS was washed with a large volume of double deionized water; the dry weight of the water-washed PCS was found to be 17.73%.

PCS in the amount of 1 kg was suspended in approximately 20 liters of double deionized water and, after the PCS settled, the water was decanted. This was repeated until the wash water was above pH 4.0, at which time the reducing sugars were lower than 0.06 g per liter. For small volume assays (e.g., 1 ml) the settled slurry was sieved through 100 Mesh screens to ensure ability to pipette. Percent dry weight content of the washed PCS was determined by drying the sample at a 105° C. oven for at least 24 hours (until constant weight) and comparing to the wet weight.

PCS hydrolysis was performed in a 1 ml volume in 96-deep-well plates (Axygen Scientific) heat sealed by an ALPS 300™ automated lab plate sealer (ABgene Inc., Rochester, N.Y., USA). PCS concentration was 10 g per liter in 50 mM sodium acetate pH 5.0. PCS hydrolysis was performed at 50° C. without additional stirring except during sampling as described. Each reaction was performed in triplicate. Released reducing sugars were analyzed by p-hydroxy benzoic acid hydrazide (PHBAH) reagent as described below.

A volume of 0.8 ml of PCS (12.5 g per liter in water) was pipetted into each well of 96-deep-well plates, followed by 0.10 ml of 0.5 M sodium acetate pH 5.0. and then 010 ml of diluted enzyme solution to start the reaction with a final reaction volume of 1.0 ml and PCS concentration of 10 g per liter. Plates were sealed. The reaction mixture was mixed by inverting the deep-well plate at the beginning of hydrolysis and before taking each sample time point. At each sample time point the plate was mixed and then the deep-well plate was centrifuged (SORVALL® RT7 with RTH-250 rotor) at 2000 rpm for 10 minutes before 20 μl of hydrolysate (supernatant) was removed and added to 180 μl of 0.4% NaOH in a 96-well microplate. This stopped solution was further diluted into the proper range of reducing sugars, when necessary. The reducing sugars released were assayed by para-hydroxy benzoic acid hydrazide reagent (PHBAH, Sigma, 4-hydroxy benzyhydrazide): 50 μl of PHBAH reagent (1.5%) were mixed with 100 μl of sample in a V-bottom 96-well THERMOWELL™ plate (Costar 6511), incubated on a plate heating block at 95° C. for 10 minutes, and then 50 μl of double deionized water was added to each well, mixed, and 100 μl was transferred to another flat-bottom 96-well plate (Costar 9017) and absorbance read at 410 nm. Reducing sugar was calculated using a glucose calibration curve under the same conditions. Percent conversion of cellulose to reducing sugars was calculated as:

% conversion=reducing sugars (mg/ml)/(cellulose added (mg/ml)×1.11)

The factor 1.11 corrects for the weight gain in hydrolyzing cellulose to glucose.

Following the 1 ml PCS hydrolysis testing, the top candidates were grown in duplicate in fermentors according to the following protocol. One hundred ml of the following shake flask medium was added to a 500 ml shake flask. The shake flask medium was composed per liter of 20 g of dextrose, 10 g of corn steep solids, 1.45 g of $(NH_4)_2SO_4$, 2.08 g of $KH_2PO_4$, 0.36 g of $CaCl_2$, 0.42 g of $MgSO_4.7H_2O$, and 0.42 ml of trace metals solution. Trace metals solution was composed per liter of 216 g of $FeCl_3.6H_2O$, 58 g of $ZnSO_4.7H_2O$, 27 g of $MnSO_4.H_2O$, 10 g of $CuSO_4.5H_2O$, 2.4 g of $H_3BO_3$, and 336 g of citric acid. The shake flask was inoculated with two plugs from a solid plate culture of *Trichoderma reesei* SMA135-04 and incubated at 28° C. on an orbital shaker at 200 rpm for 48 hours. Fifty ml of the shake flask broth was used to inoculate a 3 liter fermentation vessel containing 1.8 liters of a fermentation batch medium composed per liter of 30 g of cellulose, 4 g of dextrose, 10 g of corn steep solids, 3.8 g of $(NH_4)_2SO_4$, 2.8 g of $KH_2PO_4$, 2.64 g of $CaCl_2$, 1.63 g of $MgSO_4.7H_2O$, 1.8 ml of antifoam, and 0.66 ml of trace metals solution. Trace metals solution was composed per liter of 216 g of $FeCl_3.6H_2O$, 58 g of $ZnSO_4.7H_2O$, 27 g of $MnSO_4.H_2O$, 10 g of $CuSO_4.5H_2O$, 2.4 g of $H_3BO_3$, and 336 g of citric acid. Fermentation feed medium was composed of dextrose and cellulose, which was dosed at a rate of 0 to 4 g/l/hr for a period of 165 hours. The fermentation vessel was maintained at a temperature of 28° C. and pH was controlled to a set-point of 4.75+/−0.1. Air was added to the vessel at a rate of 1 vvm and the broth was agitated by Rushton impeller rotating at 1100 to 1300 rpm.

Total protein concentration was determined and broths were re-tested in 50 g PCS hydrolysis reactions as described below. Enzyme dilutions were prepared fresh before each experiment from stock enzyme solutions, which were stored at 4° C.

Hydrolysis of PCS was conducted using 125 ml screw-top Erlenmeyer flasks (VWR, West Chester, Pa., USA) using a total reaction mass of 50 g according to NREL Laboratory Analytical Protocol #008. In this protocol hydrolysis of PCS (approximately 11.4% in PCS and 6.8% cellulose in aqueous 50 mM sodium acetate pH 5.0 buffer) was performed using different protein loadings (expressed as mg of protein per gram of cellulose) of the 2 liter fermentation broth samples, described above. Testing of PCS hydrolyzing capability was performed at 50° C. with orbital shaking at 150 rpm using an INNOVA® 4080 Incubator (New Brunswick Scientific, Edison, N.J., USA), Aliquots were taken during the course of hydrolysis at 72, 120, and 168 hours and centrifuged, and the supernatant liquid was filtered using a MULTI-SCREEN® HV 0.45 μm membrane (Millipore, Billerica, Mass., USA) by centrifugation at 2000 rpm for 10 minutes using a SORVALL® RT7 plate centrifuge (Thermo Fisher Scientific, Waltham, Mass., USA). When not used immediately, filtered sugary aliquots were frozen at −20° C. Sugar concentrations of samples diluted in 0.005 M $H_2SO_4$ were measured after elution by 0.005 M $H_2SO_4$ at a flow rate of 0.4 ml per minute from a 4.6×250 mm AMINEX® HPX-87H column (Bio-Rad, Hercules, Calif., USA) at 65° C. with quantitation by integration of glucose and cellobiose signals from refractive index detection using a CHEMSTATION®AGILENT® 1100 HPLC (Agilent Technologies, Santa Clara, Calif., USA) calibrated by pure sugar samples. The resultant equivalents were used to calculate the percentage of cellulose conversion for each reaction.

The degree of cellulose conversion to glucose plus cellobiose sugars (conversion, %) was calculated using the following equation:

$$\text{Conversion}_{(\%)}(\text{glucose}+\text{cellobiose} \times 1.053)_{(mg/ml)} \times 100 \times 162/(\text{cellulose}_{(mg/ml)} \times 180) = (\text{glucose}+\text{cellobiose} \times 1.053)_{(mg/ml)} \times 100/(\text{cellulose}_{(mg/ml)} \times 1.111)$$

In this equation the factor 1.111 reflects the weight gain in converting cellulose to glucose, and the factor 1.053 reflects the weight gain in converting cellobiose to glucose.

The results of the PCS hydrolysis reactions in the 50 g flask assay described above are shown in Table 1. One strain that produced the highest performing broth was designated *Trichoderma reesei* SaMe-MF268.

TABLE 1

Percent conversion to sugars at 168 hour timepoint

| Broth ID-Strain Name | Percent conversion (glucose plus cellobiose) for protein loading | |
|---|---|---|
| | 2.5 mg/g cellulose | 4.0 mg/g cellulose |
| XCL-461-SaMe-MF268 | 66.29 | 80.08 |
| XCL-465-SaMe-MF268 | 69.13 | 82.80 |
| XCL-462-SaMe-MF330 | 62.98 | 77.99 |
| XCL-466-SaMe-MF330 | 63.34 | 77.90 |
| XCL-463-SaMe-MF377 | 64.03 | 78.45 |
| XCL-467-SaMe-MF377 | 64.19 | 79.06 |

Example 21

Preparation of *Trichoderma reesei* Broths Containing *Thermoascus Aurantiacus* Polypeptide GH61A and *Aspergillus Oryzae* Beta-Glucosidase Fusion Protein Fermentation broth samples, prepared as described in Example 20, were cleared of cellular debris by centrifuging for approximately 20 minutes at 9500×g. Cleared broth samples were then filtered using a MILLEX® GP ExpresS™ membrane, polyethersulfone, 022 μm (Millipore, Bedford, Mass., USA). The filtered broth samples were then desalted using a HIPREP™ 26/10 Desalting Column (AKTA™, GE Healthcare, Piscataway, N.J., USA). Protein concentrations of the desalted material were determined using a BCA™ Protein Assay Kit (Pierce, Rockford, Ill., USA) in which bovine serum albumin was used as a protein standard and calculation made for protein in filtered broth. Aliquots were typically analyzed on 8-16% CRITERION™ SDS-PAGE gels (Bio-Rad, Hercules, Calif.; 200 V for 1 hour) in which PRECISION PLUS PROTEIN™ molecular weight standards (Bio-Rad, Hercules, Calif., USA) were included. Gels were stained for protein using BIO-SAFE™ Coomassie Stain (Bio-Rad. Hercules, Calif. USA) and destained using deionized water. Estimates for the amount of *Thermoascus aurantiacus* GH61A polypeptide and fusion protein comprising *Humicola insolens* GH45 core protein and *Aspergillus oryzae* beta-glucosidase were made from quantitation of scans of stained gels or by peak size after analysis by EXPERION™ capillary electrophoresis (Bio-Rad. Hercules, Calif., USA).

Example 22

Increase in Cellulolytic Activity of *Trichoderma reesei* Broth Containing *Aspergillus Oryzae* Beta-Glucosidase Fusion Protein when Combined With Metal Ions and *Thermoascus Aurantiacus* Polypeptide GH61A Corn stover was pretreated at the U.S. Department of Energy National Renewable Energy Laboratory (NREL) using dilute sulfuric acid. The following conditions were used for the pretreatment 1.4 wt % sulfuric acid at 195° C. for 4.5 minutes. According to limit digestion with excess cellulase enzymes, the water-insoluble solids in the pretreated corn stover (PCS) contained 59.2% cellulose. Prior to enzymatic hydrolysis, the PCS was washed with a large volume of deionized water until soluble acid and sugars were removed. The dry weight of the water-washed PCS was found to be 19.16%.

Hydrolysis of PCS was conducted using 125 ml screw-top Erlenmeyer flasks (VMR, West Chester, Pa., USA) using a total reaction mass of 50 g according to NREL Laboratory Analytical Protocol #008. In this protocol hydrolysis of PCS (approximately 11.3% in PCS and 6.7% cellulose in aqueous 50 mM sodium acetate pH 5.0 buffer) was performed using different protein loadings (expressed as mg of protein per gram of cellulose) of the *Trichoderma reesei* fermentation broth containing the *Thermoascus aurantiacus* GH61A polypeptide having cellulolytic enhancing activity and *Aspergillus oryzae* beta-glucosidase fusion protein with and without addition of 10 mM final concentration of divalent metal ions in the form shown in Table 1. Testing of PCS hydrolyzing capability was performed at 50° C. with orbital shaking at 150 rpm using an INNOVA® 4080 incubator (New Brunswick Scientific, Edison, N.J., USA). Aliquots were taken during the course of hydrolysis at 72 and 120 hours, Aliquots were centrifuged, and the supernatant liquid was filtered using a MULTISCREEN® HV 0.45 μm membrane by centrifugation at 2000 rpm for 15 minutes using a SORVALL® RT7 plate centrifuge. When not used immediately, filtered sugary aliquots were frozen at −20° C. Sugar concentrations of samples diluted in 0.005 M $H_2SO_4$ were measured after elution by 0.005 M $H_2SO_4$ at a flow rate of 0.4 ml per minute from a 4.6×250 mm AMINEX® HPX-87H column at 65"C with quantitation by integration of glucose and cellobiose signal from refractive index detection using a CHEMSTATION®. AGILENT® 1100 HPLC (Agilent Technologies. Santa Clara, Calif., USA) calibrated by pure sugar samples. The resultant equivalents were used to calculate the percentage of cellulose conversion for each reaction.

The degree of cellulose conversion to glucose plus cellobiose sugars (conversion, %) was calculated using the following equation:

$$\% \text{ Conversion} = (\text{glucose}+\text{cellobiose} \times 1.053)_{(mg/ml)} \times 100 \times 162/(\text{cellulose}_{(mg/ml)} \times 180) = (\text{glucose}+\text{cellobiose} \times 1.053)_{(mg/ml)} \times 100/(\text{cellulose}_{(mg/ml)} \times 1.111)$$

In this equation the factor 1.111 reflects the weight gain in converting cellulose to glucose, and the factor 1.053 reflects the weight gain in converting cellobiose to glucose. Cellulose in PCS was determined by a limit digest of PCS to release glucose and cellobiose.

Enzyme dilutions were prepared fresh before each experiment from stock enzyme solutions, which were stored at 4° C.

Figure 16:
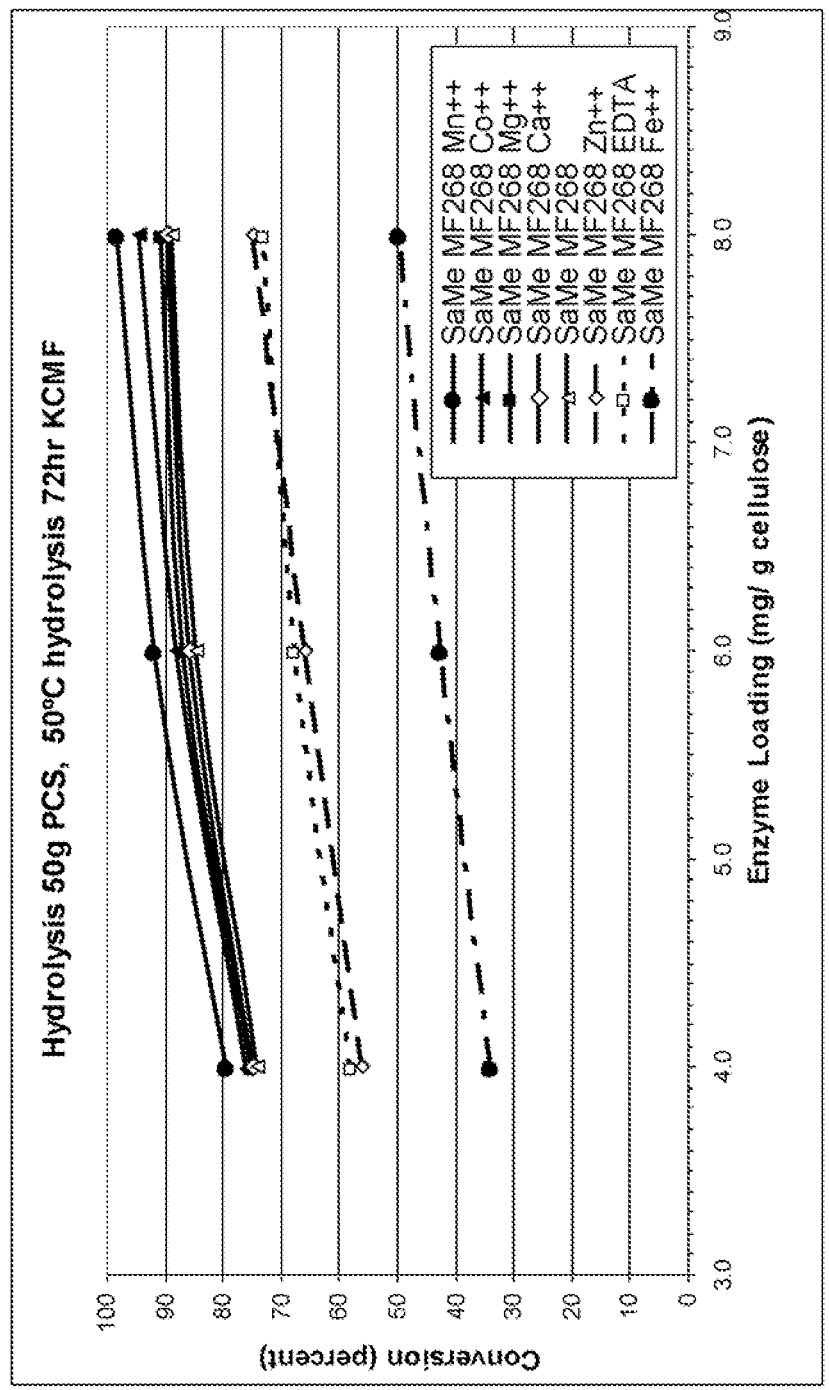
FIG. 16 shows the conversion of cellulose in pretreated corn stover to glucose and cellobiose with addition of various soluble divalent metal ions to a final concentration of 10 mM to mixtures including a fermentation broth that comprises *Trichoderma reesei* cellulolytic enzymes, an *Aspergillus oryzae* beta-glucosidase fusion protein, and a *Thermoascus aurantiacus* GH61A polypeptide having cellulolytic enhancing activity.

The results shown in Table 2 demonstrated that addition of 10 mM $MnSO_4$ increased conversion to glucose above that obtained by equivalent amounts of fermentation broth alone at protein levels from 4 to 8 mg/g cellulose. Similarly, $CaCl_2$, $MgCl_2$, or $CoCl_2$ added to 10 mM increased conversion to glucose above that obtained by equivalent amounts of fermentation broth alone at protein levels from 4 to 8 mg/g cellulose. Addition of other divalent metal salts such as 10 mM $ZnCl_2$ or $FeSO_4$, or the addition of 10 mM EDTA, a chelator of divalent cations, decreased the yield of glucose and cellobiose. The results for 72 hour hydrolysis are shown in FIG. 16.

The addition of 10 mM $MnSO_4$, $CaCl_2$, $Mg Cl_2$, or $CoCl_2$ to cellulase-containing solutions increased, therefore, the yield of glucose and cellobiose upon hydrolysis of acid-pretreated corn stover (PCS) in comparison to addition other metals salts.

Example 23

The Increase in Cellulolytic Activity of Desalted *Trichoderma reesei* Broth *Aspergillus Oryzae* Beta-Glucosidase when Combined with Metal Ions is Specific to Mixtures Containing Polypeptide GH61A The *Thermoascus aurantiacus* polypeptide GH61A having cellulolytic enhancing activity was recombinantly produced in *Aspergillus oryzae* JaL250 according to WO 2005/074656. Fungal broth expressing *Aspergillus oryzae* beta-glucosidase and *Trichoderma reesei* cellulases was recombinantly produced in *Trichoderma reesei* strain SMA135-04. Fermentations were run for each of these proteins as described below.

For fermentations involving *Aspergillus oryzae,* 100 ml of a shake flask medium was added to a 500 ml shake flask. The

TABLE 2

| Experiment | Mixture of enzymes and metal | Actual % Biomass Content (w/w) | Actual % Cellulose Content (w/w) | Actual total protein mg/g cellulose | Conversion 72 hr | Conversion 120 hr |
|---|---|---|---|---|---|---|
| 1 | SaMe MF268 | 11.32 | 6.70 | 4.00 | 74.10 | 84.62 |
| 2 | SaMe MF268 | 11.32 | 6.70 | 6.00 | 84.59 | 91.94 |
| 3 | SaMe MF268 | 11.32 | 6.70 | 8.00 | 88.68 | 95.20 |
| 7 | SaMe MF268 Ca++ | 11.32 | 6.70 | 4.00 | 74.79 | 86.14 |
| 8 | SaMe MF268 Ca++ | 11.32 | 6.70 | 6.00 | 85.77 | 95.11 |
| 9 | SaMe MF268 Ca++ | 11.32 | 6.70 | 8.00 | 89.54 | 96.29 |
| 10 | SaMe MF268 Mg++ | 11.32 | 6.70 | 4.00 | 75.31 | 87.08 |
| 11 | SaMe MF268 Mg++ | 11.32 | 6.70 | 6.00 | 86.99 | 95.12 |
| 12 | SaMe MF268 Mg++ | 11.32 | 6.70 | 8.00 | 90.49 | 97.56 |
| 13 | SaMe MF268 Mn++ | 11.32 | 6.70 | 4.00 | 79.30 | 86.77 |
| 14 | SaMe MF268 Mn++ | 11.33 | 6.70 | 6.00 | 91.65 | 95.23 |
| 15 | SaMe MF268 Mn++ | 11.32 | 6.70 | 8.00 | 98.03 | 98.70 |
| 16 | SaMe MF268 Zn++ | 11.32 | 6.70 | 4.00 | 56.00 | 63.38 |
| 17 | SaMe MF268 Zn++ | 11.32 | 6.70 | 6.00 | 65.79 | 75.03 |
| 18 | SaMe MF268 Zn++ | 11.32 | 6.70 | 8.00 | 74.88 | 84.22 |
| 19 | SaMe MF268 Fe++ | 11.32 | 6.70 | 4.00 | 33.80 | 35.83 |
| 20 | SaMe MF268 Fe++ | 11.32 | 6.70 | 6.00 | 42.50 | 44.88 |
| 21 | SaMe MF268 Fe++ | 11.32 | 6.70 | 8.00 | 49.74 | 50.21 |
| 22 | SaMe MF268 Co++ | 11.33 | 6.70 | 4.00 | 75.98 | 85.88 |
| 23 | SaMe MF268 Co++ | 11.32 | 6.70 | 6.00 | 87.86 | 94.33 |
| 24 | SaMe MF268 Co++ | 11.32 | 6.70 | 8.00 | 94.26 | 97.05 |
| 25 | SaMe MF268 EDTA | 11.31 | 6.69 | 4.00 | 57.94 | 65.94 |
| 26 | SaMe MF268 EDTA | 11.32 | 6.70 | 6.00 | 67.67 | 74.35 |
| 27 | SaMe MF268 EDTA | 11.32 | 6.70 | 8.00 | 72.85 | 77.69 | shake flask medium was composed per liter of 50 g of sucrose, 10 g of $KH_2PO_4$, 0.5 g of $CaCl_2$, 2 g of $MgSO_4.7H_2O$, 2 g of $K_2SO_4$, 2 g of urea, 10 g of yeast extract, 2 g of citric acid, and 0.5 ml of trace metals solution. Trace metals solution was composed per liter of 13.8 g of $FeSO_4.7H_2O$, 14.3 g of $ZnSO_4.7H_2O$, 8.5 g of $MnSO_4.H_2O$, 2.5 g of $CuSO_4.5H_2O$, and 3 g of citric acid. The shake flask was inoculated with two plugs from a solid plate culture of *Aspergillus oryzae* and incubated at 34° C. on an orbital shaker at 200 rpm for 24 hours, Fifty ml of the shake flask broth was used to inoculate a 3 liter fermentation vessel containing 1.8 liters of a fermentation batch medium composed per liter of 10 g of yeast extract, 24 g of sucrose, 5 g of $(NH_4)_2SO_4$, 2 g of $KH_2PO_4$, 0.5 g of $CaCl_2.2H_2O$, 2 g of $MgSO_4.7H_2O$, 1 g of citric acid, 2 g of $K_2SO_4$, 0.5 ml of anti-foam, and 0.5 ml of trace metals solution. Trace metals solution was composed per liter of 13.8 g of $FeSO_4.7H_2O$, 14.3 g of $ZnSO_4.7H_2O$, 8.5 g of $MnSO_4.H_2O$, 2.5 g of $CuSO_4.5H_2O$, and 3 g of citric acid. Fermentation feed medium was composed of maltose and antifoam. The fermentation feed medium was dosed at a rate of 0 to 4.4 g/l/hr for a period of 185 hours. The fermentation vessel was maintained at a temperature of 34° C. and pH was controlled to a set-point of 6.1+/−0.1. Air was added to the vessel at a rate of 1 vvm and the broth was agitated by Rushton impeller rotating at 1100 to 1300 rpm.

Fermentations involving *Trichoderma reesei* were performed as described in Example 20.

Crude broth samples were cleared of cellular debris by centrifuging for approximately 20 minutes at 9500×g. Cleared broth samples were then filtered using a MILLEX® GP Express™ membrane, polyethersulfone, 0.22 μm. The filtered broth samples were then desalted using a HIPREP™ 26/10 Desalting Column, Protein concentrations of the desalted material were determined using a BCA™ Protein Assay Kit in which bovine serum albumin was used as a protein standard and calculation made for protein in filtered broth. Aliquots were typically analyzed on 8-16% CRITERION™ SDS-PAGE gels (200 V for 1 hour) in which PRECISION PLUS PROTEIN™ molecular weight standards were included. Gels were stained for protein using BIO-SAFE™ Coomassie Stain (and destained using deionized water. Proteins were also prepared by desalting as above to remove metal ions dissolved in fermentation broths and are indicated by the prefix ds as seen in Tables 3 and 4.

Hydrolysis of PCS was conducted using 125 ml screw-top Erlenmeyer flasks with a total reaction mass of 50 g according to NREL Laboratory Analytical Protocol #008. In this protocol hydrolysis of PCS (approximately 11.3% in PCS and 6.7% cellulose in aqueous 50 mM sodium acetate pH 5.0 buffer) was performed using constant total protein loading (expressed as mg of enzyme per gram of cellulose) of a fermentation broth containing *Trichoderma reesei* broth containing *Aspergillus oryzae* beta-glucosidase with and without addition of *Thermoascus aurantiacus* polypeptide GH61A with and without 1 mM final concentration of divalent metal ions in the form shown in Table 2. Testing of PCS hydrolyzing capability was performed as described in Example 22. The degree of cellulose conversion to glucose plus cellobiose sugars (% conversion) was calculated using the equation described in Example 22.

Enzyme dilutions were prepared fresh before each experiment from stock enzyme solutions, which were stored at 4° C.

Figure 17:
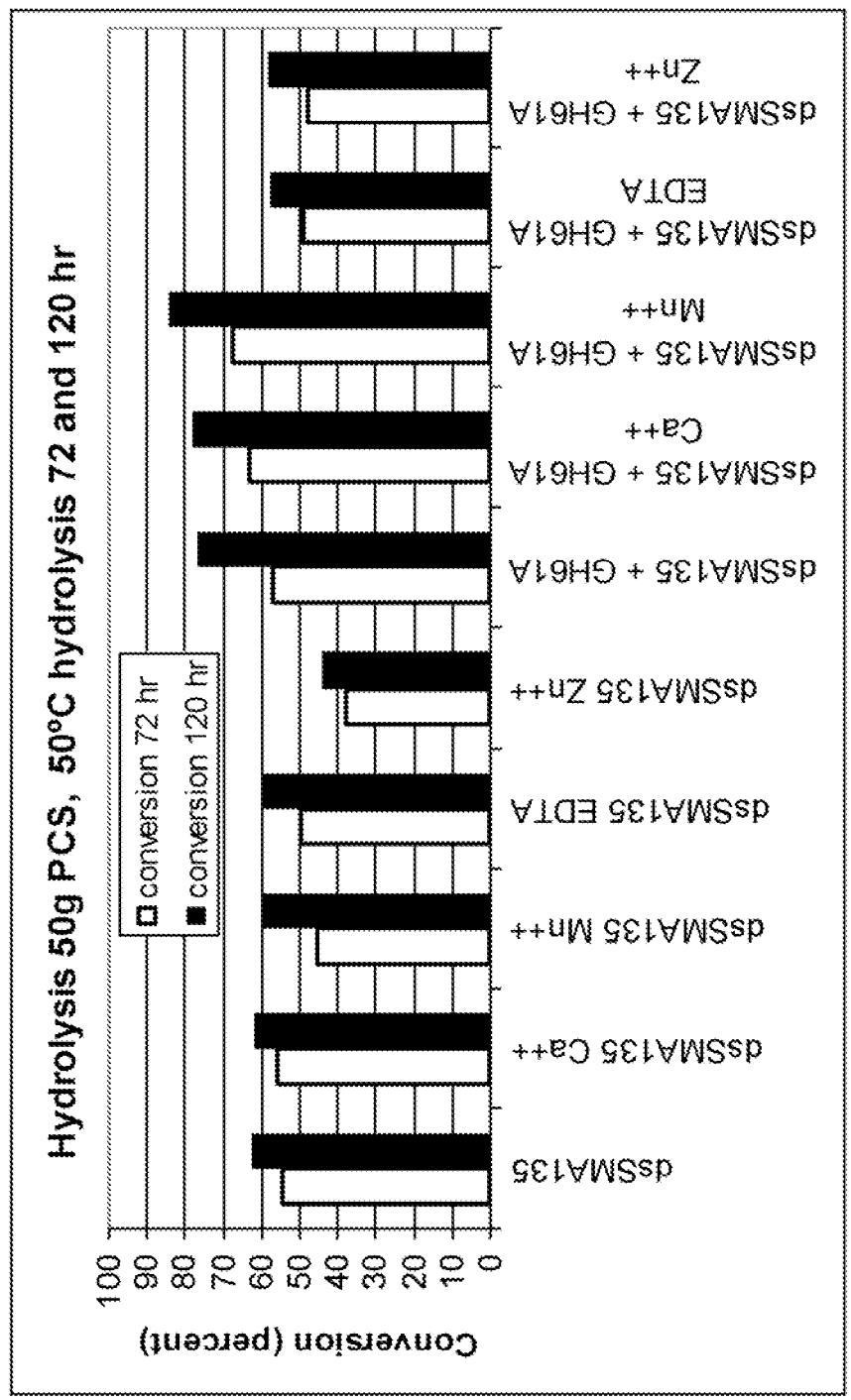
FIG. 17 shows the conversion of cellulose in pretreated corn stover to glucose and cellobiose with addition of various divalent metal ions to a final concentration of 1 mM in mixtures including a fermentation broth that comprises *Trichoderma reesei* cellulolytic enzymes and an *Aspergillus oryzae* beta-glucosidase with and without addition of a *Thermoascus aurantiacus* GH61A polypeptide having cellulolytic enhancing activity.

The results shown in Table 3 demonstrated that addition of 1 mM divalent cations alone did not increase glucose conversion above that obtained by equivalent amounts of fermentation broth without inclusion of *Thermoascus aurantiacus* GH61A polypeptide having cellulolytic enhancing activity. Similarly, inclusion of the GH61A polypeptide without addition of divalent metal cations did not increase glucose conversion. The results for 72 hour hydrolysis are plotted in FIG. 17.

The addition of 1 mM $MnSO_4$ or $CaCl_2$ to cellulase-containing solutions with *Thermoascus aurantiacus* GH61A polypeptide having cellulolytic enhancing activity increased, therefore, the yield of glucose and cellobiose upon hydrolysis of acid-pretreated corn stover (PCS). The increase was dependent on the presence of *Thermoascus aurantiacus* GH61A polypeptide. The addition of 1 mM of other metals such as Zn++ and Fe++ or chelation of metals by 1 mM EDTA reduced the yield of glucose and cellobiose upon hydrolysis of acid-pretreated corn stover (PCS).

TABLE 3

| Experiment | Mixture of enzymes and metal | Conversion 72 hr | Conversion 120 hr |
|---|---|---|---|
| 56 | dsSMA135 | 54.42 | 62.65 |
| 58 | dsSMA135 Ca++ | 55.48 | 61.52 |
| 60 | dsSMA135 Mn++ | 45.19 | 60.11 |
| 62 | dsSMA135 EDTA | 49.65 | 59.52 |
| 64 | dsSMA135 Zn++ | 37.61 | 43.59 |
| 65 | dsSMA135 + GH61A | 56.97 | 76.41 |
| 66 | dsSMA135 + GH61A Ca++ | 63.23 | 77.79 |
| 67 | dsSMA135 + GH61A Mn++ | 67.43 | 84.02 |
| 68 | dsSMA135 + GH61A EDTA | 49.03 | 57.49 |
| 69 | dsSMA135 + GH61A Zn++ | 47.39 | 58.01 |

Example 24

The Increase in Cellulolytic Activity of *Trichoderma reesei* Broth Containing *Aspergillus Oryzae* Beta-Glucosidase Fusion Protein and *Thermoascus Aurantiacus* GH61A Polypeptide when Combined with $MnSO_4$ and $MgCl_2$

*Thermoascus aurantiacus* GH61A polypeptide having cellulolytic enhancing activity and a fusion protein consisting of the *Humicola insolens* GH45A core with *Aspergillus oryzae* beta-glucosidase was recombinantly produced in *Trichoderma reesei* SaMe MF268 as described in Example 20.

Crude broth samples were cleared of cellular debris by centrifuging cultures for approximately 20 minutes at 9500× g. Cleared broth samples were then filtered using a MILLEX® GP Express™ membrane, polyethersulfone, 0.22 μm. The filtered broth samples were then desalted using a HIPREP™ 26/10 Desalting Column. Protein concentrations of the desalted material were determined using a BCA™ Protein Assay Kit in which bovine serum albumin was used as a protein standard and calculation made for protein in filtered broth, Aliquots were typically analyzed on 8-16% CRITERION™ SDS-PAGE gels (200 V for 1 hour) in which PRECISION PLUS PROTEIN™ molecular weight standards were included. Gels were stained for protein using 1310-SAFE™ Coomassie Stain (and destained using deionized water. Proteins were also prepared by desalting as above to remove metal ions dissolved in fermentation broths.

Hydrolysis of PCS was conducted using 125 ml screw-top Erlenmeyer flasks with a total reaction mass of 50 g according to NREL Laboratory Analytical Protocol #008. In this protocol hydrolysis of PCS (approximately 11.3% in PCS and 6.7% cellulose in aqueous 50 mM sodium acetate pH 5.0 buffer) was performed using constant total protein loading (expressed as mg of enzyme per gram of cellulose) of desalted or undesalted *Trichoderma reesei* fermentation broth containing *Aspergillus oryzae* beta-glucosidase fusion protein and without *Thermoascus aurantiacus* GH61A polypeptide with increasing final concentration of $MnSO_4$ and $MgCl_2$ as shown in Table 4. Testing of PCS hydrolyzing capability was performed as described in Example 22. The degree of cellulose conversion to glucose plus cellobiose sugars (conversion, %) was calculated using the equation described in Example 22.

Enzyme dilutions were prepared fresh before each experiment from stock enzyme solutions, which were stored at 4° C.

Figure 18:
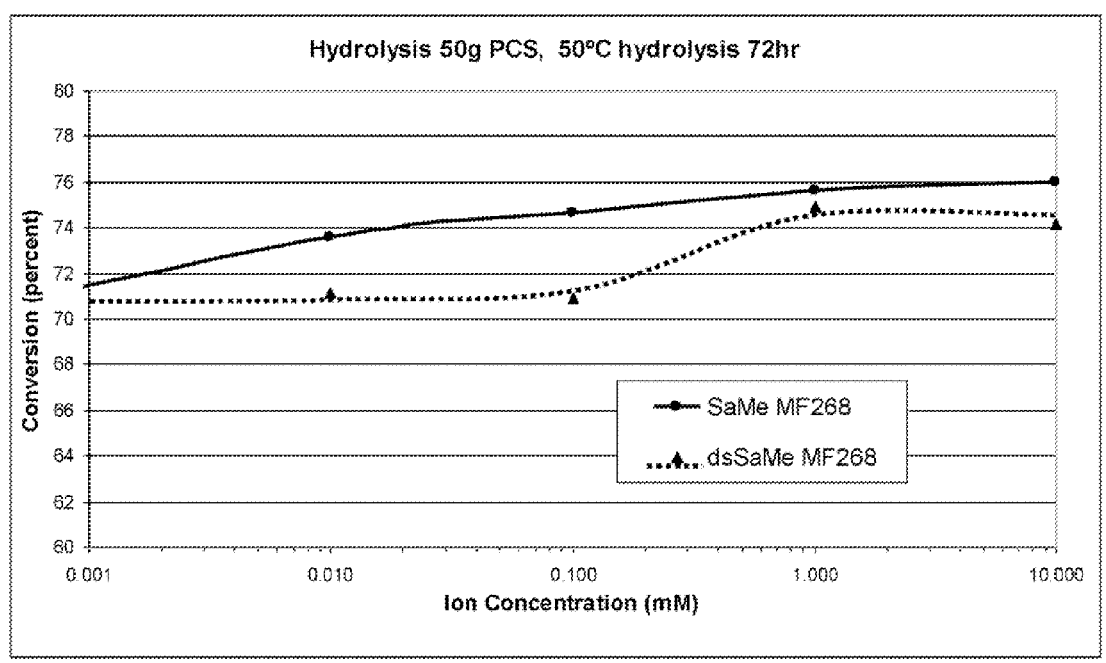
FIG. 18 shows the conversion of cellulose in pretreated corn stover to glucose and cellobiose with addition of $MgCl_2$ and $MnSO_4$ a final concentration of 0.0001 to 10 mM in mixtures including desalted or un-desalted fermentation broth that comprises *Trichoderma reesei* cellulolytic enzymes, an *Aspergillus oryzae* beta-glucosidase fusion protein, and a *Thermoascus aurantiacus* GH61A polypeptide having cellulolytic enhancing activity.

The results shown in Table 4 demonstrated that addition of increasing concentration of $MnSO_4$ and $MgCl_2$ from 0.001, 001, 0.1, 1, or 10 mM increased glucose conversion above that obtained by equivalent amounts of *Trichoderma reesei* SaMe MF268 without $MnSO_4$. Similarly, addition of $MnSO_4$ at increasing concentrations of 0.001, 0.01, 0.1, 1, or 10 mM showed no increase until approximately 1 mM when added to desalted *Trichoderma reesei* SaMe MF268 fermentation broth. The results for 72 hour hydrolysis are shown in FIG. 18.

The addition of $MnSO_4$ and $MgCl_2$ to a final concentration of 0.001, 0.01, 0.1, 1, or 10 mM of each metal on to solutions containing *Trichoderma reesei* SaMe MF268 fermentation broth increased, therefore, the yield of glucose and cellobiose upon hydrolysis of acid-pretreated corn stover (PCS). The addition of $MnSO_4$ and $MgCl_2$ to a final concentration of 1 mM or 10 mM to solutions containing desalted *Trichoderma reesei* SaMe MF268 fermentation broth increased, therefore, the yield of glucose and cellobiose upon hydrolysis of acid-pretreated corn stover (PCS).

Deposits of Biological Material

The following biological material has been deposited under the terms of the Budapest Treaty with the Agricultural Research Service Patent Culture Collection, Northern Regional Research Center, 1815 University Street, Peoria, Ill., 61604, and given the following accession numbers:

| Deposit | Accession Number | Date of Deposit |
| --- | --- | --- |
| *E. coli* strain pEJG120 | NRRL B-30699 | Dec. 19, 2003 |
| *E. coli* strain pTter61C | NRRL B-30823 | Jan. 21, 2005 |
| *E. coli* strain pTter61D | NRRL B-30812 | Jan. 21, 2005 |
| *E. coli* strain pTter61E | NRRL B-30814 | Jan. 21, 2005 |
| *E. coli* strain pTter61G | NRRL B-30811 | Jan. 21, 2005 |
| *E. coli* strain pDZA2-7 | NRRL B-30704 | Jan. 30, 2004 |
| *E. coli* strain pTr3337 | NRRL B-30878 | Sep. 20, 2005 |
| *E. coli* TOP10 (pEJG113) | NRRL B-30695 | Oct. 17, 2003 |
| *E. coli* TOP10 pKKAB | NRRL B-30860 | Jul. 8, 2005 |
| NN049573 | DSM 14240 | Apr. 19, 2001 |

The strains have been deposited under conditions that assure that access to the cultures will be available during the pendency of this patent application to one determined by the Commissioner of Patents and Trademarks to be entitled thereto under 37 C.F.R. §1.14 and 35 U.S.C. §122. The deposits represent substantially pure cultures of the deposited strains. The deposits are available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

TABLE 4

| Experiment | Mixture of enzymes and metal | Actual % Biomass Content (w/w) | Actual % Cellulose Content (w/w) | Actual total protein mg/g cellulose | Conversion 72 hr | Conversion 120 hr |
| --- | --- | --- | --- | --- | --- | --- |
| 46 | SaMe MF268 | 11.32 | 6.70 | 4.03 | 69.20 | 80.61 |
| 47 | SaMe MF268 0.01 mM ions | 11.32 | 6.70 | 4.03 | 73.56 | 82.98 |
| 48 | SaMe MF268 0.1 mM ions | 11.31 | 6.69 | 4.03 | 74.59 | 84.82 |
| 49 | SaMe MF268 1 mM ions | 11.21 | 6.63 | 4.03 | 75.62 | 84.56 |
| 50 | SaMe MF268 10 mM ions | 10.29 | 6.09 | 4.03 | 76.02 | 84.45 |
| 51 | dsSaMe MF268 | 11.32 | 6.70 | 4.02 | 70.93 | 79.11 |
| 52 | dsSaMe MF268 0.01 mM ions | 11.32 | 6.70 | 4.02 | 71.16 | 83.63 |
| 53 | dsSaMe MF268 0.1 mM ions | 11.31 | 6.69 | 4.02 | 70.88 | 83.30 |
| 54 | dsSaMe MF268 1 mM ions | 11.21 | 6.63 | 4.02 | 74.90 | 83.22 |
| 55 | dsSaMe MF268 10 mM ions | 10.29 | 6.09 | 4.02 | 74.17 | 79.01 |

What is claimed is:

1. A method of increasing the activity of a Family 61 glycoside hydrolase (GH61) polypeptide having cellulolytic enhancing activity, comprising: adding a soluble activating divalent metal cation to a composition comprising the GH61 polypeptide having cellulolytic enhancing activity, wherein the soluble activating divalent metal cation is present at an effective concentration of about 0.001 mM to about 50 mM during degradation or conversion of a cellulose-containing material and the presence of the soluble activating divalent metal cation and the GH61 polypeptide having cellulolytic enhancing activity increases the degradation or conversion of the cellulose-containing material by a cellulolytic enzyme composition compared to the GH61 polypeptide having cellulolytic enhancing activity without the soluble activating divalent metal cation, wherein the soluble activating divalent metal cation is selected from the group consisting of $Mn^{++}$, $Co^{++}$, $Mg^{++}$, $Ca^{++}$, and a combination thereof.

2. The method of claim 1, wherein the soluble activating divalent metal cation is $Mn^{++}$.

3. The method of claim 1, wherein the GH61 polypeptide having cellulolytic enhancing activity is selected from the group consisting of:
  (a) a GH61 polypeptide having cellulolytic enhancing activity comprising [ILMV]-P-X (4,5)-G-X-Y-[ILMV]-X-R-X-[EQ]-X(4)-[HNQ] (SEQ ID NO: 97 or SEQ ID NO: 98) and [FW]-[TF]-K-[AIV] (SEQ ID NO: 104), wherein X is any amino acid, X(4,5) is any amino acid at 4 or 5 contiguous positions, and X(4) is any amino acid at 4 contiguous positions; and
  (b) a GH61 polypeptide having cellulolytic enhancing activity comprising [ILMV]-P-x(4,5)-G-x-Y-[ILMV]-x-R-x-[EQ]-x(3)-A-[HNQ] (SEQ ID NO: 102 or SEQ ID NO: 103), wherein x is any amino acid, x(4,5) is any amino acid at 4 or 5 contiguous positions, and x(3) is any amino acid at 3 contiguous positions;
  wherein the GH61 polypeptide having cellulolytic enhancing activity comprising [ILMV]-P-X(4,5)-G-X-Y-[ILMV]-X-R-X-[EQ]-X(4)-[HNQ] (SEQ ID NO: 97 or SEQ ID NO: 98) and [FW]-[TF]-K-[AIV] (SEQ ID NO: 104) optionally further comprises:

```
                            (SEQ ID NO: 99 or SEQ ID NO: 100)
H-X(1,2)-G-P-X(3)-[YW]-[AILMV], (SEQ ID NO: 101)
[EQ]-X-Y-X(2)-C-X-[EHQN]-[FILV]-X-[ILV],
or
                            (SEQ ID NO: 99 or SEQ ID NO: 100)
H-X(1,2)-G-P-X(3)-[YW]-[AILMV] and [EQ]-X-Y-X(2)-
C-X-[EHQN]-[FILV]-X-[ILV],(SEQ ID NO: 101)
``` wherein X is any amino acid, X(1,2) is any amino acid at 1 position or 2 contiguous positions, X(3) is any amino acid at 3 contiguous positions, and X(2) is any amino acid at 2 contiguous positions.

4. The method of claim 1, wherein the GH61 polypeptide having cellulolytic enhancing activity is selected from the group consisting of:
  (a) a GH61 polypeptide comprising an amino acid sequence having at least 90% sequence identity to the mature polypeptide of SEQ ID NO: 12;
  (b) a GH61 polypeptide encoded by a polynucleotide comprising a nucleotide sequence having at least 90% sequence identity to the mature polypeptide coding sequence of SEQ ID NO: 11; and
  (c) a GH61 polypeptide comprising the mature polypeptide of SEQ ID NO: 12; or a fragment thereof having cellulolytic enhancing activity.

5. The method of claim 4, wherein the GH61 polypeptide having cellulolytic enhancing activity is encoded by the polynucleotide contained in plasmid pDZA2-7 which is contained in E. coli NRRL B-30704.

6. The method of claim 1, wherein the soluble activating divalent metal cation is $Co^{++}$.

7. The method of claim 1, wherein the soluble activating divalent metal cation is $Mg^{++}$.

8. The method of claim 1, wherein the soluble activating divalent metal cation is $Ca^{++}$.

9. The method of claim 4, wherein the GH61 polypeptide comprises an amino acid sequence having at least 95% sequence identity to the mature polypeptide of SEQ ID NO: 12.

10. The method of claim 9, wherein the GH61 polypeptide comprises an amino acid sequence having at least 96% sequence identity to the mature polypeptide of SEQ ID NO: 12.

11. The method of claim 10, wherein the GH61 polypeptide comprises an amino acid sequence having at least 97% sequence identity to the mature polypeptide of SEQ ID NO: 12.

12. The method of claim 11, wherein the GH61 polypeptide comprises an amino acid sequence having at least 98% sequence identity to the mature polypeptide of SEQ ID NO: 12.

13. The method of claim 12, wherein the GH61 polypeptide comprises an amino acid sequence having at least 99% sequence identity to the mature polypeptide of SEQ ID NO: 12.

14. The method of claim 4, wherein the GH61 polypeptide is encoded by a polynucleotide comprising a nucleotide sequence having at least 95% sequence identity to the mature polypeptide coding sequence of SEQ ID NO: 11.

15. The method of claim 14, wherein the GH61 polypeptide is encoded by a polynucleotide comprising a nucleotide sequence having at least 96% sequence identity to the mature polypeptide coding sequence of SEQ ID NO: 11.

16. The method of claim 15, wherein the GH61 polypeptide is encoded by a polynucleotide comprising a nucleotide sequence having at least 97% sequence identity to the mature polypeptide coding sequence of SEQ ID NO: 11.

17. The method of claim 16, wherein the GH61 polypeptide is encoded by a polynucleotide comprising a nucleotide sequence having at least 98% sequence identity to the mature polypeptide coding sequence of SEQ ID NO: 11.

18. The method of claim 17, wherein the GH61 polypeptide is encoded by a polynucleotide comprising a nucleotide sequence having at least 99% sequence identity to the mature polypeptide coding sequence of SEQ ID NO: 11.

19. The method of claim 4, where the GH61 polypeptide comprises the mature polypeptide of SEQ ID NO: 12 or a fragment thereof having cellulolytic enhancing activity.

20. The method of claim 18, where the GH61 polypeptide consists of the mature polypeptide of SEQ ID NO: 12.

* * * * *

SEQUENCE LISTING

<160> NUMBER OF SEQ ID NOS: 104

<210> SEQ ID NO 1
<211> LENGTH: 1846
<212> TYPE: DNA
<213> ORGANISM: Thielavia terrestris

<400> SEQUENCE: 1

| | | | | | | |
|---|---|---|---|---|---|---|
| aattgaagga | gggagtggcg | gagtggccac | caagtcaggc | ggctgtcaac | taaccaagga | 60 |
| tgggaacagt | tcggctcgcc | ttgcccgagg | gcagcgttcc | ctgatgggga | cgaaccatgg | 120 |
| gactggggtc | agctgctgta | taaaagttca | aatcgatgat | ctctcagatg | gcgctgctgg | 180 |
| ggtgttctgc | gcttttccat | cctcgcaacc | tggtatccca | ctagtccagc | gttcggcacc | 240 |
| atgaagtcgt | tcaccattgc | cgccttggca | gccctatggg | cccaggaggc | cgccgcccac | 300 |
| gcgaccttcc | aggacctctg | gattgatgga | gtcgactacg | gctcgcaatg | tgtccgcctc | 360 |
| ccggcgtcca | actcccccgt | caccaatgtt | gcgtccgacg | atatccgatg | caatgtcggc | 420 |
| acctcgaggc | ccaccgtcaa | gtgcccggtc | aaggccggct | ccacggtcac | gatcgagatg | 480 |
| caccaggttc | gcacgcctct | ctgcgtaggc | cccccagcta | ctatatggca | ctaacacgac | 540 |
| ctccagcaac | ctggcgaccg | gtcttgcgcc | aacgaggcta | tcggcggcga | ccactacggc | 600 |
| cccgtaatgg | tgtacatgtc | caaggtcgat | gacgcggtga | cagccgacgg | ttcatcgggc | 660 |
| tggttcaagg | tgttccagga | cagctgggcc | aagaacccgt | cgggttcgac | gggcgacgac | 720 |
| gactactggg | gcaccaagga | cctcaactcg | tgctgcggca | agatgaacgt | caagatcccc | 780 |
| gaagacatcg | agccgggcga | ctacctgctc | cgcgccgagg | ttatcgcgct | gcacgtggcc | 840 |
| gccagctcgg | gcggcgcgca | gttctacatg | tcctgctacc | agctgaccgt | gacgggctcc | 900 |
| ggcagcgcca | cccccctcgac | cgtgaatttc | ccgggcgcct | actcggccag | cgacccgggc | 960 |
| atcctgatca | acatccacgc | gcccatgtcg | acctacgtcg | tcccgggccc | gaccgtgtac | 1020 |
| gcgggcggct | cgaccaagtc | ggctggcagc | tcctgctccg | gctgcgaggc | gacctgcacg | 1080 |
| gttggttccg | gccccagcgc | gacactgacg | cagcccacct | ccaccgcgac | cgcgaccctcc | 1140 |
| gccccctggcg | gcggcggctc | cggctgcacg | gcggccaagt | accagcagtg | cggcggcacc | 1200 |
| ggctacactg | ggtgcaccac | ctgcgctgta | agttccctcg | tgatatgcag | cggaacaccg | 1260 |
| tctggactgt | tttgctaact | cgcgtcgtag | tccgggtcta | cctgcagcgc | cgtctcgcct | 1320 |
| ccgtactact | cgcagtgcct | ctaagccggg | agcgcttgct | cagcgggctg | ctgtgaagga | 1380 |
| gctccatgtc | cccatgccgc | catggccgga | gtaccgggct | gagcgcccaa | ttcttgtata | 1440 |
| tagttgagtt | ttcccaatca | tgaatacata | tgcatctgca | tggactgttg | cgtcgtcagt | 1500 |
| ctacatcctt | tgctccactg | aactgtgaga | ccccatgtca | tccggaccat | tcgatcggtg | 1560 |
| ctcgctctac | catctcggtt | gatgggtctg | ggcttgagag | tcactggcac | gtcctcggcg | 1620 |
| gtaatgaaat | gtggaggaaa | gtgtgagctg | tctgacgcac | tcggcgctga | tgagacgttg | 1680 |
| agcgcggccc | acactggtgt | tctgtaagcc | agcacacaaa | agaatactcc | aggatggccc | 1740 |
| atagcggcaa | atatacagta | tcagggatgc | aaaaagtgca | aaagtaaggg | gctcaatcgg | 1800 |
| ggatcgaacc | cgagacctcg | cacatgactt | atttcaagtc | aggggt | 1846 |

<210> SEQ ID NO 2
<211> LENGTH: 326
<212> TYPE: PRT
<213> ORGANISM: Thielavia terrestris

<400> SEQUENCE: 2

```
Met Lys Ser Phe Thr Ile Ala Ala Leu Ala Ala Leu Trp Ala Gln Glu
1               5                   10                  15

Ala Ala Ala His Ala Thr Phe Gln Asp Leu Trp Ile Asp Gly Val Asp
            20                  25                  30

Tyr Gly Ser Gln Cys Val Arg Leu Pro Ala Ser Asn Ser Pro Val Thr
        35                  40                  45

Asn Val Ala Ser Asp Asp Ile Arg Cys Asn Val Gly Thr Ser Arg Pro
    50                  55                  60

Thr Val Lys Cys Pro Val Lys Ala Gly Ser Thr Val Thr Ile Glu Met
65                  70                  75                  80

His Gln Gln Pro Gly Asp Arg Ser Cys Ala Asn Glu Ala Ile Gly Gly
                85                  90                  95

Asp His Tyr Gly Pro Val Met Val Tyr Met Ser Lys Val Asp Asp Ala
            100                 105                 110

Val Thr Ala Asp Gly Ser Ser Gly Trp Phe Lys Val Phe Gln Asp Ser
        115                 120                 125

Trp Ala Lys Asn Pro Ser Gly Ser Thr Gly Asp Asp Tyr Trp Gly
    130                 135                 140

Thr Lys Asp Leu Asn Ser Cys Cys Gly Lys Met Asn Val Lys Ile Pro
145                 150                 155                 160

Glu Asp Ile Glu Pro Gly Asp Tyr Leu Leu Arg Ala Glu Val Ile Ala
                165                 170                 175

Leu His Val Ala Ala Ser Ser Gly Gly Ala Gln Phe Tyr Met Ser Cys
        180                 185                 190

Tyr Gln Leu Thr Val Thr Gly Ser Gly Ser Ala Thr Pro Ser Thr Val
    195                 200                 205

Asn Phe Pro Gly Ala Tyr Ser Ala Ser Asp Pro Gly Ile Leu Ile Asn
210                 215                 220

Ile His Ala Pro Met Ser Thr Tyr Val Val Pro Gly Pro Thr Val Tyr
225                 230                 235                 240

Ala Gly Gly Ser Thr Lys Ser Ala Gly Ser Ser Cys Ser Gly Cys Glu
                245                 250                 255

Ala Thr Cys Thr Val Gly Ser Gly Pro Ser Ala Thr Leu Thr Gln Pro
        260                 265                 270

Thr Ser Thr Ala Thr Ala Thr Ser Ala Pro Gly Gly Gly Ser Gly
    275                 280                 285

Cys Thr Ala Ala Lys Tyr Gln Gln Cys Gly Gly Thr Gly Tyr Thr Gly
290                 295                 300

Cys Thr Thr Cys Ala Ser Gly Ser Thr Cys Ser Ala Val Ser Pro Pro
305                 310                 315                 320

Tyr Tyr Ser Gln Cys Leu
                325

<210> SEQ ID NO 3
<211> LENGTH: 880
<212> TYPE: DNA
<213> ORGANISM: Thielavia terrestris

<400> SEQUENCE: 3
accccgggat cactgcccct aggaaccagc acacctcggt ccaatcatgc ggttcgacgc    60
cctctccgcc ctcgctcttg cgccgcttgt ggctggccac ggcgccgtga ccagctacat   120
catcggcggc aaaaccctat ccggctacga gggcttctcg cctgcctcga gcccgccgac   180
gatccagtac cagtggcccg actacaaccc gaccctgagc gtgaccgacc cgaagatgcg   240
```

```
ctgcaacggc ggcacctcgg cagagctcag cgcgcccgtc caggccggcg agaacgtgac    300
ggccgtctgg aagcagtgga cccaccagca aggccccgtc atggtctgga tgttcaagtg    360
ccccggcgac ttctcgtcgt gccacggcga cggcaagggc tggttcaaga tcgaccagct    420
gggcctgtgg ggcaacaacc tcaactcgaa caactgggca ccgcgatcg tctacaagac     480 cctccagtgg agcaacccga tccccaagaa cctcgcgccg ggcaactacc tcatccgcca    540
cgagctgctc gccctgcacc aggccaacac gccgcagttc tacgccgagt gcgcccagct    600
ggtcgtctcc ggcagcggct ccgccctgcc cccgtccgac tacctctaca gcatccccgt    660
ctacgcgccc cagaacgacc ccggcatcac cgtgagtggg cttccgttcc gcggcgagct    720
ctgtggaaat cttgctgacg atgggctagg ttgacatcta caacggcggg cttacctcct    780
acaccccgcc cggcggcccc gtctggtctg gcttcgagtt ttaggcgcat tgagtcgggg    840
gctacgaggg gaaggcatct gttcgcatga gcgtgggtac                         880
```

<210> SEQ ID NO 4
<211> LENGTH: 478
<212> TYPE: PRT
<213> ORGANISM: Thielavia terrestris

<400> SEQUENCE: 4

```
Met Arg Phe Asp Ala Leu Ser Ala Leu Ala Leu Ala Pro Leu Val Ala
1               5                   10                  15

Gly His Gly Ala Val Thr Ser Tyr Ile Ile Gly Gly Lys Thr Tyr Pro
            20                  25                  30

Gly Tyr Glu Gly Phe Ser Pro Ala Ser Ser Pro Pro Thr Ile Gln Tyr
        35                  40                  45

Gln Trp Pro Asp Tyr Asn Pro Thr Leu Ser Val Thr Asp Pro Lys Met
    50                  55                  60

Arg Cys Asn Gly Gly Thr Ser Ala Glu Leu Ser Ala Pro Val Gln Ala
65                  70                  75                  80

Gly Glu Asn Val Thr Ala Val Trp Lys Gln Trp Thr His Gln Gln Gly
                85                  90                  95

Pro Val Met Val Trp Met Phe Lys Cys Pro Gly Asp Phe Ser Ser
            100                 105                 110

His Gly Asp Gly Lys Gly Trp Phe Lys Ile Asp Gln Leu Gly Leu Trp
        115                 120                 125

Gly Asn Asn Leu Asn Ser Asn Asn Trp Gly Thr Ala Ile Val Tyr Lys
    130                 135                 140

Thr Leu Gln Trp Ser Asn Pro Ile Pro Lys Asn Leu Ala Pro Gly Asn
145                 150                 155                 160

Tyr Leu Ile Arg His Glu Leu Leu Ala Leu His Gln Ala Asn Thr Pro
                165                 170                 175

Gln Phe Tyr Ala Glu Cys Ala Gln Leu Val Val Ser Gly Ser Gly Ser
            180                 185                 190

Ala Leu Pro Pro Ser Asp Tyr Leu Tyr Ser Ile Pro Val Tyr Ala Pro
        195                 200                 205

Gln Asn Asp Pro Gly Ile Thr Val Asp Ile Tyr Asn Gly Gly Leu Thr
    210                 215                 220

Ser Tyr Thr Pro Pro Gly Gly Pro Val Trp Ser Gly Phe Glu Phe Met
225                 230                 235                 240

Arg Phe Asp Ala Leu Ser Ala Leu Ala Leu Ala Pro Leu Val Ala Gly
                245                 250                 255
```

```
His Gly Ala Val Thr Ser Tyr Ile Ile Gly Gly Lys Thr Tyr Pro Gly
            260                 265                 270

Tyr Glu Gly Phe Ser Pro Ala Ser Ser Pro Thr Ile Gln Tyr Gln
        275                 280                 285

Trp Pro Asp Tyr Asn Pro Thr Leu Ser Val Thr Asp Pro Lys Met Arg
    290                 295                 300

Cys Asn Gly Gly Thr Ser Ala Glu Leu Ser Ala Pro Val Gln Ala Gly
305                 310                 315                 320

Glu Asn Val Thr Ala Val Trp Lys Gln Trp Thr His Gln Gln Gly Pro
                325                 330                 335

Val Met Val Trp Met Phe Lys Cys Pro Gly Asp Phe Ser Ser His
            340                 345                 350

Gly Asp Gly Lys Gly Trp Phe Lys Ile Asp Gln Leu Gly Leu Trp Gly
                355                 360                 365

Asn Asn Leu Asn Ser Asn Asn Trp Gly Thr Ala Ile Val Tyr Lys Thr
            370                 375                 380

Leu Gln Trp Ser Asn Pro Ile Pro Lys Asn Leu Ala Pro Gly Asn Tyr
385                 390                 395                 400

Leu Ile Arg His Glu Leu Leu Ala Leu His Gln Ala Asn Thr Pro Gln
                405                 410                 415

Phe Tyr Ala Glu Cys Ala Gln Leu Val Val Ser Gly Ser Gly Ser Ala
            420                 425                 430

Leu Pro Pro Ser Asp Tyr Leu Tyr Ser Ile Pro Val Tyr Ala Pro Gln
                435                 440                 445

Asn Asp Pro Gly Ile Thr Val Asp Ile Tyr Asn Gly Gly Leu Thr Ser
450                 455                 460

Tyr Thr Pro Pro Gly Gly Pro Val Trp Ser Gly Phe Glu Phe
465                 470                 475

<210> SEQ ID NO 5
<211> LENGTH: 1000
<212> TYPE: DNA
<213> ORGANISM: Thielavia terrestris

<400> SEQUENCE: 5
ctcctgttcc tgggccaccg cttgttgcct gcactattgg tagagttggt ctattgctag      60
agttggccat gcttctcaca tcagtcctcg gctcggctgc cctgcttgct agcggcgctg     120
cggcacacgg cgccgtgacc agctacatca tcgccggcaa gaattacccg ggtgggtag      180 ctgattattg agggcgcatt caaggttcat accggtgtgc atggctgaca accggctggc     240
agataccaag gcttttctcc tgcgaactcg ccgaacgtca tccaatggca atggcatgac     300
tacaaccccg tcttgtcgtg cagcgactcg aagcttcgct gcaacggcgg cacgtcggcc     360
accctgaacg ccacggccgc accgggcgac accatcaccg ccatctgggc gcagtggacg     420
cacagccagg gccccatcct ggtgtggatg tacaagtgcc cgggctcctt cagctcctgt     480
gacggctccg gcgctggctg gttcaagatc gacgaggccg gcttccacgg cgacggcgtc     540
aaggtcttcc tcgacaccga gaacccgtcc ggctgggaca tcgccaagct cgtcggcggc     600
aacaagcagt ggagcagcaa ggtccccgag ggcctcgccc ccggcaacta cctcgtccgc     660
cacgagttga tcgccctgca ccaggccaac aacccgcagt tctacccgga gtgcgcccag     720
gtcgtcatca ccggctccgg caccgcgcag ccggatgcct catacaaggc ggctatcccc     780
ggctactgca accagaatga cccgaacatc aaggtgagat ccaggcgtaa tgcagtctac     840
tgctggaaag aaagtggtcc aagctaaacc gcgctccagg tgcccatcaa cgaccactcc     900
```

```
atccctcaga cctacaagat tcccggccct cccgtcttca agggcaccgc cagcaagaag    960
gcccgggact tcaccgcctg aagttgttga atcgatggag                          1000
```

<210> SEQ ID NO 6
<211> LENGTH: 516
<212> TYPE: PRT
<213> ORGANISM: Thielavia terrestris

<400> SEQUENCE: 6

```
Met Leu Leu Thr Ser Val Leu Gly Ser Ala Ala Leu Ala Ser Gly
1               5                   10                  15

Ala Ala Ala His Gly Ala Val Thr Ser Tyr Ile Ile Ala Gly Lys Asn
                20                  25                  30

Tyr Pro Gly Tyr Gln Gly Phe Ser Pro Ala Asn Ser Pro Asn Val Ile
            35                  40                  45

Gln Trp Gln Trp His Asp Tyr Asn Pro Val Leu Ser Cys Ser Asp Ser
    50                  55                  60

Lys Leu Arg Cys Asn Gly Gly Thr Ser Ala Thr Leu Asn Ala Thr Ala
65                  70                  75                  80

Ala Pro Gly Asp Thr Ile Thr Ala Ile Trp Ala Gln Trp Thr His Ser
                85                  90                  95

Gln Gly Pro Ile Leu Val Trp Met Tyr Lys Cys Pro Gly Ser Phe Ser
            100                 105                 110

Ser Cys Asp Gly Ser Gly Ala Gly Trp Phe Lys Ile Asp Glu Ala Gly
        115                 120                 125

Phe His Gly Asp Gly Val Lys Val Phe Leu Asp Thr Glu Asn Pro Ser
    130                 135                 140

Gly Trp Asp Ile Ala Lys Leu Val Gly Gly Asn Lys Gln Trp Ser Ser
145                 150                 155                 160

Lys Val Pro Glu Gly Leu Ala Pro Gly Asn Tyr Leu Val Arg His Glu
                165                 170                 175

Leu Ile Ala Leu His Gln Ala Asn Asn Pro Gln Phe Tyr Pro Glu Cys
            180                 185                 190

Ala Gln Val Val Ile Thr Gly Ser Gly Thr Ala Gln Pro Asp Ala Ser
        195                 200                 205

Tyr Lys Ala Ala Ile Pro Gly Tyr Cys Asn Gln Asn Asp Pro Asn Ile
    210                 215                 220

Lys Val Pro Ile Asn Asp His Ser Ile Pro Gln Thr Tyr Lys Ile Pro
225                 230                 235                 240

Gly Pro Pro Val Phe Lys Gly Thr Ala Ser Lys Lys Ala Arg Asp Phe
                245                 250                 255

Thr Ala Met Leu Leu Thr Ser Val Leu Gly Ser Ala Ala Leu Leu Ala
            260                 265                 270

Ser Gly Ala Ala Ala His Gly Ala Val Thr Ser Tyr Ile Ile Ala Gly
        275                 280                 285

Lys Asn Tyr Pro Gly Tyr Gln Gly Phe Ser Pro Ala Asn Ser Pro Asn
    290                 295                 300

Val Ile Gln Trp Gln Trp His Asp Tyr Asn Pro Val Leu Ser Cys Ser
305                 310                 315                 320

Asp Ser Lys Leu Arg Cys Asn Gly Gly Thr Ser Ala Thr Leu Asn Ala
                325                 330                 335

Thr Ala Ala Pro Gly Asp Thr Ile Thr Ala Ile Trp Ala Gln Trp Thr
            340                 345                 350
```

```
His Ser Gln Gly Pro Ile Leu Val Trp Met Tyr Lys Cys Pro Gly Ser
            355                 360                 365
Phe Ser Ser Cys Asp Gly Ser Gly Ala Gly Trp Phe Lys Ile Asp Glu
    370                 375                 380
Ala Gly Phe His Gly Asp Gly Val Lys Val Phe Leu Asp Thr Glu Asn
385                 390                 395                 400
Pro Ser Gly Trp Asp Ile Ala Lys Leu Val Gly Gly Asn Lys Gln Trp
                405                 410                 415
Ser Ser Lys Val Pro Glu Gly Leu Ala Pro Gly Asn Tyr Leu Val Arg
            420                 425                 430
His Glu Leu Ile Ala Leu His Gln Ala Asn Asn Pro Gln Phe Tyr Pro
        435                 440                 445
Glu Cys Ala Gln Val Val Ile Thr Gly Ser Gly Thr Ala Gln Pro Asp
    450                 455                 460
Ala Ser Tyr Lys Ala Ala Ile Pro Gly Tyr Cys Asn Gln Asn Asp Pro
465                 470                 475                 480
Asn Ile Lys Val Pro Ile Asn Asp His Ser Ile Pro Gln Thr Tyr Lys
                485                 490                 495
Ile Pro Gly Pro Pro Val Phe Lys Gly Thr Ala Ser Lys Lys Ala Arg
            500                 505                 510
Asp Phe Thr Ala
            515

<210> SEQ ID NO 7
<211> LENGTH: 681
<212> TYPE: DNA
<213> ORGANISM: Thielavia terrestris

<400> SEQUENCE: 7
atgctcgcaa acggtgccat cgtcttcctg gccgccgccc tcggcgtcag tggccactac      60
acctggccac gggttaacga cggcgccgac tggcaacagg tccgtaaggc ggacaactgg     120
caggacaacg gctacgtcgg ggatgtcacg tcgccacaga tccgctgttt ccaggcgacc     180
ccgtccccgg ccccatccgt cctcaacacc acggccggct cgaccgtgac ctactgggcc     240
aaccccgacg tctaccaccc cgggcctgtg cagttttaca tggcccgcgt gcccgatggc     300
gaggacatca actcgtggaa cggcgacggc gccgtgtggt tcaaggtgta cgaggaccat     360
cctacctttg gcgctcagct cacatggccc agcacgggca gagctcgtt cgcggttccc     420
atccccccgt gcatcaagtc cggctactac ctcctccggg cggagcaaat cggcctgcac     480
gtcgcccaga gcgtaggcgg agcgcagttc tacatctcat gcgcccagct cagcgtcacc     540
ggcggcggca gcaccgagcc gccgaacaag gtggccttcc ccggcgctta cagtgcgacg     600
gacccgggca ttctgatcaa catctactac cctgttccca cgtcctacca gaaccccggc     660
ccggccgtct tcagctgctg a                                              681

<210> SEQ ID NO 8
<211> LENGTH: 452
<212> TYPE: PRT
<213> ORGANISM: Thielavia terrestris

<400> SEQUENCE: 8

Met Leu Ala Asn Gly Ala Ile Val Phe Leu Ala Ala Ala Leu Gly Val
1               5                   10                  15
Ser Gly His Tyr Thr Trp Pro Arg Val Asn Asp Gly Ala Asp Trp Gln
            20                  25                  30
```

```
Gln Val Arg Lys Ala Asp Asn Trp Gln Asp Asn Gly Tyr Val Gly Asp
         35                  40                  45

Val Thr Ser Pro Gln Ile Arg Cys Phe Gln Ala Thr Pro Ser Pro Ala
 50                  55                  60

Pro Ser Val Leu Asn Thr Thr Ala Gly Ser Thr Val Thr Tyr Trp Ala
 65                  70                  75                  80

Asn Pro Asp Val Tyr His Pro Gly Pro Val Gln Phe Tyr Met Ala Arg
                 85                  90                  95

Val Pro Asp Gly Glu Asp Ile Asn Ser Trp Asn Gly Asp Gly Ala Val
             100                 105                 110

Trp Phe Lys Val Tyr Glu Asp His Pro Thr Phe Gly Ala Gln Leu Thr
         115                 120                 125

Trp Pro Ser Thr Gly Lys Ser Ser Phe Ala Val Pro Ile Pro Pro Cys
 130                 135                 140

Ile Lys Ser Gly Tyr Tyr Leu Leu Arg Ala Glu Gln Ile Gly Leu His
 145                 150                 155                 160

Val Ala Gln Ser Val Gly Gly Ala Gln Phe Tyr Ile Ser Cys Ala Gln
                 165                 170                 175

Leu Ser Val Thr Gly Gly Gly Ser Thr Glu Pro Pro Asn Lys Val Ala
             180                 185                 190

Phe Pro Gly Ala Tyr Ser Ala Thr Asp Pro Gly Ile Leu Ile Asn Ile
         195                 200                 205

Tyr Tyr Pro Val Pro Thr Ser Tyr Gln Asn Pro Gly Pro Ala Val Phe
 210                 215                 220

Ser Cys Met Leu Ala Asn Gly Ala Ile Val Phe Leu Ala Ala Ala Leu
225                 230                 235                 240

Gly Val Ser Gly His Tyr Thr Trp Pro Arg Val Asn Asp Gly Ala Asp
                 245                 250                 255

Trp Gln Gln Val Arg Lys Ala Asp Asn Trp Gln Asp Asn Gly Tyr Val
             260                 265                 270

Gly Asp Val Thr Ser Pro Gln Ile Arg Cys Phe Gln Ala Thr Pro Ser
         275                 280                 285

Pro Ala Pro Ser Val Leu Asn Thr Thr Ala Gly Ser Thr Val Thr Tyr
 290                 295                 300

Trp Ala Asn Pro Asp Val Tyr His Pro Gly Pro Val Gln Phe Tyr Met
305                 310                 315                 320

Ala Arg Val Pro Asp Gly Glu Asp Ile Asn Ser Trp Asn Gly Asp Gly
                 325                 330                 335

Ala Val Trp Phe Lys Val Tyr Glu Asp His Pro Thr Phe Gly Ala Gln
             340                 345                 350

Leu Thr Trp Pro Ser Thr Gly Lys Ser Ser Phe Ala Val Pro Ile Pro
         355                 360                 365

Pro Cys Ile Lys Ser Gly Tyr Tyr Leu Leu Arg Ala Glu Gln Ile Gly
 370                 375                 380

Leu His Val Ala Gln Ser Val Gly Gly Ala Gln Phe Tyr Ile Ser Cys
385                 390                 395                 400

Ala Gln Leu Ser Val Thr Gly Gly Gly Ser Thr Glu Pro Pro Asn Lys
                 405                 410                 415

Val Ala Phe Pro Gly Ala Tyr Ser Ala Thr Asp Pro Gly Ile Leu Ile
             420                 425                 430

Asn Ile Tyr Tyr Pro Val Pro Thr Ser Tyr Gln Asn Pro Gly Pro Ala
         435                 440                 445

Val Phe Ser Cys
```

<210> SEQ ID NO 9
<211> LENGTH: 960
<212> TYPE: DNA
<213> ORGANISM: Thielavia terrestris

<400> SEQUENCE: 9

```
atgaagggac ttttcagtgc cgccgccctc tccctggccg tcggccaggc ttcggcccat     60
tacatcttcc agcaactctc catcaacggg aaccagtttc cggtgtacca atatattcgc    120
aagaacacca attataacag tcccgttacc gatctcacgt ccgacgatct tcggtgcaat    180
gtcggcgccc agggtgctgg gacagacacc gtcacggtga aggccggcga ccagttcacc    240
ttcacccttg acacccctgt ttaccaccag gggcccatct ccatctacat gtccaaggcc    300
ccgggcgcgg cgtcagacta cgatggcagc ggcggctggt tcaagatcaa ggactggggc    360
ccgactttca cgccgacgg cacggccacc tgggacatgg ccggctcata cacctacaac    420
atcccgacct gcattcccga cggcgactat ctgctccgca tccagtcgct ggccatccac    480
aaccccctggc cggcgggcat cccgcagttc tacatctcct cgcccagat caccgtgacc    540
ggcggcggca acggcaaccc tggcccgacg cccctcatcc ccggcgcctt caaggacacc    600
gacccgggct acacggtgaa catctacacg aacttccaca actacacggt tccggcccg    660
gaggtcttca gctgcaacgg cggcggctcg aacccgcccc gccggtgag tagcagcacg    720
cccgcgacca cgacgctggt cacgtcgacg cgcaccacgt cctccacgtc ctccgcctcg    780
acgccggcct cgaccggcgg ctgcaccgtc gccaagtggg gccagtgcgg cggcaacggg    840
tacaccggct gcacgacctg cgcggccggg tccacctgca gcaagcagaa cgactactac    900
tcgcagtgct tgtaagggag gccgcaaagc atgaggtgtt tgaagaggag gagaggggtc    960
```

<210> SEQ ID NO 10
<211> LENGTH: 608
<212> TYPE: PRT
<213> ORGANISM: Thielavia terrestris

<400> SEQUENCE: 10

```
Met Lys Gly Leu Phe Ser Ala Ala Leu Ser Leu Ala Val Gly Gln
1               5                   10                  15

Ala Ser Ala His Tyr Ile Phe Gln Gln Leu Ser Ile Asn Gly Asn Gln
            20                  25                  30

Phe Pro Val Tyr Gln Tyr Ile Arg Lys Asn Thr Asn Tyr Asn Ser Pro
        35                  40                  45

Val Thr Asp Leu Thr Ser Asp Asp Leu Arg Cys Asn Val Gly Ala Gln
    50                  55                  60

Gly Ala Gly Thr Asp Thr Val Thr Val Lys Ala Gly Asp Gln Phe Thr
65                  70                  75                  80

Phe Thr Leu Asp Thr Pro Val Tyr His Gln Gly Pro Ile Ser Ile Tyr
                85                  90                  95

Met Ser Lys Ala Pro Gly Ala Ala Ser Asp Tyr Asp Gly Ser Gly Gly
            100                 105                 110

Trp Phe Lys Ile Lys Asp Trp Gly Pro Thr Phe Asn Ala Asp Gly Thr
        115                 120                 125

Ala Thr Trp Asp Met Ala Gly Ser Tyr Thr Tyr Asn Ile Pro Thr Cys
    130                 135                 140

Ile Pro Asp Gly Asp Tyr Leu Leu Arg Ile Gln Ser Leu Ala Ile His
145                 150                 155                 160
```

```
Asn Pro Trp Pro Ala Gly Ile Pro Gln Phe Tyr Ile Ser Cys Ala Gln
                165                 170                 175

Ile Thr Val Thr Gly Gly Asn Gly Asn Pro Gly Pro Thr Ala Leu
            180                 185                 190

Ile Pro Gly Ala Phe Lys Asp Thr Asp Pro Gly Tyr Thr Val Asn Ile
            195                 200                 205

Tyr Thr Asn Phe His Asn Tyr Thr Val Pro Gly Pro Glu Val Phe Ser
210                 215                 220

Cys Asn Gly Gly Ser Asn Pro Pro Pro Val Ser Ser Ser Thr
225                 230                 235                 240

Pro Ala Thr Thr Thr Leu Val Thr Ser Thr Arg Thr Thr Ser Ser Thr
                245                 250                 255

Ser Ser Ala Ser Thr Pro Ala Ser Thr Gly Gly Cys Thr Val Ala Lys
            260                 265                 270

Trp Gly Gln Cys Gly Gly Asn Gly Tyr Thr Gly Cys Thr Thr Cys Ala
            275                 280                 285

Ala Gly Ser Thr Cys Ser Lys Gln Asn Asp Tyr Tyr Ser Gln Cys Leu
            290                 295                 300

Met Lys Gly Leu Phe Ser Ala Ala Leu Ser Leu Ala Val Gly Gln
305                 310                 315                 320

Ala Ser Ala His Tyr Ile Phe Gln Gln Leu Ser Ile Asn Gly Asn Gln
                325                 330                 335

Phe Pro Val Tyr Gln Tyr Ile Arg Lys Asn Thr Asn Tyr Asn Ser Pro
            340                 345                 350

Val Thr Asp Leu Thr Ser Asp Asp Leu Arg Cys Asn Val Gly Ala Gln
            355                 360                 365

Gly Ala Gly Thr Asp Thr Val Thr Val Lys Ala Gly Asp Gln Phe Thr
            370                 375                 380

Phe Thr Leu Asp Thr Pro Val Tyr His Gln Gly Pro Ile Ser Ile Tyr
385                 390                 395                 400

Met Ser Lys Ala Pro Gly Ala Ala Ser Asp Tyr Asp Gly Ser Gly Gly
                405                 410                 415

Trp Phe Lys Ile Lys Asp Trp Gly Pro Thr Phe Asn Ala Asp Gly Thr
            420                 425                 430

Ala Thr Trp Asp Met Ala Gly Ser Tyr Thr Tyr Asn Ile Pro Thr Cys
            435                 440                 445

Ile Pro Asp Gly Asp Tyr Leu Leu Arg Ile Gln Ser Leu Ala Ile His
            450                 455                 460

Asn Pro Trp Pro Ala Gly Ile Pro Gln Phe Tyr Ile Ser Cys Ala Gln
465                 470                 475                 480

Ile Thr Val Thr Gly Gly Asn Gly Asn Pro Gly Pro Thr Ala Leu
                485                 490                 495

Ile Pro Gly Ala Phe Lys Asp Thr Asp Pro Gly Tyr Thr Val Asn Ile
            500                 505                 510

Tyr Thr Asn Phe His Asn Tyr Thr Val Pro Gly Pro Glu Val Phe Ser
            515                 520                 525

Cys Asn Gly Gly Ser Asn Pro Pro Pro Val Ser Ser Ser Thr
530                 535                 540

Pro Ala Thr Thr Thr Leu Val Thr Ser Thr Arg Thr Thr Ser Ser Thr
545                 550                 555                 560

Ser Ser Ala Ser Thr Pro Ala Ser Thr Gly Gly Cys Thr Val Ala Lys
                565                 570                 575
```

```
Trp Gly Gln Cys Gly Gly Asn Gly Tyr Thr Gly Cys Thr Thr Cys Ala
            580                 585                 590
Ala Gly Ser Thr Cys Ser Lys Gln Asn Asp Tyr Tyr Ser Gln Cys Leu
        595                 600                 605

<210> SEQ ID NO 11
<211> LENGTH: 799
<212> TYPE: DNA
<213> ORGANISM: Thermoascus aurantiacus

<400> SEQUENCE: 11
atgtcctttt ccaagataat tgctactgcc ggcgttcttg cctctgcttc tctagtggct      60
ggccatggct tcgttcagaa catcgtgatt gatggtaaaa agtatgtcat tgcaagacgc     120
acataagcgg caacagctga caatcgacag ttatggcggg tatctagtga accagtatcc     180
atacatgtcc aatcctccag aggtcatcgc ctggtctact acggcaactg atcttggatt     240
tgtggacggt actggatacc aaaccccaga tatcatctgc catagggcg ccaagcctgg      300 agccctgact gctccagtct ctccaggagg aactgttgag cttcaatgga ctccatggcc     360
tgattctcac catggcccag ttatcaacta ccttgctccg tgcaatggtg attgttccac     420
tgtggataag acccaattag aattcttcaa aattgccgag agcggtctca tcaatgatga     480
caatcctcct gggatctggg cttcagacaa tctgatagca gccaacaaca gctggactgt     540
caccattcca accacaattg cacctggaaa ctatgttctg aggcatgaga ttattgctct     600
tcactcagct cagaaccagg atggtgccca gaactatccc cagtgcatca atctgcaggt     660
cactggaggt ggttctgata accctgctgg aactcttgga acggcactct accacgatac     720
cgatcctgga attctgatca acatctatca gaaactttcc agctatatca tccctggtcc     780
tcctctgtat actggttaa                                                  799

<210> SEQ ID NO 12
<211> LENGTH: 250
<212> TYPE: PRT
<213> ORGANISM: Thermoascus aurantiacus

<400> SEQUENCE: 12

Met Ser Phe Ser Lys Ile Ile Ala Thr Ala Gly Val Leu Ala Ser Ala
1               5                   10                  15

Ser Leu Val Ala Gly His Gly Phe Val Gln Asn Ile Val Ile Asp Gly
            20                  25                  30

Lys Lys Tyr Tyr Gly Gly Tyr Leu Val Asn Gln Tyr Pro Tyr Met Ser
        35                  40                  45

Asn Pro Pro Glu Val Ile Ala Trp Ser Thr Thr Ala Thr Asp Leu Gly
    50                  55                  60

Phe Val Asp Gly Thr Gly Tyr Gln Thr Pro Asp Ile Ile Cys His Arg
65                  70                  75                  80

Gly Ala Lys Pro Gly Ala Leu Thr Ala Pro Val Ser Pro Gly Gly Thr
                85                  90                  95

Val Glu Leu Gln Trp Thr Pro Trp Pro Asp Ser His His Gly Pro Val
            100                 105                 110

Ile Asn Tyr Leu Ala Pro Cys Asn Gly Asp Cys Ser Thr Val Asp Lys
        115                 120                 125

Thr Gln Leu Glu Phe Phe Lys Ile Ala Glu Ser Gly Leu Ile Asn Asp
    130                 135                 140

Asp Asn Pro Pro Gly Ile Trp Ala Ser Asp Asn Leu Ile Ala Ala Asn
145                 150                 155                 160
```

```
Asn Ser Trp Thr Val Thr Ile Pro Thr Thr Ile Ala Pro Gly Asn Tyr
            165                 170                 175

Val Leu Arg His Glu Ile Ile Ala Leu His Ser Ala Gln Asn Gln Asp
        180                 185                 190

Gly Ala Gln Asn Tyr Pro Gln Cys Ile Asn Leu Gln Val Thr Gly Gly
        195                 200                 205

Gly Ser Asp Asn Pro Ala Gly Thr Leu Gly Thr Ala Leu Tyr His Asp
    210                 215                 220

Thr Asp Pro Gly Ile Leu Ile Asn Ile Tyr Gln Lys Leu Ser Ser Tyr
225                 230                 235                 240

Ile Ile Pro Gly Pro Pro Leu Tyr Thr Gly
                245                 250

<210> SEQ ID NO 13
<211> LENGTH: 1172
<212> TYPE: DNA
<213> ORGANISM: Trichoderma reesei

<400> SEQUENCE: 13
ggatctaagc cccatcgata tgaagtcctg cgccattctt gcagcccttg gctgtcttgc      60
cgggagcgtt ctcggccatg gacaagtcca aaacttcacg atcaatggac aatacaatca    120
gggtttcatt ctcgattact actatcagaa gcagaatact ggtcacttcc ccaacgttgc    180
tggctggtac gccgaggacc tagacctggg cttcatctcc cctgaccaat acaccacgcc    240
cgacattgtc tgtcacaaga acgcggcccc aggtgccatt tctgccactg cagcggccgg    300
cagcaacatc gtcttccaat ggggccctgg cgtctggcct caccctacg gtcccatcgt     360 tacctacgtg gctgagtgca gcggatcgtg cacgaccgtg aacaagaaca acctgcgctg    420
ggtcaagatt caggaggccg gcatcaacta taacacccaa gtctgggcgc agcaggatct    480
gatcaaccag gcaacaagt ggactgtgaa gatcccgtcg agcctcaggc ccggaaacta     540
tgtcttccgc catgaacttc ttgctgccca tggtgcctct agtgcgaacg gcatgcagaa    600
ctatcctcag tgcgtgaaca tcgccgtcac aggctcgggc acgaaagcgc tccctgccgg    660
aactcctgca actcagctct acaagcccac tgaccctggc atcttgttca accccttacac    720 aacaatcacg agctacacca tccctggccc agccctgtgg caaggctaga tccaggggta    780
cggtgttggc gttcgtgaag tcggagctgt tgacaaggat atctgatgat gaacggagag    840
gactgatggg cgtgactgag tgtatatatt tttgatgacc aaattgtata cgaaatccga    900
acgcatggtg atcattgttt atccctgtag tatattgtct ccaggctgct aagagcccac    960
cgggtgtatt acggcaacaa agtcaggaat ttgggtggca atgaacgcag gtctccatga   1020
atgtatatgt gaagaggcat cggctggcat gggcattacc agatataggc cctgtgaaac   1080
atatagtact tgaacgtgct actggaacgg atcataagca agtcatcaac atgtgaaaaa   1140
acactacatg taaaaaaaaa aaaaaaaaaa aa                                  1172

<210> SEQ ID NO 14
<211> LENGTH: 249
<212> TYPE: PRT
<213> ORGANISM: Trichoderma reesei

<400> SEQUENCE: 14

Met Lys Ser Cys Ala Ile Leu Ala Ala Leu Gly Cys Leu Ala Gly Ser
1               5                   10                  15

Val Leu Gly His Gly Gln Val Gln Asn Phe Thr Ile Asn Gly Gln Tyr
```

```
                    20                  25                  30
Asn Gln Gly Phe Ile Leu Asp Tyr Tyr Tyr Gln Lys Gln Asn Thr Gly
                35                  40                  45

His Phe Pro Asn Val Ala Gly Trp Tyr Ala Glu Asp Leu Asp Leu Gly
        50                  55                  60

Phe Ile Ser Pro Asp Gln Tyr Thr Thr Pro Asp Ile Val Cys His Lys
65                  70                  75                  80

Asn Ala Ala Pro Gly Ala Ile Ser Ala Thr Ala Ala Gly Ser Asn
                85                  90                  95

Ile Val Phe Gln Trp Gly Pro Val Trp Pro His Pro Tyr Gly Pro
                100                 105                 110

Ile Val Thr Tyr Val Val Glu Cys Ser Gly Ser Cys Thr Thr Val Asn
            115                 120                 125

Lys Asn Asn Leu Arg Trp Val Lys Ile Gln Glu Ala Gly Ile Asn Tyr
        130                 135                 140

Asn Thr Gln Val Trp Ala Gln Gln Asp Leu Ile Asn Gln Gly Asn Lys
145                 150                 155                 160

Trp Thr Val Lys Ile Pro Ser Ser Leu Arg Pro Gly Asn Tyr Val Phe
                165                 170                 175

Arg His Glu Leu Leu Ala Ala His Gly Ala Ser Ser Ala Asn Gly Met
                180                 185                 190

Gln Asn Tyr Pro Gln Cys Val Asn Ile Ala Val Thr Gly Ser Gly Thr
            195                 200                 205

Lys Ala Leu Pro Ala Gly Thr Pro Ala Thr Gln Leu Tyr Lys Pro Thr
        210                 215                 220

Asp Pro Gly Ile Leu Phe Asn Pro Tyr Thr Thr Ile Thr Ser Tyr Thr
225                 230                 235                 240

Ile Pro Gly Pro Ala Leu Trp Gln Gly
                245

<210> SEQ ID NO 15
<211> LENGTH: 2771
<212> TYPE: DNA
<213> ORGANISM: Aspergillus oryzae

<400> SEQUENCE: 15
ctgttctgct ggttacctgc cacgttatca tgaagcttgg ttggatcgag gtggccgcat      60
tggcggctgc ctcagtagtc agtgccaagg atgatctcgc gtactcccct cctttctacc    120
cttccccatg ggcagatggt cagggtgaat gggcggaagt atacaaacgc gctgtagaca    180
tagtttccca gatgacgttg acagagaaag tcaacttaac gactggaaca ggatggcaac    240
tagagaggtg tgttggacaa actggcagtg ttcccagact caacatcccc agcttgtgtt    300
tgcaggatag tcctcttggt attcgtttct cggactacaa ttcagctttc cctgcgggtg    360
ttaatgtcgc tgccacctgg acaagacgc tcgcctacct tcgtggtcag caatgggtg     420 aggagttcag tgataagggt attgacgttc agctgggtcc tgctgctggc cctctcggtg    480
ctcatccgga tggcggtaga actgggaag gtttctcacc agatccagcc ctcaccggtg    540
tactttttgc ggagacgatt aagggtattc aagatgctgg tgtcattgcg acagctaagc    600
attatatcat gaacgaacaa gagcatttcc gccaacaacc cgaggctgcg ggttacggat    660
tcaacgtaag cgacagtttg agttccaacg ttgatgacaa gactatgcat gaattgtacc    720
tctggccctt cgcggatgca gtacgcgctg gagtcggtgc tgtcatgtgc tcttacaacc    780
aaatcaacaa cagctacggt tgcgagaata gcgaaactct gaacaagctt ttgaaggcgg    840
```

```
agcttggttt ccaaggcttc gtcatgagtg attggaccgc tcatcacagc ggcgtaggcg    900
ctgctttagc aggtctggat atgtcgatgc ccggtgatgt taccttcgat agtggtacgt    960
ctttctgggg tgcaaacttg acggtcggtg tccttaacgg tacaatcccc caatggcgtg   1020
ttgatgacat ggctgtccgt atcatggccg cttattacaa ggttggccgc gacaccaaat   1080
acaccccctcc caacttcagc tcgtggacca gggacgaata tggtttcgcg cataaccatg   1140
tttcggaagg tgcttacgag agggtcaacg aattcgtgga cgtgcaacgc gatcatgccg   1200
acctaatccg tcgcatcggc gcgcagagca ctgttctgct gaagaacaag ggtgccttgc   1260
ccttgagccg caaggaaaag ctggtcgccc ttctgggaga ggatgcgggt tccaactcgt   1320
ggggcgctaa cggctgtgat gaccgtggtt gcgataacgg taccttgcc atggcctggg   1380
gtagcggtac tgcgaatttc ccatacctcg tgacaccaga gcaggcgatt cagaacgaag   1440
ttcttcaggg ccgtggtaat gtcttcgccg tgaccgacag ttgggcgctc gacaagatcg   1500
ctgcggctgc ccgccaggcc agcgtatctc tcgtgttcgt caactccgac tcaggagaaa   1560
gctatcttag tgtggatgga aatgagggcg atcgtaacaa catcactctg tggaagaacg   1620
gcgacaatgt ggtcaagacc gcagcgaata actgtaacaa caccgtggtc atcatccact   1680
ccgtcggacc agttttgatc gatgaatggt atgaccaccc caatgtcact ggtattctct   1740
gggctggtct gccaggccag gagtctggta actccatcgc cgatgtgctg tacggtcgtg   1800
tcaaccctgg cgccaagtct cctttcactt ggggcaagac ccgggagtcg tatggttctc   1860
ccttggtcaa ggatgccaac aatggcaacg gagcgcccca gtctgatttc acccagggtg   1920
ttttcatcga ttaccgccat ttcgataagt tcaatgagac ccctatctac gagtttggct   1980
acggcttgag ctacaccacc ttcgagctct ccgacctcca tgttcagccc ctgaacgcgt   2040
cccgatacac tcccaccagt ggcatgactg aagctgcaaa gaactttggt gaaattggcg   2100
atgcgtcgga gtacgtgtat ccggaggggc tggaaaggat ccatgagttt atctatccct   2160
ggatcaactc taccgacctg aaggcatcgt ctgacgattc taactacggc tgggaagact   2220
ccaagtatat tcccgaaggc gccacggatg ggtctgccca gccccgtttg cccgctagtg   2280
gtggtgccgg aggaaacccc ggtctgtacg aggatctttt ccgcgtctct gtgaaggtca   2340
agaacacggg caatgtcgcc ggtgatgaag ttcctcagct gtacgtttcc ctaggcggcc   2400
cgaatgagcc caaggtggta ctgcgcaagt ttgagcgtat tcacttggcc ccttcgcagg   2460
aggccgtgtg gacaacgacc cttacccgtc gtgaccttgc aaactgggac gtttcggctc   2520
aggactggac cgtcactcct taccccaaga cgatctacgt tggaaactcc tcacggaaac   2580
tgccgctcca ggcctcgctg cctaaggccc agtaaggggc aagtcctgat tgtacagagc   2640
atttcgagat ttatgatgta catgtttatg aatgacctag ggtagggtaa tacttagtag   2700
ggttagttct aattcttgga gtcaagtatt gactcactgg gccgataaaa aaaaaaaaa   2760
aaaaaaaaa a                                                          2771

<210> SEQ ID NO 16
<211> LENGTH: 861
<212> TYPE: PRT
<213> ORGANISM: Aspergillus oryzae

<400> SEQUENCE: 16

Met Lys Leu Gly Trp Ile Glu Val Ala Ala Leu Ala Ala Ala Ser Val
1               5                   10                  15

Val Ser Ala Lys Asp Asp Leu Ala Tyr Ser Pro Pro Phe Tyr Pro Ser
```

```
            20                  25                  30
Pro Trp Ala Asp Gly Gln Gly Glu Trp Ala Glu Val Tyr Lys Arg Ala
            35                  40                  45
Val Asp Ile Val Ser Gln Met Thr Leu Thr Glu Lys Val Asn Leu Thr
            50                  55                  60
Thr Gly Thr Gly Trp Gln Leu Glu Arg Cys Val Gly Gln Thr Gly Ser
65                  70                  75                  80
Val Pro Arg Leu Asn Ile Pro Ser Leu Cys Leu Gln Asp Ser Pro Leu
                85                  90                  95
Gly Ile Arg Phe Ser Asp Tyr Asn Ser Ala Phe Pro Ala Gly Val Asn
            100                 105                 110
Val Ala Ala Thr Trp Asp Lys Thr Leu Ala Tyr Leu Arg Gly Gln Ala
            115                 120                 125
Met Gly Glu Glu Phe Ser Asp Lys Gly Ile Asp Val Gln Leu Gly Pro
            130                 135                 140
Ala Ala Gly Pro Leu Gly Ala His Pro Asp Gly Gly Arg Asn Trp Glu
145                 150                 155                 160
Gly Phe Ser Pro Asp Pro Ala Leu Thr Gly Val Leu Phe Ala Glu Thr
                165                 170                 175
Ile Lys Gly Ile Gln Asp Ala Gly Val Ile Ala Thr Ala Lys His Tyr
            180                 185                 190
Ile Met Asn Glu Gln Glu His Phe Arg Gln Pro Glu Ala Ala Gly
            195                 200                 205
Tyr Gly Phe Asn Val Ser Asp Ser Leu Ser Ser Asn Val Asp Asp Lys
            210                 215                 220
Thr Met His Glu Leu Tyr Leu Trp Pro Phe Ala Asp Ala Val Arg Ala
225                 230                 235                 240
Gly Val Gly Ala Val Met Cys Ser Tyr Asn Gln Ile Asn Asn Ser Tyr
                245                 250                 255
Gly Cys Glu Asn Ser Glu Thr Leu Asn Lys Leu Leu Lys Ala Glu Leu
            260                 265                 270
Gly Phe Gln Gly Phe Val Met Ser Asp Trp Thr Ala His His Ser Gly
            275                 280                 285
Val Gly Ala Ala Leu Ala Gly Leu Asp Met Ser Met Pro Gly Asp Val
            290                 295                 300
Thr Phe Asp Ser Gly Thr Ser Phe Trp Gly Ala Asn Leu Thr Val Gly
305                 310                 315                 320
Val Leu Asn Gly Thr Ile Pro Gln Trp Arg Val Asp Asp Met Ala Val
                325                 330                 335
Arg Ile Met Ala Ala Tyr Tyr Lys Val Gly Arg Asp Thr Lys Tyr Thr
            340                 345                 350
Pro Pro Asn Phe Ser Ser Trp Thr Arg Asp Glu Tyr Gly Phe Ala His
            355                 360                 365
Asn His Val Ser Glu Gly Ala Tyr Glu Arg Val Asn Glu Phe Val Asp
            370                 375                 380
Val Gln Arg Asp His Ala Asp Leu Ile Arg Arg Ile Gly Ala Gln Ser
385                 390                 395                 400
Thr Val Leu Leu Lys Asn Lys Gly Ala Leu Pro Leu Ser Arg Lys Glu
                405                 410                 415
Lys Leu Val Ala Leu Leu Gly Glu Asp Ala Gly Ser Asn Ser Trp Gly
            420                 425                 430
Ala Asn Gly Cys Asp Asp Arg Gly Cys Asp Asn Gly Thr Leu Ala Met
            435                 440                 445
```

-continued

Ala Trp Gly Ser Gly Thr Ala Asn Phe Pro Tyr Leu Val Thr Pro Glu
    450                 455                 460

Gln Ala Ile Gln Asn Glu Val Leu Gln Gly Arg Gly Asn Val Phe Ala
465                 470                 475                 480

Val Thr Asp Ser Trp Ala Leu Asp Lys Ile Ala Ala Ala Arg Gln
                485                 490                 495

Ala Ser Val Ser Leu Val Phe Val Asn Ser Asp Ser Gly Glu Ser Tyr
                500                 505                 510

Leu Ser Val Asp Gly Asn Glu Gly Asp Arg Asn Asn Ile Thr Leu Trp
            515                 520                 525

Lys Asn Gly Asp Asn Val Val Lys Thr Ala Ala Asn Cys Asn Asn
530                 535                 540

Thr Val Val Ile Ile His Ser Val Gly Pro Val Leu Ile Asp Glu Trp
545                 550                 555                 560

Tyr Asp His Pro Asn Val Thr Gly Ile Leu Trp Ala Gly Leu Pro Gly
                565                 570                 575

Gln Glu Ser Gly Asn Ser Ile Ala Asp Val Leu Tyr Gly Arg Val Asn
                580                 585                 590

Pro Gly Ala Lys Ser Pro Phe Thr Trp Gly Lys Thr Arg Glu Ser Tyr
            595                 600                 605

Gly Ser Pro Leu Val Lys Asp Ala Asn Gly Asn Gly Ala Pro Gln
    610                 615                 620

Ser Asp Phe Thr Gln Gly Val Phe Ile Asp Tyr Arg His Phe Asp Lys
625                 630                 635                 640

Phe Asn Glu Thr Pro Ile Tyr Glu Phe Gly Tyr Gly Leu Ser Tyr Thr
                645                 650                 655

Thr Phe Glu Leu Ser Asp Leu His Val Gln Pro Leu Asn Ala Ser Arg
            660                 665                 670

Tyr Thr Pro Thr Ser Gly Met Thr Glu Ala Ala Lys Asn Phe Gly Glu
    675                 680                 685

Ile Gly Asp Ala Ser Glu Tyr Val Tyr Pro Glu Gly Leu Glu Arg Ile
    690                 695                 700

His Glu Phe Ile Tyr Pro Trp Ile Asn Ser Thr Asp Leu Lys Ala Ser
705                 710                 715                 720

Ser Asp Asp Ser Asn Tyr Gly Trp Glu Asp Ser Lys Tyr Ile Pro Glu
                725                 730                 735

Gly Ala Thr Asp Gly Ser Ala Gln Pro Arg Leu Pro Ala Ser Gly Gly
            740                 745                 750

Ala Gly Gly Asn Pro Gly Leu Tyr Glu Asp Leu Phe Arg Val Ser Val
    755                 760                 765

Lys Val Lys Asn Thr Gly Asn Val Ala Gly Asp Glu Val Pro Gln Leu
770                 775                 780

Tyr Val Ser Leu Gly Gly Pro Asn Glu Pro Lys Val Val Leu Arg Lys
785                 790                 795                 800

Phe Glu Arg Ile His Leu Ala Pro Ser Gln Glu Ala Val Trp Thr Thr
                805                 810                 815

Thr Leu Thr Arg Arg Asp Leu Ala Asn Trp Asp Val Ser Ala Gln Asp
            820                 825                 830

Trp Thr Val Thr Pro Tyr Pro Lys Thr Ile Tyr Val Gly Asn Ser Ser
    835                 840                 845

Arg Lys Leu Pro Leu Gln Ala Ser Leu Pro Lys Ala Gln
    850                 855                 860

<210> SEQ ID NO 17
<211> LENGTH: 3060
<212> TYPE: DNA
<213> ORGANISM: Aspergillus fumigatus

<400> SEQUENCE: 17

| | | | | | | |
|---|---|---|---|---|---|---|
| atgagattcg | gttggctcga | ggtggccgct | ctgacggccg | cttctgtagc | caatgcccag | 60 |
| gtttgtgatg | ctttcccgtc | attgtttcgg | atatagttga | caatagtcat | ggaaataatc | 120 |
| aggaattggc | tttctctcca | ccattctacc | cttcgccttg | ggctgatggc | cagggagagt | 180 |
| gggcagatgc | ccatcgacgc | gccgtcgaga | tcgtttctca | gatgacactg | gcggagaagg | 240 |
| ttaaccttac | aacgggtact | gggtgggttg | cgactttttt | gttgacagtg | agctttcttc | 300 |
| actgaccatc | tacacagatg | ggaaatggac | cgatgcgtcg | gtcaaaccgg | cagcgttccc | 360 |
| aggtaagctt | gcaattctgc | aacaacgtgc | aagtgtagtt | gctaaaacgc | ggtggtgcag | 420 |
| acttggtatc | aactgggtc | tttgtggcca | ggattcccct | tgggtatcc | gtttctgtga | 480 |
| gctatacccg | cggagtcttt | cagtcctgt | attatgtgct | gatgattgtc | tctgtatagc | 540 |
| tgacctcaac | tccgccttcc | ctgctggtac | taatgtcgcc | gcgacatggg | acaagacact | 600 |
| cgcctacctt | cgtggcaagg | ccatgggtga | ggaattcaac | gacaagggcg | tggacatttt | 660 |
| gctggggcct | gctgctggtc | ctctcggcaa | atacccggac | ggcggcagaa | tctgggaagg | 720 |
| cttctctcct | gatccggttc | tcactggtgt | acttttcgcc | gaaactatca | agggtatcca | 780 |
| agacgcgggt | gtgattgcta | ctgccaagca | ttacattctg | aatgaacagg | agcatttccg | 840 |
| acaggttggc | gaggcccagg | gatatggtta | caacatcacg | gagacgatca | gctccaacgt | 900 |
| ggatgacaag | accatgcacg | agttgtacct | tggtgagta | gttgacactg | caaatgagga | 960 |
| ccttgattga | tttgactgac | ctggaatgca | ggccctttgc | agatgctgtg | cgcggtaaga | 1020 |
| ttttccgtag | acttgacctc | gcgacgaaga | aatcgctgac | gaaccatcgt | agctggcgtt | 1080 |
| ggcgctgtca | tgtgttccta | caatcaaatc | aacaacagct | acggttgtca | aaacagtcaa | 1140 |
| actctcaaca | agctcctcaa | ggctgagctg | gcttccaag | gcttcgtcat | gagtgactgg | 1200 |
| agcgctcacc | acagcggtgt | cggcgctgcc | ctcgctgggt | tggatatgtc | gatgcctgga | 1260 |
| gacatttcct | tcgacgacgg | actctccttc | tggggcacga | acctaactgt | cagtgttctt | 1320 |
| aacggcaccg | ttccagcctg | gcgtgtcgat | gacatggctg | ttcgtatcat | gaccgcgtac | 1380 |
| tacaaggttg | gtcgtgaccg | tcttcgtatt | ccccctaact | tcagctcctg | gacccgggat | 1440 |
| gagtacggct | gggagcattc | tgctgtctcc | gagggagcct | ggaccaaggt | gaacgacttc | 1500 |
| gtcaatgtgc | agcgcagtca | ctctcagatc | atccgtgaga | ttggtgccgc | tagtacagtg | 1560 |
| ctcttgaaga | acacgggtgc | tcttcctttg | accggcaagg | aggttaaagt | gggtgttctc | 1620 |
| ggtgaagacg | ctggttccaa | cccgtggggt | gctaacggct | gccccgaccg | cggctgtgat | 1680 |
| aacggcactc | ttgctatggc | ctggggtagt | ggtactgcca | acttccctta | ccttgtcacc | 1740 |
| cccgagcagg | ctatccagcg | agaggtcatc | agcaacggcg | gcaatgtctt | tgctgtgact | 1800 |
| gataacgggg | ctctcagcca | gatggcagat | gttgcatctc | aatccaggtg | agtgcgggct | 1860 |
| cttagaaaaa | gaacgttctc | tgaatgaagt | ttttaacca | ttgcgaacag | cgtgtctttg | 1920 |
| gtgtttgtca | acgccgactc | tggagagggt | ttcatcagtg | tcgacggcaa | cgagggtgac | 1980 |
| cgcaaaaatc | tcactctgtg | gaagaacggc | gaggccgtca | ttgacactgt | tgtcagccac | 2040 |
| tgcaacaaca | cgattgtggt | tattcacagt | gttgggcccg | tcttgatcga | ccggtggtat | 2100 |
| gataacccca | acgtcactgc | catcatctgg | gccggcttgc | ccggtcagga | gagtggcaac | 2160 |

```
tccctggtcg acgtgctcta tggccgcgtc aacccagcg ccaagacccc gttcacctgg   2220
ggcaagactc ggagtctta cgggctccc ttgctcaccg agcctaacaa tggcaatggt   2280
gctccccagg atgatttcaa cgagggcgtc ttcattgact accgtcactt tgacaagcgc   2340
aatgagaccc ccatttatga gtttggccat ggcttgagct acaccacctt tggttactct   2400
caccttcggg ttcaggccct caatagttcg agttcggcat atgtcccgac tagcggagag   2460
accaagcctg cgccaaccta tggtgagatc ggtagtgccg ccgactacct gtatcccgag   2520
ggtctcaaaa gaattaccaa gtttatttac ccttggctca actcgaccga cctcgaggat   2580
tcttctgacg acccgaacta cggctgggag gactcggagt acattcccga aggcgctagg   2640
gatgggtctc ctcaacccct cctgaaggct ggcggcgctc ctggtggtaa ccctacccct   2700
tatcaggatc ttgttagggt gtcggccacc ataaccaaca ctggtaacgt cgccggttat   2760
gaagtccctc aattggtgag tgacccgcat gttccttgcg ttgcaatttg gctaactcgc   2820
ttctagtatg tttcactggg cggaccgaac gagcctcggg tcgttctgcg caagttcgac   2880
cgaatcttcc tggctcctgg ggagcaaaag gtttggacca cgactcttaa ccgtcgtgat   2940
ctcgccaatt gggatgtgga ggctcaggac tgggtcatca caaagtaccc caagaaagtg   3000
cacgtcggca gctcctcgcg taagctgcct ctgagagcgc ctctgccccg tgtctactag   3060
```

<210> SEQ ID NO 18
<211> LENGTH: 863
<212> TYPE: PRT
<213> ORGANISM: Aspergillus fumigatus

<400> SEQUENCE: 18

```
Met Arg Phe Gly Trp Leu Glu Val Ala Ala Leu Thr Ala Ala Ser Val
1               5                   10                  15

Ala Asn Ala Gln Glu Leu Ala Phe Ser Pro Pro Phe Tyr Pro Ser Pro
                20                  25                  30

Trp Ala Asp Gly Gln Gly Glu Trp Ala Asp Ala His Arg Arg Ala Val
            35                  40                  45

Glu Ile Val Ser Gln Met Thr Leu Ala Glu Lys Val Asn Leu Thr Thr
        50                  55                  60

Gly Thr Gly Trp Glu Met Asp Arg Cys Val Gly Gln Thr Gly Ser Val
65                  70                  75                  80

Pro Arg Leu Gly Ile Asn Trp Gly Leu Cys Gly Gln Asp Ser Pro Leu
                85                  90                  95

Gly Ile Arg Phe Ser Asp Leu Asn Ser Ala Phe Pro Gly Thr Asn
                100                 105                 110

Val Ala Ala Thr Trp Asp Lys Thr Leu Ala Tyr Leu Arg Gly Lys Ala
            115                 120                 125

Met Gly Glu Glu Phe Asn Asp Lys Gly Val Asp Ile Leu Leu Gly Pro
        130                 135                 140

Ala Ala Gly Pro Leu Gly Lys Tyr Pro Asp Gly Gly Arg Ile Trp Glu
145                 150                 155                 160

Gly Phe Ser Pro Asp Pro Val Leu Thr Gly Val Leu Phe Ala Glu Thr
                165                 170                 175

Ile Lys Gly Ile Gln Asp Ala Gly Val Ile Ala Thr Ala Lys His Tyr
                180                 185                 190

Ile Leu Asn Glu Gln Glu His Phe Arg Gln Val Gly Glu Ala Gln Gly
            195                 200                 205

Tyr Gly Tyr Asn Ile Thr Glu Thr Ile Ser Ser Asn Val Asp Asp Lys
```

```
                   210                 215                 220
Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                    245                 250                 255

Gly Cys Gln Asn Ser Gln Thr Leu Asn Lys Leu Leu Lys Ala Glu Leu
                260                 265                 270

Gly Phe Gln Gly Phe Val Met Ser Asp Trp Ser Ala His His Ser Gly
                275                 280                 285

Val Gly Ala Ala Leu Ala Gly Leu Asp Met Ser Met Pro Gly Asp Ile
290                 295                 300

Ser Phe Asp Asp Gly Leu Ser Phe Trp Gly Thr Asn Leu Thr Val Ser
305                 310                 315                 320

Val Leu Asn Gly Thr Val Pro Ala Trp Arg Val Asp Asp Met Ala Val
                325                 330                 335

Arg Ile Met Thr Ala Tyr Tyr Lys Val Gly Arg Asp Arg Leu Arg Ile
                340                 345                 350

Pro Pro Asn Phe Ser Ser Trp Thr Arg Asp Glu Tyr Gly Trp Glu His
                355                 360                 365

Ser Ala Val Ser Glu Gly Ala Trp Thr Lys Val Asn Asp Phe Val Asn
370                 375                 380

Val Gln Arg Ser His Ser Gln Ile Ile Arg Glu Ile Gly Ala Ala Ser
385                 390                 395                 400

Thr Val Leu Leu Lys Asn Thr Gly Ala Leu Pro Leu Thr Gly Lys Glu
                405                 410                 415

Val Lys Val Gly Val Leu Gly Glu Asp Ala Gly Ser Asn Pro Trp Gly
                420                 425                 430

Ala Asn Gly Cys Pro Asp Arg Gly Cys Asp Asn Gly Thr Leu Ala Met
                435                 440                 445

Ala Trp Gly Ser Gly Thr Ala Asn Phe Pro Tyr Leu Val Thr Pro Glu
450                 455                 460

Gln Ala Ile Gln Arg Glu Val Ile Ser Asn Gly Gly Asn Val Phe Ala
465                 470                 475                 480

Val Thr Asp Asn Gly Ala Leu Ser Gln Met Ala Asp Val Ala Ser Gln
                485                 490                 495

Ser Ser Val Ser Leu Val Phe Val Asn Ala Asp Ser Gly Glu Gly Phe
                500                 505                 510

Ile Ser Val Asp Gly Asn Glu Gly Asp Arg Lys Asn Leu Thr Leu Trp
                515                 520                 525

Lys Asn Gly Glu Ala Val Ile Asp Thr Val Val Ser His Cys Asn Asn
530                 535                 540

Thr Ile Val Val Ile His Ser Val Gly Pro Val Leu Ile Asp Arg Trp
545                 550                 555                 560

Tyr Asp Asn Pro Asn Val Thr Ala Ile Ile Trp Ala Gly Leu Pro Gly
                565                 570                 575

Gln Glu Ser Gly Asn Ser Leu Val Asp Val Leu Tyr Gly Arg Val Asn
                580                 585                 590

Pro Ser Ala Lys Thr Pro Phe Thr Trp Gly Lys Thr Arg Glu Ser Tyr
                595                 600                 605

Gly Ala Pro Leu Leu Thr Glu Pro Asn Asn Gly Asn Gly Ala Pro Gln
                610                 615                 620

Asp Asp Phe Asn Glu Gly Val Phe Ile Asp Tyr Arg His Phe Asp Lys
625                 630                 635                 640
```

```
Arg Asn Glu Thr Pro Ile Tyr Glu Phe Gly His Gly Leu Ser Tyr Thr
                645                 650                 655

Thr Phe Gly Tyr Ser His Leu Arg Val Gln Ala Leu Asn Ser Ser Ser
            660                 665                 670

Ser Ala Tyr Val Pro Thr Ser Gly Glu Thr Lys Pro Ala Pro Thr Tyr
        675                 680                 685

Gly Glu Ile Gly Ser Ala Ala Asp Tyr Leu Tyr Pro Glu Gly Leu Lys
    690                 695                 700

Arg Ile Thr Lys Phe Ile Tyr Pro Trp Leu Asn Ser Thr Asp Leu Glu
705                 710                 715                 720

Asp Ser Ser Asp Asp Pro Asn Tyr Gly Trp Glu Asp Ser Glu Tyr Ile
                725                 730                 735

Pro Glu Gly Ala Arg Asp Gly Ser Pro Gln Pro Leu Leu Lys Ala Gly
            740                 745                 750

Gly Ala Pro Gly Gly Asn Pro Thr Leu Tyr Gln Asp Leu Val Arg Val
        755                 760                 765

Ser Ala Thr Ile Thr Asn Thr Gly Asn Val Ala Gly Tyr Glu Val Pro
    770                 775                 780

Gln Leu Tyr Val Ser Leu Gly Gly Pro Asn Glu Pro Arg Val Val Leu
785                 790                 795                 800

Arg Lys Phe Asp Arg Ile Phe Leu Ala Pro Gly Glu Gln Lys Val Trp
                805                 810                 815

Thr Thr Thr Leu Asn Arg Arg Asp Leu Ala Asn Trp Asp Val Glu Ala
            820                 825                 830

Gln Asp Trp Val Ile Thr Lys Tyr Pro Lys Lys Val His Val Gly Ser
        835                 840                 845

Ser Ser Arg Lys Leu Pro Leu Arg Ala Pro Leu Pro Arg Val Tyr
    850                 855                 860

<210> SEQ ID NO 19
<211> LENGTH: 2800
<212> TYPE: DNA
<213> ORGANISM: Penicillium brasilianum

<400> SEQUENCE: 19
tgaaaatgca gggttctaca atctttctgg ctttcgcctc atgggcgagc caggttgctg      60
ccattgcgca gcccatacag aagcacgagg tttgttttat cttgctcatg gacgtgcttt     120
gacttgacta attgttttac atacagcccg gatttctgca cgggccccaa gccatagaat     180
cgttctcaga accgttctac ccgtcgccct ggatgaatcc tcacgccgag ggctgggagg     240
ccgcatatca gaaagctcaa gattttgtct cgcaactcac tatcttggag aaaataaatc     300
tgaccaccgg tgttgggtaa gtctctccga ctgcttctgg gtcacggtgc gacgagccac     360
tgactttttg aagctgggaa atgggccgt gtgtaggaaa cactggatca attcctcgtc      420
tcggattcaa aggattttgt acccaggatt caccacaggg tgttcggttc gcagattatt     480
cctccgcttt cacatctagc caaatggccg ccgcaacatt tgaccgctca attctttatc     540
aacgaggcca agccatggca caggaacaca aggctaaggg tatcacaatt caattgggcc     600
ctgttgccgg ccctctcggt cgcatccccg agggcggccg caactgggaa ggattctccc     660
ctgatcctgt cttgactggt atagccatgg ctgagacaat aagggcatg caggatactg       720 gagtgattgc ttgcgctaaa cattatattg gaaacgagca ggagcacttc cgtcaagtgg     780
gtgaagctgc gggtcacgga tacactattt ccgatactat ttcatctaat attgacgacc     840
```

```
gtgctatgca tgagctatac ttgtggccat tgctgatgc cgttcgcgct ggtgtgggtt    900
ctttcatgtg ctcatactct cagatcaaca actcctacgg atgccaaaac agtcagaccc    960
tcaacaagct cctcaagagc gaattgggct tccaaggctt tgtcatgagc gattggggtg   1020
cccatcactc tggagtgtca tcggcgctag ctggacttga tatgagcatg ccgggtgata   1080
ccgaatttga ttctggcttg agcttctggg gctctaacct caccattgca attctgaacg   1140
gcacggttcc cgaatggcgc ctggatgaca tggcgatgcg aattatggct gcatacttca   1200
aagttggcct tactattgag atcaaccag atgtcaactt caatgcctgg acccatgaca   1260
cctacggata taaatacgct tatagcaagg aagattacga gcaggtcaac tggcatgtcg   1320
atgttcgcag cgaccacaat aagctcattc gcgagactgc cgcgaagggt acagttctgc   1380
tgaagaacaa ctttcatgct ctccctctga agcagcccag gttcgtggcc gtcgttggtc   1440
aggatgccgg gccaaacccc aagggcccta acggctgcgc agaccgagga tgcgaccaag   1500
gcactctcgc aatgggatgg ggctcagggt ctaccgaatt cccttacctg gtcactcctg   1560
acactgctat tcagtcaaag gtcctcgaat acggggtcg atacgagagt attttgata    1620
actatgacga caatgctatc ttgtcgcttg tctcacagcc tgatgcaacc tgtatcgttt   1680
ttgcaaatgc cgattccggt gaaggctaca tcactgtcga caacaactgg ggtgaccgca   1740
acaatctgac cctctggcaa aatgccgatc aagtgattag cactgtcagc tcgcgatgca   1800
acaacacaat cgttgttctc cactctgtcg gaccagtgtt gctaaatggt atatatgagc   1860
acccgaacat cacagctatt gtctgggcag ggatgccagg cgaagaatct ggcaatgctc   1920
tcgtggatat tctttggggc aatgttaacc ctgccggtcg cactccgttc acctgggcca   1980
aaagtcgaga ggactatggc actgatataa tgtacgagcc caacaacggc cagcgtgcgc   2040
ctcagcagga tttcaccgag agcatctacc tcgactaccg ccatttcgac aaagctggta   2100
tcgagccaat ttacgagttt ggattcggcc tctcctatac caccttcgaa tactctgacc   2160
tccgtgttgt gaagaagtat gttcaaccat acagtcccac gaccggcacc ggtgctcaag   2220
caccttccat cggacagcca cctagccaga acctggatac ctacaagttc cctgctacat   2280
acaagtacat caaaaccttc atttatccct acctgaacag cactgtctcc ctccgcgctg   2340
cttccaagga tcccgaatac ggtcgtacag actttatccc accccacgcg cgtgatggct   2400
cccctcaacc tctcaacccc gctggagacc cagtggccag tggtgaaaac aacatgctct   2460
acgacgaact ttacgaggtc actgcacaga tcaaaaacac tggcgacgtg gccggcgacg   2520
aagtcgtcca gctttacgta gatctcgggg gtgacaaccc gcctcgtcag ttgagaaact   2580
ttgacaggtt ttatctgctg cccggtcaga gctcaacatt ccgggctaca ttgacgcgcc   2640
gtgatttgag caactgggat attgaggcgc agaactggcg agttacggaa tcgcctaaga   2700
gagtgtatgt tggacggtcg agtcgggatt tgccgctgag ctcacaattg gagtaatgat   2760
catgtctacc aatagatgtt gaatgtctgg tgtggatatt                          2800
```

<210> SEQ ID NO 20
<211> LENGTH: 878
<212> TYPE: PRT
<213> ORGANISM: Penicillium brasilianum
<400> SEQUENCE: 20

Met Gln Gly Ser Thr Ile Phe Leu Ala Phe Ala Ser Trp Ala Ser Gln
1               5                   10                  15

Val Ala Ala Ile Ala Gln Pro Ile Gln Lys His Glu Pro Gly Phe Leu
            20                  25                  30

-continued

```
His Gly Pro Gln Ala Ile Glu Ser Phe Ser Glu Pro Phe Tyr Pro Ser
    35                  40                  45
Pro Trp Met Asn Pro His Ala Glu Gly Trp Glu Ala Ala Tyr Gln Lys
 50                  55                  60
Ala Gln Asp Phe Val Ser Gln Leu Thr Ile Leu Glu Lys Ile Asn Leu
 65                  70                  75                  80
Thr Thr Gly Val Gly Trp Glu Asn Gly Pro Cys Val Gly Asn Thr Gly
                 85                  90                  95
Ser Ile Pro Arg Leu Gly Phe Lys Gly Phe Cys Thr Gln Asp Ser Pro
                100                 105                 110
Gln Gly Val Arg Phe Ala Asp Tyr Ser Ser Ala Phe Thr Ser Ser Gln
                115                 120                 125
Met Ala Ala Thr Phe Asp Arg Ser Ile Leu Tyr Gln Arg Gly Gln
130                 135                 140
Ala Met Ala Gln Glu His Lys Ala Lys Gly Ile Thr Ile Gln Leu Gly
145                 150                 155                 160
Pro Val Ala Gly Pro Leu Gly Arg Ile Pro Glu Gly Arg Asn Trp
                165                 170                 175
Glu Gly Phe Ser Pro Asp Pro Val Leu Thr Gly Ile Ala Met Ala Glu
                180                 185                 190
Thr Ile Lys Gly Met Gln Asp Thr Gly Val Ile Ala Cys Ala Lys His
                195                 200                 205
Tyr Ile Gly Asn Glu Gln Glu His Phe Arg Gln Val Gly Glu Ala Ala
    210                 215                 220
Gly His Gly Tyr Thr Ile Ser Asp Thr Ile Ser Asn Ile Asp Asp
225                 230                 235                 240
Arg Ala Met His Glu Leu Tyr Leu Trp Pro Phe Ala Asp Ala Val Arg
                245                 250                 255
Ala Gly Val Gly Ser Phe Met Cys Ser Tyr Ser Gln Ile Asn Asn Ser
                260                 265                 270
Tyr Gly Cys Gln Asn Ser Gln Thr Leu Asn Lys Leu Leu Lys Ser Glu
    275                 280                 285
Leu Gly Phe Gln Gly Phe Val Met Ser Asp Trp Gly Ala His His Ser
    290                 295                 300
Gly Val Ser Ser Ala Leu Ala Gly Leu Asp Met Ser Met Pro Gly Asp
305                 310                 315                 320
Thr Glu Phe Asp Ser Gly Leu Ser Phe Trp Gly Ser Asn Leu Thr Ile
                325                 330                 335
Ala Ile Leu Asn Gly Thr Val Pro Glu Trp Arg Leu Asp Asp Met Ala
                340                 345                 350
Met Arg Ile Met Ala Ala Tyr Phe Lys Val Gly Leu Thr Ile Glu Asp
                355                 360                 365
Gln Pro Asp Val Asn Phe Asn Ala Trp Thr His Asp Thr Tyr Gly Tyr
370                 375                 380
Lys Tyr Ala Tyr Ser Lys Glu Asp Tyr Glu Gln Val Asn Trp His Val
385                 390                 395                 400
Asp Val Arg Ser Asp His Asn Lys Leu Ile Arg Glu Thr Ala Ala Lys
                405                 410                 415
Gly Thr Val Leu Leu Lys Asn Asn Phe His Ala Leu Pro Leu Lys Gln
                420                 425                 430
Pro Arg Phe Val Ala Val Val Gly Gln Asp Ala Gly Pro Asn Pro Lys
                435                 440                 445
```

```
Gly Pro Asn Gly Cys Ala Asp Arg Gly Cys Asp Gln Gly Thr Leu Ala
    450                 455                 460

Met Gly Trp Gly Ser Gly Ser Thr Glu Phe Pro Tyr Leu Val Thr Pro
465                 470                 475                 480

Asp Thr Ala Ile Gln Ser Lys Val Leu Glu Tyr Gly Gly Arg Tyr Glu
                485                 490                 495

Ser Ile Phe Asp Asn Tyr Asp Asn Ala Ile Leu Ser Leu Val Ser
                500                 505                 510

Gln Pro Asp Ala Thr Cys Ile Val Phe Ala Asn Ala Asp Ser Gly Glu
                515                 520                 525

Gly Tyr Ile Thr Val Asp Asn Asn Trp Gly Asp Arg Asn Asn Leu Thr
    530                 535                 540

Leu Trp Gln Asn Ala Asp Gln Val Ile Ser Thr Val Ser Ser Arg Cys
545                 550                 555                 560

Asn Asn Thr Ile Val Val Leu His Ser Val Gly Pro Val Leu Leu Asn
                565                 570                 575

Gly Ile Tyr Glu His Pro Asn Ile Thr Ala Ile Val Trp Ala Gly Met
                580                 585                 590

Pro Gly Glu Glu Ser Gly Asn Ala Leu Val Asp Ile Leu Trp Gly Asn
                595                 600                 605

Val Asn Pro Ala Gly Arg Thr Pro Phe Thr Trp Ala Lys Ser Arg Glu
    610                 615                 620

Asp Tyr Gly Thr Asp Ile Met Tyr Glu Pro Asn Asn Gly Gln Arg Ala
625                 630                 635                 640

Pro Gln Gln Asp Phe Thr Glu Ser Ile Tyr Leu Asp Tyr Arg His Phe
                645                 650                 655

Asp Lys Ala Gly Ile Glu Pro Ile Tyr Glu Phe Gly Phe Gly Leu Ser
                660                 665                 670

Tyr Thr Thr Phe Glu Tyr Ser Asp Leu Arg Val Val Lys Lys Tyr Val
                675                 680                 685

Gln Pro Tyr Ser Pro Thr Thr Gly Thr Gly Ala Gln Ala Pro Ser Ile
    690                 695                 700

Gly Gln Pro Pro Ser Gln Asn Leu Asp Thr Tyr Lys Phe Pro Ala Thr
705                 710                 715                 720

Tyr Lys Tyr Ile Lys Thr Phe Ile Tyr Pro Tyr Leu Asn Ser Thr Val
                725                 730                 735

Ser Leu Arg Ala Ala Ser Lys Asp Pro Glu Tyr Gly Arg Thr Asp Phe
                740                 745                 750

Ile Pro Pro His Ala Arg Asp Gly Ser Pro Gln Pro Leu Asn Pro Ala
    755                 760                 765

Gly Asp Pro Val Ala Ser Gly Gly Asn Asn Met Leu Tyr Asp Glu Leu
770                 775                 780

Tyr Glu Val Thr Ala Gln Ile Lys Asn Thr Gly Asp Val Ala Gly Asp
785                 790                 795                 800

Glu Val Val Gln Leu Tyr Val Asp Leu Gly Gly Asp Asn Pro Pro Arg
                805                 810                 815

Gln Leu Arg Asn Phe Asp Arg Phe Tyr Leu Leu Pro Gly Gln Ser Ser
                820                 825                 830

Thr Phe Arg Ala Thr Leu Thr Arg Arg Asp Leu Ser Asn Trp Asp Ile
                835                 840                 845

Glu Ala Gln Asn Trp Arg Val Thr Glu Ser Pro Lys Arg Val Tyr Val
    850                 855                 860

Gly Arg Ser Ser Arg Asp Leu Pro Leu Ser Ser Gln Leu Glu
```

<210> SEQ ID NO 21
<211> LENGTH: 2583
<212> TYPE: DNA
<213> ORGANISM: Aspergillus niger

<400> SEQUENCE: 21

| | | | | | |
|---|---|---|---|---|---|
| atgaggttca | ctttgatcga | ggcggtggct | ctgactgccg | tctcgctggc | cagcgctgat | 60 |
| gaattggcct | actccccacc | gtattaccca | tcccccttggg | ccaatggcca | gggcgactgg | 120 |
| gcgcaggcat | accagcgcgc | tgttgatatt | gtctcgcaaa | tgacattgga | tgagaaggtc | 180 |
| aatctgacca | caggaactgg | atgggaattg | gaactatgtg | ttggtcagac | tggcggtgtt | 240 |
| ccccgattgg | gagttccggg | aatgtgttta | caggatagcc | ctctgggcgt | tcgcgactcc | 300 |
| gactacaact | ctgctttccc | tgccggcatg | aacgtggctg | caacctggga | caagaatctg | 360 |
| gcataccttc | gcggcaaggc | tatgggtcag | gaatttagtg | acaagggtgc | cgatatccaa | 420 |
| ttgggtccag | ctgccggccc | tctcggtaga | agtcccgacg | gtggtcgtaa | ctgggagggc | 480 |
| ttctccccag | accctgccct | aagtggtgtg | ctctttgccg | agaccatcaa | gggtatccaa | 540 |
| gatgctggtg | tggttgcgac | ggctaagcac | tacattgctt | acgagcaaga | gcatttccgt | 600 |
| caggcgcctg | aagcccaagg | ttttggattt | aatatttccg | agagtggaag | tgcgaacctc | 660 |
| gatgataaga | ctatgcacga | gctgtacctc | tggcccttcg | cggatgccat | ccgtgcaggt | 720 |
| gctggcgctg | tgatgtgctc | ctacaaccag | atcaacaaca | gttatggctg | ccagaacagc | 780 |
| tacactctga | acaagctgct | caaggccgag | ctgggcttcc | agggctttgt | catgagtgat | 840 |
| tgggctgctc | accatgctgg | tgtgagtggt | gctttggcag | gattggatat | gtctatgcca | 900 |
| ggagacgtcg | actacgacag | tggtacgtct | tactggggta | caaacttgac | cattagcgtg | 960 |
| ctcaacggaa | cggtgcccca | tggcgtgtt | gatgacatgg | ctgtccgcat | catggccgcc | 1020 |
| tactacaagg | tcgccgtgac | ccgtctgtgg | actcctccca | acttcagctc | atggaccaga | 1080 |
| gatgaatacg | gctacaagta | ctactacgtg | tcggagggac | cgtacgagaa | ggtcaaccag | 1140 |
| tacgtgaatg | tgcaacgcaa | ccacagcgaa | ctgattcgcc | gcattggagc | ggacagcacg | 1200 |
| gtgctcctca | agaacgacgg | cgctctgcct | ttgactggta | aggagcgcct | ggtcgcgctt | 1260 |
| atcggagaag | atgcgggctc | caaccctttat | ggtgccaacg | gctgcagtga | ccgtggatgc | 1320 |
| gacaatggaa | cattggcgat | gggctgggga | agtggtactg | ccaacttccc | atacctggtg | 1380 |
| accccccgagc | aggccatctc | aaacgaggtg | cttaagcaca | gaatggtgt | attcaccgcc | 1440 |
| accgataact | gggctatcga | tcagattgag | gcgcttgcta | agaccgccag | tgtctctctt | 1500 |
| gtctttgtca | cgccgactc | tggtgagggt | tacatcaatg | tggacggaaa | cctgggtgac | 1560 |
| cgcaggaacc | tgaccctgtg | gaggaacggc | gataatgtga | tcaaggctgc | tgctagcaac | 1620 |
| tgcaacaaca | caatcgttgt | cattcactct | gtcggaccag | tcttggttaa | cgagtggtac | 1680 |
| gacaaccccca | atgttaccgc | tatcctctgg | ggtggtttgc | ccggtcagga | gtctggcaac | 1740 |
| tctcttgccg | acgtcctcta | tggccgtgtc | aaccccggtg | ccaagtcgcc | ctttacctgg | 1800 |
| ggcaagactc | gtgaggccta | ccaagactac | ttggtcaccg | agcccaacaa | cggcaacgga | 1860 |
| gccccctcagg | aagactttgt | cgagggcgtc | ttcattgact | accgtggatt | tgacaagcgc | 1920 |
| aacgagaccc | cgatctacga | gttcggctat | ggtctgagct | acaccacttt | caactactcg | 1980 |
| aaccttgagg | tgcaggtgct | gagcgcccct | gcatacgagc | tgcttcgggg | tgagaccgag | 2040 |
| gcagcgccaa | ccttcggaga | ggttggaaat | gcgtcggatt | acctctaccc | cagcggattg | 2100 |

-continued

```
cagagaatta ccaagttcat ctacccctgg ctcaacggta ccgatctcga ggcatcttcc    2160
ggggatgcta gctacgggca ggactcctcc gactatcttc ccgagggagc accgatggc     2220 tctgcgcaac cgatcctgcc tgccggtggc ggtcctggcg gcaaccctcg cctgtacgac    2280
gagctcatcc gcgtgtcagt gaccatcaag aacaccggca aggttgctgg tgatgaagtt    2340
ccccaactgt atgtttccct tggcggtccc aatgagccca agatcgtgct gcgtcaattc    2400
gagcgcatca cgctgcagcc gtcggaggag acgaagtgga gcacgactct gacgcgccgt    2460
gaccttgcaa actggaatgt tgagaagcag gactgggaga ttacgtcgta tcccaagatg    2520
gtgtttgtcg gaagctcctc gcggaagctg ccgctccggg cgtctctgcc tactgttcac    2580
taa                                                                  2583
```

<210> SEQ ID NO 22
<211> LENGTH: 860
<212> TYPE: PRT
<213> ORGANISM: Aspergillus niger

<400> SEQUENCE: 22

```
Met Arg Phe Thr Leu Ile Glu Ala Val Ala Leu Thr Ala Val Ser Leu
1               5                   10                  15

Ala Ser Ala Asp Glu Leu Ala Tyr Ser Pro Pro Tyr Pro Ser Pro
            20                  25                  30

Trp Ala Asn Gly Gln Gly Asp Trp Ala Gln Ala Tyr Gln Arg Ala Val
        35                  40                  45

Asp Ile Val Ser Gln Met Thr Leu Asp Glu Lys Val Asn Leu Thr Thr
    50                  55                  60

Gly Thr Gly Trp Glu Leu Glu Leu Cys Val Gly Gln Thr Gly Val
65                  70                  75                  80

Pro Arg Leu Gly Val Pro Gly Met Cys Leu Gln Asp Ser Pro Leu Gly
                85                  90                  95

Val Arg Asp Ser Asp Tyr Asn Ser Ala Phe Pro Ala Gly Met Asn Val
            100                 105                 110

Ala Ala Thr Trp Asp Lys Asn Leu Ala Tyr Leu Arg Gly Lys Ala Met
        115                 120                 125

Gly Gln Glu Phe Ser Asp Lys Gly Ala Asp Ile Gln Leu Gly Pro Ala
    130                 135                 140

Ala Gly Pro Leu Gly Arg Ser Pro Asp Gly Gly Arg Asn Trp Glu Gly
145                 150                 155                 160

Phe Ser Pro Asp Pro Ala Leu Ser Gly Val Leu Phe Ala Glu Thr Ile
                165                 170                 175

Lys Gly Ile Gln Asp Ala Gly Val Val Ala Thr Ala Lys His Tyr Ile
            180                 185                 190

Ala Tyr Glu Gln Glu His Phe Arg Gln Ala Pro Glu Ala Gln Gly Phe
        195                 200                 205

Gly Phe Asn Ile Ser Glu Ser Gly Ser Ala Asn Leu Asp Asp Lys Thr
    210                 215                 220

Met His Glu Leu Tyr Leu Trp Pro Phe Ala Asp Ala Ile Arg Ala Gly
225                 230                 235                 240

Ala Gly Ala Val Met Cys Ser Tyr Asn Gln Ile Asn Asn Ser Tyr Gly
                245                 250                 255

Cys Gln Asn Ser Tyr Thr Leu Asn Lys Leu Leu Lys Ala Glu Leu Gly
            260                 265                 270

Phe Gln Gly Phe Val Met Ser Asp Trp Ala Ala His His Ala Gly Val
```

```
                275                 280                 285
Ser Gly Ala Leu Ala Gly Leu Asp Met Ser Met Pro Gly Asp Val Asp
            290                 295                 300
Tyr Asp Ser Gly Thr Ser Tyr Trp Gly Thr Asn Leu Thr Ile Ser Val
305                 310                 315                 320
Leu Asn Gly Thr Val Pro Gln Trp Arg Val Asp Asp Met Ala Val Arg
                325                 330                 335
Ile Met Ala Ala Tyr Tyr Lys Val Gly Arg Asp Arg Leu Trp Thr Pro
                340                 345                 350
Pro Asn Phe Ser Ser Trp Thr Arg Asp Glu Tyr Gly Tyr Lys Tyr Tyr
                355                 360                 365
Tyr Val Ser Glu Gly Pro Tyr Glu Lys Val Asn Gln Tyr Val Asn Val
            370                 375                 380
Gln Arg Asn His Ser Glu Leu Ile Arg Arg Ile Gly Ala Asp Ser Thr
385                 390                 395                 400
Val Leu Leu Lys Asn Asp Gly Ala Leu Pro Leu Thr Gly Lys Glu Arg
                405                 410                 415
Leu Val Ala Leu Ile Gly Glu Asp Ala Gly Ser Asn Pro Tyr Gly Ala
                420                 425                 430
Asn Gly Cys Ser Asp Arg Gly Cys Asp Asn Gly Thr Leu Ala Met Gly
            435                 440                 445
Trp Gly Ser Gly Thr Ala Asn Phe Pro Tyr Leu Val Thr Pro Glu Gln
            450                 455                 460
Ala Ile Ser Asn Glu Val Leu Lys His Lys Asn Gly Val Phe Thr Ala
465                 470                 475                 480
Thr Asp Asn Trp Ala Ile Asp Gln Ile Glu Ala Leu Ala Lys Thr Ala
                485                 490                 495
Ser Val Ser Leu Val Phe Val Asn Ala Asp Ser Gly Glu Gly Tyr Ile
            500                 505                 510
Asn Val Asp Gly Asn Leu Gly Asp Arg Arg Asn Leu Thr Leu Trp Arg
            515                 520                 525
Asn Gly Asp Asn Val Ile Lys Ala Ala Ala Ser Asn Cys Asn Asn Thr
            530                 535                 540
Ile Val Val Ile His Ser Val Gly Pro Val Leu Val Asn Glu Trp Tyr
545                 550                 555                 560
Asp Asn Pro Asn Val Thr Ala Ile Leu Trp Gly Gly Leu Pro Gly Gln
                565                 570                 575
Glu Ser Gly Asn Ser Leu Ala Asp Val Leu Tyr Gly Arg Val Asn Pro
            580                 585                 590
Gly Ala Lys Ser Pro Phe Thr Trp Gly Lys Thr Arg Glu Ala Tyr Gln
            595                 600                 605
Asp Tyr Leu Val Thr Glu Pro Asn Asn Gly Asn Gly Ala Pro Gln Glu
            610                 615                 620
Asp Phe Val Glu Gly Val Phe Ile Asp Tyr Arg Gly Phe Asp Lys Arg
625                 630                 635                 640
Asn Glu Thr Pro Ile Tyr Glu Phe Gly Tyr Gly Leu Ser Tyr Thr Thr
                645                 650                 655
Phe Asn Tyr Ser Asn Leu Glu Val Gln Val Leu Ser Ala Pro Ala Tyr
                660                 665                 670
Glu Pro Ala Ser Gly Glu Thr Glu Ala Ala Pro Thr Phe Gly Glu Val
            675                 680                 685
Gly Asn Ala Ser Asp Tyr Leu Tyr Pro Ser Gly Leu Gln Arg Ile Thr
            690                 695                 700
```

```
Lys Phe Ile Tyr Pro Trp Leu Asn Gly Thr Asp Leu Glu Ala Ser Ser
705                 710                 715                 720

Gly Asp Ala Ser Tyr Gly Gln Asp Ser Asp Tyr Leu Pro Glu Gly
            725                 730                 735

Ala Thr Asp Gly Ser Ala Gln Pro Ile Leu Pro Ala Gly Gly Pro
            740                 745                 750

Gly Gly Asn Pro Arg Leu Tyr Asp Glu Leu Ile Arg Val Ser Val Thr
        755                 760                 765

Ile Lys Asn Thr Gly Lys Val Ala Gly Asp Glu Val Pro Gln Leu Tyr
770                 775                 780

Val Ser Leu Gly Gly Pro Asn Glu Pro Lys Ile Val Leu Arg Gln Phe
785                 790                 795                 800

Glu Arg Ile Thr Leu Gln Pro Ser Glu Glu Thr Lys Trp Ser Thr Thr
                805                 810                 815

Leu Thr Arg Arg Asp Leu Ala Asn Trp Asn Val Glu Lys Gln Asp Trp
            820                 825                 830

Glu Ile Thr Ser Tyr Pro Lys Met Val Phe Val Gly Ser Ser Ser Arg
835                 840                 845

Lys Leu Pro Leu Arg Ala Ser Leu Pro Thr Val His
    850                 855                 860

<210> SEQ ID NO 23
<211> LENGTH: 2583
<212> TYPE: DNA
<213> ORGANISM: Aspergillus aculeatus

<400> SEQUENCE: 23
atgaagctca gttggcttga ggcggctgcc ttgacggctg cttcagtcgt cagcgctgat      60
gaactggcgt tctctcctcc tttctacccc tctccgtggg ccaatggcca gggagagtgg     120
gcggaagcct accagcgtgc agtggccatt gtatcccaga tgactctgga tgagaaggtc     180
aacctgacca ccggaactgg atgggagctg agaagtgcg tcggtcagac tggtggtgtc      240
ccaagactga acatcggtgg catgtgtctt caggacagtc ccttgggaat tcgtgatagt     300
gactacaatt cggctttccc tgctggtgtc aacgttgctg cgacatggga caagaacctt     360
gcttatctac gtggtcaggc tatgggtcaa gagttcagtg acaaaggaat tgatgttcaa     420
ttgggaccgg ccgcgggtcc cctcggcagg agccctgatg gaggtcgcaa ctgggaaggt     480
ttctctccag acccggctct tactggtgtg ctctttgcgg agacgattaa gggtattcaa     540
gacgctggtg tcgtggcgac agccaagcat acattctca atgagcaaga gcatttccgc       600
caggtcgcag aggctgcggg ctacggattc aatatctccg acacgatcag ctctaacgtt     660
gatgacaaga ccattcatga aatgtacctc tggcccttcg cggatgccgt tcgcgccggc     720
gttggcgcca tcatgtgttc ctacaaccag atcaacaaca gctacggttg ccagaacagt     780
tacactctga caagcttct gaaggccgag ctcggcttcc agggctttgt gatgtctgac      840
tggggtgctc accacagtgg tgttggctct gctttggccg gcttggatat gtcaatgcct     900
ggcgatatca ccttcgattc tgccactagt ttctggggta ccaacctgac cattgctgtg     960
ctcaacggta ccgtcccgca gtggcgcgtt gacgacatgg ctgtccgtat catggctgcc    1020
tactacaagg ttggccgcga ccgcctgtac cagccgccta acttcagctc ctggactcgc    1080
gatgaatacg gcttcaagta tttctacccc caggaagggc cctatgagaa ggtcaatcac    1140
tttgtcaatg tgcagcgcaa ccacagcgag gttattcgca agttgggagc agacagtact    1200
```

```
gttctactga agaacaacaa tgccctgccg ctgaccggaa aggagcgcaa agttgcgatc    1260
ctgggtgaag atgctggatc caactcgtac ggtgccaatg ctgctctga ccgtggctgt    1320
gacaacggta ctcttgctat ggcttgtggt agcggcactg ccgaattccc atatctcgtg    1380
accccctgagc aggctattca agccgaggtg ctcaagcata agggcagcgt ctacgccatc    1440
acggacaact gggcgctgag ccaggtggag accctcgcta acaagccag tgtctctctt    1500
gtatttgtca actcggacgc gggagagggc tatatctccg tggacggaaa cgagggcgac    1560
cgcaacaacc tcaccctctg gaagaacggc gacaacctca tcaaggctgc tgcaaacaac    1620
tgcaacaaca ccatcgttgt catccactcc gttggacctg ttttggttga cgagtggtat    1680
gaccacccca acgttactgc catcctctgg gcgggcttgc ctggccagga gtctggcaac    1740
tccttggctg acgtgctcta cggccgcgtc aacccgggcg ccaaatctcc attcacctgg    1800
ggcaagacga gggaggcgta cggggattac cttgtccgtg agctcaacaa cggcaacgga    1860
gctccccaag atgatttctc ggaaggtgtt ttcattgact accgcggatt cgacaagcgc    1920
aatgagaccc cgatctacga gttcggacat ggtctgagct acaccacttt caactactct    1980
ggccttcaca tccaggttct caacgcttcc tccaacgctc aagtagccac tgagactggc    2040
gccgctccca ccttcggaca gtcggcaat gcctctgact acgtgtaccc tgagggattg    2100
accagaatca gcaagttcat ctatccctgg cttaattcca cagacctgaa ggcctcatct    2160
ggcgacccgt actatggagt cgacaccgcg agcacgtgc ccgagggtgc tactgatggc    2220
tctccgcagc ccgttctgcc tgccggtggt ggctctggtg gtaacccgcg cctctacgat    2280
gagttgatcc gtgtttcggt gacagtcaag aacactggtc gtgttgccgg tgatgctgtg    2340
cctcaattgt atgttccct tggtggaccc aatgagccca aggttgtgtt gcgcaaattc    2400
gaccgcctca ccctcaagcc ctccgaggag acggtgtgga cgactaccct gacccgccgc    2460
gatctgtcta ctgggacgt tgcggctcag gactgggtca tcacttctta cccgaagaag    2520
gtccatgttg gtagctcttc gcgtcagctg ccccttcacg cggcgctccc gaaggtgcaa    2580
tga                                                                 2583
```

<210> SEQ ID NO 24  
<211> LENGTH: 860  
<212> TYPE: PRT  
<213> ORGANISM: Aspergillus aculeatus
<400> SEQUENCE: 24

```
Met Lys Leu Ser Trp Leu Glu Ala Ala Ala Leu Thr Ala Ala Ser Val
1               5                   10                  15

Val Ser Ala Asp Glu Leu Ala Phe Ser Pro Pro Phe Tyr Pro Ser Pro
            20                  25                  30

Trp Ala Asn Gly Gln Gly Glu Trp Ala Glu Ala Tyr Gln Arg Ala Val
        35                  40                  45

Ala Ile Val Ser Gln Met Thr Leu Asp Glu Lys Val Asn Leu Thr Thr
    50                  55                  60

Gly Thr Gly Trp Glu Leu Glu Lys Cys Val Gly Gln Thr Gly Gly Val
65                  70                  75                  80

Pro Arg Leu Asn Ile Gly Gly Met Cys Leu Gln Asp Ser Pro Leu Gly
                85                  90                  95

Ile Arg Asp Ser Asp Tyr Asn Ser Ala Phe Pro Ala Gly Val Asn Val
            100                 105                 110

Ala Ala Thr Trp Asp Lys Asn Leu Ala Tyr Leu Arg Gly Gln Ala Met
        115                 120                 125
```

```
Gly Gln Glu Phe Ser Asp Lys Gly Ile Asp Val Gln Leu Gly Pro Ala
    130                 135                 140
Ala Gly Pro Leu Gly Arg Ser Pro Asp Gly Gly Arg Asn Trp Glu Gly
145                 150                 155                 160
Phe Ser Pro Asp Pro Ala Leu Thr Gly Val Leu Phe Ala Glu Thr Ile
                165                 170                 175
Lys Gly Ile Gln Asp Ala Gly Val Val Ala Thr Ala Lys His Tyr Ile
                180                 185                 190
Leu Asn Glu Gln Glu His Phe Arg Gln Val Ala Glu Ala Ala Gly Tyr
            195                 200                 205
Gly Phe Asn Ile Ser Asp Thr Ile Ser Ser Asn Val Asp Asp Lys Thr
    210                 215                 220
Ile His Glu Met Tyr Leu Trp Pro Phe Ala Asp Ala Val Arg Ala Gly
225                 230                 235                 240
Val Gly Ala Ile Met Cys Ser Tyr Asn Gln Ile Asn Asn Ser Tyr Gly
                245                 250                 255
Cys Gln Asn Ser Tyr Thr Leu Asn Lys Leu Leu Lys Ala Glu Leu Gly
                260                 265                 270
Phe Gln Gly Phe Val Met Ser Asp Trp Gly Ala His His Ser Gly Val
            275                 280                 285
Gly Ser Ala Leu Ala Gly Leu Asp Met Ser Met Pro Gly Asp Ile Thr
    290                 295                 300
Phe Asp Ser Ala Thr Ser Phe Trp Gly Thr Asn Leu Thr Ile Ala Val
305                 310                 315                 320
Leu Asn Gly Thr Val Pro Gln Trp Arg Val Asp Met Ala Val Arg
                325                 330                 335
Ile Met Ala Ala Tyr Tyr Lys Val Gly Arg Asp Arg Leu Tyr Gln Pro
                340                 345                 350
Pro Asn Phe Ser Ser Trp Thr Arg Asp Glu Tyr Gly Phe Lys Tyr Phe
            355                 360                 365
Tyr Pro Gln Glu Gly Pro Tyr Glu Lys Val Asn His Phe Val Asn Val
    370                 375                 380
Gln Arg Asn His Ser Glu Val Ile Arg Lys Leu Gly Ala Asp Ser Thr
385                 390                 395                 400
Val Leu Leu Lys Asn Asn Asn Ala Leu Pro Leu Thr Gly Lys Glu Arg
                405                 410                 415
Lys Val Ala Ile Leu Gly Glu Asp Ala Gly Ser Asn Ser Tyr Gly Ala
                420                 425                 430
Asn Gly Cys Ser Asp Arg Gly Cys Asp Asn Gly Thr Leu Ala Met Ala
            435                 440                 445
Trp Gly Ser Gly Thr Ala Glu Phe Pro Tyr Leu Val Thr Pro Glu Gln
    450                 455                 460
Ala Ile Gln Ala Glu Val Leu Lys His Lys Gly Ser Val Tyr Ala Ile
465                 470                 475                 480
Thr Asp Asn Trp Ala Leu Ser Gln Val Glu Thr Leu Ala Lys Gln Ala
                485                 490                 495
Ser Val Ser Leu Val Phe Val Asn Ser Asp Ala Gly Glu Gly Tyr Ile
                500                 505                 510
Ser Val Asp Gly Asn Glu Gly Asp Arg Asn Asn Leu Thr Leu Trp Lys
            515                 520                 525
Asn Gly Asp Asn Leu Ile Lys Ala Ala Ala Asn Cys Asn Asn Thr
    530                 535                 540
```

Ile Val Val Ile His Ser Val Gly Pro Val Leu Val Asp Glu Trp Tyr
545                 550                 555                 560

Asp His Pro Asn Val Thr Ala Ile Leu Trp Ala Gly Leu Pro Gly Gln
                565                 570                 575

Glu Ser Gly Asn Ser Leu Ala Asp Val Leu Tyr Gly Arg Val Asn Pro
            580                 585                 590

Gly Ala Lys Ser Pro Phe Thr Trp Gly Lys Thr Arg Glu Ala Tyr Gly
        595                 600                 605

Asp Tyr Leu Val Arg Glu Leu Asn Asn Gly Asn Gly Ala Pro Gln Asp
    610                 615                 620

Asp Phe Ser Glu Gly Val Phe Ile Asp Tyr Arg Gly Phe Asp Lys Arg
625                 630                 635                 640

Asn Glu Thr Pro Ile Tyr Glu Phe Gly His Gly Leu Ser Tyr Thr Thr
                645                 650                 655

Phe Asn Tyr Ser Gly Leu His Ile Gln Val Leu Asn Ala Ser Ser Asn
                660                 665                 670

Ala Gln Val Ala Thr Glu Thr Gly Ala Ala Pro Thr Phe Gly Gln Val
            675                 680                 685

Gly Asn Ala Ser Asp Tyr Val Tyr Pro Glu Gly Leu Thr Arg Ile Ser
        690                 695                 700

Lys Phe Ile Tyr Pro Trp Leu Asn Ser Thr Asp Leu Lys Ala Ser Ser
705                 710                 715                 720

Gly Asp Pro Tyr Tyr Gly Val Asp Thr Ala Glu His Val Pro Glu Gly
                725                 730                 735

Ala Thr Asp Gly Ser Pro Gln Pro Val Leu Pro Ala Gly Gly Gly Ser
            740                 745                 750

Gly Gly Asn Pro Arg Leu Tyr Asp Glu Leu Ile Arg Val Ser Val Thr
        755                 760                 765

Val Lys Asn Thr Gly Arg Val Ala Gly Asp Ala Val Pro Gln Leu Tyr
770                 775                 780

Val Ser Leu Gly Gly Pro Asn Glu Pro Lys Val Val Leu Arg Lys Phe
785                 790                 795                 800

Asp Arg Leu Thr Leu Lys Pro Ser Glu Glu Thr Val Trp Thr Thr Thr
                805                 810                 815

Leu Thr Arg Arg Asp Leu Ser Asn Trp Asp Val Ala Ala Gln Asp Trp
                820                 825                 830

Val Ile Thr Ser Tyr Pro Lys Lys Val His Val Gly Ser Ser Ser Arg
            835                 840                 845

Gln Leu Pro Leu His Ala Ala Leu Pro Lys Val Gln
        850                 855                 860

<210> SEQ ID NO 25
<211> LENGTH: 3294
<212> TYPE: DNA
<213> ORGANISM: Aspergillus oryzae

<400> SEQUENCE: 25
atgcgttcct cccccctcct ccgctccgcc gttgtggccg ccctgccggt gttggccctt    60
gccgctgatg caggtccac ccgctactgg gactgctgca agccttcgtg cggctgggcc    120
aagaaggctc ccgtgaacca gcctgtcttt tcctgcaacg ccaacttcca gcgtatcacg    180
gacttcgacg ccaagtccgg ctgcgagccg ggcggtgtcg cctactcgtg cgccgaccag    240
acccatgggg ctgtgaacga cgacttcgcg ctcggttttg ctgccacctc tattgccggc    300
agcaatgagg cgggctggtg ctgcgcctgc tacgagctca ccttcacatc cggtcctgtt    360

-continued

```
gctggcaaga agatggtcgt ccagtccacc agcactggcg gtgatcttgg cagcaaccac    420
ttcgatctca acatccccgg cggcggcgtc ggcatcttcg acggatgcac tccccagttc    480
ggtggtctgc ccggccagcg ctacggcggc atctcgtccc gcaacgagtg cgatcggttc    540
cccgacgccc tcaagcccgg ctgctactgg cgcttcgact ggttcaagaa cgccgacaat    600
ccgagcttca gcttccgtca ggtccagtgc ccagccgagc tcgtcgctcg caccggatgc    660
cgccgcaacg acgacggcaa cttccctgcc gtccagatcc ccatgcgttc ctcccccctc    720
ctccgctccg ccgttgtggc cgccctgccg gtgttggccc ttgccaagga tgatctcgcg    780
tactcccctc ctttctaccc ttccccatgg gcagatggtc agggtgaatg ggcggaagta    840
tacaaacgcg ctgtagacat agtttcccag atgacgttga cagagaaagt caacttaacg    900
actggaacag gatggcaact agagaggtgt gttggacaaa ctggcagtgt tcccagactc    960
aacatcccca gcttgtgttt gcaggatagt cctcttggta ttcgtttctc ggactacaat   1020
tcagctttcc ctgcgggtgt taatgtcgct gccacctggg acaagacgct cgcctacctt   1080
cgtggtcagg caatgggtga ggagttcagt gataagggta ttgacgttca gctgggtcct   1140
gctgctggcc ctctcggtgc tcatccggat ggcggtagaa actgggaaag tttctcacca   1200
gatccagccc tcaccggtgt acttttttgcg gagacgatta agggtattca agatgctggt   1260
gtcattgcga cagctaagca ttatatcatg aacgaacaag agcatttccg ccaacaaccc   1320
gaggctgcgg gttacggatt caacgtaagc gacagtttga gttccaacgt tgatgacaag   1380
actatgcatg aattgtacct ctggcccttc gcggatgcag tacgcgctgg agtcggtgct   1440
gttatgtgct cttacaacca aatcaacaac agctacggtt gcgagaatag cgaaactctg   1500
aacaagcttt tgaaggcgga gcttggtttc caaggcttcg tcatgagtga ttggaccgct   1560
caacacagcg gcgtaggcgc tgctttagca ggtctggata tgtcgatgcc cggtgatgtt   1620
accttcgata gtggtacgtc tttctggggt gcaaacttga cggtcggtgt ccttaacggt   1680
acaatccccc aatggcgtgt tgatgacatg gctgtccgta tcatggccgc ttattacaag   1740
gttggccgcg acaccaaata caccccctccc aacttcagct cgtggaccag ggacgaatat   1800
ggtttcgcgc ataaccatgt ttcggaaggt gcttacgaga gggtcaacga attcgtggac   1860
gtgcaacgcg atcatgccga cctaatccgt cgcatcggcg cgcagagcac tgttctgctg   1920
aagaacaagg gtgccttgcc cttgagccgc aaggaaaagc tggtcgccct tctgggagag   1980
gatgcgggtt ccaactcgtg gggcgctaac ggctgtgatg accgtggttg cgataacggt   2040
acccttgcca tggcctgggg tagcggtact gcgaatttcc cataccctcgt gacaccagag   2100 caggcgattc agaacgaagt tcttcagggc cgtggtaatg tcttcgccgt gaccgacagt   2160
tgggcgctca acaagatcgc tgcggctgcc cgccaggcca gcgtatctct cgtgttcgtc   2220
aactccgact caggagaagg ctatcttagt gtggatggaa atgagggcga tcgtaacaac   2280
atcactctgt ggaagaacgg cgacaatgtg gtcaagaccg cagcgaataa ctgtaacaac   2340
accgttgtca tcatccactc cgtcggacca gttttgatcg atgaatggta tgaccacccc   2400
aatgtcactg gtattctctg ggctggtctg ccaggccagg agtctggtaa ctccattgcc   2460
gatgtgctgt acgtcgtgt caaccctggc gccaagtctc ctttcacttg gggcaagacc   2520
cgggagtcgt atggttctcc cttggtcaag gatgccaaca atggcaacgg agcgccccag   2580
tctgatttca cccagggtgt tttcatcgat taccgccatt tcgataagtt caatgagacc   2640
cctatctacg agtttggcta cggcttgagc tacaccacct tcgagctctc cgacctccat   2700
```

```
gttcagcccc tgaacgcgtc ccgatacact cccaccagtg gcatgactga agctgcaaag   2760
aactttggtg aaattggcga tgcgtcggag tacgtgtatc cggaggggct ggaaaggatc   2820
catgagttta tctatccctg gatcaactct accgacctga aggcatcgtc tgacgattct   2880
aactacggct gggaagactc caagtatatt cccgaaggcg ccacggatgg gtctgcccag   2940
ccccgtttgc ccgctagtgg tggtgccgga ggaaaccccg gtctgtacga ggatcttttc   3000
cgcgtctctg tgaaggtcaa gaacacgggc aatgtcgccg gtgatgaagt tcctcagctg   3060
tacgtttccc taggcggccc gaatgagccc aaggtggtac tgcgcaagtt tgagcgtatt   3120
cacttggccc cttcgcagga ggccgtgtgg acaacgaccc ttacccgtcg tgaccttgca   3180
aactgggacg tttcggctca ggactggacc gtcactcctt accccaagac gatctacgtt   3240
ggaaactcct cacggaaact gccgctccag gcctcgctgc ctaaggccca gtaa          3294
```

<210> SEQ ID NO 26
<211> LENGTH: 1097
<212> TYPE: PRT
<213> ORGANISM: Aspergillus oryzae

<400> SEQUENCE: 26

```
Met Arg Ser Ser Pro Leu Leu Arg Ser Ala Val Val Ala Ala Leu Pro
1               5                   10                  15

Val Leu Ala Leu Ala Ala Asp Gly Arg Ser Thr Arg Tyr Trp Asp Cys
            20                  25                  30

Cys Lys Pro Ser Cys Gly Trp Ala Lys Lys Ala Pro Val Asn Gln Pro
        35                  40                  45

Val Phe Ser Cys Asn Ala Asn Phe Gln Arg Ile Thr Asp Phe Asp Ala
    50                  55                  60

Lys Ser Gly Cys Glu Pro Gly Gly Val Ala Tyr Ser Cys Ala Asp Gln
65                  70                  75                  80

Thr Pro Trp Ala Val Asn Asp Asp Phe Ala Leu Gly Phe Ala Ala Thr
                85                  90                  95

Ser Ile Ala Gly Ser Asn Glu Ala Gly Trp Cys Cys Ala Cys Tyr Glu
            100                 105                 110

Leu Thr Phe Thr Ser Gly Pro Val Ala Gly Lys Lys Met Val Val Gln
        115                 120                 125

Ser Thr Ser Thr Gly Gly Asp Leu Gly Ser Asn His Phe Asp Leu Asn
    130                 135                 140

Ile Pro Gly Gly Gly Val Gly Ile Phe Asp Gly Cys Thr Pro Gln Phe
145                 150                 155                 160

Gly Gly Leu Pro Gly Gln Arg Tyr Gly Gly Ile Ser Ser Arg Asn Glu
                165                 170                 175

Cys Asp Arg Phe Pro Asp Ala Leu Lys Pro Gly Cys Tyr Trp Arg Phe
            180                 185                 190

Asp Trp Phe Lys Asn Ala Asp Asn Pro Ser Phe Ser Phe Arg Gln Val
        195                 200                 205

Gln Cys Pro Ala Glu Leu Val Ala Arg Thr Gly Cys Arg Arg Asn Asp
    210                 215                 220

Asp Gly Asn Phe Pro Ala Val Gln Ile Pro Met Arg Ser Ser Pro Leu
225                 230                 235                 240

Leu Arg Ser Ala Val Val Ala Ala Leu Pro Val Leu Ala Leu Ala Lys
                245                 250                 255

Asp Asp Leu Ala Tyr Ser Pro Pro Phe Tyr Pro Ser Pro Trp Ala Asp
            260                 265                 270
```

Gly Gln Gly Glu Trp Ala Glu Val Tyr Lys Arg Ala Val Asp Ile Val
        275                 280                 285

Ser Gln Met Thr Leu Thr Glu Lys Val Asn Leu Thr Thr Gly Thr Gly
        290                 295                 300

Trp Gln Leu Glu Arg Cys Val Gly Gln Thr Gly Ser Val Pro Arg Leu
305                 310                 315                 320

Asn Ile Pro Ser Leu Cys Leu Gln Asp Ser Pro Leu Gly Ile Arg Phe
                325                 330                 335

Ser Asp Tyr Asn Ser Ala Phe Pro Ala Gly Val Asn Val Ala Ala Thr
                    340                 345                 350

Trp Asp Lys Thr Leu Ala Tyr Leu Arg Gly Gln Ala Met Gly Glu Glu
            355                 360                 365

Phe Ser Asp Lys Gly Ile Asp Val Gln Leu Gly Pro Ala Ala Gly Pro
370                 375                 380

Leu Gly Ala His Pro Asp Gly Arg Asn Trp Glu Ser Phe Ser Pro
385                 390                 395                 400

Asp Pro Ala Leu Thr Gly Val Leu Phe Ala Glu Thr Ile Lys Gly Ile
                405                 410                 415

Gln Asp Ala Gly Val Ile Ala Thr Ala Lys His Tyr Ile Met Asn Glu
            420                 425                 430

Gln Glu His Phe Arg Gln Pro Glu Ala Ala Gly Tyr Gly Phe Asn
        435                 440                 445

Val Ser Asp Ser Leu Ser Ser Asn Val Asp Asp Lys Thr Met His Glu
        450                 455                 460

Leu Tyr Leu Trp Pro Phe Ala Asp Ala Val Arg Ala Gly Val Gly Ala
465                 470                 475                 480

Val Met Cys Ser Tyr Asn Gln Ile Asn Asn Ser Tyr Gly Cys Glu Asn
                485                 490                 495

Ser Glu Thr Leu Asn Lys Leu Leu Lys Ala Glu Leu Gly Phe Gln Gly
                500                 505                 510

Phe Val Met Ser Asp Trp Thr Ala Gln His Ser Gly Val Gly Ala Ala
            515                 520                 525

Leu Ala Gly Leu Asp Met Ser Met Pro Gly Asp Val Thr Phe Asp Ser
530                 535                 540

Gly Thr Ser Phe Trp Gly Ala Asn Leu Thr Val Gly Val Leu Asn Gly
545                 550                 555                 560

Thr Ile Pro Gln Trp Arg Val Asp Asp Met Ala Val Arg Ile Met Ala
                565                 570                 575

Ala Tyr Tyr Lys Val Gly Arg Asp Thr Lys Tyr Thr Pro Pro Asn Phe
            580                 585                 590

Ser Ser Trp Thr Arg Asp Glu Tyr Gly Phe Ala His Asn His Val Ser
        595                 600                 605

Glu Gly Ala Tyr Glu Arg Val Asn Glu Phe Val Asp Val Gln Arg Asp
    610                 615                 620

His Ala Asp Leu Ile Arg Arg Ile Gly Ala Gln Ser Thr Val Leu Leu
625                 630                 635                 640

Lys Asn Lys Gly Ala Leu Pro Leu Ser Arg Lys Glu Lys Leu Val Ala
                645                 650                 655

Leu Leu Gly Glu Asp Ala Gly Ser Asn Ser Trp Gly Ala Asn Gly Cys
                660                 665                 670

Asp Asp Arg Gly Cys Asp Asn Gly Thr Leu Ala Met Ala Trp Gly Ser
            675                 680                 685

Gly Thr Ala Asn Phe Pro Tyr Leu Val Thr Pro Glu Gln Ala Ile Gln

```
              690                 695                700
Asn Glu Val Leu Gln Gly Arg Gly Asn Val Phe Ala Val Thr Asp Ser
705                 710                715                720

Trp Ala Leu Asp Lys Ile Ala Ala Ala Arg Gln Ala Ser Val Ser
            725                 730                735

Leu Val Phe Val Asn Ser Asp Ser Gly Glu Gly Tyr Leu Ser Val Asp
            740                 745                750

Gly Asn Glu Gly Asp Arg Asn Asn Ile Thr Leu Trp Lys Asn Gly Asp
            755                 760                765

Asn Val Val Lys Thr Ala Ala Asn Asn Cys Asn Asn Thr Val Val Ile
            770                 775                780

Ile His Ser Val Gly Pro Val Leu Ile Asp Glu Trp Tyr Asp His Pro
785                 790                795                800

Asn Val Thr Gly Ile Leu Trp Ala Gly Leu Pro Gly Gln Glu Ser Gly
            805                 810                815

Asn Ser Ile Ala Asp Val Leu Tyr Gly Arg Val Asn Pro Gly Ala Lys
            820                 825                830

Ser Pro Phe Thr Trp Gly Lys Thr Arg Glu Ser Tyr Gly Ser Pro Leu
            835                 840                845

Val Lys Asp Ala Asn Asn Gly Asn Gly Ala Pro Gln Ser Asp Phe Thr
            850                 855                860

Gln Gly Val Phe Ile Asp Tyr Arg His Phe Asp Lys Phe Asn Glu Thr
865                 870                875                880

Pro Ile Tyr Glu Phe Gly Tyr Gly Leu Ser Tyr Thr Thr Phe Glu Leu
            885                 890                895

Ser Asp Leu His Val Gln Pro Leu Asn Ala Ser Arg Tyr Thr Pro Thr
            900                 905                910

Ser Gly Met Thr Glu Ala Ala Lys Asn Phe Gly Glu Ile Gly Asp Ala
            915                 920                925

Ser Glu Tyr Val Tyr Pro Glu Gly Leu Glu Arg Ile His Glu Phe Ile
            930                 935                940

Tyr Pro Trp Ile Asn Ser Thr Asp Leu Lys Ala Ser Ser Asp Asp Ser
945                 950                955                960

Asn Tyr Gly Trp Glu Asp Ser Lys Tyr Ile Pro Glu Gly Ala Thr Asp
            965                 970                975

Gly Ser Ala Gln Pro Arg Leu Pro Ala Ser Gly Gly Ala Gly Gly Asn
            980                 985                990

Pro Gly Leu Tyr Glu Asp Leu Phe Arg Val Ser Val Lys Val Lys Asn
            995                 1000               1005

Thr Gly Asn Val Ala Gly Asp Glu Val Pro Gln Leu Tyr Val Ser
1010                1015               1020

Leu Gly Gly Pro Asn Glu Pro Lys Val Val Leu Arg Lys Phe Glu
1025                1030               1035

Arg Ile His Leu Ala Pro Ser Gln Glu Ala Val Trp Thr Thr Thr
1040                1045               1050

Leu Thr Arg Arg Asp Leu Ala Asn Trp Asp Val Ser Ala Gln Asp
1055                1060               1065

Trp Thr Val Thr Pro Tyr Pro Lys Thr Ile Tyr Val Gly Asn Ser
1070                1075               1080

Ser Arg Lys Leu Pro Leu Gln Ala Ser Leu Pro Lys Ala Gln
1085                1090               1095
```

<210> SEQ ID NO 27

<211> LENGTH: 3294
<212> TYPE: DNA
<213> ORGANISM: Aspergillus oryzae

<400> SEQUENCE: 27

```
atgcgttcct ccccctcct ccgctccgcc gttgtggccg ccctgccggt gttggccctt    60
gccgctgatg gcaggtccac ccgctactgg gactgctgca agccttcgtg cggctgggcc   120
aagaaggctc ccgtgaacca gcctgtcttt tcctgcaacg ccaacttcca gcgtatcacg   180
gacttcgacg ccaagtccgg ctgcgagccg ggcggtgtcg cctactcgtg cgccgaccag   240
accccatggg ctgtgaacga cgacttcgcg ctcggttttg ctgccacctc tattgccggc   300
agcaatgagg cgggctggtg ctgcgcctgc tacgagctca ccttcacatc cggtcctgtt   360
gctggcaaga gatggtcgt ccagtccacc agcactggcg gtgatcttgg cagcaaccac   420
ttcgatctca acatccccgg cggcggcgtc ggcatcttcg acggatgcac tccccagttc   480
ggtggtctgc ccggccagcg ctacggcggc atctcgtccc gcaacgagtg cgatcggttc   540
cccgacgccc tcaagcccgg ctgctactgg cgcttcgact ggttcaagaa cgccgacaat   600
ccgagcttca gcttccgtca ggtccagtgc ccagccgagc tcgtcgctcg caccggatgc   660
cgccgcaacg acgacggcaa cttccctgcc gtccagatcc ccatgcgttc ctccccctc   720
ctccgctccg ccgttgtggc cgccctgccg gtgttggccc ttgccaagga tgatctcgcg   780
tactcccctc ctttctaccc ttcccatgg gcagatggtc agggtgaatg gcggaagta   840
tacaaacgcg ctgtagacat agttcccag atgacgttga cagagaaagt caacttaacg   900
actggaacag gatggcaact agagaggtgt gttggacaaa ctggcagtgt cccagactc   960
aacatcccca gcttgtgttt gcaggatagt cctcttggta ttcgtttctc ggactacaat  1020
tcagctttcc ctgcgggtgt taatgtcgct gccacctggg acaagacgct cgcctacctt  1080
cgtggtcagg caatgggtga ggagttcagt gataagggta ttgacgttca gctgggtcct  1140
gctgctggcc ctctcggtgc tcatccggat ggcggtagaa actgggaagg ttctctcacca  1200
gatccagccc tcaccggtgt acttttgcg gagacgatta agggtattca agatgctggt  1260
gtcattgcga cagctaagca ttatatcatg aacgaacaag agcatttccg ccaacaaccc  1320
gaggctgcgg gttacggatt caacgtaagc gacagtttga gttccaacgt tgatgacaag  1380
actatgcatg aattgtacct ctggcccttc gcggatgcag tacgcgctgg agtcggtgct  1440
gtcatgtgct cttacaacca aatcaacaac agctacggtt gcgagaatag cgaaactctg  1500
aacaagcttt tgaaggcgga gcttggtttc caaggcttcg tcatgagtga ttggaccgct  1560
catcacagcg gcgtaggcgc tgctttagca ggtctggata tgtcgatgcc cggtgatgtt  1620
accttcgata gtggtacgtc tttctggggt gcaaacttga cggtcggtgt ccttaacggt  1680
acaatccccc aatggcgtgt tgatgacatg gctgtccgta tcatggccgc ttattacaag  1740
gttggccgcg acaccaaata caccctccc aacttcagct cgtggaccag ggacgaatat  1800
ggtttcgcgc ataaccatgt ttcggaaggt gcttacgaga gggtcaacga attcgtggac  1860
gtgcaacgcg atcatgccga cctaatccgt cgcatcggcg cgcagagcac tgttctgctg  1920
aagaacaagg gtgccttgcc cttgagccgc aaggaaaagc tggtcgccct tctgggagag  1980
gatgcgggtt ccaactcgtg gggcgctaac ggctgtgatg accgtggttg cgataacggt  2040
acccttgcca tggcctgggg tagcggtact gcgaatttcc catacctcgt gacaccagag  2100
caggcgattc agaacgaagt tcttcagggc cgtggtaatg tcttcgccgt gaccgacagt  2160
tgggcgctcg acaagatcgc tgcggctgcc cgccaggcca gcgtatctct cgtgttcgtc  2220
```

-continued

```
aactccgact caggagaagg ctatcttagt gtggatggaa atgagggcga tcgtaacaac    2280
atcactctgt ggaagaacgg cgacaatgtg gtcaagaccg cagcgaataa ctgtaacaac    2340
accgttgtca tcatccactc cgtcggacca gttttgatcg atgaatggta tgaccacccc    2400
aatgtcactg gtattctctg ggctggtctg ccaggccagg agtctggtaa ctccattgcc    2460
gatgtgctgt acgtcgtgt caaccctggc gccaagtctc ctttcacttg gggcaagacc    2520
cgggagtcgt atggttctcc cttggtcaag gatgccaaca atggcaacgg agcgcccag    2580 tctgatttca cccagggtgt tttcatcgat taccgccatt tcgataagtt caatgagacc    2640
cctatctacg agtttggcta cggcttgagc tacaccacct tcgagctctc cgacctccat    2700
gttcagcccc tgaacgcgtc ccgatacact cccaccagtg gcatgactga agctgcaaag    2760
aactttggtg aaattggcga tgcgtcggag tacgtgtatc cggaggggct ggaaaggatc    2820
catgagttta tctatccctg gatcaactct accgacctga aggcatcgtc tgacgattct    2880
aactacggct gggaagactc caagtatatt cccgaaggcg ccacggatgg gtctgcccag    2940
ccccgtttgc ccgctagtgg tggtgccgga ggaaaccccg gtctgtacga ggatcttttc    3000
cgcgtctctg tgaaggtcaa gaacacgggc aatgtcgccg tgatgaagt tcctcagctg    3060 tacgtttccc taggcggccc gaatgagccc aaggtggtac tgcgcaagtt tgagcgtatt    3120
cacttggccc cttcgcagga ggccgtgtgg acaacgaccc ttacccgtcg tgaccttgca    3180
aactgggacg tttcggctca ggactggacc gtcactcctt accccaagac gatctacgtt    3240
ggaaactcct cacggaaact gccgctccag gcctcgctgc ctaaggccca gtaa          3294
```

<210> SEQ ID NO 28
<211> LENGTH: 1097
<212> TYPE: PRT
<213> ORGANISM: Aspergillus oryzae

<400> SEQUENCE: 28

```
Met Arg Ser Ser Pro Leu Leu Arg Ser Ala Val Ala Ala Leu Pro
1               5                   10                  15

Val Leu Ala Leu Ala Ala Asp Gly Arg Ser Thr Arg Tyr Trp Asp Cys
            20                  25                  30

Cys Lys Pro Ser Cys Gly Trp Ala Lys Lys Ala Pro Val Asn Gln Pro
        35                  40                  45

Val Phe Ser Cys Asn Ala Asn Phe Gln Arg Ile Thr Asp Phe Asp Ala
    50                  55                  60

Lys Ser Gly Cys Glu Pro Gly Gly Val Ala Tyr Ser Cys Ala Asp Gln
65                  70                  75                  80

Thr Pro Trp Ala Val Asn Asp Asp Phe Ala Leu Gly Phe Ala Ala Thr
                85                  90                  95

Ser Ile Ala Gly Ser Asn Glu Ala Gly Trp Cys Cys Ala Cys Tyr Glu
            100                 105                 110

Leu Thr Phe Thr Ser Gly Pro Val Ala Gly Lys Lys Met Val Val Gln
        115                 120                 125

Ser Thr Ser Thr Gly Gly Asp Leu Gly Ser Asn His Phe Asp Leu Asn
    130                 135                 140

Ile Pro Gly Gly Gly Val Gly Ile Phe Asp Gly Cys Thr Pro Gln Phe
145                 150                 155                 160

Gly Gly Leu Pro Gly Gln Arg Tyr Gly Gly Ile Ser Ser Arg Asn Glu
                165                 170                 175

Cys Asp Arg Phe Pro Asp Ala Leu Lys Pro Gly Cys Tyr Trp Arg Phe
```

```
            180                 185                 190
Asp Trp Phe Lys Asn Ala Asp Asn Pro Ser Phe Ser Phe Arg Gln Val
            195                 200                 205

Gln Cys Pro Ala Glu Leu Val Ala Arg Thr Gly Cys Arg Arg Asn Asp
            210                 215                 220

Asp Gly Asn Phe Pro Ala Val Gln Ile Pro Met Arg Ser Ser Pro Leu
225                 230                 235                 240

Leu Arg Ser Ala Val Val Ala Ala Leu Pro Val Leu Ala Leu Ala Lys
                245                 250                 255

Asp Asp Leu Ala Tyr Ser Pro Pro Phe Tyr Pro Ser Pro Trp Ala Asp
                260                 265                 270

Gly Gln Gly Glu Trp Ala Glu Val Tyr Lys Arg Ala Val Asp Ile Val
            275                 280                 285

Ser Gln Met Thr Leu Thr Glu Lys Val Asn Leu Thr Thr Gly Thr Gly
            290                 295                 300

Trp Gln Leu Glu Arg Cys Val Gly Gln Thr Gly Ser Val Pro Arg Leu
305                 310                 315                 320

Asn Ile Pro Ser Leu Cys Leu Gln Asp Ser Pro Leu Gly Ile Arg Phe
                325                 330                 335

Ser Asp Tyr Asn Ser Ala Phe Pro Ala Gly Val Asn Val Ala Ala Thr
                340                 345                 350

Trp Asp Lys Thr Leu Ala Tyr Leu Arg Gly Gln Ala Met Gly Glu Glu
            355                 360                 365

Phe Ser Asp Lys Gly Ile Asp Val Gln Leu Gly Pro Ala Ala Gly Pro
            370                 375                 380

Leu Gly Ala His Pro Asp Gly Gly Arg Asn Trp Glu Gly Phe Ser Pro
385                 390                 395                 400

Asp Pro Ala Leu Thr Gly Val Leu Phe Ala Glu Thr Ile Lys Gly Ile
                405                 410                 415

Gln Asp Ala Gly Val Ile Ala Thr Ala Lys His Tyr Ile Met Asn Glu
            420                 425                 430

Gln Glu His Phe Arg Gln Gln Pro Glu Ala Ala Gly Tyr Gly Phe Asn
            435                 440                 445

Val Ser Asp Ser Leu Ser Ser Asn Val Asp Asp Lys Thr Met His Glu
            450                 455                 460

Leu Tyr Leu Trp Pro Phe Ala Asp Ala Val Arg Ala Gly Val Gly Ala
465                 470                 475                 480

Val Met Cys Ser Tyr Asn Gln Ile Asn Asn Ser Tyr Gly Cys Glu Asn
                485                 490                 495

Ser Glu Thr Leu Asn Lys Leu Leu Lys Ala Glu Leu Gly Phe Gln Gly
            500                 505                 510

Phe Val Met Ser Asp Trp Thr Ala His His Ser Gly Val Gly Ala Ala
            515                 520                 525

Leu Ala Gly Leu Asp Met Ser Met Pro Gly Asp Val Thr Phe Asp Ser
530                 535                 540

Gly Thr Ser Phe Trp Gly Ala Asn Leu Thr Val Gly Val Leu Asn Gly
545                 550                 555                 560

Thr Ile Pro Gln Trp Arg Val Asp Asp Met Ala Val Arg Ile Met Ala
                565                 570                 575

Ala Tyr Tyr Lys Val Gly Arg Asp Thr Lys Tyr Thr Pro Pro Asn Phe
            580                 585                 590

Ser Ser Trp Thr Arg Asp Glu Tyr Gly Phe Ala His Asn His Val Ser
            595                 600                 605
```

-continued

```
Glu Gly Ala Tyr Glu Arg Val Asn Glu Phe Val Asp Val Gln Arg Asp
            610                 615                 620

His Ala Asp Leu Ile Arg Arg Ile Gly Ala Gln Ser Thr Val Leu Leu
625                 630                 635                 640

Lys Asn Lys Gly Ala Leu Pro Leu Ser Arg Lys Glu Lys Leu Val Ala
            645                 650                 655

Leu Leu Gly Glu Asp Ala Gly Ser Asn Ser Trp Gly Ala Asn Gly Cys
            660                 665                 670

Asp Asp Arg Gly Cys Asp Asn Gly Thr Leu Ala Met Ala Trp Gly Ser
            675                 680                 685

Gly Thr Ala Asn Phe Pro Tyr Leu Val Thr Pro Glu Gln Ala Ile Gln
    690                 695                 700

Asn Glu Val Leu Gln Gly Arg Gly Asn Val Phe Ala Val Thr Asp Ser
705                 710                 715                 720

Trp Ala Leu Asp Lys Ile Ala Ala Ala Arg Gln Ala Ser Val Ser
                725                 730                 735

Leu Val Phe Val Asn Ser Asp Ser Gly Glu Gly Tyr Leu Ser Val Asp
                740                 745                 750

Gly Asn Glu Gly Asp Arg Asn Asn Ile Thr Leu Trp Lys Asn Gly Asp
            755                 760                 765

Asn Val Val Lys Thr Ala Ala Asn Asn Cys Asn Asn Thr Val Val Ile
770                 775                 780

Ile His Ser Val Gly Pro Val Leu Ile Asp Glu Trp Tyr Asp His Pro
785                 790                 795                 800

Asn Val Thr Gly Ile Leu Trp Ala Gly Leu Pro Gly Gln Glu Ser Gly
                805                 810                 815

Asn Ser Ile Ala Asp Val Leu Tyr Gly Arg Val Asn Pro Gly Ala Lys
            820                 825                 830

Ser Pro Phe Thr Trp Gly Lys Thr Arg Glu Ser Tyr Gly Ser Pro Leu
            835                 840                 845

Val Lys Asp Ala Asn Asn Gly Asn Gly Ala Pro Gln Ser Asp Phe Thr
850                 855                 860

Gln Gly Val Phe Ile Asp Tyr Arg His Phe Asp Lys Phe Asn Glu Thr
865                 870                 875                 880

Pro Ile Tyr Glu Phe Gly Tyr Gly Leu Ser Tyr Thr Thr Phe Glu Leu
                885                 890                 895

Ser Asp Leu His Val Gln Pro Leu Asn Ala Ser Arg Tyr Thr Pro Thr
            900                 905                 910

Ser Gly Met Thr Glu Ala Ala Lys Asn Phe Gly Glu Ile Gly Asp Ala
            915                 920                 925

Ser Glu Tyr Val Tyr Pro Glu Gly Leu Glu Arg Ile His Glu Phe Ile
930                 935                 940

Tyr Pro Trp Ile Asn Ser Thr Asp Leu Lys Ala Ser Ser Asp Asp Ser
945                 950                 955                 960

Asn Tyr Gly Trp Glu Asp Ser Lys Tyr Ile Pro Glu Gly Ala Thr Asp
                965                 970                 975

Gly Ser Ala Gln Pro Arg Leu Pro Ala Ser Gly Gly Ala Gly Gly Asn
            980                 985                 990

Pro Gly Leu Tyr Glu Asp Leu Phe Arg Val Ser Val Lys Val Lys Asn
            995                 1000                1005

Thr Gly Asn Val Ala Gly Asp Glu Val Pro Gln Leu Tyr Val Ser
    1010                1015                1020
```

```
Leu Gly Gly Pro Asn Glu Pro Lys Val Val Leu Arg Lys Phe Glu
    1025                1030                1035

Arg Ile His Leu Ala Pro Ser Gln Glu Ala Val Trp Thr Thr Thr
    1040                1045                1050

Leu Thr Arg Arg Asp Leu Ala Asn Trp Asp Val Ser Ala Gln Asp
    1055                1060                1065

Trp Thr Val Thr Pro Tyr Pro Lys Thr Ile Tyr Val Gly Asn Ser
    1070                1075                1080

Ser Arg Lys Leu Pro Leu Gln Ala Ser Leu Pro Lys Ala Gln
    1085                1090                1095

<210> SEQ ID NO 29
<211> LENGTH: 29
<212> TYPE: DNA
<213> ORGANISM: Trichoderma reesei

<400> SEQUENCE: 29
aacgttaatt aaggaatcgt tttgtgttt                                    29

<210> SEQ ID NO 30
<211> LENGTH: 29
<212> TYPE: DNA
<213> ORGANISM: Trichoderma reesei

<400> SEQUENCE: 30
agtactagta gctccgtggc gaaagcctg                                    29

<210> SEQ ID NO 31
<211> LENGTH: 918
<212> TYPE: DNA
<213> ORGANISM: Humicola insolens

<400> SEQUENCE: 31
atgcgttcct ccccctcct cccgtccgcc gttgtggccg ccctgccggt gttggccctt    60
gccgctgatg gcaggtccac ccgctactgg gactgctgca agccttcgtg cggctgggcc   120
aagaaggctc ccgtgaacca gcctgtcttt tcctgcaacg ccaacttcca gcgtatcacg   180
gacttcgacg ccaagtccgg ctgcgagccg ggcggtgtcg cctactcgtg cgccgaccag   240
accccatggg ctgtgaacga cgacttcgcg ctcggttttg ctgccacctc tattgccggc   300
agcaatgagg cgggctggtg ctgcgcctgc tacgagctca ccttcacatc cggtcctgtt   360
gctggcaaga gatggtcgt ccagtccacc agcactggcg tgatcttgg cagcaaccac   420 ttcgatctca acatccccgg cggcggcgtc ggcatcttcg acggatgcac tccccagttc   480
ggcggtctgc ccggccagcg ctacggcggc atctcgtccc gcaacgagtg cgatcggttc   540
cccgacgccc tcaagcccgg ctgctactgg cgcttcgact ggttcaagaa cgccgacaat   600
ccgagcttca gcttccgtca ggtccagtgc ccagccgagc tcgtcgctcg caccggatgc   660
cgccgcaacg acgacggcaa cttccctgcc gtccagatcc cctccagcag caccagctct   720
ccggtcaacc agcctaccag caccagcacc acgtccacct ccaccacctc gagcccgcca   780
gtccagccta cgactcccag cggctgcact gctgagaggt gggctcagtg cggcggcaat   840
ggctggagcg gctgcaccac ctgcgtcgct ggcagcactt gcacgaagat taatgactgg   900
taccatcagt gcctgtag                                                918

<210> SEQ ID NO 32
<211> LENGTH: 305
<212> TYPE: PRT
```

<213> ORGANISM: Humicola insolens

<400> SEQUENCE: 32

Met Arg Ser Ser Pro Leu Leu Arg Ser Ala Val Val Ala Ala Leu Pro
1               5                   10                  15

Val Leu Ala Leu Ala Ala Asp Gly Arg Ser Thr Arg Tyr Trp Asp Cys
            20                  25                  30

Cys Lys Pro Ser Cys Gly Trp Ala Lys Lys Ala Pro Val Asn Gln Pro
        35                  40                  45

Val Phe Ser Cys Asn Ala Asn Phe Gln Arg Ile Thr Asp Phe Asp Ala
    50                  55                  60

Lys Ser Gly Cys Glu Pro Gly Val Ala Tyr Ser Cys Ala Asp Gln
65                  70                  75                  80

Thr Pro Trp Ala Val Asn Asp Asp Phe Ala Leu Gly Phe Ala Ala Thr
                85                  90                  95

Ser Ile Ala Gly Ser Asn Glu Ala Gly Trp Cys Cys Ala Cys Tyr Glu
            100                 105                 110

Leu Thr Phe Thr Ser Gly Pro Val Ala Gly Lys Lys Met Val Val Gln
        115                 120                 125

Ser Thr Ser Thr Gly Gly Asp Leu Gly Ser Asn His Phe Asp Leu Asn
    130                 135                 140

Ile Pro Gly Gly Gly Val Gly Ile Phe Asp Gly Cys Thr Pro Gln Phe
145                 150                 155                 160

Gly Gly Leu Pro Gly Gln Arg Tyr Gly Gly Ile Ser Ser Arg Asn Glu
                165                 170                 175

Cys Asp Arg Phe Pro Asp Ala Leu Lys Pro Gly Cys Tyr Trp Arg Phe
            180                 185                 190

Asp Trp Phe Lys Asn Ala Asp Asn Pro Ser Phe Ser Phe Arg Gln Val
        195                 200                 205

Gln Cys Pro Ala Glu Leu Val Ala Arg Thr Gly Cys Arg Arg Asn Asp
    210                 215                 220

Asp Gly Asn Phe Pro Ala Val Gln Ile Pro Ser Ser Ser Thr Ser Ser
225                 230                 235                 240

Pro Val Asn Gln Pro Thr Ser Thr Ser Thr Ser Thr Ser Thr Ser Thr
                245                 250                 255

Ser Ser Pro Pro Val Gln Pro Thr Thr Pro Ser Gly Cys Thr Ala Glu
            260                 265                 270

Arg Trp Ala Gln Cys Gly Gly Asn Gly Trp Ser Gly Cys Thr Thr Cys
        275                 280                 285

Val Ala Gly Ser Thr Cys Thr Lys Ile Asn Asp Trp Tyr His Gln Cys
    290                 295                 300

Leu
305

<210> SEQ ID NO 33
<211> LENGTH: 31
<212> TYPE: DNA
<213> ORGANISM: Saccharomyces cerevisiae

<400> SEQUENCE: 33
ttgaattgaa aatagattga tttaaaactt c                               31

<210> SEQ ID NO 34
<211> LENGTH: 25
<212> TYPE: DNA
<213> ORGANISM: Saccharomyces cerevisiae

```
<210> SEQ ID NO 34
<211> LENGTH: 25
<212> TYPE: DNA
<213> ORGANISM: Saccharomyces cerevisiae

<400> SEQUENCE: 34
ttgcatgcgt aatcatggtc atagc                                            25

<210> SEQ ID NO 35
<211> LENGTH: 26
<212> TYPE: DNA
<213> ORGANISM: Saccharomyces cerevisiae

<400> SEQUENCE: 35
ttgaattcat gggtaataac tgatat                                           26

<210> SEQ ID NO 36
<211> LENGTH: 32
<212> TYPE: DNA
<213> ORGANISM: Saccharomyces cerevisiae

<400> SEQUENCE: 36
aaatcaatct attttcaatt caattcatca tt                                    32

<210> SEQ ID NO 37
<211> LENGTH: 11
<212> TYPE: DNA
<213> ORGANISM: Aspergillus niger

<400> SEQUENCE: 37
gtactaaaac c                                                           11

<210> SEQ ID NO 38
<211> LENGTH: 11
<212> TYPE: DNA
<213> ORGANISM: Aspergillus niger

<400> SEQUENCE: 38
ccgttaaatt t                                                           11

<210> SEQ ID NO 39
<211> LENGTH: 45
<212> TYPE: DNA
<213> ORGANISM: Aspergillus niger

<400> SEQUENCE: 39
ggatgctgtt gactccggaa atttaacggt ttggtcttgc atccc                      45

<210> SEQ ID NO 40
<211> LENGTH: 14
<212> TYPE: DNA
<213> ORGANISM: Aspergillus niger

<400> SEQUENCE: 40
atgcaattta aact                                                        14

<210> SEQ ID NO 41
<211> LENGTH: 14
<212> TYPE: DNA
<213> ORGANISM: Aspergillus niger

<400> SEQUENCE: 41
cggcaattta acgg                                                        14

<210> SEQ ID NO 42
<211> LENGTH: 44
<212> TYPE: DNA
```

<213> ORGANISM: Aspergillus niger

<400> SEQUENCE: 42
ggtattgtcc tgcagacggc aatttaacgg cttctgcgaa tcgc                44

<210> SEQ ID NO 43
<211> LENGTH: 29
<212> TYPE: DNA
<213> ORGANISM: Humicola insolens

<400> SEQUENCE: 43
aagcttaagc atgcgttcct cccccctcc                                 29

<210> SEQ ID NO 44
<211> LENGTH: 32
<212> TYPE: DNA
<213> ORGANISM: Humicola insolens

<400> SEQUENCE: 44
ctgcagaatt ctacaggcac tgatggtacc ag                             32

<210> SEQ ID NO 45
<211> LENGTH: 32
<212> TYPE: DNA
<213> ORGANISM: Trichoderma reesei

<400> SEQUENCE: 45
ctgcagaatt ctacaggcac tgatggtacc ag                             32

<210> SEQ ID NO 46
<211> LENGTH: 36
<212> TYPE: DNA
<213> ORGANISM: Trichoderma reesei

<400> SEQUENCE: 46
accgcggact gcgcatcatg cgttcctccc ccctcc                         36

<210> SEQ ID NO 47
<211> LENGTH: 29
<212> TYPE: DNA
<213> ORGANISM: Trichoderma reesei

<400> SEQUENCE: 47
aaacgtcgac cgaatgtagg attgttatc                                 29

<210> SEQ ID NO 48
<211> LENGTH: 17
<212> TYPE: DNA
<213> ORGANISM: Trichoderma reesei

<400> SEQUENCE: 48
gatgcgcagt ccgcggt                                              17

<210> SEQ ID NO 49
<211> LENGTH: 29
<212> TYPE: DNA
<213> ORGANISM: Trichoderma reesei

<400> SEQUENCE: 49
aaacgtcgac cgaatgtagg attgttatc                                 29

<210> SEQ ID NO 50
<211> LENGTH: 36

```
<212> TYPE: DNA
<213> ORGANISM: Trichoderma reesei

<400> SEQUENCE: 50 ggaggggga ggaacgcatg atgcgcagtc cgcggt                                    36

<210> SEQ ID NO 51
<211> LENGTH: 29
<212> TYPE: DNA
<213> ORGANISM: Trichoderma reesei

<400> SEQUENCE: 51
aaacgtcgac cgaatgtagg attgttatc                                           29

<210> SEQ ID NO 52
<211> LENGTH: 32
<212> TYPE: DNA
<213> ORGANISM: Trichoderma reesei

<400> SEQUENCE: 52
ctgcagaatt ctacaggcac tgatggtacc ag                                       32

<210> SEQ ID NO 53
<211> LENGTH: 46
<212> TYPE: DNA
<213> ORGANISM: Aspergillus oryzae

<400> SEQUENCE: 53
atagtcaacc gcggactgcg catcatgaag cttggttgga tcgagg                        46

<210> SEQ ID NO 54
<211> LENGTH: 26
<212> TYPE: DNA
<213> ORGANISM: Aspergillus oryzae

<400> SEQUENCE: 54
actagtttac tgggccttag gcagcg                                              26

<210> SEQ ID NO 55
<211> LENGTH: 26
<212> TYPE: DNA
<213> ORGANISM: Trichoderma reesei

<400> SEQUENCE: 55
gtcgactcga agcccgaatg taggat                                              26

<210> SEQ ID NO 56
<211> LENGTH: 45
<212> TYPE: DNA
<213> ORGANISM: Trichoderma reesei

<400> SEQUENCE: 56
cctcgatcca accaagcttc atgatgcgca gtccgcggtt gacta                         45

<210> SEQ ID NO 57
<211> LENGTH: 57
<212> TYPE: DNA
<213> ORGANISM: Aspergillus oryzae

<400> SEQUENCE: 57
atgaagcttg gttggatcga ggtggccgca ttggcggctg cctcagtagt cagtgcc            57

<210> SEQ ID NO 58
```

```
<211> LENGTH: 19
<212> TYPE: PRT
<213> ORGANISM: Aspergillus oryzae

<400> SEQUENCE: 58

Met Lys Leu Gly Trp Ile Glu Val Ala Ala Leu Ala Ala Ala Ser Val
1               5                   10                  15

Val Ser Ala

<210> SEQ ID NO 59
<211> LENGTH: 42
<212> TYPE: DNA
<213> ORGANISM: Aspergillus oryzae

<400> SEQUENCE: 59
tgccggtgtt ggcccttgcc aaggatgatc tcgcgtactc cc                              42

<210> SEQ ID NO 60
<211> LENGTH: 28
<212> TYPE: DNA
<213> ORGANISM: Aspergillus oryzae

<400> SEQUENCE: 60
gactagtctt actgggcctt aggcagcg                                              28

<210> SEQ ID NO 61
<211> LENGTH: 63
<212> TYPE: DNA
<213> ORGANISM: Humicola insolens

<400> SEQUENCE: 61
atgcgttcct cccccctcct ccgctccgcc gttgtggccg ccctgccggt gttggccctt           60
gcc                                                                        63

<210> SEQ ID NO 62
<211> LENGTH: 21
<212> TYPE: PRT
<213> ORGANISM: Humicola insolens

<400> SEQUENCE: 62

Met Arg Ser Ser Pro Leu Leu Arg Ser Ala Val Val Ala Ala Leu Pro
1               5                   10                  15

Val Leu Ala Leu Ala
            20

<210> SEQ ID NO 63
<211> LENGTH: 30
<212> TYPE: DNA
<213> ORGANISM: Trichoderma reesei

<400> SEQUENCE: 63
acgcgtcgac cgaatgtagg attgttatcc                                            30

<210> SEQ ID NO 64
<211> LENGTH: 42
<212> TYPE: DNA
<213> ORGANISM: Trichoderma reesei

<400> SEQUENCE: 64
gggagtacgc gagatcatcc ttggcaaggg ccaacaccgg ca                              42

<210> SEQ ID NO 65
```

```
<210> SEQ ID NO 65
<211> LENGTH: 20
<212> TYPE: DNA
<213> ORGANISM: Trichoderma reesei

<400> SEQUENCE: 65
cccaagctta gccaagaaca                                              20

<210> SEQ ID NO 66
<211> LENGTH: 29
<212> TYPE: DNA
<213> ORGANISM: Trichoderma reesei

<400> SEQUENCE: 66
gggggaggaa cgcatgggat ctggacggc                                    29

<210> SEQ ID NO 67
<211> LENGTH: 30
<212> TYPE: DNA
<213> ORGANISM: Aspergillus oryzae

<400> SEQUENCE: 67
gccgtccaga tccccatgcg ttcctccccc                                   30

<210> SEQ ID NO 68
<211> LENGTH: 20
<212> TYPE: DNA
<213> ORGANISM: Aspergillus oryzae

<400> SEQUENCE: 68
ccaagcttgt tcagagtttc                                              20

<210> SEQ ID NO 69
<211> LENGTH: 20
<212> TYPE: DNA
<213> ORGANISM: Aspergillus oryzae

<400> SEQUENCE: 69
ggactgcgca gcatgcgttc                                              20

<210> SEQ ID NO 70
<211> LENGTH: 30
<212> TYPE: DNA
<213> ORGANISM: Aspergillus oryzae

<400> SEQUENCE: 70
agttaattaa ttactgggcc ttaggcagcg                                   30

<210> SEQ ID NO 71
<211> LENGTH: 28
<212> TYPE: DNA
<213> ORGANISM: Thermoascus aurantiacus

<400> SEQUENCE: 71
atgtcctttt ccaagataat tgctactg                                     28

<210> SEQ ID NO 72
<211> LENGTH: 26
<212> TYPE: DNA
<213> ORGANISM: Thermoascus aurantiacus

<400> SEQUENCE: 72
gcttaattaa ccagtataca gaggag                                       26
```

<210> SEQ ID NO 73
<211> LENGTH: 1377
<212> TYPE: DNA
<213> ORGANISM: Trichoderma reesei

<400> SEQUENCE: 73

```
atggcgccct cagttacact gccgttgacc acggccatcc tggccattgc ccggctcgtc      60
gccgcccagc aaccgggtac cagcaccccc gaggtccatc ccaagttgac aacctacaag     120
tgtacaaagt ccggggggtg cgtggcccag gacacctcgg tggtccttga ctggaactac     180
cgctggatgc acgacgcaaa ctacaactcg tgcaccgtca acggcggcgt caacaccacg     240
ctctgccctg acgaggcgac ctgtggcaag aactgcttca tcgagggcgt cgactacgcc     300
gcctcgggcg tcacgacctc gggcagcagc ctcaccatga ccagtacat gcccagcagc      360
tctggcggct acagcagcgt ctctcctcgg ctgtatctcc tggactctga cggtgagtac     420
gtgatgctga agctcaacgg ccaggagctg agcttcgacg tcgacctctc tgctctgccg     480
tgtggagaga acggctcgct ctacctgtct cagatggacg agaacggggg cgccaaccag     540
tataacacgg ccggtgccaa ctacgggagc ggctactgcg atgctcagtg ccccgtccag     600
acatggagga acggcaccct caacactagc caccagggct tctgctgcaa cgagatggat     660
atcctggagg gcaactcgag ggcgaatgcc ttgaccectc actcttgcac ggccacggcc     720
tgcgactctg ccgttgcgg cttcaacccc tatggcagcg gctacaaaag ctactacggc     780
cccggagata ccgttgacac ctccaagacc ttcaccatca tcacccagtt caacacggac     840
aacggctcgc cctcgggcaa ccttgtgagc atcacccgca agtaccagca aaacggcgtc     900
gacatcccca gcgcccagcc cggcggcgac accatctcgt cctgcccgtc cgcctcagcc     960
tacggcggcc tcgccaccat gggcaaggcc ctgagcagcg gcatggtgct cgtgttcagc    1020
atttggaacg acaacagcca gtacatgaac tggctcgaca gcggcaacgc cggcccctgc    1080
agcagcaccg agggcaaccc atccaacatc ctggccaaca accccaacac gcacgtcgtc    1140
ttctccaaca tccgctgggg agacattggg tctactacga actcgactgc gccccgccc     1200
ccgcctgcgt ccagcacgac gttttcgact acacggagga gctcgacgac ttcgagcagc    1260
ccgagctgca cgcagactca ctgggggcag tgcggtggca ttgggtacag cgggtgcaag    1320
acgtgcacgt cgggcactac gtgccagtat agcaacgact actactcgca atgcctt       1377
```

<210> SEQ ID NO 74
<211> LENGTH: 459
<212> TYPE: PRT
<213> ORGANISM: Trichoderma reesei

<400> SEQUENCE: 74

```
Met Ala Pro Ser Val Thr Leu Pro Leu Thr Thr Ala Ile Leu Ala Ile
1               5                   10                  15

Ala Arg Leu Val Ala Ala Gln Gln Pro Gly Thr Ser Thr Pro Glu Val
                20                  25                  30

His Pro Lys Leu Thr Thr Tyr Lys Cys Thr Lys Ser Gly Gly Cys Val
            35                  40                  45

Ala Gln Asp Thr Ser Val Val Leu Asp Trp Asn Tyr Arg Trp Met His
        50                  55                  60

Asp Ala Asn Tyr Asn Ser Cys Thr Val Asn Gly Gly Val Asn Thr Thr
65                  70                  75                  80

Leu Cys Pro Asp Glu Ala Thr Cys Gly Lys Asn Cys Phe Ile Glu Gly
                85                  90                  95
```

-continued

```
Val Asp Tyr Ala Ala Ser Gly Val Thr Thr Ser Gly Ser Ser Leu Thr
            100                 105                 110

Met Asn Gln Tyr Met Pro Ser Ser Gly Gly Tyr Ser Ser Val Ser
        115                 120                 125

Pro Arg Leu Tyr Leu Leu Asp Ser Asp Gly Glu Tyr Val Met Leu Lys
    130                 135                 140

Leu Asn Gly Gln Glu Leu Ser Phe Asp Val Asp Leu Ser Ala Leu Pro
145                 150                 155                 160

Cys Gly Glu Asn Gly Ser Leu Tyr Leu Ser Gln Met Asp Glu Asn Gly
                165                 170                 175

Gly Ala Asn Gln Tyr Asn Thr Ala Gly Ala Asn Tyr Gly Ser Gly Tyr
            180                 185                 190

Cys Asp Ala Gln Cys Pro Val Gln Thr Trp Arg Asn Gly Thr Leu Asn
        195                 200                 205

Thr Ser His Gln Gly Phe Cys Cys Asn Glu Met Asp Ile Leu Glu Gly
    210                 215                 220

Asn Ser Arg Ala Asn Ala Leu Thr Pro His Ser Cys Thr Ala Thr Ala
225                 230                 235                 240

Cys Asp Ser Ala Gly Cys Gly Phe Asn Pro Tyr Gly Ser Gly Tyr Lys
                245                 250                 255

Ser Tyr Tyr Gly Pro Gly Asp Thr Val Asp Thr Ser Lys Thr Phe Thr
            260                 265                 270

Ile Ile Thr Gln Phe Asn Thr Asp Asn Gly Ser Pro Ser Gly Asn Leu
        275                 280                 285

Val Ser Ile Thr Arg Lys Tyr Gln Gln Asn Gly Val Asp Ile Pro Ser
    290                 295                 300

Ala Gln Pro Gly Gly Asp Thr Ile Ser Ser Cys Pro Ser Ala Ser Ala
305                 310                 315                 320

Tyr Gly Gly Leu Ala Thr Met Gly Lys Ala Leu Ser Ser Gly Met Val
                325                 330                 335

Leu Val Phe Ser Ile Trp Asn Asp Asn Ser Gln Tyr Met Asn Trp Leu
            340                 345                 350

Asp Ser Gly Asn Ala Gly Pro Cys Ser Ser Thr Glu Gly Asn Pro Ser
        355                 360                 365

Asn Ile Leu Ala Asn Asn Pro Asn Thr His Val Val Phe Ser Asn Ile
    370                 375                 380

Arg Trp Gly Asp Ile Gly Ser Thr Thr Asn Ser Thr Ala Pro Pro Pro
385                 390                 395                 400

Pro Pro Ala Ser Ser Thr Thr Phe Ser Thr Thr Arg Arg Ser Ser Thr
                405                 410                 415

Thr Ser Ser Ser Pro Ser Cys Thr Gln Thr His Trp Gly Gln Cys Gly
            420                 425                 430

Gly Ile Gly Tyr Ser Gly Cys Lys Thr Cys Thr Ser Gly Thr Thr Cys
        435                 440                 445

Gln Tyr Ser Asn Asp Tyr Tyr Ser Gln Cys Leu
    450                 455
```

<210> SEQ ID NO 75
<211> LENGTH: 1254
<212> TYPE: DNA
<213> ORGANISM: Trichoderma reesei

<400> SEQUENCE: 75
atgaacaagt ccgtggctcc attgctgctt gcagcgtcca tactatatgg cggcgccgtc    60

-continued

```
gcacagcaga ctgtctgggg ccagtgtgga ggtattggtt ggagcggacc tacgaattgt    120
gctcctggct cagcttgttc gaccctcaat ccttattatg cgcaatgtat tccgggagcc    180
actactatca ccacttcgac ccggccacca tccggtccaa ccaccaccac cagggctacc    240
tcaacaagct catcaactcc acccacgagc tctggggtcc gatttgccgg cgttaacatc    300
gcgggttttg actttggctg taccacagat ggcacttgcg ttacctcgaa ggtttatcct    360
ccgttgaaga acttcaccgg ctcaaacaac taccccgatg catcggcca  gatgcagcac    420 ttcgtcaacg aggacgggat gactatttc  cgcttacctg tcggatggca gtacctcgtc    480
aacaacaatt tgggcggcaa tcttgattcc acgagcattt ccaagtatga tcagcttgtt    540 cagggggtgcc tgtctctggg cgcatactgc atcgtcgaca tccacaatta tgctcgatgg    600
aacggtggga tcattggtca gggcggccct actaatgctc aattcacgag cctttggtcg    660
cagttggcat caaagtacgc atctcagtcg agggtgtggt tcggcatcat gaatgagccc    720
cacgacgtga acatcaacac ctgggctgcc acggtccaag aggttgtaac cgcaatccgc    780
aacgctggtg ctacgtcgca attcatctct ttgcctggaa atgattggca atctgctggg    840
gctttcatat ccgatggcag tgcagccgcc ctgtctcaag tcacgaaccc ggatgggtca    900
acaacgaatc tgattttgta cgtgcacaaa tacttggact cagacaactc cggtactcac    960
gccgaatgta ctacaaataa cattgacggc gccttttctc cgcttgccac ttggctccga   1020
cagaacaatc gccaggctat cctgacagaa accggtggtg caacgttca  gtcctgcata   1080 caagacatgt gccagcaaat ccaatatctc aaccagaact cagatgtcta tcttggctat   1140
gttggttggg gtgccggatc atttgatagc acgtatgtcc tgacggaaac accgactagc   1200
agtggtaact catggacgga cacatccttg gtcagctcgt gtctcgcaag aaag        1254
```

<210> SEQ ID NO 76
<211> LENGTH: 418
<212> TYPE: PRT
<213> ORGANISM: Trichoderma reesei

<400> SEQUENCE: 76

```
Met Asn Lys Ser Val Ala Pro Leu Leu Leu Ala Ser Ile Leu Tyr
1               5                   10                  15

Gly Gly Ala Val Ala Gln Gln Thr Val Trp Gly Gln Cys Gly Gly Ile
            20                  25                  30

Gly Trp Ser Gly Pro Thr Asn Cys Ala Pro Gly Ser Ala Cys Ser Thr
        35                  40                  45

Leu Asn Pro Tyr Tyr Ala Gln Cys Ile Pro Gly Ala Thr Thr Ile Thr
    50                  55                  60

Thr Ser Thr Arg Pro Pro Ser Gly Pro Thr Thr Thr Arg Ala Thr
65                  70                  75                  80

Ser Thr Ser Ser Ser Thr Pro Pro Thr Ser Ser Gly Val Arg Phe Ala
                85                  90                  95

Gly Val Asn Ile Ala Gly Phe Asp Phe Gly Cys Thr Thr Asp Gly Thr
            100                 105                 110

Cys Val Thr Ser Lys Val Tyr Pro Pro Leu Lys Asn Phe Thr Gly Ser
        115                 120                 125

Asn Asn Tyr Pro Asp Gly Ile Gly Gln Met Gln His Phe Val Asn Glu
    130                 135                 140

Asp Gly Met Thr Ile Phe Arg Leu Pro Val Gly Trp Gln Tyr Leu Val
145                 150                 155                 160

Asn Asn Asn Leu Gly Gly Asn Leu Asp Ser Thr Ser Ile Ser Lys Tyr
```

```
                165                 170                 175
Asp Gln Leu Val Gln Gly Cys Leu Ser Leu Gly Ala Tyr Cys Ile Val
                180                 185                 190

Asp Ile His Asn Tyr Ala Arg Trp Asn Gly Gly Ile Ile Gly Gln Gly
                195                 200                 205

Gly Pro Thr Asn Ala Gln Phe Thr Ser Leu Trp Ser Gln Leu Ala Ser
            210                 215                 220

Lys Tyr Ala Ser Gln Ser Arg Val Trp Phe Gly Ile Met Asn Glu Pro
225                 230                 235                 240

His Asp Val Asn Ile Asn Thr Trp Ala Ala Thr Val Gln Glu Val Val
                    245                 250                 255

Thr Ala Ile Arg Asn Ala Gly Ala Thr Ser Gln Phe Ile Ser Leu Pro
                260                 265                 270

Gly Asn Asp Trp Gln Ser Ala Gly Ala Phe Ile Ser Asp Gly Ser Ala
            275                 280                 285

Ala Ala Leu Ser Gln Val Thr Asn Pro Asp Gly Ser Thr Thr Asn Leu
        290                 295                 300

Ile Phe Asp Val His Lys Tyr Leu Asp Ser Asp Asn Ser Gly Thr His
305                 310                 315                 320

Ala Glu Cys Thr Thr Asn Asn Ile Asp Gly Ala Phe Ser Pro Leu Ala
                    325                 330                 335

Thr Trp Leu Arg Gln Asn Asn Arg Gln Ala Ile Leu Thr Glu Thr Gly
                340                 345                 350

Gly Gly Asn Val Gln Ser Cys Ile Gln Asp Met Cys Gln Gln Ile Gln
            355                 360                 365

Tyr Leu Asn Gln Asn Ser Asp Val Tyr Leu Gly Tyr Val Gly Trp Gly
        370                 375                 380

Ala Gly Ser Phe Asp Ser Thr Tyr Val Leu Thr Glu Thr Pro Thr Ser
385                 390                 395                 400

Ser Gly Asn Ser Trp Thr Asp Thr Ser Leu Val Ser Ser Cys Leu Ala
                    405                 410                 415

Arg Lys

<210> SEQ ID NO 77
<211> LENGTH: 702
<212> TYPE: DNA
<213> ORGANISM: Trichoderma reesei

<400> SEQUENCE: 77
atgaagttcc ttcaagtcct ccctgccctc ataccggccg ccctggccca aaccagctgt    60
gaccagtggg caaccttcac tggcaacggc tacacagtca gcaacaacct tggggagca    120 tcagccggct ctgatttggg ctgcgtgacg gcggtatcgc tcagcggcgg ggcctcctgg    180
cacgcagact ggcagtggtc cggcggccag aacaacgtca agtcgtacca gaactctcag    240
attgccattc cccagaagag gaccgtcaac agcatcagca gcatgcccac cactgccagc    300
tggagctaca gcgggagcaa catccgcgct aatgttgcgt atgacttgtt caccgcagcc    360
aacccgaatc atgtcacgta ctcgggagac tacgaactca tgatctggct tggcaaatac    420
ggcgatattg gccgattggg tcctcacag gaacagtca acgtcggtgg ccagagctgg    480
acgtctacta tggctacaa cggagccatg caagtctatt cctttgtggc ccagaccaac    540
actaccaact acagcggaga tgtcaagaac ttcttcaatt atctccgaga caataaagga    600
tacaacgctg caggccaata tgttcttagc taccaatttg gtaccgagcc cttcacgggc    660
```
agtggaactc tgaacgtcgc atcctggacc gcatctatca ac  702

<210> SEQ ID NO 78
<211> LENGTH: 234
<212> TYPE: PRT
<213> ORGANISM: Trichoderma reesei

<400> SEQUENCE: 78

```
Met Lys Phe Leu Gln Val Leu Pro Ala Leu Ile Pro Ala Ala Leu Ala
1               5                   10                  15

Gln Thr Ser Cys Asp Gln Trp Ala Thr Phe Thr Gly Asn Gly Tyr Thr
            20                  25                  30

Val Ser Asn Asn Leu Trp Gly Ala Ser Ala Gly Ser Gly Phe Gly Cys
        35                  40                  45

Val Thr Ala Val Ser Leu Ser Gly Gly Ala Ser Trp His Ala Asp Trp
    50                  55                  60

Gln Trp Ser Gly Gly Gln Asn Asn Val Lys Ser Tyr Gln Asn Ser Gln
65                  70                  75                  80

Ile Ala Ile Pro Gln Lys Arg Thr Val Asn Ser Ile Ser Ser Met Pro
                85                  90                  95

Thr Thr Ala Ser Trp Ser Tyr Ser Gly Ser Asn Ile Arg Ala Asn Val
            100                 105                 110

Ala Tyr Asp Leu Phe Thr Ala Ala Asn Pro Asn His Val Thr Tyr Ser
        115                 120                 125

Gly Asp Tyr Glu Leu Met Ile Trp Leu Gly Lys Tyr Gly Asp Ile Gly
    130                 135                 140

Pro Ile Gly Ser Ser Gln Gly Thr Val Asn Val Gly Gly Gln Ser Trp
145                 150                 155                 160

Thr Leu Tyr Tyr Gly Tyr Asn Gly Ala Met Gln Val Tyr Ser Phe Val
                165                 170                 175

Ala Gln Thr Asn Thr Thr Asn Tyr Ser Gly Asp Val Lys Asn Phe Phe
            180                 185                 190

Asn Tyr Leu Arg Asp Asn Lys Gly Tyr Asn Ala Ala Gly Gln Tyr Val
        195                 200                 205

Leu Ser Tyr Gln Phe Gly Thr Glu Pro Phe Thr Gly Ser Gly Thr Leu
    210                 215                 220

Asn Val Ala Ser Trp Thr Ala Ser Ile Asn
225                 230
```

<210> SEQ ID NO 79
<211> LENGTH: 726
<212> TYPE: DNA
<213> ORGANISM: Trichoderma reesei

<400> SEQUENCE: 79
atgaaggcaa ctctggttct cggctccctc attgtaggcg ccgtttccgc gtacaaggcc  60
accaccacgc gctactacga tgggcaggag ggtgcttgcg gatgcggctc gagctccggc  120
gcattcccgt ggcagctcgg catcggcaac ggagtctaca cggctgccgg ctcccaggct  180
ctcttcgaca cggccggagc ttcatggtgc ggcgccggct gcggtaaatg ctaccagctc  240
acctcgacgg gccaggcgcc ctgctccagc tgcggcacgg gcgtgctgc tggccagagc  300 atcatcgtca tggtgaccaa cctgtgcccg aacaatggga acgcgcagtg gtgcccggtg  360
gtcggcggca ccaaccaata cggctacagc taccattttcg acatcatggc cagaacgag  420 atctttggag acaatgtcgt cgtcgacttt gagcccattg cttgccccgg gcaggctgcc  480

```
tctgactggg ggacgtgcct ctgcgtggga cagcaagaga cggatcccac gcccgtcctc      540
ggcaacgaca cgggctcaac tcctcccggg agctcgccgc cagcgacatc gtcgagtccg      600
ccgtctggcg gcggccagca gacgctctat ggccagtgtg gaggtgccgg ctggacggga      660
cctacgacgt gccaggcccc agggacctgc aaggttcaga accagtggta ctcccagtgt      720
cttcct                                                                 726
```

<210> SEQ ID NO 80
<211> LENGTH: 242
<212> TYPE: PRT
<213> ORGANISM: Trichoderma reesei

<400> SEQUENCE: 80

```
Met Lys Ala Thr Leu Val Leu Gly Ser Leu Ile Val Gly Ala Val Ser
1               5                   10                  15

Ala Tyr Lys Ala Thr Thr Thr Arg Tyr Tyr Asp Gly Gln Glu Gly Ala
            20                  25                  30

Cys Gly Cys Gly Ser Ser Ser Gly Ala Phe Pro Trp Gln Leu Gly Ile
        35                  40                  45

Gly Asn Gly Val Tyr Thr Ala Ala Gly Ser Gln Ala Leu Phe Asp Thr
    50                  55                  60

Ala Gly Ala Ser Trp Cys Gly Ala Gly Cys Gly Lys Cys Tyr Gln Leu
65                  70                  75                  80

Thr Ser Thr Gly Gln Ala Pro Cys Ser Ser Cys Gly Thr Gly Gly Ala
                85                  90                  95

Ala Gly Gln Ser Ile Ile Val Met Val Thr Asn Leu Cys Pro Asn Asn
            100                 105                 110

Gly Asn Ala Gln Trp Cys Pro Val Val Gly Gly Thr Asn Gln Tyr Gly
        115                 120                 125

Tyr Ser Tyr His Phe Asp Ile Met Ala Gln Asn Glu Ile Phe Gly Asp
    130                 135                 140

Asn Val Val Val Asp Phe Glu Pro Ile Ala Cys Pro Gly Gln Ala Ala
145                 150                 155                 160

Ser Asp Trp Gly Thr Cys Leu Cys Val Gly Gln Gln Glu Thr Asp Pro
                165                 170                 175

Thr Pro Val Leu Gly Asn Asp Thr Gly Ser Thr Pro Gly Ser Ser
            180                 185                 190

Pro Pro Ala Thr Ser Ser Pro Ser Gly Gly Gln Gln Thr
        195                 200                 205

Leu Tyr Gly Gln Cys Gly Gly Ala Gly Trp Thr Gly Pro Thr Thr Cys
    210                 215                 220

Gln Ala Pro Gly Thr Cys Lys Val Gln Asn Gln Trp Tyr Ser Gln Cys
225                 230                 235                 240

Leu Pro
```

<210> SEQ ID NO 81
<211> LENGTH: 1371
<212> TYPE: DNA
<213> ORGANISM: Myceliophthora thermophila

<400> SEQUENCE: 81

```
atgggtcgcg gcgctgcttt cctaggcctc gcctcgctcc tcgtgggcgc ggccaaggcc      60
cagacgcccg gcgagggcga ggaggtgcac ccgcagatca cgacgtaccg ctgcaccaag     120
gcggacgggt gcgaggagaa gaccaactac atcgtgctgg acgccctatc gcacccggtc     180
```

```
caccaggtcg acaacccgta caactgcggc gactggggcc agaagcccaa cgagacggcc      240 tgccccggacc tcgagtcgtg cgccaggaac tgcatcatgg acccggtctc ggactacggc     300
cggcacggtg tctcgaccga cggcacctcg ctgcgcctca gcagctagt cggcggcaac      360 gtcgtcagcc cgcgcgtcta cctgctcgac gagaccaagg agcgctacga gatgctcaag     420
ctgaccggca acgagttcac ctttgacgtc gacgccacca agctgccctg cggcatgaac    480
agcgccctct acctctccga gatggacgcc accggcgccc ggagcgagct caacccgggc    540
ggcgccacct ttggcaccgg ctactgcgac gcccagtgct acgtcacccc cttcatcaac    600
ggcctcggca acatcgaggg caagggcgcg tgctgcaacg agatggatat ctggaggcc     660 aacgcgcggg cgcagcacat cgcgccgcac ccgtgcagca aggcggggcc gtacctgtgc    720
gagggcgccg agtgcgagtt cgacggcgtg tgcgacaaga acggctgcgc ctggaacccg    780
taccgggtca acgtgacgga ctactacggc gagggcgccg agttcagggt ggacacgacc   840
cggcccttct cggtcgtcac gcagttccgc gccggcggcg acgcgggggg cggcaagctc   900
gagagcatct accggctctt cgtccaggac ggcagggtga ttgagtcgta cgtcgtcgac   960
aagcccggcc tgcccccgac ggaccgcatg acggacgagt tctgcgccgc caccggcgcc  1020
gcccgcttca cggagctcgg cgccatggag gccatgggcg acgccctgac gcgcggcatg  1080
gtcctcgccc tcagcatctg gtggagcgag ggcgacaaca tgaactggct cgactcgggc  1140
gaggccggcc cctgcgaccc ggacgagggc aacccgtcca acatcatccg cgtccagccc  1200
gacccggagg tcgtcttcag caacctgcgc tggggcgaga tcggctcaac ctacgagtcc  1260
gccgtcgacg ggcccgtcgg caagggcaag gcaagggca agggcaaggc tcccgccggc  1320
gacggcaacg ggaaggagaa gagcaatggc aagcgcttca ggaggttctg a            1371
```

<210> SEQ ID NO 82
<211> LENGTH: 456
<212> TYPE: PRT
<213> ORGANISM: Myceliophthora thermophila

<400> SEQUENCE: 82

```
Met Gly Arg Gly Ala Ala Phe Leu Gly Leu Ala Ser Leu Leu Val Gly
1               5                   10                  15

Ala Ala Lys Ala Gln Thr Pro Gly Glu Gly Glu Val His Pro Gln
            20                  25                  30

Ile Thr Thr Tyr Arg Cys Thr Lys Ala Asp Gly Cys Glu Glu Lys Thr
        35                  40                  45

Asn Tyr Ile Val Leu Asp Ala Leu Ser His Pro Val His Gln Val Asp
    50                  55                  60

Asn Pro Tyr Asn Cys Gly Asp Trp Gly Gln Lys Pro Asn Glu Thr Ala
65                  70                  75                  80

Cys Pro Asp Leu Glu Ser Cys Ala Arg Asn Cys Ile Met Asp Pro Val
                85                  90                  95

Ser Asp Tyr Gly Arg His Gly Val Ser Thr Asp Gly Thr Ser Leu Arg
            100                 105                 110

Leu Lys Gln Leu Val Gly Gly Asn Val Val Ser Pro Arg Val Tyr Leu
        115                 120                 125

Leu Asp Glu Thr Lys Glu Arg Tyr Glu Met Leu Lys Leu Thr Gly Asn
    130                 135                 140

Glu Phe Thr Phe Asp Val Asp Ala Thr Lys Leu Pro Cys Gly Met Asn
145                 150                 155                 160

Ser Ala Leu Tyr Leu Ser Glu Met Asp Ala Thr Gly Ala Arg Ser Glu
```

```
                165                 170                 175
Leu Asn Pro Gly Gly Ala Thr Phe Gly Thr Gly Tyr Cys Asp Ala Gln
            180                 185                 190
Cys Tyr Val Thr Pro Phe Ile Asn Gly Leu Gly Asn Ile Glu Gly Lys
        195                 200                 205

Gly Ala Cys Cys Asn Glu Met Asp Ile Trp Glu Ala Asn Ala Arg Ala
    210                 215                 220
Gln His Ile Ala Pro His Pro Cys Ser Lys Ala Gly Pro Tyr Leu Cys
225                 230                 235                 240
Glu Gly Ala Glu Cys Glu Phe Asp Gly Val Cys Asp Lys Asn Gly Cys
                245                 250                 255
Ala Trp Asn Pro Tyr Arg Val Asn Val Thr Asp Tyr Tyr Gly Glu Gly
            260                 265                 270
Ala Glu Phe Arg Val Asp Thr Thr Arg Pro Phe Ser Val Val Thr Gln
        275                 280                 285

Phe Arg Ala Gly Gly Asp Ala Gly Gly Gly Lys Leu Glu Ser Ile Tyr
    290                 295                 300
Arg Leu Phe Val Gln Asp Gly Arg Val Ile Glu Ser Tyr Val Val Asp
305                 310                 315                 320
Lys Pro Gly Leu Pro Pro Thr Asp Arg Met Thr Asp Glu Phe Cys Ala
                325                 330                 335
Ala Thr Gly Ala Ala Arg Phe Thr Glu Leu Gly Ala Met Glu Ala Met
            340                 345                 350
Gly Asp Ala Leu Thr Arg Gly Met Val Leu Ala Leu Ser Ile Trp Trp
        355                 360                 365

Ser Glu Gly Asp Asn Met Asn Trp Leu Asp Ser Gly Glu Ala Gly Pro
    370                 375                 380
Cys Asp Pro Asp Glu Gly Asn Pro Ser Asn Ile Ile Arg Val Gln Pro
385                 390                 395                 400
Asp Pro Glu Val Val Phe Ser Asn Leu Arg Trp Gly Glu Ile Gly Ser
                405                 410                 415
Thr Tyr Glu Ser Ala Val Asp Gly Pro Val Gly Lys Gly Lys Gly Lys
            420                 425                 430
Gly Lys Gly Lys Ala Pro Ala Gly Asp Gly Asn Gly Lys Glu Lys Ser
        435                 440                 445

Asn Gly Lys Arg Phe Arg Arg Phe
    450                 455
```

<210> SEQ ID NO 83
<211> LENGTH: 744
<212> TYPE: DNA
<213> ORGANISM: Chrysosporium lucknowense

<400> SEQUENCE: 83

```
atgcagccgt ttctgctctt gttcctctcg tcggtcacgg cggcgagccc cctgacggcg      60
ctcgacaagc ggcagcaggc gacgttgtgc gagcagtacg gctactggtc gggcaacggt     120
tacgaggtca acaacaacaa ctggggcaag gattcggcct cgggcggcca tcagtgcacc     180
tacgtcgaca gcagcagctc cagcggcgtc gcctggcaca cgacctggca gtgggaagga     240
ggccagaacc aggtcaagag cttcgccaac tgcggcctgc aggtgcccaa gggcaggacc     300
atctcgtcca tcagcaacct gcagacctcc atctcgtggt cctacagcaa caccaacatc     360
cgcgccaacg tggcctacga cctcttcacc gcggcagacc cgaaccacgc gaccagcagc     420
ggcgactacg agctcatgat ctggctggcg agattcggcg acgtctaccc catcggctcg     480
```

```
tcccagggcc acgtcaacgt ggccggccag gactgggagc tgtggacggg cttcaacggc       540
aacatgcggg tctacagctt cgtagcgccc agccccgca acagcttcag cgccaacgtc       600
aaggacttct tcaactatct ccagtccaac cagggcttcc cggccagcag ccaataccct       660
ctcatcttcc aggcgggcac cgagcccttc accggcggcg agaccaccct taccgtcaac       720
aactactctg caagggttgc ttaa                                              744
```

<210> SEQ ID NO 84
<211> LENGTH: 247
<212> TYPE: PRT
<213> ORGANISM: Chrysosporium lucknowense

<400> SEQUENCE: 84

```
Met Gln Pro Phe Leu Leu Leu Phe Leu Ser Ser Val Thr Ala Ala Ser
1               5                   10                  15

Pro Leu Thr Ala Leu Asp Lys Arg Gln Gln Ala Thr Leu Cys Glu Gln
            20                  25                  30

Tyr Gly Tyr Trp Ser Gly Asn Gly Tyr Glu Val Asn Asn Asn Trp
        35                  40                  45

Gly Lys Asp Ser Ala Ser Gly Gly His Gln Cys Thr Tyr Val Asp Ser
    50                  55                  60

Ser Ser Ser Ser Gly Val Ala Trp His Thr Thr Trp Gln Trp Glu Gly
65                  70                  75                  80

Gly Gln Asn Gln Val Lys Ser Phe Ala Asn Cys Gly Leu Gln Val Pro
                85                  90                  95

Lys Gly Arg Thr Ile Ser Ser Ile Ser Asn Leu Gln Thr Ser Ile Ser
            100                 105                 110

Trp Ser Tyr Ser Asn Thr Asn Ile Arg Ala Asn Val Ala Tyr Asp Leu
        115                 120                 125

Phe Thr Ala Ala Asp Pro Asn His Ala Thr Ser Ser Gly Asp Tyr Glu
    130                 135                 140

Leu Met Ile Trp Leu Ala Arg Phe Gly Asp Val Tyr Pro Ile Gly Ser
145                 150                 155                 160

Ser Gln Gly His Val Asn Val Ala Gly Gln Asp Trp Glu Leu Trp Thr
                165                 170                 175

Gly Phe Asn Gly Asn Met Arg Val Tyr Ser Phe Val Ala Pro Ser Pro
            180                 185                 190

Arg Asn Ser Phe Ser Ala Asn Val Lys Asp Phe Phe Asn Tyr Leu Gln
        195                 200                 205

Ser Asn Gln Gly Phe Pro Ala Ser Ser Gln Tyr Leu Leu Ile Phe Gln
    210                 215                 220

Ala Gly Thr Glu Pro Phe Thr Gly Gly Glu Thr Thr Leu Thr Val Asn
225                 230                 235                 240

Asn Tyr Ser Ala Arg Val Ala
                245
```

<210> SEQ ID NO 85
<211> LENGTH: 678
<212> TYPE: DNA
<213> ORGANISM: Chrysosporium lucknowense

<400> SEQUENCE: 85

```
atgcatctct ccgccaccac cgggttcctc gccctccgg ccctggccct ggccagctc        60 tcgggcagcg gccagacgac ccggtactgg gactgctgca gccgagctg

```
ggcaagggcc cctcgtctcc ggtgcaggcc tgcgacaaga acgacaaccc gctcaacgac      180
ggcggctcca cccggtccgg ctgcgacgcg ggcggcagcg cctacatgtg ctcctcccag      240
agccctgggg ccgtcagcga cgagctgtcg tacggctggg cggccgtcaa gctcgccggc      300
agctccgagt cgcagtggtg ctgcgcctgc tacgagctga ccttcaccag cgggccggtc      360
gcgggcaaga agatgattgt gcaggcgacc aacaccggtg gcgacctggg cgacaaccac      420
tttgacctgg ccatccccgg tggcggtgtc ggtattttca acgcctgcac cgaccagtac      480
ggcgctcccc cgaacggctg gggcgaccgc tacgcggca tccattccaa ggaagagtgc       540
gaatccttcc cggaggccct caagcccggc tgcaactggc gcttcgactg gttccaaaac      600
gccgacaacc cgtcggtcac cttccaggag gtggcctgcc cgtcggagct cacgtccaag      660
agcggctgct cccgttaa                                                   678
```

```
<210> SEQ ID NO 86
<211> LENGTH: 225
<212> TYPE: PRT
<213> ORGANISM: Chrysosporium lucknowense

<400> SEQUENCE: 86

Met His Leu Ser Ala Thr Thr Gly Phe Leu Ala Leu Pro Ala Leu Ala
1               5                   10                  15

Leu Ala Gln Leu Ser Gly Ser Gly Gln Thr Thr Arg Tyr Trp Asp Cys
            20                  25                  30

Cys Lys Pro Ser Cys Ala Trp Pro Gly Lys Gly Pro Ser Ser Pro Val
        35                  40                  45

Gln Ala Cys Asp Lys Asn Asn Pro Leu Asn Asp Gly Gly Ser Thr
    50                  55                  60

Arg Ser Gly Cys Asp Ala Gly Gly Ser Ala Tyr Met Cys Ser Ser Gln
65                  70                  75                  80

Ser Pro Trp Ala Val Ser Asp Glu Leu Ser Tyr Gly Trp Ala Ala Val
                85                  90                  95

Lys Leu Ala Gly Ser Ser Glu Ser Gln Trp Cys Cys Ala Cys Tyr Glu
            100                 105                 110

Leu Thr Phe Thr Ser Gly Pro Val Ala Gly Lys Lys Met Ile Val Gln
        115                 120                 125

Ala Thr Asn Thr Gly Gly Asp Leu Gly Asp Asn His Phe Asp Leu Ala
    130                 135                 140

Ile Pro Gly Gly Gly Val Gly Ile Phe Asn Ala Cys Thr Asp Gln Tyr
145                 150                 155                 160

Gly Ala Pro Pro Asn Gly Trp Gly Asp Arg Tyr Gly Gly Ile His Ser
                165                 170                 175

Lys Glu Glu Cys Glu Ser Phe Pro Glu Ala Leu Lys Pro Gly Cys Asn
            180                 185                 190

Trp Arg Phe Asp Trp Phe Gln Asn Ala Asp Asn Pro Ser Val Thr Phe
        195                 200                 205

Gln Glu Val Ala Cys Pro Ser Glu Leu Thr Ser Lys Ser Gly Cys Ser
    210                 215                 220

Arg
225

<210> SEQ ID NO 87
<211> LENGTH: 1542
<212> TYPE: DNA
<213> ORGANISM: Trichoderma reesei
```

<400> SEQUENCE: 87

```
atgtatcgga agttggccgt catctcggcc ttcttggcca cagctcgtgc tcagtcggcc      60
tgcactctcc aatcggagac tcacccgcct ctgacatggc agaaatgctc gtctggtggc     120
acgtgcactc aacagacagg ctccgtggtc atcgacgcca actggcgctg gactcacgct     180
acgaacagca gcacgaactg ctacgatggc aacacttgga gctcgaccct atgtcctgac     240
aacgagacct cgcgcaagaa ctgctgtctg acggtgccg cctacgcgtc cacgtacgga      300
gttaccacga gcggtaacag cctctccatt ggctttgtca cccagtctgc gcagaagaac     360
gttggcgctc gcctttacct tatggcgagc gacacgacct accaggaatt caccctgctt     420
ggcaacgagt tctctttcga tgttgatgtt tcgcagctgc cgtgcggctt gaacggagct     480
ctctacttcg tgtccatgga cgcggatggt ggcgtgagca agtatcccac caacaccgct     540
ggcgccaagt acggcacggg gtactgtgac agccagtgtc cccgcgatct gaagttcatc     600
aatggccagg ccaacgttga gggctgggag ccgtcatcca acaacgcgaa cacgggcatt     660
ggaggacacg gaagctgctg ctctgagatg gatatctggg aggccaactc catctccgag     720
gctcttaccc ccaccccttg cacgactgtc ggccaggaga tctgcgaggg tgatgggtgc     780
ggcggaactt actccgataa cagatatggc ggcacttgcg atcccgatgg ctgcgactgg     840
aacccatacc gcctgggcaa caccagcttc tacggccctg gctcaagctt accctcgat     900
accaccaaga aattgaccgt tgtcacccag ttcgagacgt cgggtgccat caaccgatac     960
tatgtccaga tggcgtcac tttccagcag cccaacgccg agcttggtag ttactctggc    1020
aacgagctca cgatgatta ctgcacagct gaggaggcag aattcggcgg atcctctttc    1080
tcagacaagg gcggcctgac tcagttcaag aaggctacct ctggcggcat ggttctggtc    1140
atgagtctgt gggatgatta ctacgccaac atgctgtggc tggactccac ctaccccgaca  1200
aacgagacct cctccacacc cggtgccgtg cgcggaagct gctccaccag ctccggtgtc    1260
cctgctcagg tcgaatctca gtctcccaac gccaaggtca ccttctccaa catcaagttc    1320
ggacccattg gcagcaccgg caaccctagc ggcggcaacc ctcccggcgg aaacccgcct    1380
ggcaccacca ccacccgccg cccagccact accactggaa gctctcccgg acctaccag    1440
tctcactacg gccagtgcgg cggtattggc tacagcggcc ccacggtctg cgccagcggc    1500
acaacttgcc aggtcctgaa cccttactac tctcagtgcc tg                       1542
```

<210> SEQ ID NO 88
<211> LENGTH: 514
<212> TYPE: PRT
<213> ORGANISM: Trichoderma reesei

<400> SEQUENCE: 88

```
Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
            20                  25                  30

Trp Gln Lys Cys Ser Ser Gly Gly Thr Cys Thr Gln Gln Thr Gly Ser
        35                  40                  45

Val Val Ile Asp Ala Asn Trp Arg Trp Thr His Ala Thr Asn Ser Ser
    50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
                85                  90                  95
```

```
Ser Thr Tyr Gly Val Thr Thr Gly Asn Ser Leu Ser Ile Gly Phe
            100                 105                 110

Val Thr Gln Ser Ala Gln Lys Asn Val Gly Ala Arg Leu Tyr Leu Met
            115                 120                 125

Ala Ser Asp Thr Thr Tyr Gln Glu Phe Thr Leu Leu Gly Asn Glu Phe
            130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Val Ser Lys Tyr Pro
            165                 170                 175

Thr Asn Thr Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
            195                 200                 205

Trp Glu Pro Ser Ser Asn Asn Ala Asn Thr Gly Ile Gly Gly His Gly
            210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
            245                 250                 255

Gly Asp Gly Cys Gly Gly Thr Tyr Ser Asp Asn Arg Tyr Gly Gly Thr
            260                 265                 270

Cys Asp Pro Asp Gly Cys Asp Trp Asn Pro Tyr Arg Leu Gly Asn Thr
            275                 280                 285

Ser Phe Tyr Gly Pro Gly Ser Ser Phe Thr Leu Asp Thr Lys Lys
            290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
            325                 330                 335

Ser Tyr Ser Gly Asn Glu Leu Asn Asp Asp Tyr Cys Thr Ala Glu Glu
            340                 345                 350

Ala Glu Phe Gly Gly Ser Ser Phe Ser Asp Lys Gly Gly Leu Thr Gln
            355                 360                 365

Phe Lys Lys Ala Thr Ser Gly Gly Met Val Leu Val Met Ser Leu Trp
            370                 375                 380

Asp Asp Tyr Tyr Ala Asn Met Leu Trp Leu Asp Ser Thr Tyr Pro Thr
385                 390                 395                 400

Asn Glu Thr Ser Ser Thr Pro Gly Ala Val Arg Gly Ser Cys Ser Thr
            405                 410                 415

Ser Ser Gly Val Pro Ala Gln Val Glu Ser Gln Ser Pro Asn Ala Lys
            420                 425                 430

Val Thr Phe Ser Asn Ile Lys Phe Gly Pro Ile Gly Ser Thr Gly Asn
            435                 440                 445

Pro Ser Gly Gly Asn Pro Pro Gly Gly Asn Pro Pro Gly Thr Thr Thr
            450                 455                 460

Thr Arg Arg Pro Ala Thr Thr Thr Gly Ser Ser Pro Gly Pro Thr Gln
465                 470                 475                 480

Ser His Tyr Gly Gln Cys Gly Gly Ile Gly Tyr Ser Gly Pro Thr Val
            485                 490                 495

Cys Ala Ser Gly Thr Thr Cys Gln Val Leu Asn Pro Tyr Tyr Ser Gln
            500                 505                 510
```

Cys Leu

<210> SEQ ID NO 89
<211> LENGTH: 1413
<212> TYPE: DNA
<213> ORGANISM: Trichoderma reesei

<400> SEQUENCE: 89

| | | |
|---|---|---|
| atgattgtcg gcattctcac cacgctggct acgctggcca cactcgcagc tagtgtgcct | 60 |
| ctagaggagc ggcaagcttg ctcaagcgtc tggggccaat gtggtggcca gaattggtcg | 120 |
| ggtccgactt gctgtgcttc cggaagcaca tgcgtctact ccaacgacta ttactcccag | 180 |
| tgtcttcccg gcgctgcaag ctcaagctcg tccacgcgcg ccgcgtcgac gacttctcga | 240 |
| gtatccccca caacatcccg gtcgagctcc gcgacgcctc cacctggttc tactactacc | 300 |
| agagtacctc cagtcggatc gggaaccgct acgtattcag gcaaccctt tgttggggtc | 360 |
| actccttggg ccaatgcata ttacgcctct gaagttagca gcctcgctat tcctagcttg | 420 |
| actggagcca tggccactgc tgcagcagct gtcgcaaagg ttccctcttt tatgtggcta | 480 |
| gatactcttg acaagacccc tctcatggag caaaccttgg ccgacatccg caccgccaac | 540 |
| aagaatggcg gtaactatgc cggacagttt gtggtgtatg acttgccgga tcgcgattgc | 600 |
| gctgcccttg cctcgaatgg cgaatactct attgccgatg gtggcgtcgc caaatataag | 660 |
| aactatatcg acaccattcg tcaaattgtc gtggaatatt ccgatatccg gaccctcctg | 720 |
| gttattgagc ctgactctct tgccaacctg gtgaccaacc tcggtactcc aaagtgtgcc | 780 |
| aatgctcagt cagcctacct tgagtgcatc aactacgccg tcacacagct gaaccttcca | 840 |
| aatgttgcga tgtatttgga cgctggccat gcaggatggc ttggctggcc ggcaaaccaa | 900 |
| gacccggccg ctcagctatt tgcaaatgtt tacaagaatg catcgtctcc gagagctctt | 960 |
| cgcggattgg caaccaatgt cgccaactac aacgggtgga acattaccag ccccccatcg | 1020 |
| tacacgcaag gcaacgctgt ctacaacgag aagctgtaca tccacgctat ggacctctct | 1080 |
| cttgccaatc acggctggtc caacgccttc ttcatcactg atcaaggtcg atcgggaaag | 1140 |
| cagcctaccg gacagcaaca gtggggagac tggtgcaatg tgatcggcac cggatttggt | 1200 |
| attcgcccat ccgcaaacac tggggactcg ttgctggatt cgtttgtctg ggtcaagcca | 1260 |
| ggcggcgagt gtgacggcac cagcgacagc agtgcgccac gatttgactc ccactgtgcg | 1320 |
| ctcccagatg ccttgcaacc ggcgcctcaa gctggtgctt ggttccaagc ctactttgtg | 1380 |
| cagcttctca aaacgcaaa cccatcgttc ctg | 1413 |

<210> SEQ ID NO 90
<211> LENGTH: 471
<212> TYPE: PRT
<213> ORGANISM: Trichoderma reesei

<400> SEQUENCE: 90

Met Ile Val Gly Ile Leu Thr Thr Leu Ala Thr Leu Ala Thr Leu Ala
1               5                   10                  15

Ala Ser Val Pro Leu Glu Glu Arg Gln Ala Cys Ser Ser Val Trp Gly
                20                  25                  30

Gln Cys Gly Gly Gln Asn Trp Ser Gly Pro Thr Cys Cys Ala Ser Gly
            35                  40                  45

Ser Thr Cys Val Tyr Ser Asn Asp Tyr Tyr Ser Gln Cys Leu Pro Gly
        50                  55                  60

Ala Ala Ser Ser Ser Ser Ser Ser Thr Arg Ala Ala Ser Thr Thr Ser Arg

```
            65                  70                  75                  80
Val Ser Pro Thr Thr Ser Arg Ser Ser Ala Thr Pro Pro Gly
                    85                  90                  95
Ser Thr Thr Arg Val Pro Val Gly Ser Gly Thr Ala Thr Tyr
            100                 105                 110
Ser Gly Asn Pro Phe Val Gly Val Thr Pro Trp Ala Asn Ala Tyr Tyr
            115                 120                 125
Ala Ser Glu Val Ser Ser Leu Ala Ile Pro Ser Leu Thr Gly Ala Met
            130                 135                 140
Ala Thr Ala Ala Ala Val Ala Lys Val Pro Ser Phe Met Trp Leu
145                 150                 155                 160
Asp Thr Leu Asp Lys Thr Pro Leu Met Glu Gln Thr Leu Ala Asp Ile
                    165                 170                 175
Arg Thr Ala Asn Lys Asn Gly Gly Asn Tyr Ala Gly Gln Phe Val Val
                    180                 185                 190
Tyr Asp Leu Pro Asp Arg Asp Cys Ala Ala Leu Ala Ser Asn Gly Glu
                    195                 200                 205
Tyr Ser Ile Ala Asp Gly Gly Val Ala Lys Tyr Lys Asn Tyr Ile Asp
            210                 215                 220
Thr Ile Arg Gln Ile Val Val Glu Tyr Ser Asp Ile Arg Thr Leu Leu
225                 230                 235                 240
Val Ile Glu Pro Asp Ser Leu Ala Asn Leu Val Thr Asn Leu Gly Thr
                    245                 250                 255
Pro Lys Cys Ala Asn Ala Gln Ser Ala Tyr Leu Glu Cys Ile Asn Tyr
                    260                 265                 270
Ala Val Thr Gln Leu Asn Leu Pro Asn Val Ala Met Tyr Leu Asp Ala
                    275                 280                 285
Gly His Ala Gly Trp Leu Gly Trp Pro Ala Asn Gln Asp Pro Ala Ala
            290                 295                 300
Gln Leu Phe Ala Asn Val Tyr Lys Asn Ala Ser Ser Pro Arg Ala Leu
305                 310                 315                 320
Arg Gly Leu Ala Thr Asn Val Ala Asn Tyr Asn Gly Trp Asn Ile Thr
                    325                 330                 335
Ser Pro Pro Ser Tyr Thr Gln Gly Asn Ala Val Tyr Asn Glu Lys Leu
                    340                 345                 350
Tyr Ile His Ala Ile Gly Pro Leu Leu Ala Asn His Gly Trp Ser Asn
                    355                 360                 365
Ala Phe Phe Ile Thr Asp Gln Gly Arg Ser Gly Lys Gln Pro Thr Gly
            370                 375                 380
Gln Gln Gln Trp Gly Asp Trp Cys Asn Val Ile Gly Thr Gly Phe Gly
385                 390                 395                 400
Ile Arg Pro Ser Ala Asn Thr Gly Asp Ser Leu Leu Asp Ser Phe Val
                    405                 410                 415
Trp Val Lys Pro Gly Gly Glu Cys Asp Gly Thr Ser Asp Ser Ser Ala
                    420                 425                 430
Pro Arg Phe Asp Ser His Cys Ala Leu Pro Asp Ala Leu Gln Pro Ala
                    435                 440                 445
Pro Gln Ala Gly Ala Trp Phe Gln Ala Tyr Phe Val Gln Leu Leu Thr
            450                 455                 460
Asn Ala Asn Pro Ser Phe Leu
465                 470

<210> SEQ ID NO 91
```

<211> LENGTH: 1648
<212> TYPE: DNA
<213> ORGANISM: Chrysosporium lucknowense
<220> FEATURE:
<221> NAME/KEY: misc_feature
<222> LOCATION: (1162)..(1162)
<223> OTHER INFORMATION: N=A,C,G, OR T

<400> SEQUENCE: 91

```
atgtacgcca agttcgcgac cctcgccgcc cttgtggctg gcgccgctgc tcagaacgcc      60
tgcactctga ccgctgagaa ccacccctcg ctgacgtggt ccaagtgcac gtctggcggc     120
agctgcacca gcgtccaggg ttccatcacc atcgacgcca actggcggtg gactcaccgg     180
accgatagcg ccaccaactg ctacgagggc aacaagtggg atacttcgta ctgcagcgat     240
ggtccttctt gcgcctccaa gtgctgcatc gacggcgctg actactcgag cacctatggc     300
atcaccacga gcggtaactc cctgaacctc aagttcgtca ccaagggcca gtactcgacc     360
aacatcggct cgcgtaccta cctgatggag agcgacacca agtaccagag taagttcctc     420
tcgcacccgg ccgccgggag atgatggcgc ccagcccgct gacgcgaatg acacagtgtt     480
ccagctcctc ggcaacgagt tcaccttcga tgtcgacgtc tccaacctcg gctgcggcct     540
caatggcgcc ctctacttcg tgtccatgga tgccgatggt ggcatgtcca agtactcggg     600
caacaaggca ggtgccaagt acggtaccgg ctactgtgat tctcagtgcc cccgcgacct     660
caagttcatc aacggcgagg ccaacgtaga gaactggcag agctcgacca acgatgccaa     720
cgccggcacg ggcaagtacg gcagctgctg ctccgagatg gacgtctggg aggccaacaa     780
catggccgcc gccttcactc cccacccttg caccgtgatc ggccagtcgc gctgcgaggg     840
cgactcgtgc ggcggtacct acagcaccga ccgctatgcc ggcatctgcg accccgacgg     900
atgcgacttc aactcgtacc gccagggcaa caagaccttc tacggcaagg gcatgacggt     960
cgacacgacc aagaagatca cggtcgtcac ccagttcctc aagaactcgg ccggcgagct    1020
ctccgagatc aagcggttct acgtccagaa cggcaaggtc atccccaact ccgagtccac    1080
catcccgggc gtcgagggca actccatcac ccaggactgg tgcgaccgcc agaaggccgc    1140
cttcggcgac gtgaccgact tncaggacaa gggcggcatg gtccagatgg gcaaggccct    1200
cgcggggccc atggtcctcg tcatgtccat ctgggacgac cacgccgtca acatgctctg    1260
gctcgactcc acctggccca tcgacggcgc cggcaagccg ggcgccgagc gcggtgcctg    1320
ccccaccacc tcgggcgtcc ccgctgaggt cgaggccgag gcccccaact ccaacgtcat    1380
cttctccaac atccgcttcg gccccatcgg ctccaccgtc tccggcctgc ccgacggcgg    1440
cagcggcaac cccaacccgc ccgtcagctc gtccaccccg gtcccctcct cgtccaccac    1500
atcctccggt tcctccggcc cgactggcgg cacgggtgtc gctaagcact atgagcaatg    1560
cggaggaatc gggttcactg gccctaccca gtgcgagagc ccctacactt gcaccaagct    1620
gaatgactgg tactcgcagt gcctgtaa                                       1648
```

<210> SEQ ID NO 92
<211> LENGTH: 526
<212> TYPE: PRT
<213> ORGANISM: Chrysosporium lucknowense
<220> FEATURE:
<221> NAME/KEY: MISC_FEATURE
<222> LOCATION: (365)..(365)
<223> OTHER INFORMATION: X=ANY AMINO ACID

<400> SEQUENCE: 92

Met Tyr Ala Lys Phe Ala Thr Leu Ala Ala Leu Val Ala Gly Ala Ala

-continued

```
1               5                   10                  15
Ala Gln Asn Ala Cys Thr Leu Thr Ala Glu Asn His Pro Ser Leu Thr
                20                  25                  30

Trp Ser Lys Cys Thr Ser Gly Gly Ser Cys Thr Ser Val Gln Gly Ser
                35                  40                  45

Ile Thr Ile Asp Ala Asn Trp Arg Trp Thr His Arg Thr Asp Ser Ala
        50                  55                  60

Thr Asn Cys Tyr Glu Gly Asn Lys Trp Asp Thr Ser Tyr Cys Ser Asp
65                  70                  75                  80

Gly Pro Ser Cys Ala Ser Lys Cys Cys Ile Asp Gly Ala Asp Tyr Ser
                85                  90                  95

Ser Thr Tyr Gly Ile Thr Thr Ser Gly Asn Ser Leu Asn Leu Lys Phe
                100                 105                 110

Val Thr Lys Gly Gln Tyr Ser Thr Asn Ile Gly Ser Arg Thr Tyr Leu
                115                 120                 125

Met Glu Ser Asp Thr Lys Tyr Gln Met Phe Gln Leu Leu Gly Asn Glu
                130                 135                 140

Phe Thr Phe Asp Val Asp Val Ser Asn Leu Gly Cys Gly Leu Asn Gly
145                 150                 155                 160

Ala Leu Tyr Phe Val Ser Met Asp Ala Asp Gly Gly Met Ser Lys Tyr
                    165                 170                 175

Ser Gly Asn Lys Ala Gly Ala Lys Tyr Gly Thr Gly Tyr Cys Asp Ser
                180                 185                 190

Gln Cys Pro Arg Asp Leu Lys Phe Ile Asn Gly Glu Ala Asn Val Glu
                195                 200                 205

Asn Trp Gln Ser Ser Thr Asn Asp Ala Asn Ala Gly Thr Gly Lys Tyr
                210                 215                 220

Gly Ser Cys Cys Ser Glu Met Asp Val Trp Glu Ala Asn Asn Met Ala
225                 230                 235                 240

Ala Ala Phe Thr Pro His Pro Cys Trp Val Ile Gly Gln Ser Arg Cys
                    245                 250                 255

Glu Gly Asp Ser Cys Gly Gly Thr Tyr Ser Thr Asp Arg Tyr Ala Gly
                260                 265                 270

Ile Cys Asp Pro Asp Gly Cys Asp Phe Asn Ser Tyr Arg Gln Gly Asn
                275                 280                 285

Lys Thr Phe Tyr Gly Lys Gly Met Thr Val Asp Thr Thr Lys Lys Ile
                290                 295                 300

Thr Val Val Thr Gln Phe Leu Lys Asn Ser Ala Gly Glu Leu Ser Glu
305                 310                 315                 320

Ile Lys Arg Phe Tyr Val Gln Asn Gly Lys Val Ile Pro Asn Ser Glu
                    325                 330                 335

Ser Thr Ile Pro Gly Val Glu Gly Asn Ser Ile Thr Gln Asp Trp Cys
                340                 345                 350

Asp Arg Gln Lys Ala Ala Phe Gly Asp Val Thr Asp Xaa Gln Asp Lys
                355                 360                 365

Gly Gly Met Val Gln Met Gly Lys Ala Leu Ala Gly Pro Met Val Leu
                370                 375                 380

Val Met Ser Ile Trp Asp Asp His Ala Val Asn Met Leu Trp Leu Asp
385                 390                 395                 400

Ser Thr Trp Pro Ile Asp Gly Ala Gly Lys Pro Gly Ala Glu Arg Gly
                    405                 410                 415

Ala Cys Pro Thr Thr Ser Gly Val Pro Ala Glu Val Glu Ala Glu Ala
                420                 425                 430
```

```
Pro Asn Ser Asn Val Ile Phe Ser Asn Ile Arg Phe Gly Pro Ile Gly
        435                 440                 445

Ser Thr Val Ser Gly Leu Pro Asp Gly Gly Ser Gly Asn Pro Asn Pro
450                 455                 460

Pro Val Ser Ser Thr Pro Val Pro Ser Ser Ser Thr Ser Thr Ser Ser
465                 470                 475                 480

Gly Ser Ser Gly Pro Thr Gly Gly Thr Gly Val Ala Lys His Tyr Glu
                485                 490                 495

Gln Cys Gly Gly Ile Gly Phe Thr Gly Pro Thr Gln Cys Glu Ser Pro
                500                 505                 510

Tyr Thr Cys Thr Lys Leu Asn Asp Trp Tyr Ser Gln Cys Leu
                515                 520                 525

<210> SEQ ID NO 93
<211> LENGTH: 1353
<212> TYPE: DNA
<213> ORGANISM: Myceliophthora thermophila

<400> SEQUENCE: 93
atgaagcagt acctccagta cctcgcggcg accctgcccc tggtgggcct ggccacggcc      60
cagcaggcgg gtaacctgca gaccgagact caccccaggc tcacttggtc caagtgcacg     120
gccccgggat cctgccaaca ggtcaacggc gaggtcgtca tcgactccaa ctggcgctgg     180
gtgcacgacg agaacgcgca gaactgctac gacggcaacc agtggaccaa cgcttgcagc     240
tctgccaccg actgcgccga gaattgcgcg ctcgagggtg ccgactacca gggcaccctat    300
ggcgcctcga ccagcggcaa tgccctgacg ctcaccttcg tcactaagca cgagtacggc     360
accaacattg gctcgcgcct ctacctcatg aacggcgcga caagtacca gatgttcacc      420
ctcaagggca cgagctggc cttcgacgtc gacctctcgg ccgtcgagtg cggcctcaac      480
agcgccctct acttcgtggc catggaggag gatggcggtg tgtcgagcta cccgaccaac     540
acggccggtg ctaagttcgg cactgggtac tgcgacgccc aatgcgcacg cgacctcaag     600
ttcgtcggcg gcaagggcaa catcgagggc tggaagccgt ccaccaacga tgccaatgcc     660
ggtgtcggtc cttatggcgg tgctgcgct  gagatcgacg tctgggagtc gaacaagtat     720
gctttcgctt tcaccccgca cggttgcgag aaccctaaat accacgtctg cgagaccacc     780
aactgcggtg gcacctactc cgaggaccgc ttcgctggtg actgcgatgc aacggctgc      840
gactacaacc cctaccgcat gggcaaccag gacttctacg gtcccggctt gacggtcgat     900
accagcaaga agttcaccgt cgtcagccag ttcgaggaga caagctcac ccagttcttc      960
gtccaggacg gcaagaagat tgagatcccc ggccccaagg tcgagggcat cgatgcggac    1020
agcgccgcta tcaccctga  gctgtgcagt gccctgttca aggccttcga tgaccgtgac    1080
cgcttctcgg aggttggcgg cttcgatgcc atcaacacgg ccctcagcac tcccatggtc    1140
ctcgtcatgt ccatctggga tgatcactac gccaatatgc tctggctcga ctcgagctac    1200
ccccctgaga aggctggcca gcctggcggt gaccgtggcc cgtgtcctca ggactctggc    1260
gtcccggccg acgttgaggc tcagtaccct aatgccaagg tcatctggtc caacatccgc    1320
ttcggcccca tcggctcgac tgtcaacgtc taa                                 1353

<210> SEQ ID NO 94
<211> LENGTH: 450
<212> TYPE: PRT
<213> ORGANISM: Myceliophthora thermophila
```

```
<400> SEQUENCE: 94

Met Lys Gln Tyr Leu Gln Tyr Leu Ala Ala Thr Leu Pro Leu Val Gly
1               5                   10                  15

Leu Ala Thr Ala Gln Gln Ala Gly Asn Leu Gln Thr Glu Thr His Pro
            20                  25                  30

Arg Leu Thr Trp Ser Lys Cys Thr Ala Pro Gly Ser Cys Gln Gln Val
        35                  40                  45

Asn Gly Glu Val Val Ile Asp Ser Asn Trp Arg Trp Val His Asp Glu
50                  55                  60

Asn Ala Gln Asn Cys Tyr Asp Gly Asn Gln Trp Thr Asn Ala Cys Ser
65                  70                  75                  80

Ser Ala Thr Asp Cys Ala Glu Asn Cys Ala Leu Glu Gly Ala Asp Tyr
                85                  90                  95

Gln Gly Thr Tyr Gly Ala Ser Thr Ser Gly Asn Ala Leu Thr Leu Thr
            100                 105                 110

Phe Val Thr Lys His Glu Tyr Gly Thr Asn Ile Gly Ser Arg Leu Tyr
        115                 120                 125

Leu Met Asn Gly Ala Asn Lys Tyr Gln Met Phe Thr Leu Lys Gly Asn
130                 135                 140

Glu Leu Ala Phe Asp Val Asp Leu Ser Ala Val Glu Cys Gly Leu Asn
145                 150                 155                 160

Ser Ala Leu Tyr Phe Val Ala Met Glu Glu Asp Gly Gly Val Ser Ser
                165                 170                 175

Tyr Pro Thr Asn Thr Ala Gly Ala Lys Phe Gly Thr Gly Tyr Cys Asp
            180                 185                 190

Ala Gln Cys Ala Arg Asp Leu Lys Phe Val Gly Gly Lys Gly Asn Ile
        195                 200                 205

Glu Gly Trp Lys Pro Ser Thr Asn Asp Ala Asn Ala Gly Val Gly Pro
210                 215                 220

Tyr Gly Cys Cys Ala Glu Ile Asp Val Trp Glu Ser Asn Lys Tyr
225                 230                 235                 240

Ala Phe Ala Phe Thr Pro His Gly Cys Glu Asn Pro Lys Tyr His Val
                245                 250                 255

Cys Glu Thr Thr Asn Cys Gly Gly Thr Tyr Ser Glu Asp Arg Phe Ala
            260                 265                 270

Gly Asp Cys Asp Ala Asn Gly Cys Asp Tyr Asn Pro Tyr Arg Met Gly
        275                 280                 285

Asn Gln Asp Phe Tyr Gly Pro Gly Leu Thr Val Asp Thr Ser Lys Lys
290                 295                 300

Phe Thr Val Val Ser Gln Phe Glu Glu Asn Lys Leu Thr Gln Phe Phe
305                 310                 315                 320

Val Gln Asp Gly Lys Lys Ile Glu Ile Pro Gly Pro Lys Val Glu Gly
                325                 330                 335

Ile Asp Ala Asp Ser Ala Ala Ile Thr Pro Glu Leu Cys Ser Ala Leu
            340                 345                 350

Phe Lys Ala Phe Asp Asp Arg Asp Arg Phe Ser Glu Val Gly Gly Phe
        355                 360                 365

Asp Ala Ile Asn Thr Ala Leu Ser Thr Pro Met Val Leu Val Met Ser
370                 375                 380

Ile Trp Asp Asp His Tyr Ala Asn Met Leu Trp Leu Asp Ser Ser Tyr
385                 390                 395                 400

Pro Pro Glu Lys Ala Gly Gln Pro Gly Gly Asp Arg Gly Pro Cys Pro
                405                 410                 415
```

Gln Asp Ser Gly Val Pro Ala Asp Val Glu Ala Gln Tyr Pro Asn Ala
            420                 425                 430

Lys Val Ile Trp Ser Asn Ile Arg Phe Gly Pro Ile Gly Ser Thr Val
        435                 440                 445

Asn Val
    450

<210> SEQ ID NO 95
<211> LENGTH: 1446
<212> TYPE: DNA
<213> ORGANISM: Thielavia terrestris

<400> SEQUENCE: 95

```
atggctcaga agctccttct cgccgccgcc cttgcggcca cgccctcgc tgctcccgtc      60
gtcgaggagc gccagaactg cggttccgtc tggagccaat gcggcggcat gggctggtcc    120
ggcgcgacct gctgcgcttc gggcaatacc tgcgttgagc tgaacccgta ctactcgcag    180
tgcctgccca acagccaggt gactacctcg accagcaaga ccacctccac caccaccagg    240
agcagcacca ccagccacag cagcggtccc accagcacga gcaccaccac caccagcagt    300
cccgtggtca ctacccccgcc gagtacctcc atccccggcg gtgcctcgtc aacggccagc    360
tggtccggca cccgttctc gggcgtgcag atgtgggcca acgactacta cgcctccgag      420
gtctcgtcgc tggccatccc cagcatgacg gcgccatgg ccaccaaggc ggccgaggtg      480
gccaaggtgc ccagcttcca gtggcttgac cgcaacgtca ccatcgacac gctgttcgcc    540
cacacgctgt cgcagatccg cgcggccaac cagaaaggcg ccaacccgcc ctacgcgggc    600
atcttcgtgg tctacgacct tccggaccgc gactgcgccg ccgccgcgtc aacggcgag     660
ttctccatcg cgaacaacgg ggcggccaac tacaagacgt acatcgacgc gatccggagc    720
ctcgtcatcc agtactcaga catccgcatc atcttcgtca tcgagcccga ctcgctggcc    780
aacatggtga ccaacctgaa cgtggccaag tgcgccaacg ccgagtcgac ctacaaggag    840
ttgaccgtct acgcgctgca gcagctgaac ctgcccaacg tggccatgta cctggacgcc    900
ggccacgccg gctggctcgg ctggcccgcc aacatccagc cggccgccaa cctcttcgcc    960
gagatctaca cgagcgccgg caagccggcc gccgtgcgcg gcctcgccac caacgtggcc   1020
aactacaacg gctggagcct ggccacgccg ccctcgtaca cccagggcga ccccaactac   1080
gacgagagcc actacgtcca ggccctcgcc ccgctgctca ccgccaacgg cttccccgcc   1140
cacttcatca ccgacaccgg ccgcaacggc aagcagccga ccggacaacg gcaatgggga   1200
gactggtgca acgttatcgg aactggcttc ggcgtgcgcc cgacgacaaa caccggcctc   1260
gacatcgagg acgccttcgt ctgggtcaag cccggcggcg agtgcgacgg cacgagcaac   1320
acgacctctc cccgctacga ctaccactgc ggcctgtcgg acgcgctgca gcctgctccg   1380
gaggccggca cttggttcca ggcctacttc gagcagctcc tgaccaacgc caacccgccc   1440
ttttaa                                                              1446
```

<210> SEQ ID NO 96
<211> LENGTH: 481
<212> TYPE: PRT
<213> ORGANISM: Thielavia terrestris

<400> SEQUENCE: 96

Met Ala Gln Lys Leu Leu Leu Ala Ala Ala Leu Ala Ala Ser Ala Leu
1               5                   10                  15

```
Ala Ala Pro Val Val Glu Glu Arg Gln Asn Cys Gly Ser Val Trp Ser
            20                  25                  30

Gln Cys Gly Gly Ile Gly Trp Ser Gly Ala Thr Cys Cys Ala Ser Gly
        35                  40                  45

Asn Thr Cys Val Glu Leu Asn Pro Tyr Tyr Ser Gln Cys Leu Pro Asn
    50                  55                  60

Ser Gln Val Thr Thr Ser Thr Ser Lys Thr Thr Ser Thr Thr Thr Arg
65                  70                  75                  80

Ser Ser Thr Thr Ser His Ser Ser Gly Pro Thr Ser Thr Ser Thr Thr
                85                  90                  95

Thr Thr Ser Ser Pro Val Val Thr Thr Pro Pro Ser Thr Ser Ile Pro
            100                 105                 110

Gly Gly Ala Ser Ser Thr Ala Ser Trp Ser Gly Asn Pro Phe Ser Gly
        115                 120                 125

Val Gln Met Trp Ala Asn Asp Tyr Tyr Ala Ser Glu Val Ser Ser Leu
    130                 135                 140

Ala Ile Pro Ser Met Thr Gly Ala Met Ala Thr Lys Ala Ala Glu Val
145                 150                 155                 160

Ala Lys Val Pro Ser Phe Gln Trp Leu Asp Arg Asn Val Thr Ile Asp
                165                 170                 175

Thr Leu Phe Ala His Thr Leu Ser Gln Ile Arg Ala Ala Asn Gln Lys
            180                 185                 190

Gly Ala Asn Pro Pro Tyr Ala Gly Ile Phe Val Val Tyr Asp Leu Pro
        195                 200                 205

Asp Arg Asp Cys Ala Ala Ala Ser Asn Gly Glu Phe Ser Ile Ala
210                 215                 220

Asn Asn Gly Ala Ala Asn Tyr Lys Thr Tyr Ile Asp Ala Ile Arg Ser
225                 230                 235                 240

Leu Val Ile Gln Tyr Ser Asp Ile Arg Ile Ile Phe Val Ile Glu Pro
                245                 250                 255

Asp Ser Leu Ala Asn Met Val Thr Asn Leu Asn Val Ala Lys Cys Ala
            260                 265                 270

Asn Ala Glu Ser Thr Tyr Lys Glu Leu Thr Val Tyr Ala Leu Gln Gln
        275                 280                 285

Leu Asn Leu Pro Asn Val Ala Met Tyr Leu Asp Ala Gly His Ala Gly
    290                 295                 300

Trp Leu Gly Trp Pro Ala Asn Ile Gln Pro Ala Ala Asn Leu Phe Ala
305                 310                 315                 320

Glu Ile Tyr Thr Ser Ala Gly Lys Pro Ala Ala Val Arg Gly Leu Ala
                325                 330                 335

Thr Asn Val Ala Asn Tyr Asn Gly Trp Ser Leu Ala Thr Pro Pro Ser
            340                 345                 350

Tyr Thr Gln Gly Asp Pro Asn Tyr Asp Glu Ser His Tyr Val Gln Ala
        355                 360                 365

Leu Ala Pro Leu Leu Thr Ala Asn Gly Phe Pro Ala His Phe Ile Thr
    370                 375                 380

Asp Thr Gly Arg Asn Gly Lys Gln Pro Thr Gly Gln Arg Gln Trp Gly
385                 390                 395                 400

Asp Trp Cys Asn Val Ile Gly Thr Gly Phe Gly Val Arg Pro Thr Thr
                405                 410                 415

Asn Thr Gly Leu Asp Ile Glu Asp Ala Phe Val Trp Val Lys Pro Gly
            420                 425                 430

Gly Glu Cys Asp Gly Thr Ser Asn Thr Thr Ser Pro Arg Tyr Asp Tyr
```

```
                    435                 440                 445
His Cys Gly Leu Ser Asp Ala Leu Gln Pro Ala Pro Glu Ala Gly Thr
        450                 455                 460

Trp Phe Gln Ala Tyr Phe Glu Gln Leu Leu Thr Asn Ala Asn Pro Pro
465                 470                 475                 480

Phe

<210> SEQ ID NO 97
<211> LENGTH: 19
<212> TYPE: PRT
<213> ORGANISM: Thielavia terrestris
<220> FEATURE:
<221> NAME/KEY: MISC_FEATURE
<222> LOCATION: (1)..(1)
<223> OTHER INFORMATION: X=I,L,M, OR V
<220> FEATURE:
<221> NAME/KEY: misc_feature
<222> LOCATION: (3)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (10)..(10)
<223> OTHER INFORMATION: X=I,L,M, OR V
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: MISC_FEATURE
<222> LOCATION: (14)..(14)
<223> OTHER INFORMATION: X=E OR Q
<220> FEATURE:
<221> NAME/KEY: misc_feature
<222> LOCATION: (15)..(18)
<223> OTHER INFORMATION: Xaa can be any naturally occurring amino acid
<220> FEATURE:
<221> NAME/KEY: MISC_FEATURE
<222> LOCATION: (19)..(19)
<223> OTHER INFORMATION: X=H,N, OR Q

<400> SEQUENCE: 97

Xaa Pro Xaa Xaa Xaa Xaa Gly Xaa Tyr Xaa Xaa Arg Xaa Xaa Xaa Xaa
1               5                   10                  15

Xaa Xaa Xaa

<210> SEQ ID NO 98
<211> LENGTH: 20
<212> TYPE: PRT
<213> ORGANISM: Thielavia terrestris
<220> FEATURE:
<221> NAME/KEY: MISC_FEATURE
<222> LOCATION: (1)..(1)
<223> OTHER INFORMATION: X=I,L,M, OR V
<220> FEATURE:
<221> NAME/KEY: misc_feature
<222> LOCATION: (3)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: MISC_FEATURE
<222> LOCATION: (11)..(11)
```

-continued

```
<223> OTHER INFORMATION: X=I,L,M, OR V
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: MISC_FEATURE
<222> LOCATION: (15)..(15)
<223> OTHER INFORMATION: X=E OR Q
<220> FEATURE:
<221> NAME/KEY: misc_feature
<222> LOCATION: (16)..(19)
<223> OTHER INFORMATION: Xaa can be any naturally occurring amino acid
<220> FEATURE:
<221> NAME/KEY: MISC_FEATURE
<222> LOCATION: (20)..(20)
<223> OTHER INFORMATION: X=H,N, OR Q

<400> SEQUENCE: 98

Xaa Pro Xaa Xaa Xaa Xaa Xaa Gly Xaa Tyr Xaa Xaa Arg Xaa Xaa Xaa
1               5                   10                  15

Xaa Xaa Xaa Xaa
            20

<210> SEQ ID NO 99
<211> LENGTH: 9
<212> TYPE: PRT
<213> ORGANISM: Thielavia terrestris
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: X= Y OR W
<220> FEATURE:
<221> NAME/KEY: MISC_FEATURE
<222> LOCATION: (9)..(9)
<223> OTHER INFORMATION: X= A,I,L,M OR V

<400> SEQUENCE: 99

His Xaa Gly Pro Xaa Xaa Xaa Xaa Xaa
1               5

<210> SEQ ID NO 100
<211> LENGTH: 10
<212> TYPE: PRT
<213> ORGANISM: Thielavia terrestris
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: X= Y OR W
<220> FEATURE:
<221> NAME/KEY: MISC_FEATURE
<222> LOCATION: (10)..(10)
<223> OTHER INFORMATION: X= A,I,L,M OR V
```

```
<400> SEQUENCE: 100

His Xaa Xaa Gly Pro Xaa Xaa Xaa Xaa Xaa
1               5                   10

<210> SEQ ID NO 101
<211> LENGTH: 11
<212> TYPE: PRT
<213> ORGANISM: Thielavia terrestris
<220> FEATURE:
<221> NAME/KEY: MISC_FEATURE
<222> LOCATION: (1)..(1)
<223> OTHER INFORMATION: X= E OR Q
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: X= E,H,Q OR N
<220> FEATURE:
<221> NAME/KEY: MISC_FEATURE
<222> LOCATION: (9)..(9)
<223> OTHER INFORMATION: X=F,I,L, OR V
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: X=I,L,OR V

<400> SEQUENCE: 101

Xaa Xaa Tyr Xaa Xaa Cys Xaa Xaa Xaa Xaa Xaa
1               5                   10

<210> SEQ ID NO 102
<211> LENGTH: 19
<212> TYPE: PRT
<213> ORGANISM: Thielavia terrestris
<220> FEATURE:
<221> NAME/KEY: MISC_FEATURE
<222> LOCATION: (1)..(1)
<223> OTHER INFORMATION: X=I,L,M OR V
<220> FEATURE:
<221> NAME/KEY: misc_feature
<222> LOCATION: (3)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (10)..(10)
<223> OTHER INFORMATION: X=I,L,M OR V
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: MISC_FEATURE
```

```
<222> LOCATION: (14)..(14)
<223> OTHER INFORMATION: X= E OR Q
<220> FEATURE:
<221> NAME/KEY: misc_feature
<222> LOCATION: (15)..(17)
<223> OTHER INFORMATION: Xaa can be any naturally occurring amino acid
<220> FEATURE:
<221> NAME/KEY: MISC_FEATURE
<222> LOCATION: (19)..(19)
<223> OTHER INFORMATION: X= H,N, OR Q

<400> SEQUENCE: 102

Xaa Pro Xaa Xaa Xaa Xaa Gly Xaa Tyr Xaa Xaa Arg Xaa Xaa Xaa Xaa
1               5                   10                  15

Xaa Ala Xaa

<210> SEQ ID NO 103
<211> LENGTH: 20
<212> TYPE: PRT
<213> ORGANISM: Thielavia terrestris
<220> FEATURE:
<221> NAME/KEY: MISC_FEATURE
<222> LOCATION: (1)..(1)
<223> OTHER INFORMATION: X=I,L,M OR V
<220> FEATURE:
<221> NAME/KEY: misc_feature
<222> LOCATION: (3)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: X=I,L,M OR V
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: MISC_FEATURE
<222> LOCATION: (15)..(15)
<223> OTHER INFORMATION: X=E OR Q
<220> FEATURE:
<221> NAME/KEY: misc_feature
<222> LOCATION: (16)..(18)
<223> OTHER INFORMATION: Xaa can be any naturally occurring amino acid
<220> FEATURE:
<221> NAME/KEY: MISC_FEATURE
<222> LOCATION: (20)..(20)
<223> OTHER INFORMATION: X= H,N, OR Q

<400> SEQUENCE: 103

Xaa Pro Xaa Xaa Xaa Xaa Xaa Gly Xaa Tyr Xaa Xaa Arg Xaa Xaa Xaa
1               5                   10                  15

Xaa Xaa Ala Xaa
            20

<210> SEQ ID NO 104
<211> LENGTH: 4
<212> TYPE: PRT
<213> ORGANISM: Thielavia terrestris
<220> FEATURE:
<221> NAME/KEY: MISC_FEATURE
<222> LOCATION: (1)..(1)
<223> OTHER INFORMATION: X = F or W
<220> FEATURE:
<221> NAME/KEY: MISC_FEATURE
```

```
<222> LOCATION: (2)..(2)
<223> OTHER INFORMATION: X = T or F
<220> FEATURE:
<221> NAME/KEY: MISC_FEATURE
<222> LOCATION: (4)..(4)
<223> OTHER INFORMATION: X = A, I or V

<400> SEQUENCE: 104

Xaa Xaa Lys Xaa
1
```